US012643876B2

(12) United States Patent
Lin et al.

(10) Patent No.: US 12,643,876 B2
(45) Date of Patent: Jun. 2, 2026

(54) DEUTERATED HPKI KINASE INHIBITOR, AND PREPARATION METHOD THEREFOR AND USE THEREOF

(71) Applicant: ZHUHAI YUFAN BIOTECHNOLOGIES CO., LTD, Guangdong (CN)

(72) Inventors: Xingyu Lin, Guangdong (CN); Tingting Lu, Guangdong (CN)

(73) Assignee: GUANGZHOU YUFAN NANTU BIOTECHNOLOGIES CO., LTD, Guangzhou (CN)

( * ) Notice: Subject to any disclaimer, the term of this patent is extended or adjusted under 35 U.S.C. 154(b) by 447 days.

(21) Appl. No.: 18/250,287

(22) PCT Filed: Oct. 15, 2021

(86) PCT No.: PCT/CN2021/124144
§ 371 (c)(1),
(2) Date: Apr. 24, 2023

(87) PCT Pub. No.: WO2022/089225
PCT Pub. Date: May 5, 2022

(65) Prior Publication Data

US 2023/0399309 A1 Dec. 14, 2023

(30) Foreign Application Priority Data

Oct. 30, 2020 (CN) ......................... 202011199799.3

(51) Int. Cl.
*C07D 401/04* (2006.01)
*C07D 417/04* (2006.01)

(52) U.S. Cl.
CPC ......... *C07D 401/04* (2013.01); *C07D 417/04* (2013.01); *C07B 2200/05* (2013.01); *C07B 2200/13* (2013.01)

(58) Field of Classification Search
CPC .................................................... C07D 401/04
See application file for complete search history.

(56) References Cited

U.S. PATENT DOCUMENTS

| | | | |
|---|---|---|---|
| 11,999,725 | B2 | 6/2024 | Liao |
| 2016/0158360 | A1 | 6/2016 | Hernandez et al. |
| 2021/0276994 | A1 | 9/2021 | Liao |
| 2022/0331435 | A1 | 10/2022 | Liao et al. |
| 2023/0097009 | A1 | 3/2023 | Kang et al. |
| 2023/0241050 | A1 | 8/2023 | Lin et al. |

FOREIGN PATENT DOCUMENTS

| | | | | |
|---|---|---|---|---|
| CN | 1777427 A | 5/2006 | | |
| CN | 101967140 | 2/2011 | | |
| CN | 103304552 | 9/2013 | | |
| CN | 104650049 | 5/2015 | | |
| CN | 110396087 * | 11/2019 | ........... | C07D 417/14 |
| CN | 110396087 A | 11/2019 | | |
| CN | 110396088 | 11/2019 | | |
| JP | 2014005265 | 1/2014 | | |
| JP | 2014526524 | 10/2014 | | |
| WO | 2006021884 A2 | 3/2006 | | |
| WO | 2012119006 | 9/2012 | | |
| WO | 2013041038 | 3/2013 | | |
| WO | 2013138210 | 9/2013 | | |
| WO | 2013192512 | 12/2013 | | |
| WO | 2015034729 | 3/2015 | | |
| WO | 2016201370 | 12/2016 | | |
| WO | 2019206049 | 10/2019 | | |
| WO | 2020193511 | 10/2020 | | |
| WO | 2020255022 | 12/2020 | | |
| WO | 2021057872 | 4/2021 | | |
| WO | 2021254118 | 12/2021 | | |
| WO | 2021254265 | 12/2021 | | |

OTHER PUBLICATIONS

Vippagunta et al. (2001).*
Wolff et al. (1995).*
Banker et al., (1996).*
International Search Report for PCT/CN2021/124144 mailed Jan. 19, 2022, 6 pages.
Written Opinion of the ISA for PCT/CN2021/124144 mailed Jan. 19, 2022, 4 pages.
Foster, A. B . . . "Deuterium isotope effects in the metabolism of drugs and xenobiotics: Implications for drug design." Advances in Drug Research 14(1985):1-40.
Ao, Wangwei et al.Synthesis of deuterium-labeled crizotinib, a potent and selective dual inhibitor of mesenchymal-epithelial transition factor (c-MET) kinase and anaplastic lymphoma kinase (ALK). J Labelled Comp Radiopharm. Dec. 2018;61(14):1036-1042. doi: 10.1002/jlcr.3678. Epub Sep. 9, 2018. PMID: 30118545.
Syroeshkin A. V., et al., The influence of deuterium on the properties of pharmaceutical substances (review), Development and Registration of Medicines, 2020; 19 pages.
Mino R. Caira, Crystalline Polymorphism of Organic Compounds, Topics in Current Chemistry, vol. 198, section 3.1, 1998, pp. 163-208.
Sawasdikosol et al., "HPK1 as a novel target for cancer immunotherapy", Immunology Institute at the Mount Sinai School of Medicine, Apr. 4, 2012, 5 pages.
Buteau, "Deuterated Drugs: Unexpectedly Nonobvious?" Journal of High Technology Law, 2009, 53 pages.
Drug discovery, "Heavyweight drugs", Chemistry & Industry, Mar. 9, 2009, 3 pages.

(Continued)

*Primary Examiner* — Paul V Ward
(74) *Attorney, Agent, or Firm* — NIXON & VANDERHYE, PC

(57) ABSTRACT

Provided in the present invention are a compound of general formula I or a pharmaceutically acceptable salt, a stereoisomer, an ester, a prodrug and a solvate thereof, a preparation method and use thereof, and in particular, the use of the compound of general formula I or the pharmaceutically acceptable salt, the stereoisomer, the ester, the prodrug and the solvate thereof as an HPK1 kinase inhibitor in the prevention and/or treatment of tumors and diseases caused by or associated with pathogen infection. The above-mentioned compound of general formula I contains at least one deuterium atom, and has high stability and good bioavailablility in an animal body.

15 Claims, 7 Drawing Sheets

(56) References Cited

OTHER PUBLICATIONS

Gannes et al., "Natural Abundance Variations in Stable Isotopes and their Potential Uses in Animal Physiological Ecology", Comp Biochem Physiol Mol Integr Physiol, 1998, vol. 119A, No. 3, pp. 725-737.

* cited by examiner

DEUTERATED HPKI KINASE INHIBITOR, AND PREPARATION METHOD THEREFOR AND USE THEREOF

This application is the U.S. national phase of International Application No. PCT/CN2021/124144 filed Oct. 15, 2021 which designated the U.S. and claims priority to CN 202011199799.3 filed Oct. 30, 2020, the entire contents of each of which are hereby incorporated by reference.

FIELD OF THE INVENTION

The present invention relates to the field of pharmaceuticals, and particularly relates to a deuterated HPK1 kinase inhibitor, a preparation method and use thereof. The present invention further relates to a crystalline form of the deuterated HPK1 kinase inhibitor (especially 4-(3-(((2-amino-S-(1-(1-trideuteromethylpiperidin-4-yl)-1H-pyrazol-4-yl)pyridin-3-yl)oxy)methyl)phenyl)-2-methylbut-3-yn-2-ol and salts thereof) described above, a preparation method and use thereof.

BACKGROUND OF THE INVENTION

HPK1 kinase is involved in many signaling cascade reactions including growth factor signaling, MAPK signaling, cytokine signaling, apoptosis signaling, antigen receptor signaling and the like. HPK1 kinase is a key functional activator of the JNK/SAPK signaling pathway, and when it is activated, the HPK1 kinase can selectively activate the MAPK signaling pathway of C-Jun N-terminal kinase (JNK).

HPK1 kinase can be used as a target of immunotherapy, and it can be activated by lymphocyte antigen receptors and inhibit AP-1. AP-1 plays a role in promoting cell proliferation, inhibiting differentiation, promoting invasion and metastasis of tumor cells and the like in the process of tumor formation and development. However, targeted disruption of alleles of the HPK1 kinase may lead to increased production of Th1 cytokines by T cells in TCR responses.

S Sawasdikosol (HPK1 as a novel target for cancer immunotherapy, *Immunol Res,* 54 (2012), pp. 262-265) reported that HPK1 kinase −/− T cells proliferate more rapidly than the monomeric wild-type and are resistant to prostaglandin E2 (PGE2)-mediated suppression. Most strikingly, mice transfected with HPK1 kinase −/− T cells were resistant to the growth of cancer tumors. The loss of HPK1 from dendritic cells (DCs) endows them with superior antigen presentation ability, enabling HPK1 −/− DCs to elicit a more potent anti-tumor immune response when used as cancer vaccine. It is probable that blocking the HPK1 kinase activity with a small molecule inhibitor may activate the superior anti-tumor activity of both cell types, resulting in a synergistic amplification of anti-tumor potential. In addition, the transfected HPK1 kinase is not expressed in major organs, suggesting that inhibitors of HPK1 kinase activity may not lead to any serious complications.

US2016158360A1 discloses a composition and method for enhancing immune responses and treating cancer, the composition comprising a PD-1 antagonist and an HPK1 antagonist, wherein the HPK1 antagonist comprises a compound that inhibits the serine/threonine kinase activity of HPK1.

It can be seen that HPK1 kinase plays a key role in disease treatment, especially in cancer treatment. The discovery of small molecule inhibitors of HPK1 kinase is currently an urgent need. Patent document CN110396087A discloses a heterocyclic compound which is useful as an HPK1 kinase inhibitor.

SUMMARY OF THE INVENTION

The present invention provides a compound of general formula I:

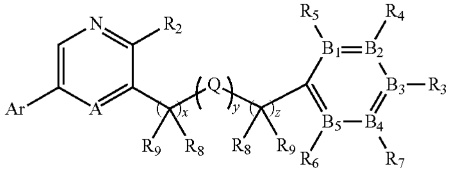

(I)

wherein,

A is selected from $CR_{10}$ and N;

Q is selected from O and S;

x and z are independently selected from integers between 0 and 6 (for example, 0, 1, 2, 3, 4, 5 or 6);

y is 0 or 1;

Ar is selected from aromatic five-membered heterocyclic group, aromatic six-membered heterocyclic group and phenyl, wherein the aromatic five-membered heterocyclic group is selected from: furyl, thienyl, pyrrolyl, pyrazolyl, imidazolyl, oxazolyl, thiazolyl and selenothiazolyl, and the aromatic six-membered heterocyclic group is selected from: pyridinyl, pyridazinyl, pyrimidinyl and pyrazinyl; optionally, H on the aromatic five-membered heterocyclic group, the aromatic six-membered heterocyclic group or the phenyl may be substituted with the following groups: -D, —$SO_2$, —$SO_2N(C_{0-10}$ alkyl)($C_{0-10}$ alkyl), —$N(C_{0-10}$ alkyl)$SO_2$($C_{0-10}$ alkyl), —$CON(C_{0-10}$ alkyl)($C_{0-10}$ alkyl), —$N(C_{0-10}$ alkyl)$CO(C_{0-10}$ alkyl), —$N(C_{0-10}$ alkyl)$COO(C_{0-10}$ alkyl), —$OCON(C_{0-10}$ alkyl)($C_{0-10}$ alkyl), halogen, —CN, —$OCH_2F$, —$OCHF_2$, —$OCF_3$, $C_{1-10}$ linear/branched alkyl, —$N(C_{0-10}$ alkyl)($C_{0-10}$ alkyl), —$OC_{0-10}$ alkyl, $C_{3-10}$ cycloalkyl, —O heterocycloalkyl, —N heterocycloalkyl, —N heterocycloaryl, —O heterocycloaryl or —S heterocycloaryl, and wherein the alkyl moieties may be optionally substituted with one or more of the following groups: —$SO_2$, —$SO_2N$($C_{0-10}$ alkyl)($C_{0-10}$ alkyl), —$N(C_{0-10}$ alkyl)$SO_2(C_{0-10}$ alkyl), —$CON(C_{0-10}$ alkyl)($C_{0-10}$ alkyl), —$N(C_{0-10}$ alkyl)$CO(C_{0-10}$ alkyl), —$N(C_{0-10}$ alkyl)$COO(C_{0-10}$ alkyl), —$OCON(C_{0-10}$ alkyl)($C_{0-10}$ alkyl), halogen, —CN, —$OCH_2F$, —$OCHF_2$, —$OCF_3$, —$N(C_{0-10}$ alkyl)($C_{0-10}$ alkyl), —$OC_{0-10}$ alkyl, —$CO(C_{0-10}$ alkyl), —$COO(C_{0-10}$ alkyl), —N heterocycloaryl, —O heterocycloaryl or —S heterocycloaryl, wherein one or more H atoms attached to the C atoms or heteroatoms may be substituted with deuterium;

$R_2$ is selected from: —H, -D, halogen, —$NO_2$, —CN, $C_{1-10}$ linear/branched alkyl, $C_{3-10}$ cycloalkyl, —$N(C_{0-10}$ alkyl)($C_{0-10}$ alkyl), —$CF_3$, —$OCF_3$, —$OCHF_2$, —$OCH_2F$ and —$OC_{0-10}$ alkyl, wherein one or more H atoms attached to the C atoms may be substituted with deuterium;

$B_1$, $B_2$, $B_3$, $B_4$ and $B_5$ are independently selected from C and N (when $B_1$, $B_2$, $B_3$, $B_4$ or $B_5$ is N, $R_3$, $R_4$, $R_5$, $R_6$ or $R_7$ corresponding thereto is not present);

$R_3$, $R_4$, $R_5$, $R_6$ and $R_7$, when present, are independently selected from: —H, -D, halogen, —CN, —$OC_{0-10}$ alkyl, —CO($C_{0-10}$ alkyl), —CON($C_{0-10}$ alkyl)($C_{0-10}$ alkyl), $C_{1-10}$ linear/branched alkyl, heteroalkyl containing O or N, —N($C_{0-10}$ alkyl)($C_{0-10}$ alkyl), $C_{3-10}$ cycloalkyl, —C≡C—$R_{10}$, —O heterocycloalkyl and —N heterocycloalkyl, or $R_5$ and $R_4$, $R_4$ and $R_3$, $R_3$ and $R_7$, $R_7$ and $R_6$, together with carbon atoms therebetween, form $C_{3-8}$ cycloalkyl or $C_{3-8}$ heterocycloalkyl containing —O— or —S—, —N heterocycloaryl, —O heterocycloaryl or —S heterocycloaryl or phenyl, wherein the alkyl moieties may be optionally substituted with one or more of the following groups: —$SO_2$, —$SO_2$N($C_{0-10}$ alkyl)($C_{0-10}$ alkyl), —N($C_{0-10}$ alkyl)$SO_2$($C_{0-10}$ alkyl), —CON($C_{0-10}$ alkyl)($C_{0-10}$ alkyl), —N($C_{0-10}$ alkyl)CO($C_{0-10}$ alkyl), —N($C_{0-10}$ alkyl)COO($C_{0-10}$ alkyl), —OCON($C_{0-10}$ alkyl)($C_{0-10}$ alkyl), halogen, —CN, —$OCH_2F$, —$OCHF_2$, —$OCF_3$, $C_{1-10}$ linear/branched alkyl, —N($C_{0-10}$ alkyl)($C_{0-10}$ alkyl), —$OC_{0-10}$ alkyl, $C_{3-10}$ cycloalkyl, —O heterocycloalkyl, —N heterocycloalkyl, —N heterocycloaryl, —O heterocycloaryl or —S heterocycloaryl, wherein one or more H atoms attached to the C atoms or heteroatoms may be substituted with deuterium;

$R_8$ and $R_9$ are independently selected from: —H, -D, halogen and $C_{1-10}$ linear/branched alkyl, wherein one or more H atoms attached to the C atoms may be substituted with deuterium;

$R_{10}$ is selected from: —H, -D, $C_{1-5}$ linear/branched alkyl, $C_{3-10}$ cycloalkyl and

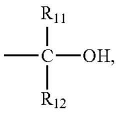

wherein one or more H atoms attached to the C atoms may be substituted with deuterium;

$R_{11}$ and $R_{12}$ are independently selected from: —H, -D, —$CF_3$, —$CHF_2$, —$CH_2F$, $C_{1-10}$ linear/branched alkyl, —CH═C($C_{0-10}$ alkyl)($C_{0-10}$ alkyl), —C≡C($C_{0-10}$ alkyl), $C_{3-10}$ cycloalkyl, an aromatic five-membered cyclic group and an aromatic six-membered cyclic group, or $R_{11}$ and $R_{12}$, together with carbon atoms between $R_{11}$ and $R_{12}$, form $C_{3-8}$ cycloalkyl or $C_{3-8}$ heterocycloalkyl containing —O— or —S—, $C_{4-9}$ fused cycloalkyl, $C_{5-10}$ spiro cycloalkyl, $C_{4-9}$ bridged cycloalkyl, $C_{3-7}$ cyclolactam, $C_{3-7}$ cyclic lactone or $C_{3-7}$ cyclic ketone, wherein the alkyl moieties may be optionally substituted with one or more of the following groups: —$SO_2$, —$SO_2$N($C_{0-10}$ alkyl)($C_{0-10}$ alkyl), —N($C_{0-10}$ alkyl)$SO_2$($C_{0-10}$ alkyl), —CON($C_{0-10}$ alkyl)($C_{0-10}$ alkyl), —N($C_{0-10}$ alkyl)CO($C_{0-10}$ alkyl), —N($C_{0-10}$ alkyl)COO($C_{0-10}$ alkyl), —OCON($C_{0-10}$ alkyl)($C_{0-10}$ alkyl), halogen, —CN, —$OCH_2F$, —$OCHF_2$, —$OCF_3$, —N($C_{0-10}$ alkyl)($C_{0-10}$ alkyl), —$OC_{0-10}$ alkyl, —N heterocycloaryl, —O heterocycloaryl or —S heterocycloaryl, wherein one or more H atoms attached to the C atoms or heteroatoms may be substituted with deuterium;

and, the compound of general formula I contains at least one deuterium atom.

In one embodiment of the present invention, A is $CR_{10}$, in particular CH.

In one embodiment of the present invention, Q is O.

In one embodiment of the present invention, x is 0.

In one embodiment of the present invention, z is 1.

In one embodiment of the present invention, y is 1.

In one embodiment of the present invention, $B_1$, $B_2$, $B_3$, $B_4$ and $B_5$ are all C, i.e., in general formula I,

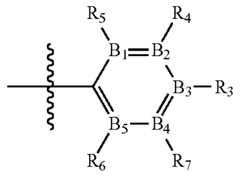

is

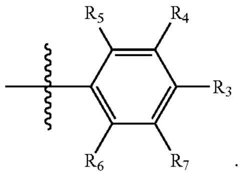

.

In another embodiment of the present invention, at least one of $B_1$, $B_2$, $B_3$, $B_4$ and $B_5$ is N.

Specifically, $B_2$ is C, and at least one of $B_1$, $B_3$, $B_4$ and $B_5$ is N.

More specifically, $B_2$ is C, and $B_1$ is N.

More specifically, $B_2$ is C, and $B_3$ is N.

More specifically, $B_2$ is C, and $B_4$ is N.

More specifically, $B_2$ is C, and $B_5$ is N.

More specifically, $B_2$ is C, $B_3$ and $B_4$ are N, or $B_3$ and $B_5$ are both N.

Specifically, Ar is selected from: thiazolyl, selenothiazolyl, imidazolyl, pyrazolyl and pyridinyl.

In one embodiment of the present invention, the compound of general formula I has the following structure:

(II)

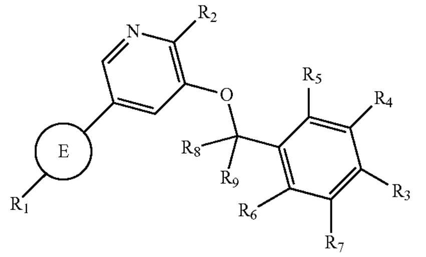

wherein the E ring is selected from:

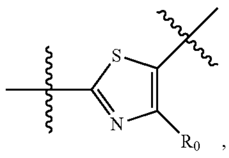

,

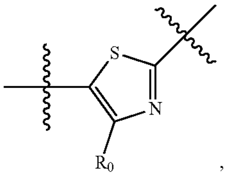

,

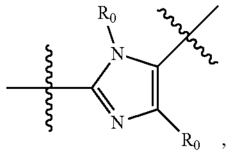

,

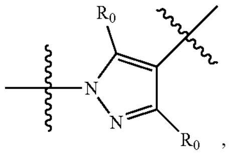

,

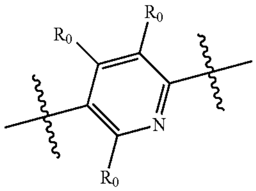

and

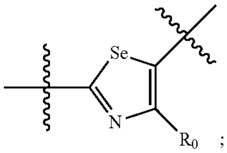

;

in the E ring, each $R_0$ is independently selected from: —H, -D, $C_{1-10}$ linear/branched alkyl, —N($C_{0-10}$ alkyl)($C_{0-10}$ alkyl), —O$C_{0-10}$ alkyl, —CO($C_{0-10}$ alkyl) and $C_{3-10}$ cycloalkyl, wherein H attached to the C atoms or heteroatoms may be substituted with deuterium;

$R_1$ is selected from: —H, -D, —O heterocycloalkyl, —N heterocycloalkyl, $C_{1-10}$ linear/branched alkyl, $C_{3-10}$ cycloalkyl, —O$C_{0-10}$ alkyl, —N($C_{0-10}$ alkyl)($C_{0-10}$ alkyl), —$SO_2$($C_{0-10}$ alkyl), —CO($C_{0-10}$ alkyl), —O-phenyl, —S($C_{0-10}$ alkyl), —N heterocycloaryl, —O heterocycloaryl and —S heterocycloaryl, wherein H attached to the C atoms or heteroatoms may be substituted with deuterium;

$R_{2-9}$ have the corresponding definitions described above in the present invention;

and, wherein at least one of $R_{0-9}$ contains a deuterium atom.

In one embodiment of the present invention, in general formula II, $R_1$ contains at least one deuterium atom; and more specifically, for example, $R_1$ contains at least one deuterium atom, while $R_{2-9}$ does not contain a deuterium atom.

In another embodiment of the present invention, in general formula II, $R_2$ contains at least one deuterium atom.

In another embodiment of the present invention, in general formula II, $R_3$ contains at least one deuterium atom.

In another embodiment of the present invention, in general formula II, $R_4$ contains at least one deuterium atom.

In another embodiment of the present invention, in general formula II, $R_5$ contains at least one deuterium atom.

In another embodiment of the present invention, in general formula II, $R_6$ contains at least one deuterium atom.

In another embodiment of the present invention, in general formula II, $R_8$ and/or $R_9$ contains at least one deuterium atom.

Specifically, each $R_0$ is independently selected from: $C_{1-5}$ linear/branched alkyl and —N($C_{0-10}$ alkyl)($C_{0-10}$ alkyl), wherein H attached to the C atoms may be substituted with deuterium.

More specifically, each $R_0$ is independently selected from: —H, -D, —$CH_3$, —$CH_2CH_3$ and —$NH_2$.

Specifically, $R_1$ is selected from: —O heterocycloalkyl, —N heterocycloalkyl, —$SO_2$($C_{0-3}$ alkyl), —O-phenyl, —S($C_{0-4}$ alkyl), $C_{3-6}$ cycloalkyl and $C_{3-5}$ linear/branched alkyl, wherein H attached to the C atoms or heteroatoms may be substituted with deuterium.

More specifically, $R_1$ is selected from:

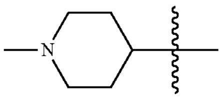, 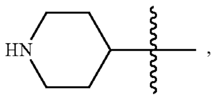,

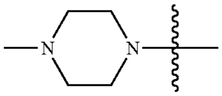, 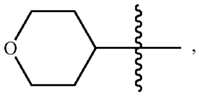,

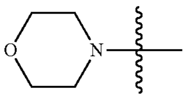, —$CH_3$, 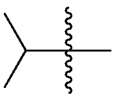,

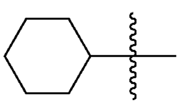, 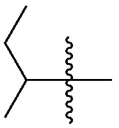,

-continued

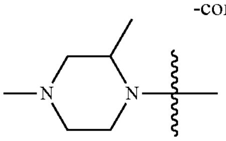, 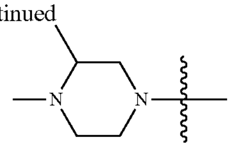,

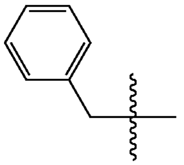, 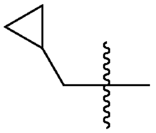,

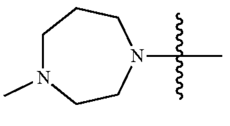, 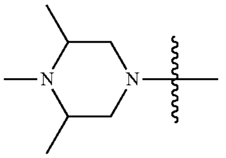,

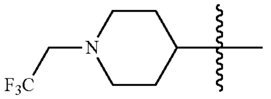, 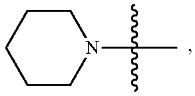,

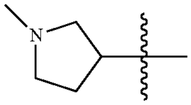, 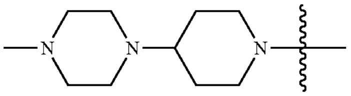,

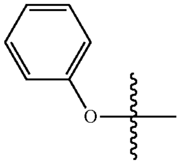, 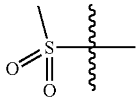,

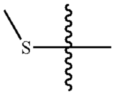, 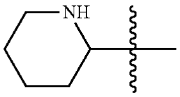,

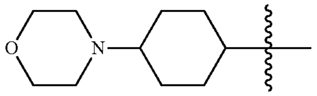,

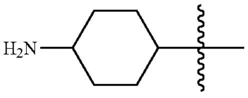 and 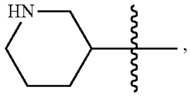, wherein H attached to the C atoms or N atoms may be substituted with deuterium.

More specifically, $R_1$ is selected from:

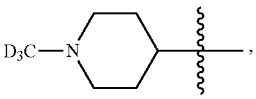, 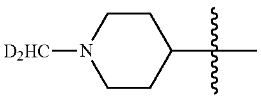,

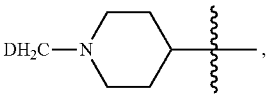, 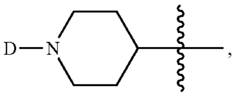,

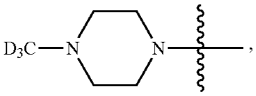, 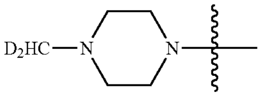,

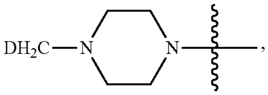, —$CH_2D$, —$CHD_2$,

-continued

—$CD_3$, 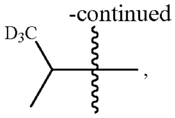, 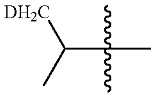,

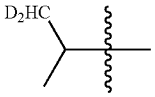, 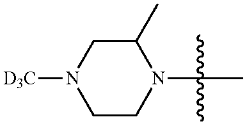,

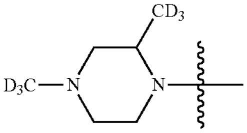, 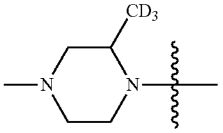,

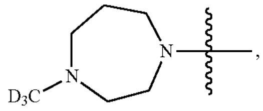, 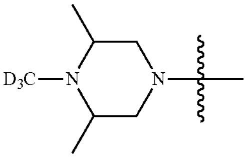,

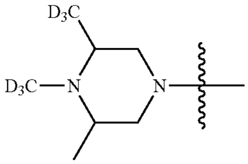, 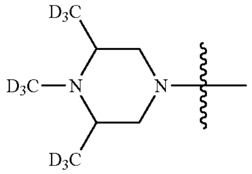,

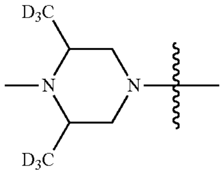, 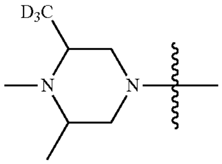,

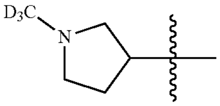,

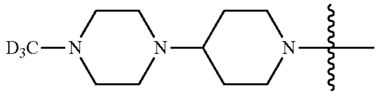,

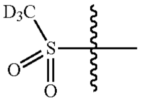, 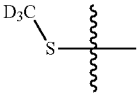,

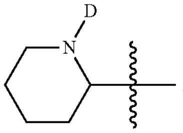, 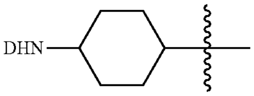,

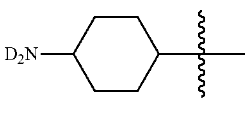 and 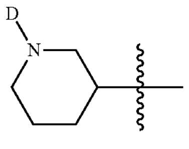.

Specifically, when $R_0$ is adjacent to $R_1$, $R_0$ and $R_1$, together with carbon atoms therebetween, form $C_{3-8}$ cycloalkyl or $C_{3-8}$ heterocycloalkyl containing —O— or —S—, —N heterocycloaryl, —O heterocycloaryl, —S heterocycloaryl or phenyl.

Specifically, $R_2$ is selected from: —H, -D, halogen, —$NO_2$, —CN, $C_{1-5}$ linear/branched alkyl, $C_{3-10}$ cycloalkyl, —N($C_{0-10}$ alkyl)($C_{0-10}$ alkyl), —$CF_3$, —$OCF_3$, —$OCHF_2$, —$OCH_2F$ and —$OC_{0-10}$ alkyl, wherein H attached to the C atoms or N atoms may be substituted with deuterium.

More specifically, $R_2$ is selected from: —$NO_2$, —N($C_{0-10}$ alkyl)($C_{0-10}$ alkyl), —$OC_{0-10}$ alkyl and —$OCF_3$, wherein H attached to the C atoms or N atoms may be substituted with deuterium.

Further specifically, $R_2$ is selected from: —$NH_2$, —NHD, —$ND_2$ and —$NO_2$.

Specifically, $R_3$ is selected from: —H, -D, halogen, —$OC_{0-10}$ alkyl, —CO($C_{0-10}$ alkyl), $C_{1-10}$ linear/branched alkyl, —N($C_{0-10}$ alkyl)($C_{0-10}$ alkyl) and $C_{3-10}$ cycloalkyl, wherein H attached to the C atoms may be substituted with deuterium.

More specifically, $R_3$ is selected from: —H, -D, halogen, —$OC_{0-10}$ alkyl and $C_{1-10}$ linear/branched alkyl, wherein H attached to the C atoms may be substituted with deuterium.

Further specifically, $R_3$ is selected from: —H, -D, —F, —$OCH_3$, —$OCH_2D$, —$OCHD_2$ and —$OCD_3$.

Specifically, $R_4$ is selected from: —H, -D, halogen, —$OC_{0-10}$ alkyl, —CO($C_{0-10}$ alkyl), —CN, $C_{3-10}$ cycloalkyl, $C_{1-10}$ linear/branched alkyl, —N($C_{0-10}$ alkyl)($C_{0-10}$ alkyl), —O heterocycloalkyl and —N heterocycloalkyl, wherein H attached to the C atoms or N atoms may be substituted with deuterium.

More specifically, $R_4$ is selected from: —H, -D, halogen, —$OC_{0-10}$ alkyl, —CN, $C_{3-10}$ cycloalkyl and —C≡C—$R_{10}$, wherein H attached to the C atoms may be substituted with deuterium. In one embodiment of the present invention, H attached to the C atoms in $R_{10}$ may be substituted with deuterium.

In one embodiment of the present invention, $R_4$ is selected from: —H, -D, —F, —Cl, —$OCH_3$, —$OCH_2D$, —$OCHD_2$, —$OCD_3$, —CN,

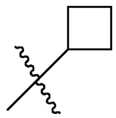 [SMILES: *C1CCC1]

and —C≡C—$R_{10}$.

Specifically, $R_5$, $R_6$ and $R_7$ are independently selected from: —H, -D, halogen, —CN, —$OC_{0-10}$ alkyl, —CO($C_{0-10}$ alkyl), $C_{1-10}$ linear/branched alkyl, —N($C_{0-10}$ alkyl)($C_{0-10}$ alkyl), $C_{3-10}$ cycloalkyl, —C≡C—$R_{10}$, —O heterocycloalkyl, —N heterocycloalkyl, and $C_{1-5}$ linear/branched alkyl containing O or N, or $R_6$ and $R_7$, together with carbon atoms between $R_6$ and $R_7$, form $C_{3-8}$ cycloalkyl or $C_{3-8}$ heterocycloalkyl containing —O— or —S—, wherein H attached to the C atoms or heteroatoms may be substituted with deuterium.

More specifically, $R_5$, $R_6$ and $R_7$ are independently selected from: —H, -D, halogen, —CN, $C_{1-3}$ linear/branched alkyl, —$OC_{0-3}$ alkyl, —CO($C_{0-3}$ alkyl) and N-containing $C_{1-3}$ linear/branched alkyl, or $R_6$ and $R_7$, together with carbon atoms between $R_6$ and $R_7$, form $C_{3-8}$ cycloalkyl or $C_{3-8}$ heterocycloalkyl containing —O—, wherein H attached to the C atoms or N atoms may be substituted with deuterium.

Further specifically, $R_5$, $R_6$ and $R_7$ are independently selected from: —H, -D, —F, —Cl, —$CH_3$, —$CH_2NH_2$, —$CH_2NH(CH_3)$, —$CH_2N(CH_3)_2$, —CN, —$OCH_3$ and —$COCH_3$, or $R_6$ and $R_7$, together with carbon atoms between $R_6$ and $R_7$, form five-membered cycloalkyl containing —O—, wherein H attached to the C atoms or N atoms may be substituted with deuterium.

In one embodiment of the present invention, $R_5$ is selected from: —H, -D, —F, —Cl, —$CH_3$, —$CH_2D$, —$CHD_2$, —$CD_3$, —$OCH_3$, —$COCH_3$, —$CH_2NH_2$, —$CH_2N(CH_3)_2$, —CN, —$OCH_2D$, —$OCHD_2$, —$OCD_3$, —$COCD_3$, —$CH_2N(CD_3)_2$ and —$CH_2N(CH_3)(CD_3)$.

In one embodiment of the present invention, $R_6$ is selected from: —H, -D, —F, —Cl, —$CH_3$, —$CH_2D$, —$CHD_2$, —$CD_3$, —$OCH_3$, —$COCH_3$, —$CH_2NH_2$, —$CH_2N(CH_3)_2$, —CN, —$OCH_2D$, —$OCHD_2$, —$OCD_3$, —$COCD_3$, —$CH_2N(CD_3)_2$ and —$CH_2N(CH_3)(CD_3)$.

In one embodiment of the present invention, $R_7$ is selected from: —H, -D, —F, —Cl, —$CH_3$, —$CH_2D$, —$CHD_2$, —$CD_3$, —$OCH_3$, —$COCH_3$, —$CH_2NH_2$, —$CH_2N(CH_3)_2$, —CN, —$OCH_2D$, —OCH, —$OCD_3$, —$COCD_3$, —$CH_2N(CD_3)_2$ and —$CH_2N(CH_3)(CD_3)$.

In one embodiment of the present invention, $R_{10}$ is

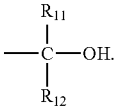

In one embodiment of the present invention, H attached to the C atoms in $R_{10}$ may be substituted with deuterium.

Specifically, $R_{11}$ and $R_{12}$ are independently selected from: —H, -D, —$CF_3$, —$CHF_2$, —$CH_2F$, $C_{1-10}$ linear/branched alkyl, —CH═C($C_{0-10}$ alkyl)($C_{0-10}$ alkyl), $C_{3-10}$ cycloalkyl and an aromatic six-membered cyclic group, or $R_{11}$ and $R_{12}$, together with carbon atoms between $R_{11}$ and $R_{12}$, form $C_{3-8}$ cycloalkyl, $C_{4-7}$ fused cycloalkyl, $C_{5-9}$ spiro cycloalkyl, $C_{4-9}$ bridged cycloalkyl, $C_{3-7}$ cyclolactam, $C_{3-7}$ cyclic lactone or $C_{3-7}$ cyclic ketone, wherein H on the C atoms may be substituted with the following groups: —$SO_2$, —$SO_2N$($C_{0-10}$ alkyl)($C_{0-10}$ alkyl), —N($C_{0-10}$ alkyl)$SO_2$($C_{0-10}$ alkyl), —CON($C_{0-10}$ alkyl)($C_{0-10}$ alkyl), —N($C_{0-10}$ alkyl)CO($C_{0-10}$ alkyl), —N($C_{0-10}$ alkyl)COO($C_{0-10}$ alkyl), —OCON($C_{0-10}$ alkyl)($C_{0-10}$ alkyl), halogen, —CN, —$OCH_2F$, —$OCHF_2$, —$OCF_3$, $C_{1-10}$ linear/branched alkyl, —N($C_{0-10}$ alkyl)($C_{0-10}$ alkyl), —$OC_{0-10}$ alkyl, —CO($C_{0-10}$ alkyl), $C_{3-10}$ cycloalkyl, —O heterocycloalkyl, —N heterocycloalkyl, —N heterocycloaryl, —O heterocycloaryl and —S heterocycloaryl, wherein the alkyl moieties may be optionally substituted with one or more of the following groups: —$SO_2$, —$SO_2N$($C_{0-10}$ alkyl)($C_{0-10}$ alkyl), —N($C_{0-10}$ alkyl)$SO_2$($C_{0-10}$ alkyl), —CON($C_{0-10}$ alkyl)($C_{0-10}$ alkyl), —N($C_{0-10}$ alkyl)CO($C_{0-10}$ alkyl), —N($C_{0-10}$ alkyl)COO($C_{0-10}$ alkyl), —OCON($C_{0-10}$ alkyl)($C_{0-10}$ alkyl), halogen, —CN, —$OCH_2F$, —$OCHF_2$, —$OCF_3$, —N($C_{0-10}$ alkyl)($C_{0-10}$ alkyl), —$OC_{0-10}$ alkyl, —CO($C_{0-10}$ alkyl), —N heterocycloaryl, —O heterocycloaryl and —S heterocycloaryl, wherein H attached to the C atoms or heteroatoms may be substituted with deuterium.

More specifically, $R_{11}$ and $R_{12}$ are independently selected from: —H, -D, —$CF_3$, —$CHF_2$, —$CH_2F$, $C_{1-5}$ linear/branched alkyl, —CH═CH($C_{0-10}$ alkyl), $C_{3-10}$ cycloalkyl and an aromatic six-membered cyclic group, or RH and Rig, together with carbon atoms between $R_{11}$ and $R_{12}$, form $C_{3-6}$ cycloalkyl, $C_{4-6}$ fused cycloalkyl, $C_{5-8}$ spiro cycloalkyl, $C_{4-8}$ bridged cycloalkyl, $C_{3-7}$ cyclolactam, $C_{3-7}$ cyclic lactone and $C_{3-7}$ cyclic ketone, wherein the alkyl moieties may be substituted with the following groups: —$SO_2$, —$SO_2N$($C_{0-10}$ alkyl)($C_{0-10}$ alkyl), —N($C_{0-10}$ alkyl)$SO_2$($C_{0-10}$ alkyl), —CON($C_{0-10}$ alkyl)($C_{0-10}$ alkyl), —N($C_{0-10}$ alkyl)CO($C_{0-10}$ alkyl), —N($C_{0-10}$ alkyl)COO($C_{0-10}$ alkyl), —OCON($C_{0-10}$ alkyl)($C_{0-10}$ alkyl), halogen, —CN, —$OCH_2F$, —$OCHF_2$, —$OCF_3$, $C_{1-10}$ linear/branched alkyl, —N($C_{0-10}$ alkyl)($C_{0-10}$ alkyl), —$OC_{0-10}$ alkyl, —CO($C_{0-10}$ alkyl), $C_{3-10}$ cycloalkyl, —O heterocycloalkyl, —N heterocycloalkyl, —N heterocycloaryl, —O heterocycloaryl and —S heterocycloaryl, wherein the alkyl moieties may be optionally substituted with one or more of the following groups: —$SO_2$, —$SO_2N$($C_{0-10}$ alkyl)($C_{0-10}$ alkyl), —N($C_{0-10}$ alkyl)$SO_2$($C_{0-10}$ alkyl), —CON($C_{0-10}$ alkyl)($C_{0-10}$ alkyl), —N($C_{0-10}$ alkyl)CO($C_{0-10}$ alkyl), —N($C_{0-10}$ alkyl)COO($C_{0-10}$ alkyl), —OCON($C_{0-10}$ alkyl)($C_{0-10}$ alkyl), halogen, —CN, —$OCH_2F$, —$OCHF_2$, —$OCF_3$, —N($C_{0-10}$ alkyl)($C_{0-10}$ alkyl), —$OC_{0-10}$ alkyl, —CO($C_{0-10}$ alkyl), —N heterocycloaryl, —O heterocycloaryl and —S heterocycloaryl, wherein H attached to the C atoms or heteroatoms may be substituted with deuterium.

Further specifically, $R_{11}$ and $R_{12}$ are independently selected from: —H, -D, —$CF_3$, —$CHF_2$, —$CH_2F$, —$CH_3$, —$CH_2CH_3$, —CH═$CH_2$,

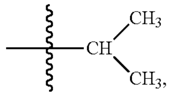 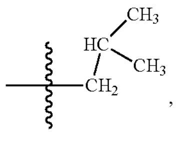 , 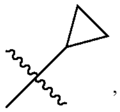 ,

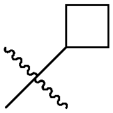 , 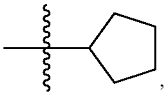 , 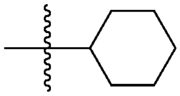 and

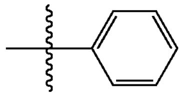 , or $R_{11}$ and $R_{12}$, together with carbon atoms between $R_{11}$ and $R_{12}$, form

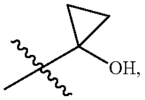 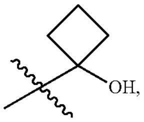 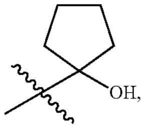

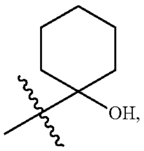 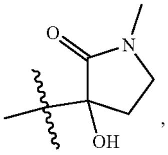 , 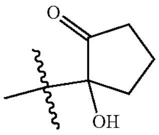 ,

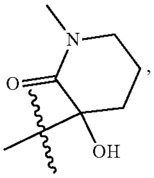 , 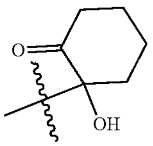 , 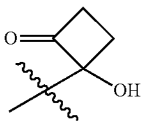 ,

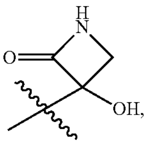 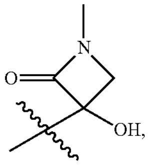 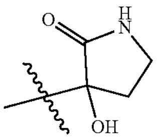 ,

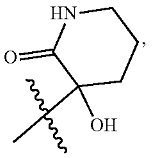 , 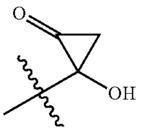 , 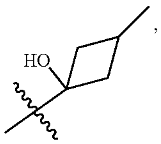 ,

-continued

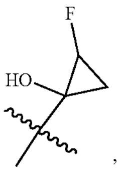,
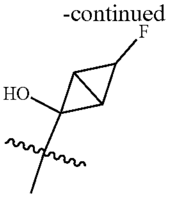
and
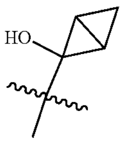, wherein H attached to the C atoms or N atoms may be substituted with deuterium.

Even more specifically, $R_{11}$ and $R_{12}$ are independently selected from: —H, -D, —$CF_3$, —$CHF_2$, —$CDF_2$, —$CH_2F$, —$CD_2F$, —$CH_3$, —$CH_2D$, —$CHD_2$, —$CD_3$, —$CH_2CH_3$, —$CH_2CD_3$,

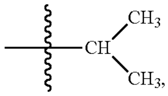
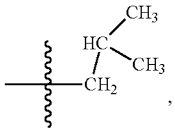,
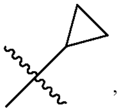,

-continued

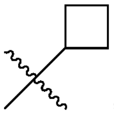,
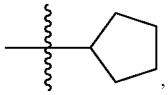,
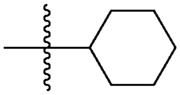
and
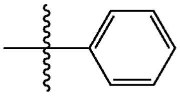.

Specifically, $R_8$ and $R_9$ are independently selected from: —H, -D and $C_{1-10}$ linear/branched alkyl, wherein H attached to the C atoms may be substituted with deuterium.

More specifically, $R_8$ and $R_9$ are independently selected from: —H, -D and $C_{1-3}$ linear/branched alkyl, wherein H attached to the C atoms may be substituted with deuterium.

Further specifically, $R_8$ and $R_9$ are independently selected from: —H, -D, —$CH_3$, —$CH_2D$, —$CHD_2$ and —$CD_3$.

Specifically, the compound of general formula I has the following structures:

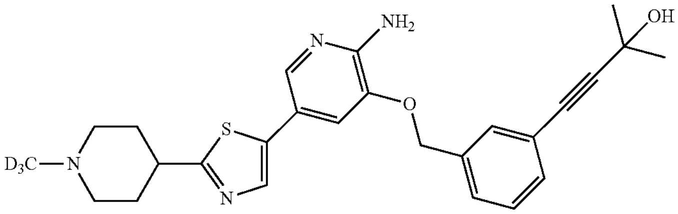
(1)

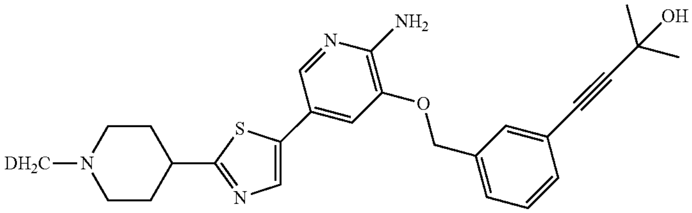

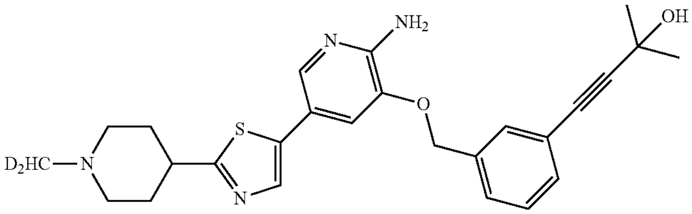

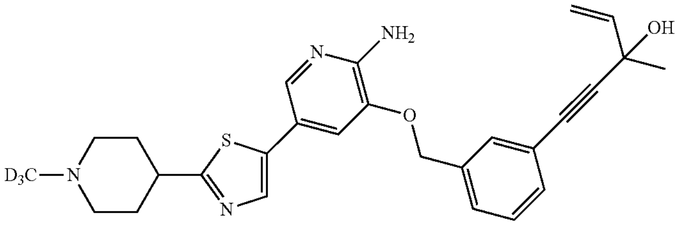

-continued
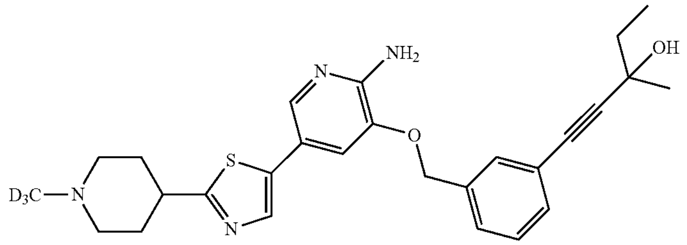
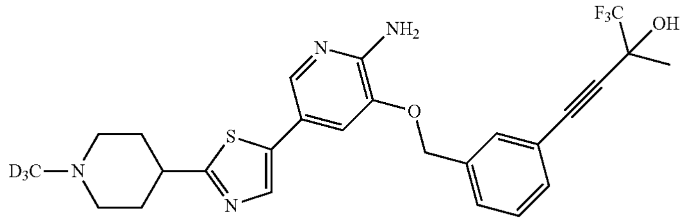
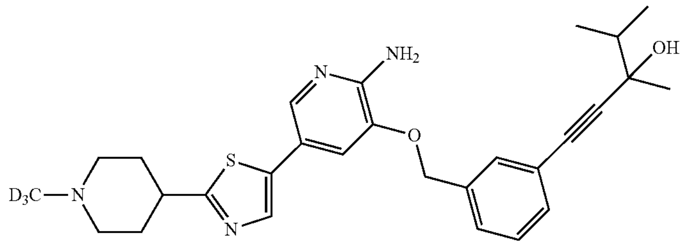
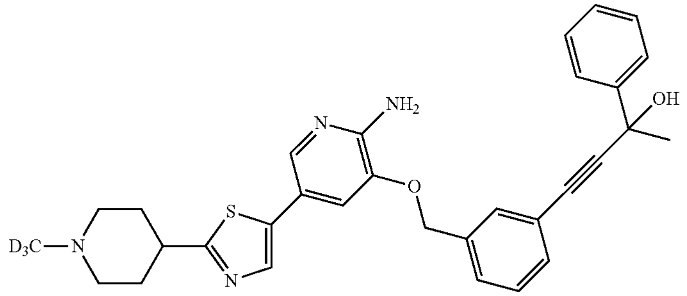
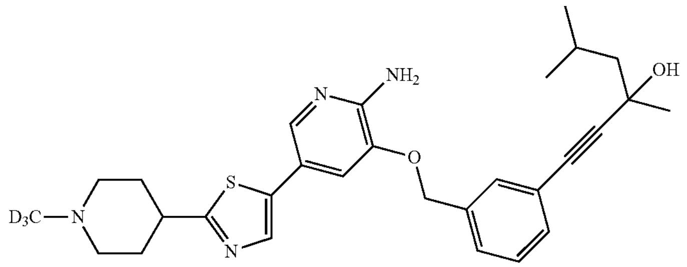
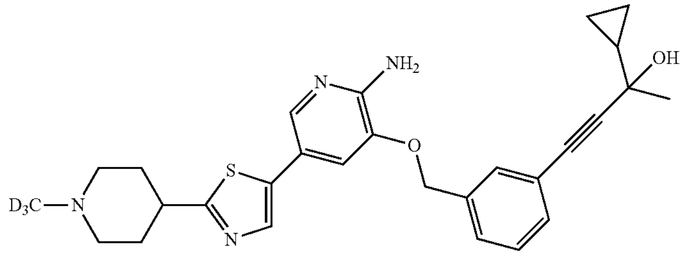

-continued
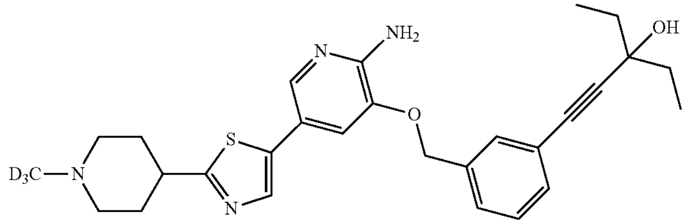
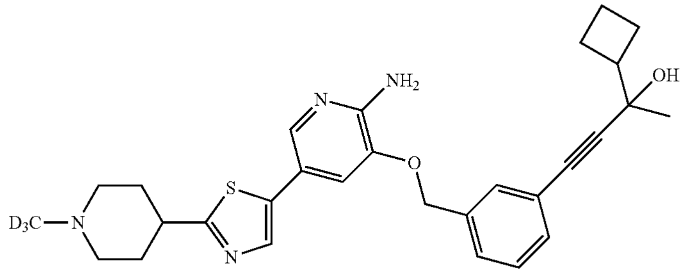
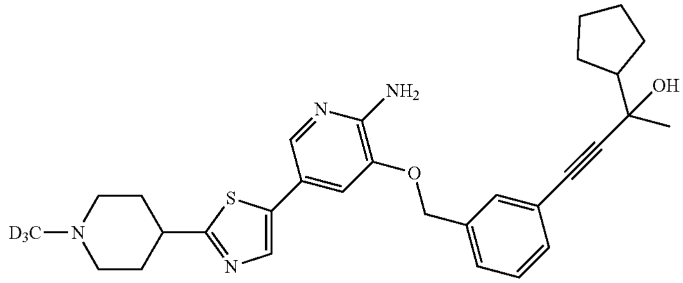
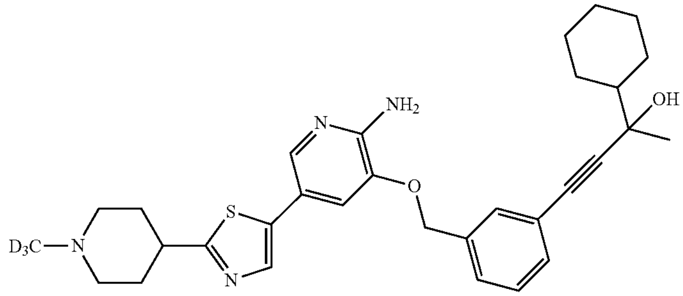
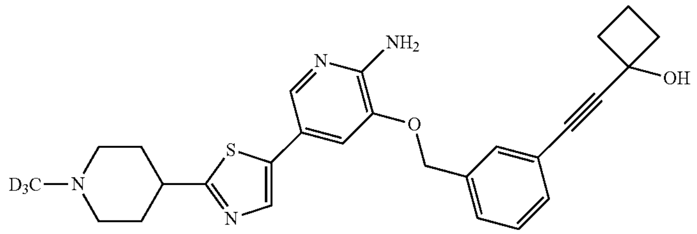
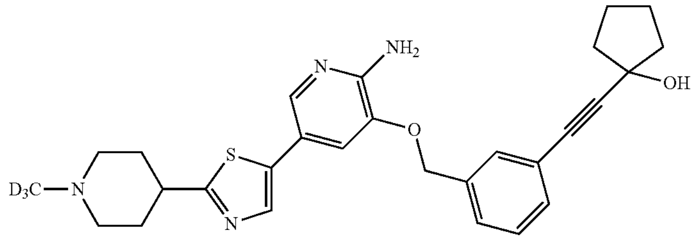

-continued
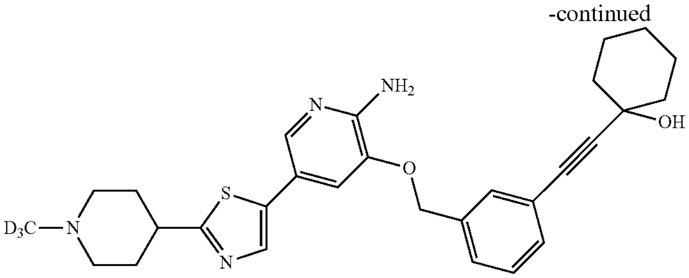
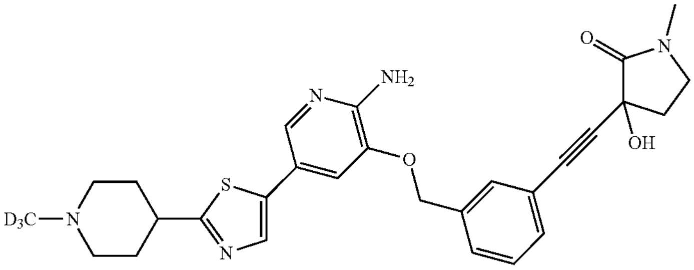
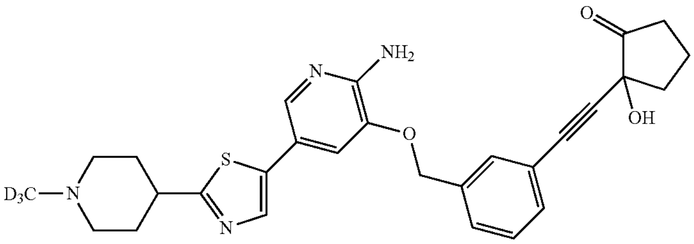
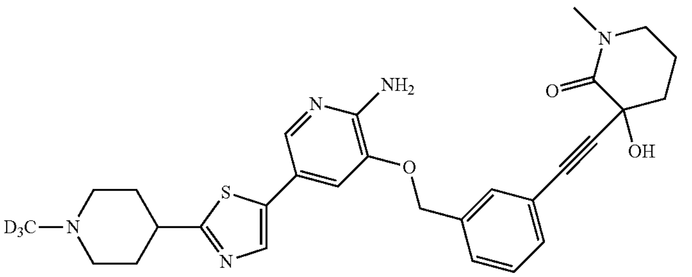
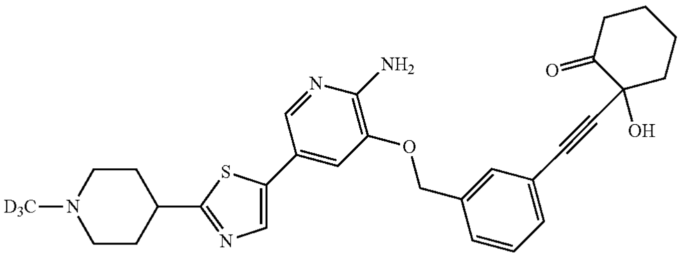
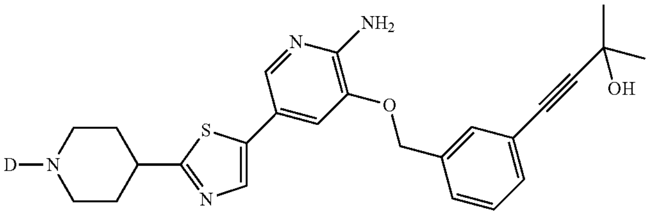

-continued
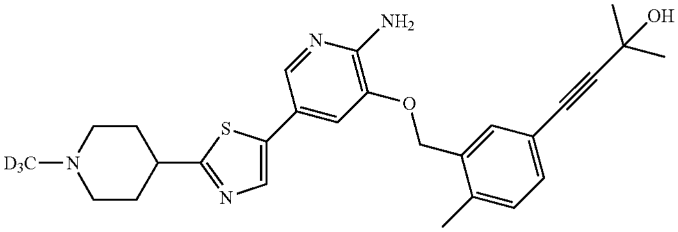
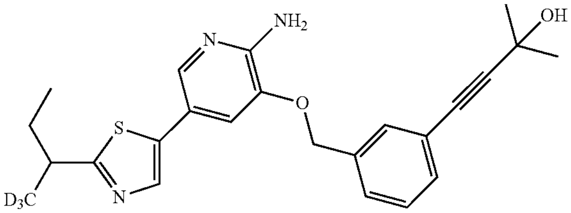
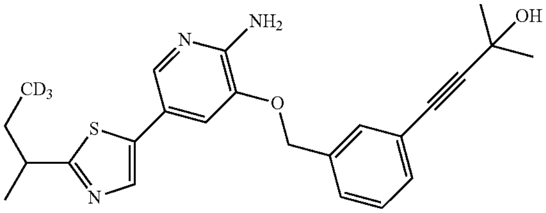
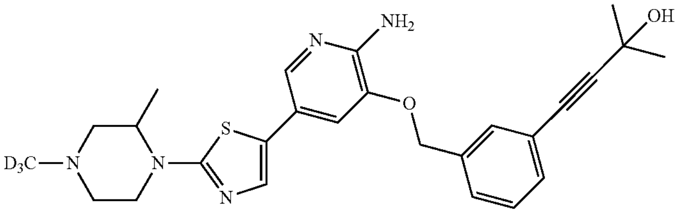
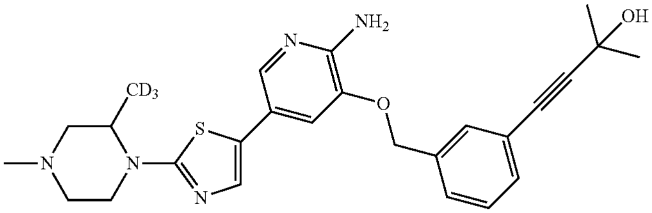
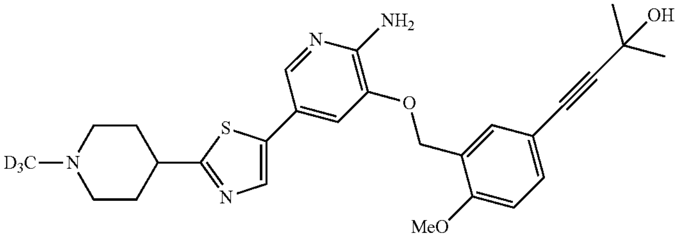
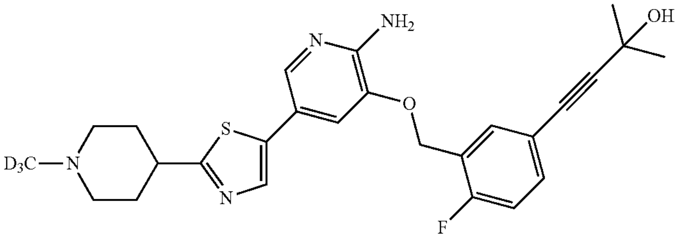

-continued
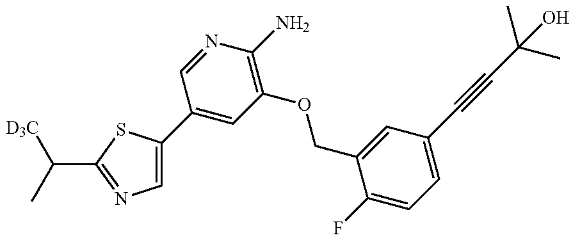
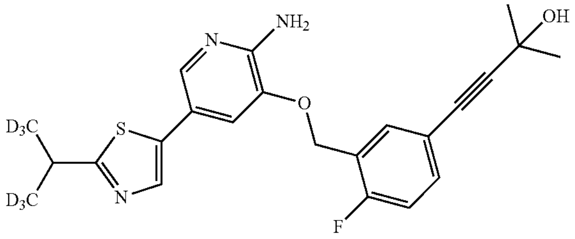
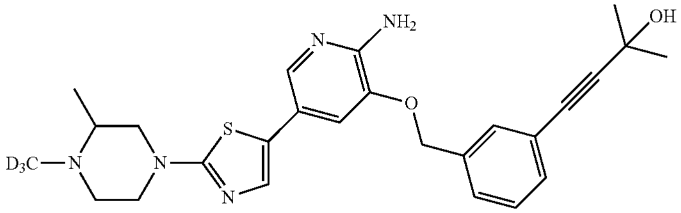
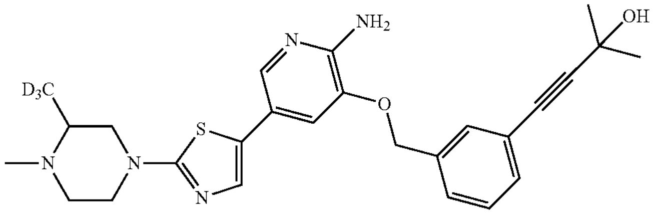
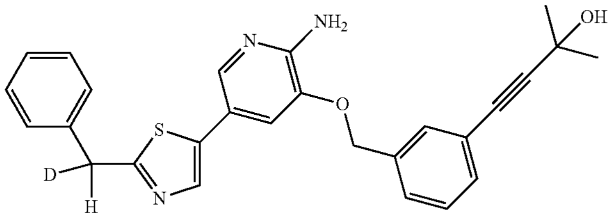
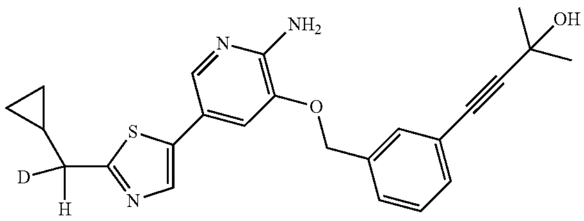
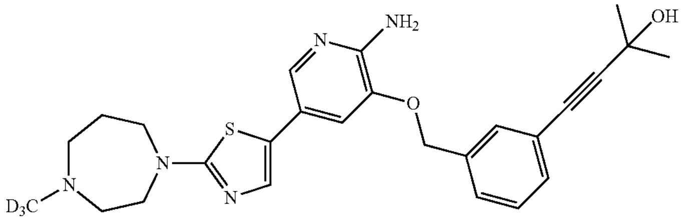

-continued
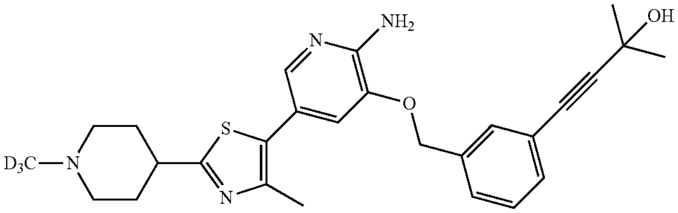
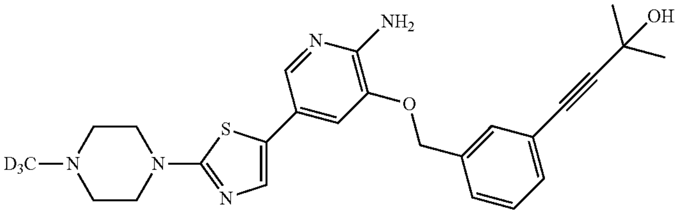
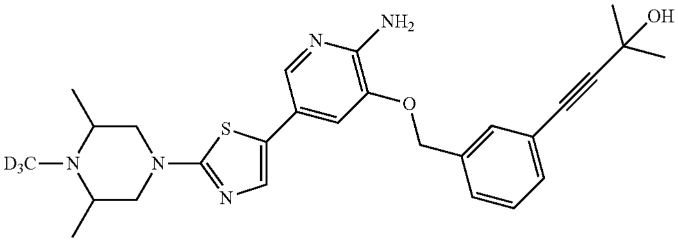
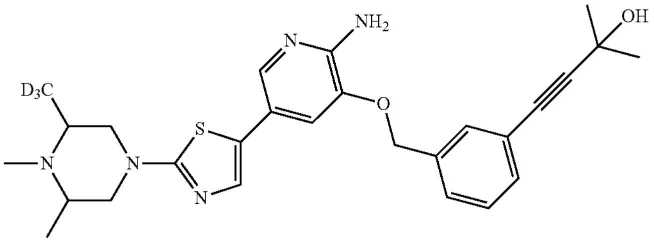
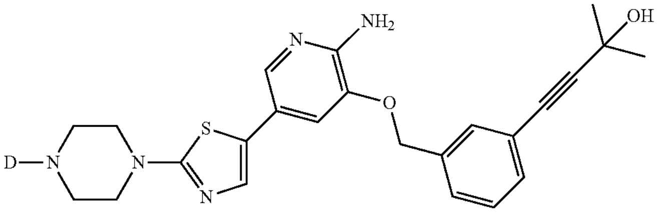
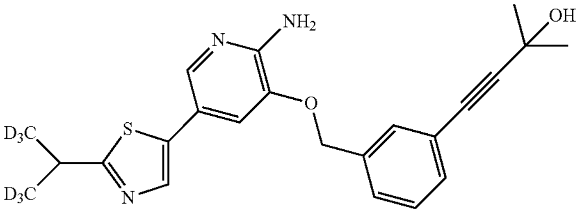
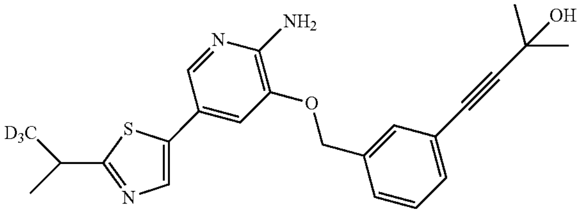
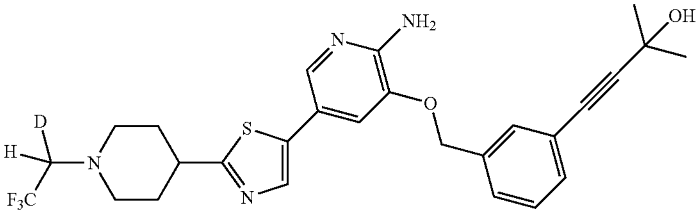

-continued
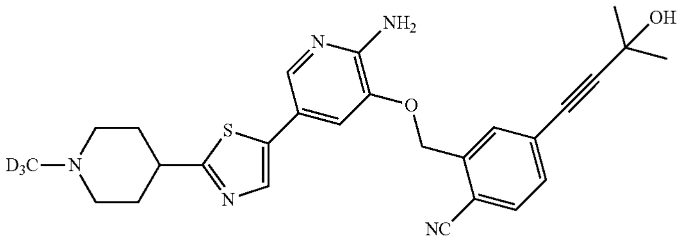
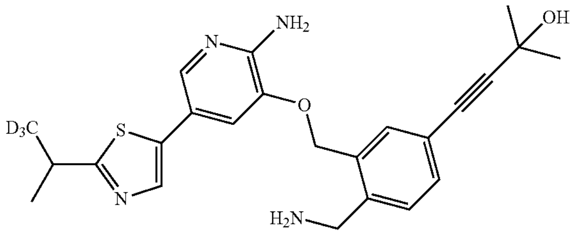
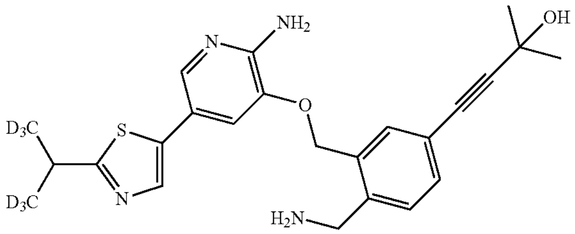
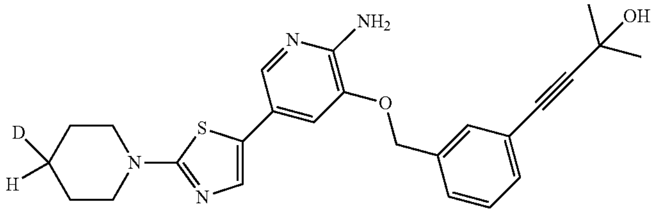
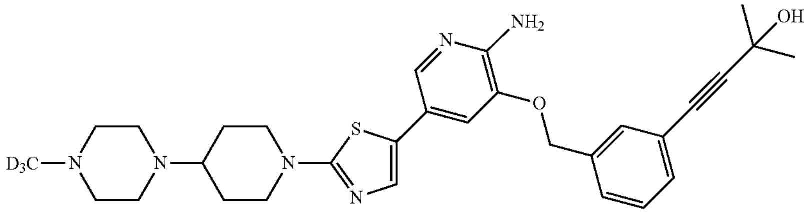
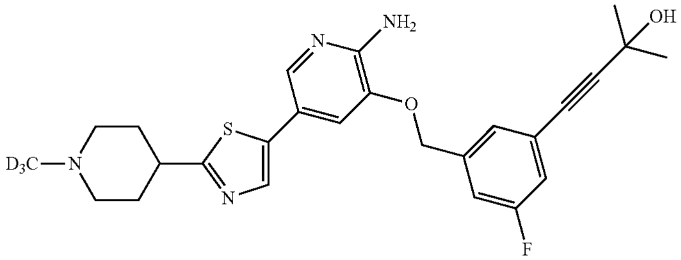
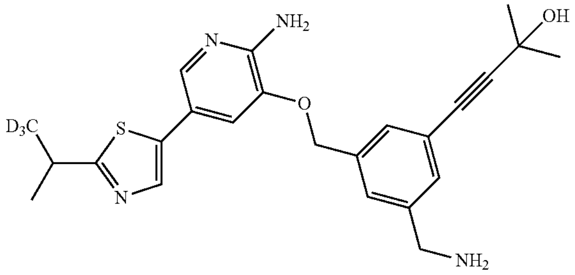
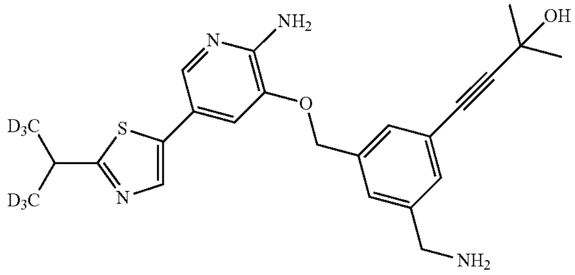
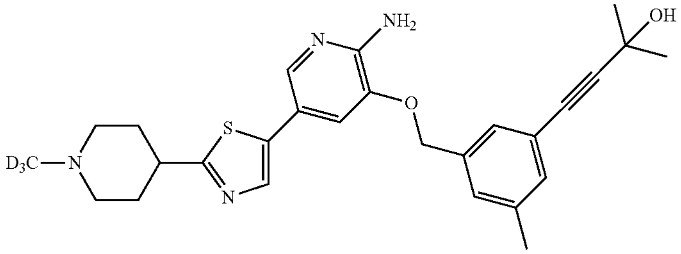

-continued
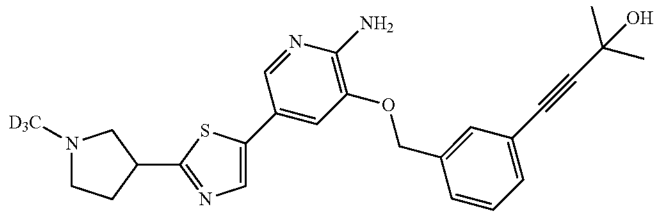
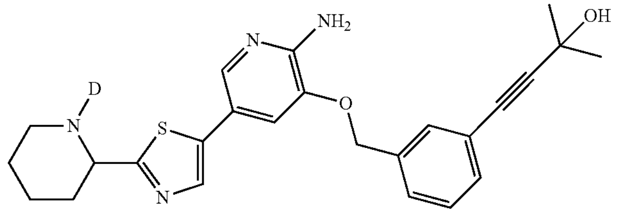
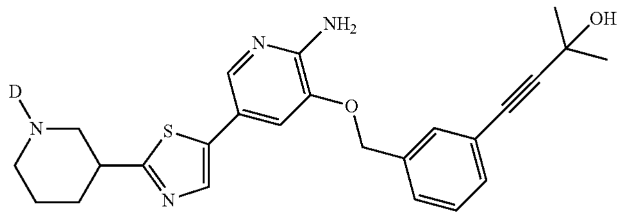
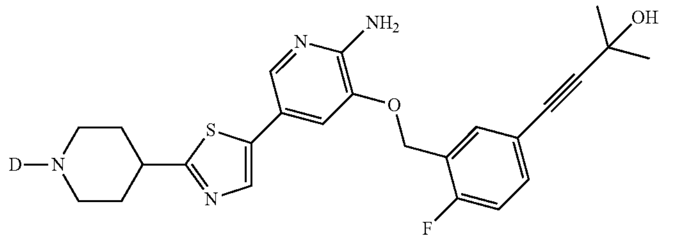
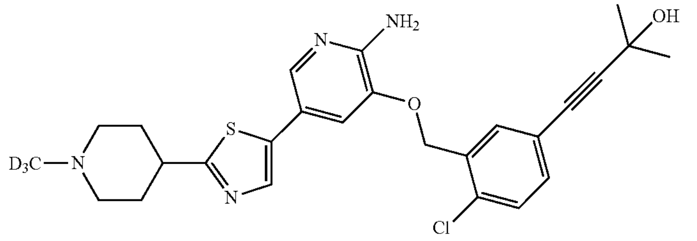
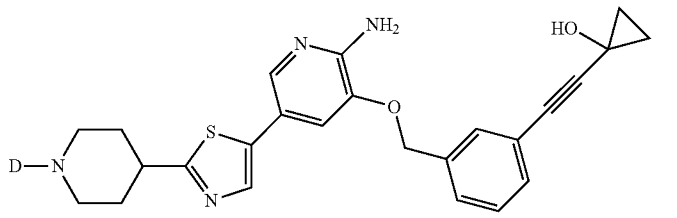
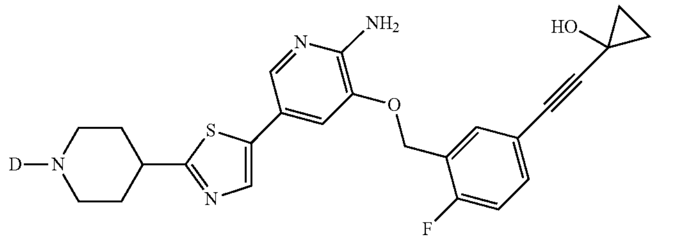

-continued
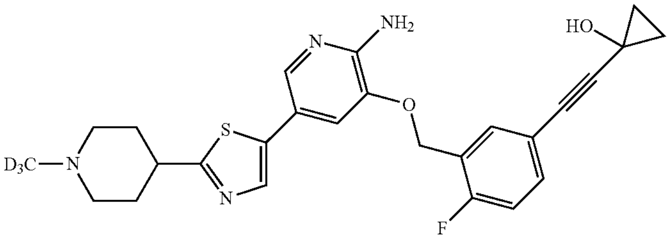
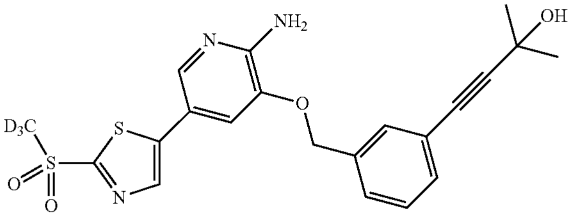
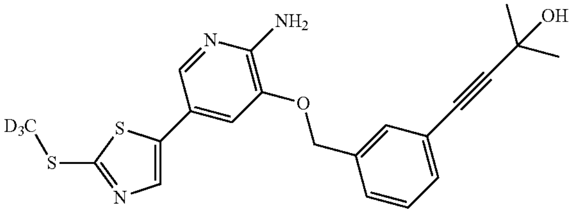
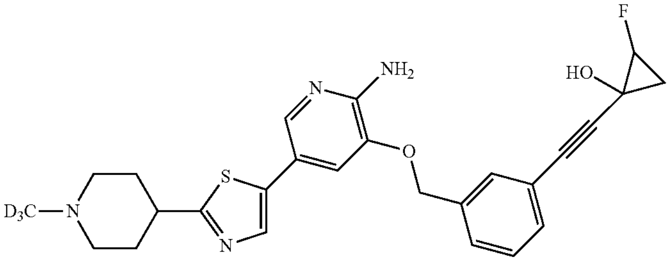
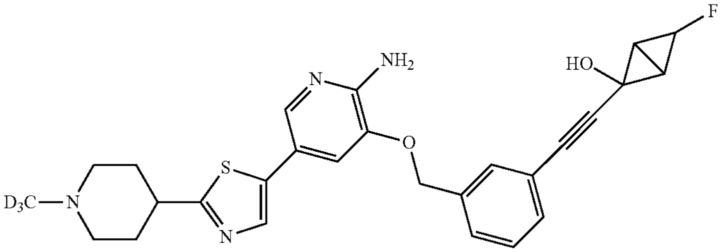
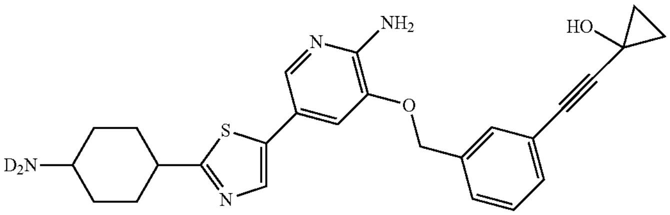
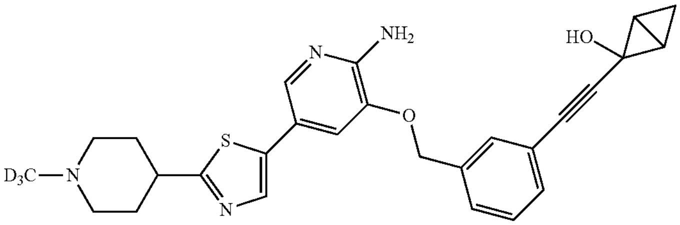
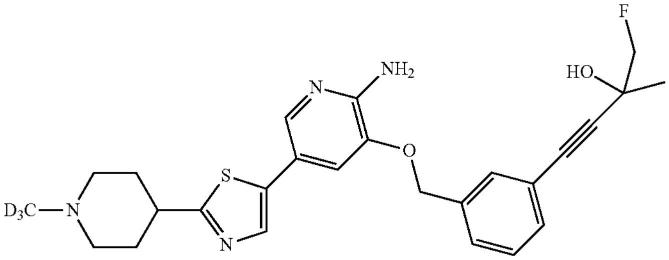

-continued
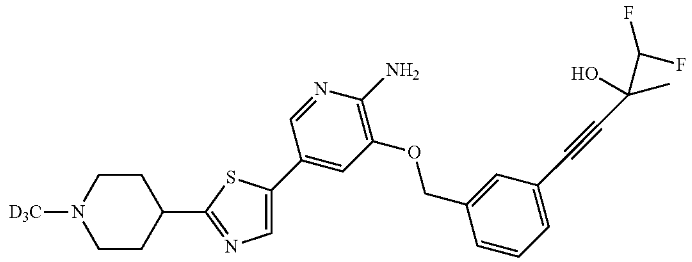
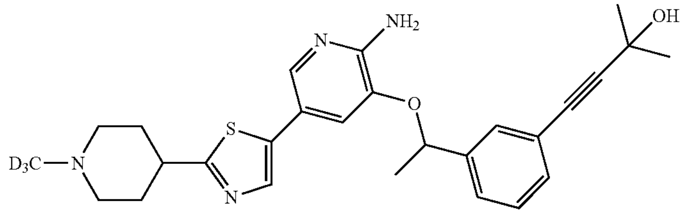
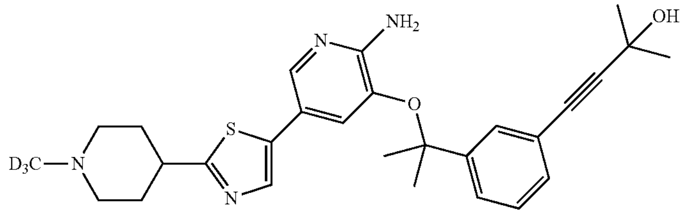
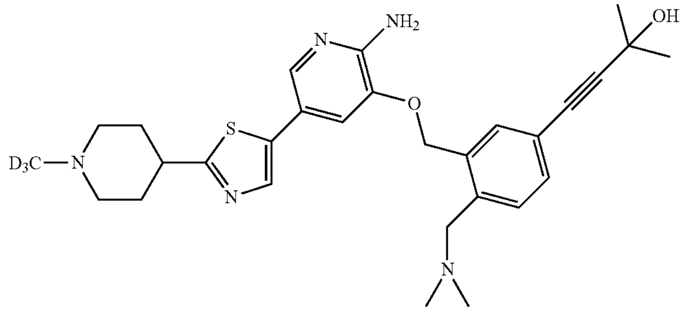
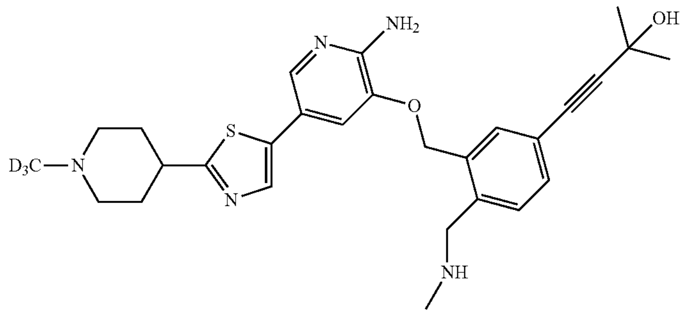
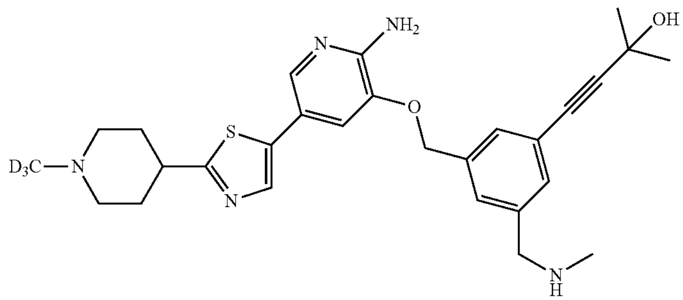

-continued
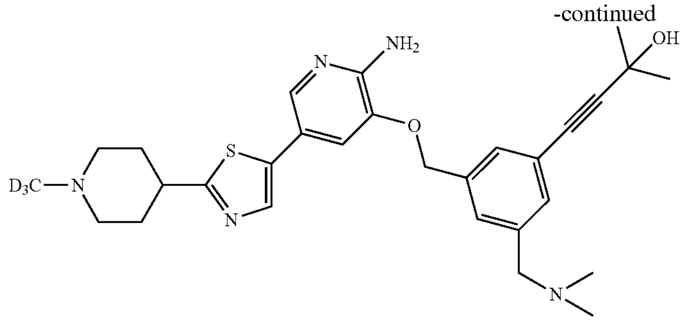
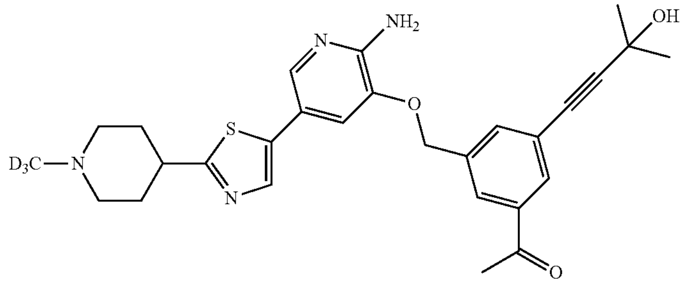
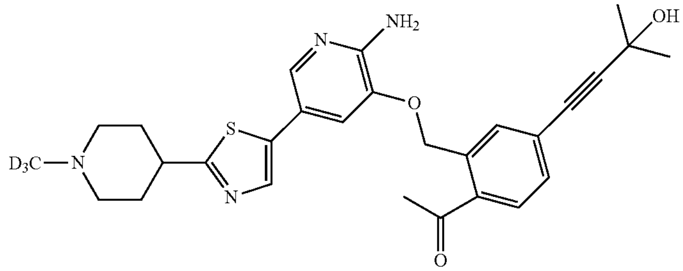
(2)
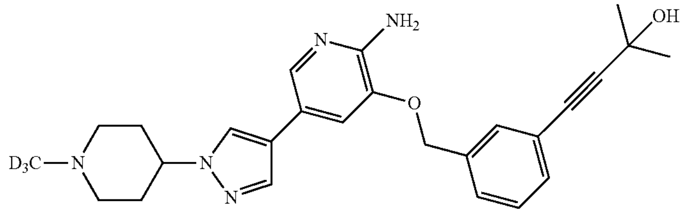
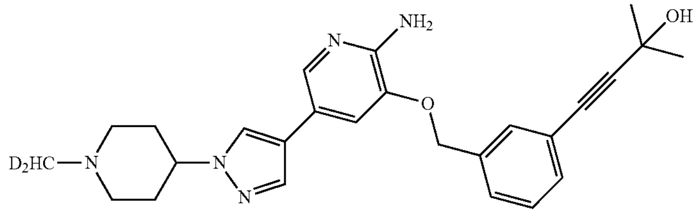
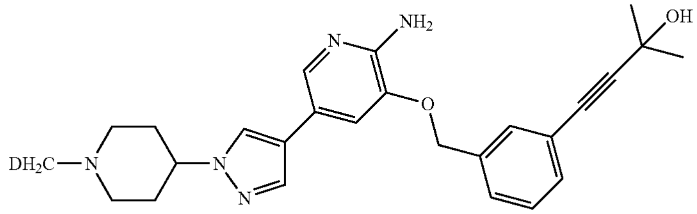
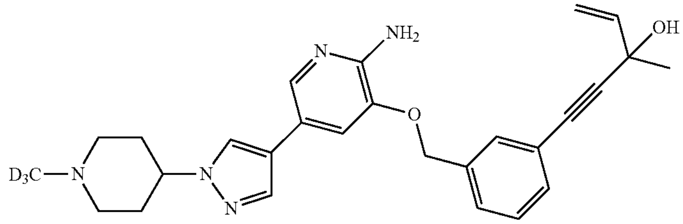

-continued
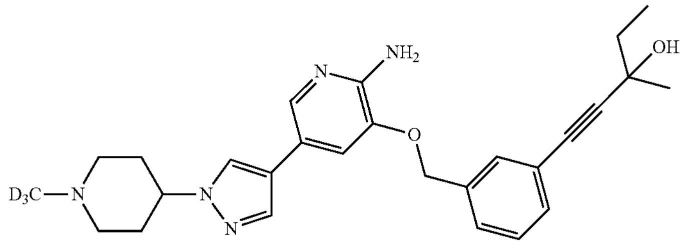
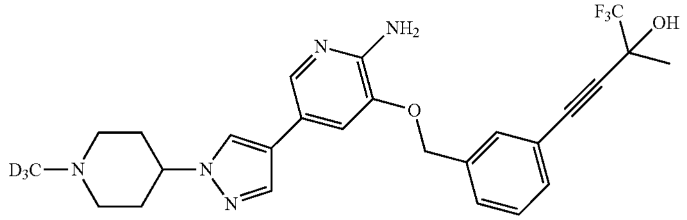
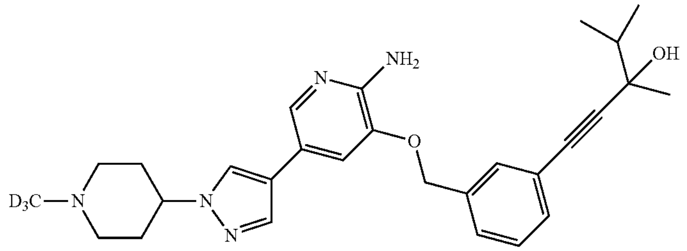
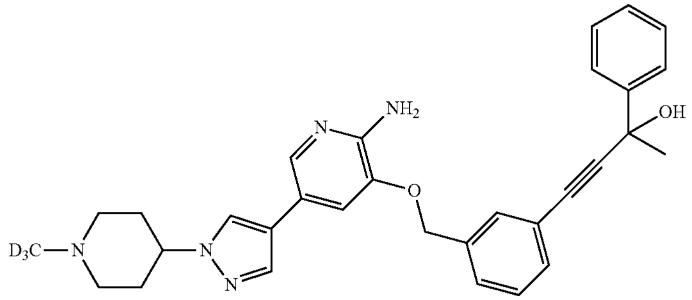
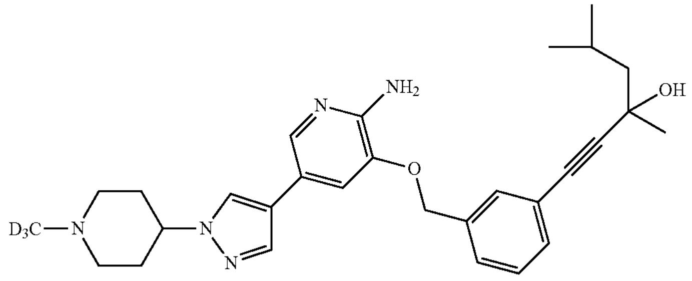
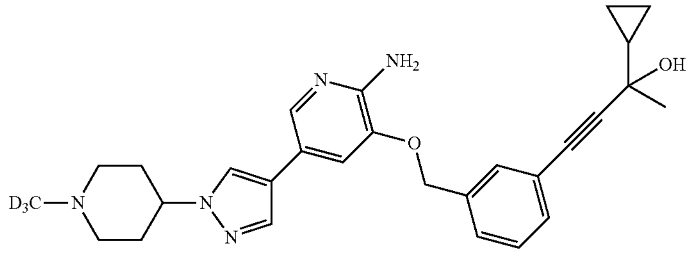

-continued
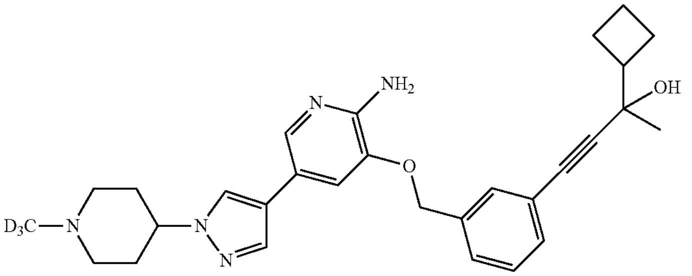
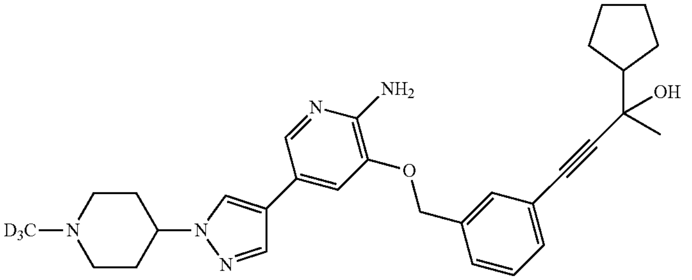
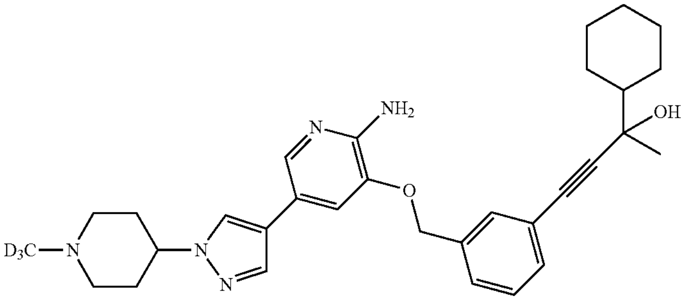
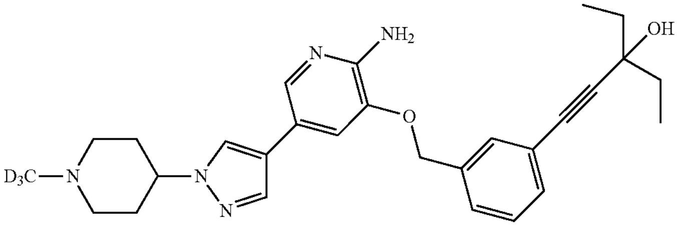
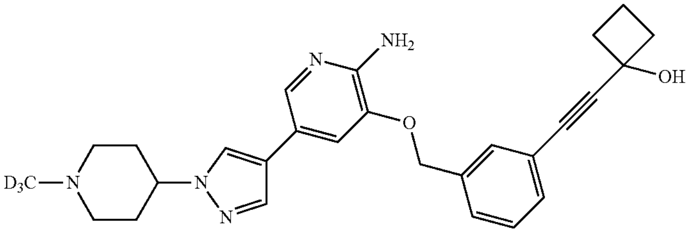
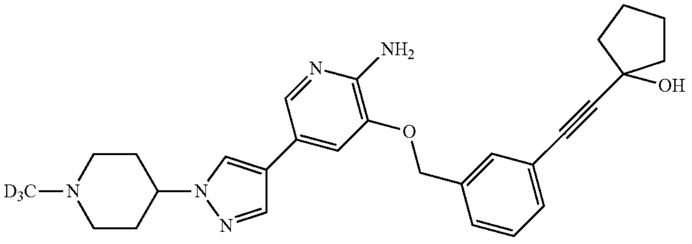

-continued
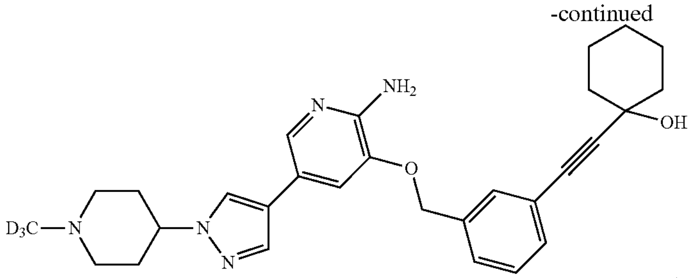
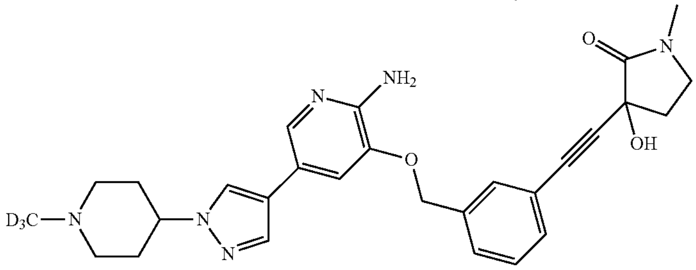
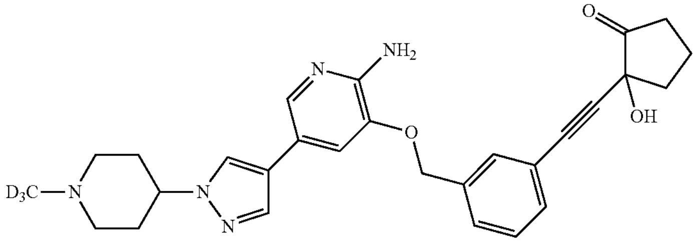
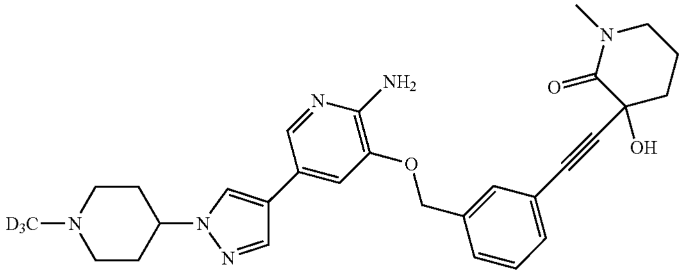
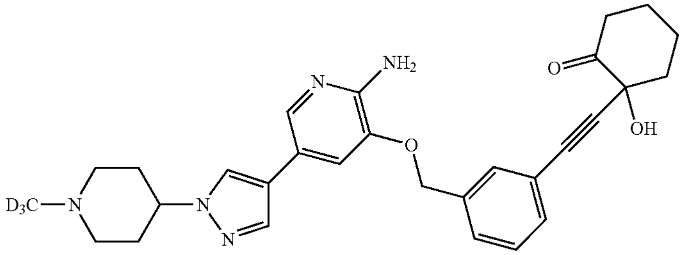
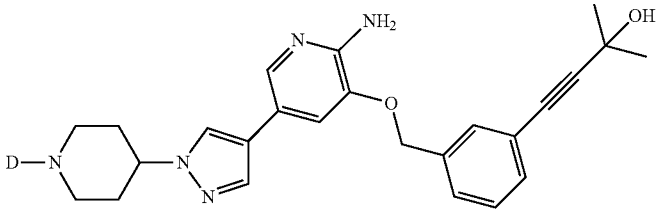
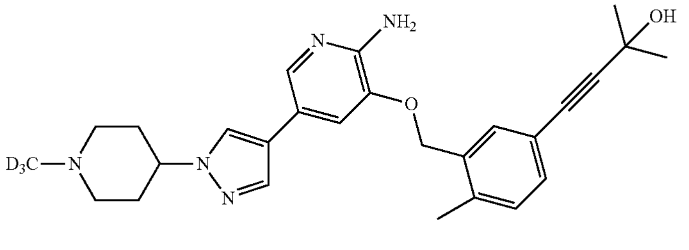

-continued
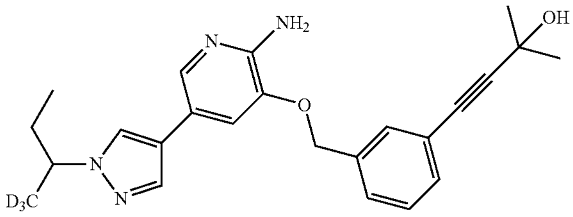
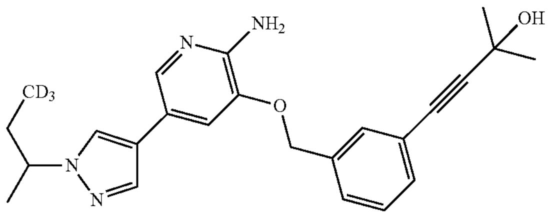
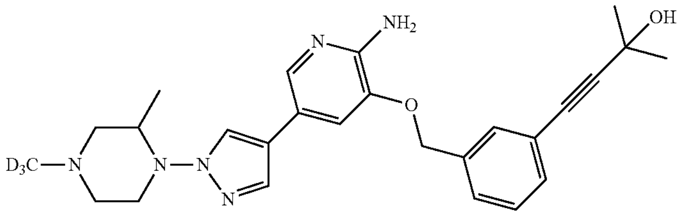
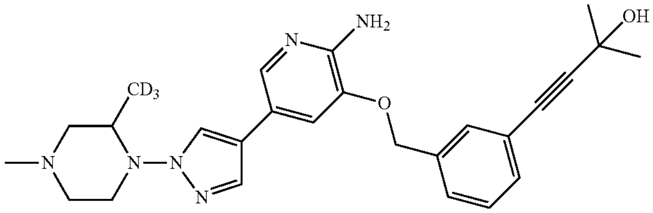
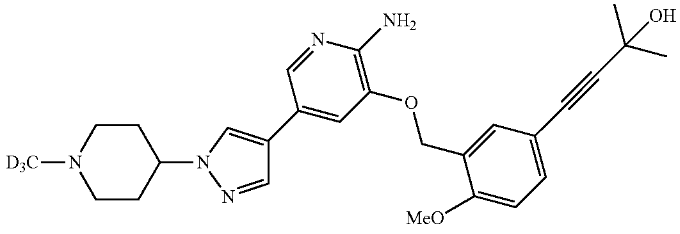
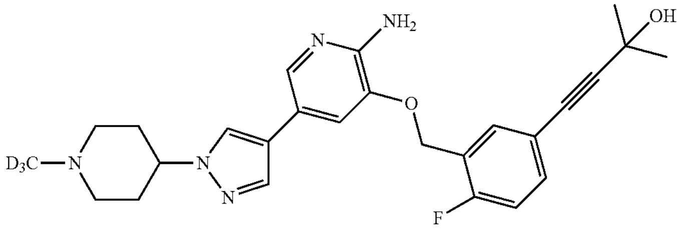
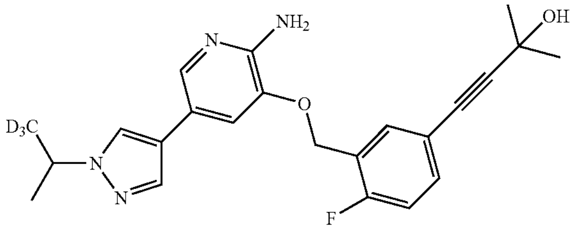
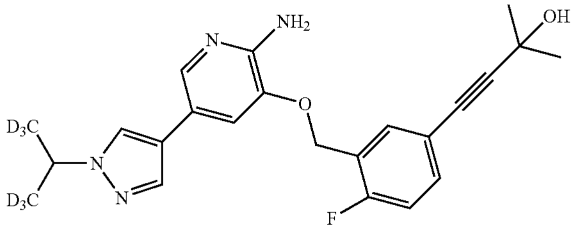
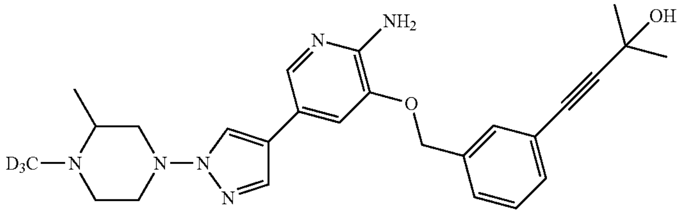

-continued
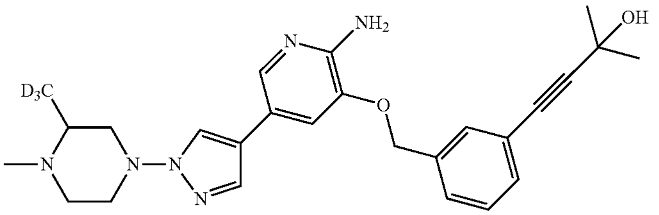
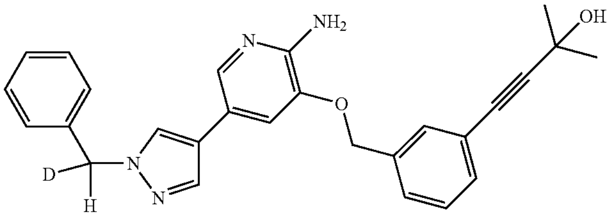
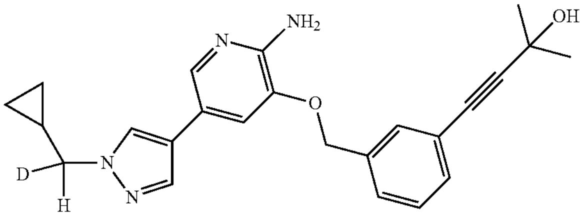
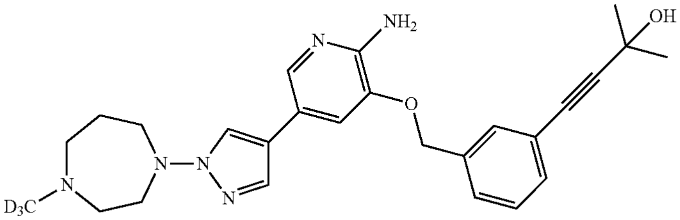
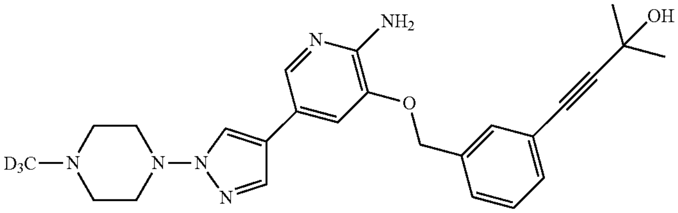
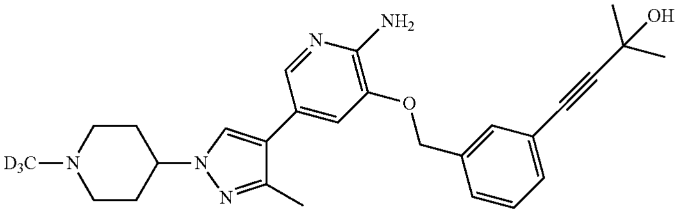
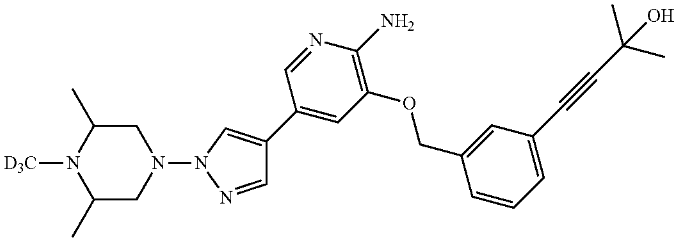

-continued
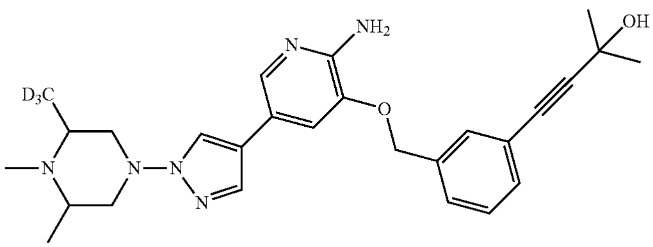
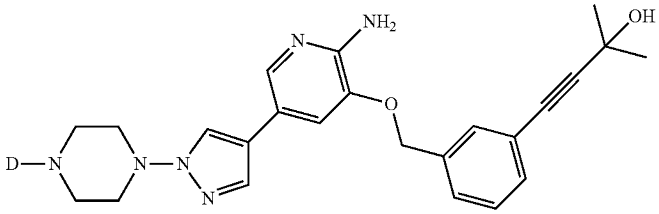
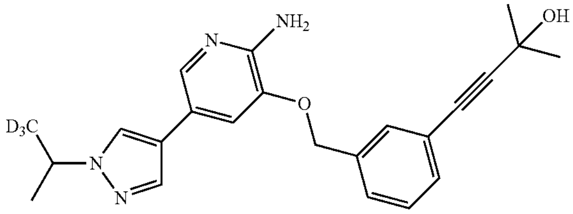
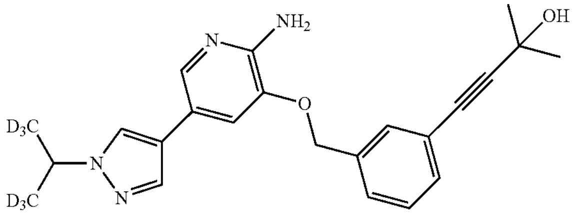
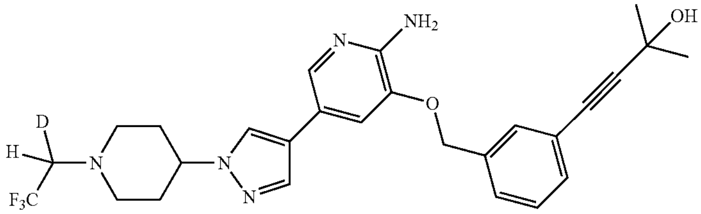
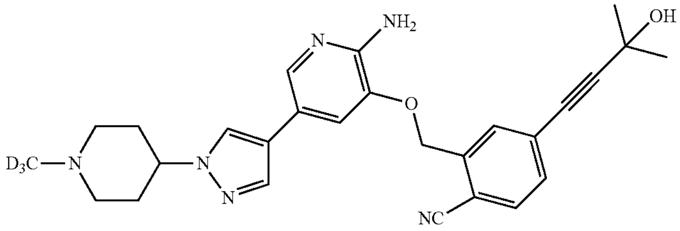
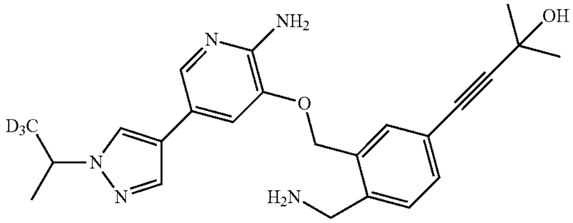
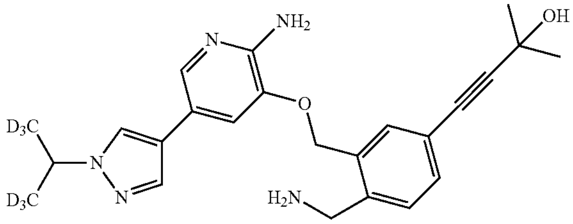
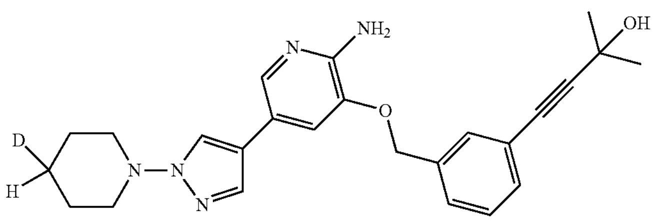

-continued
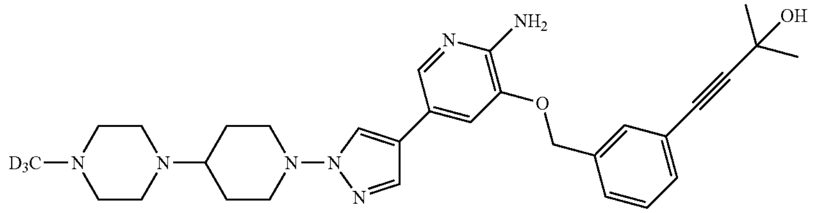
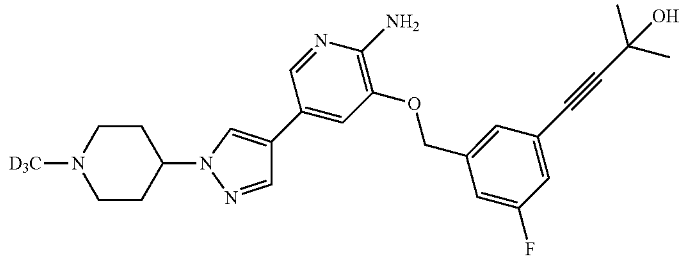
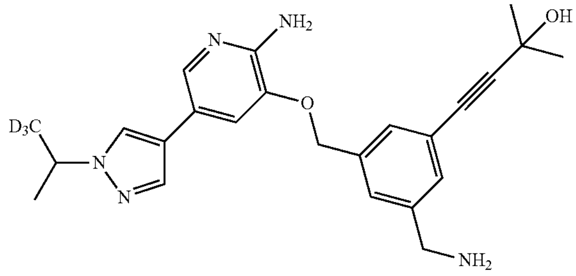
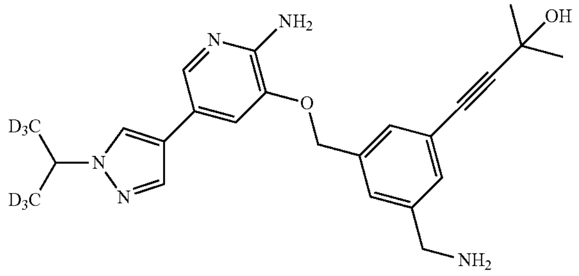
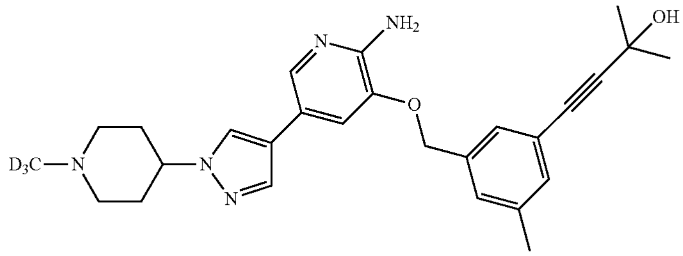
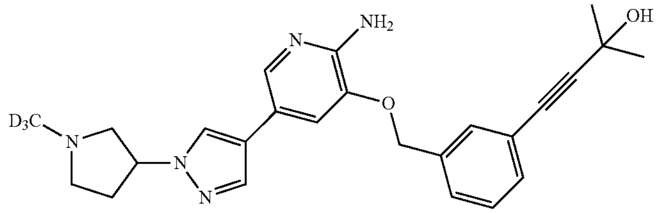
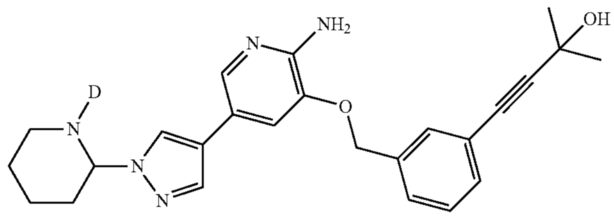
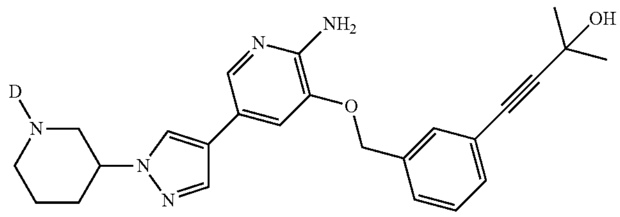

-continued
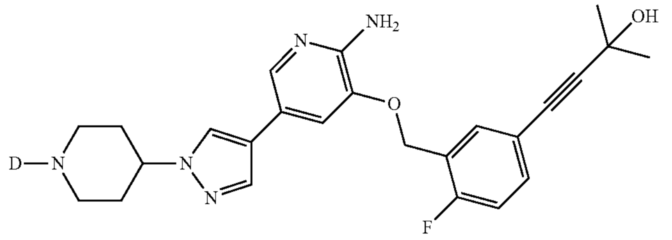
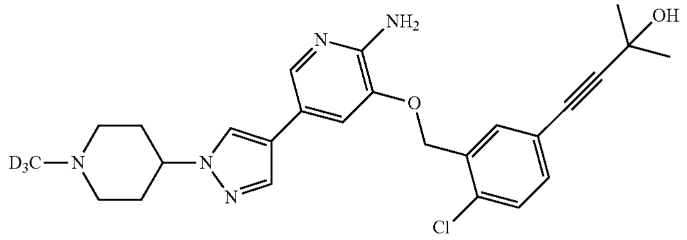
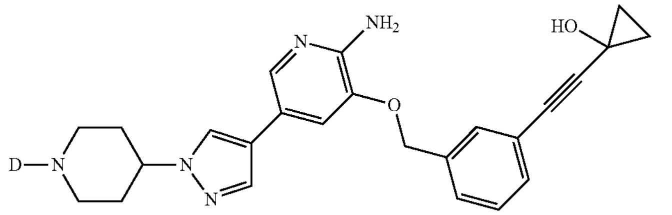
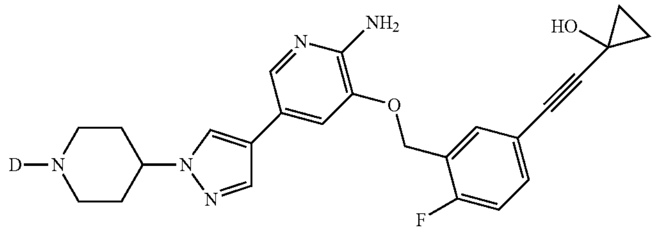
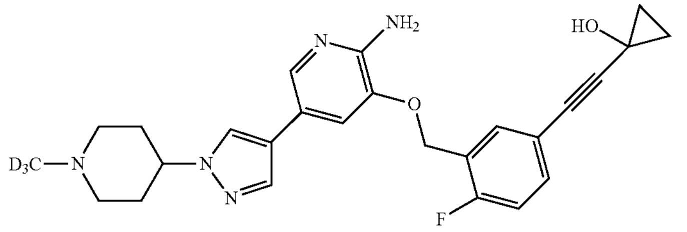
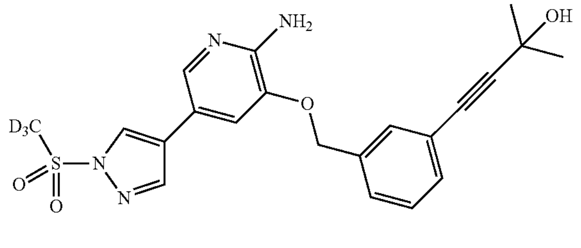
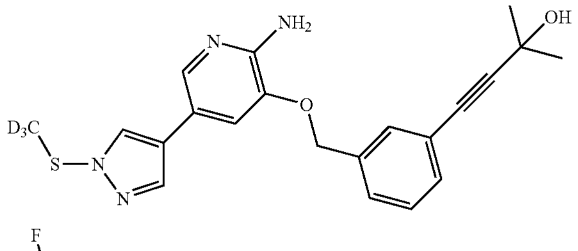
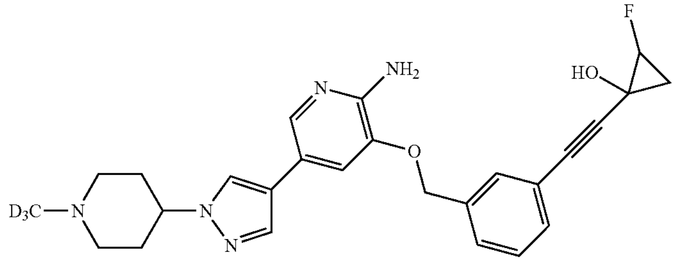

-continued
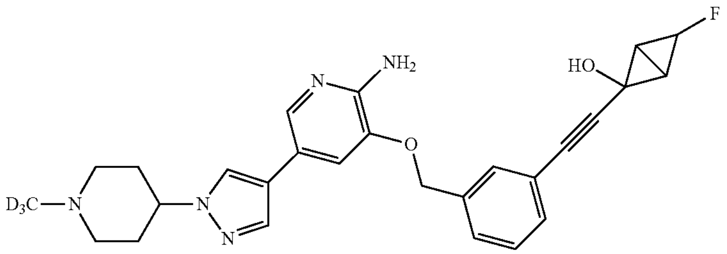
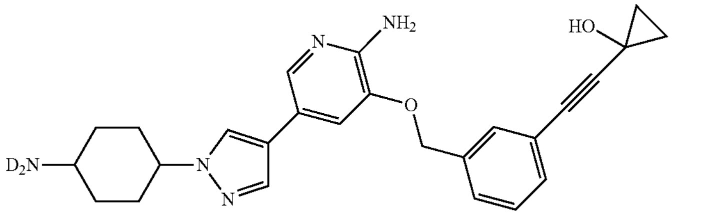
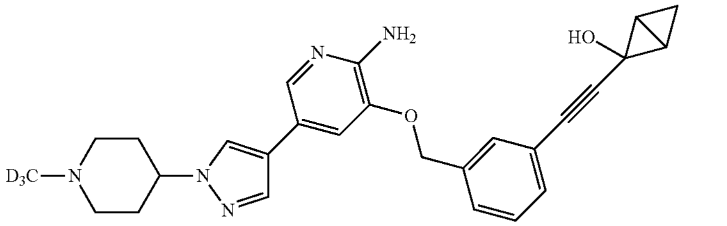
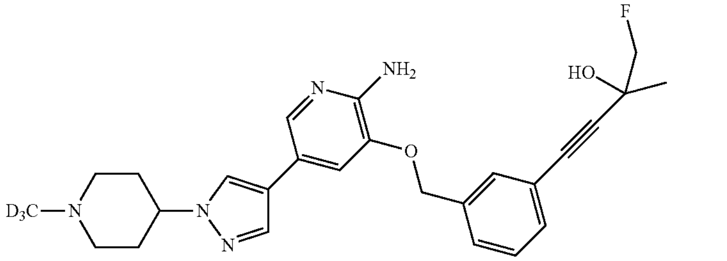
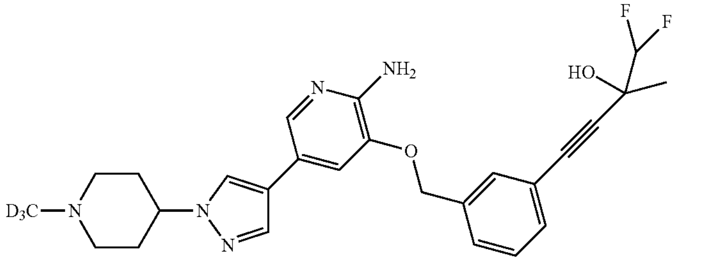
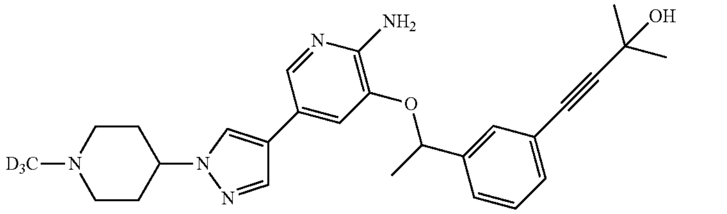
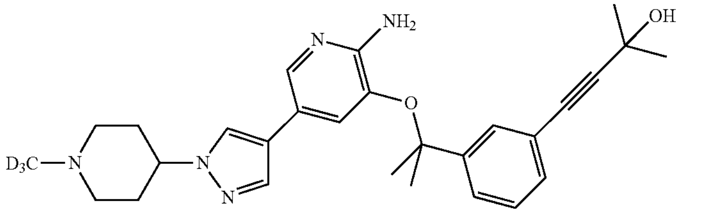

-continued
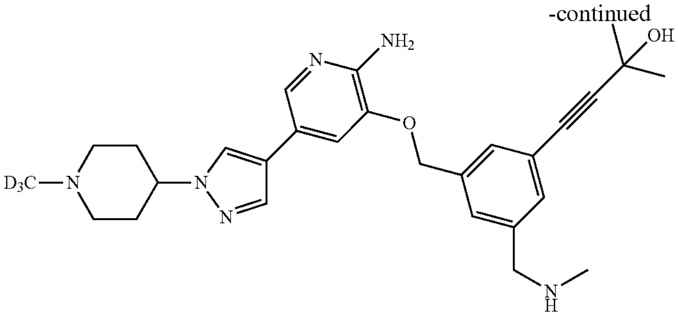
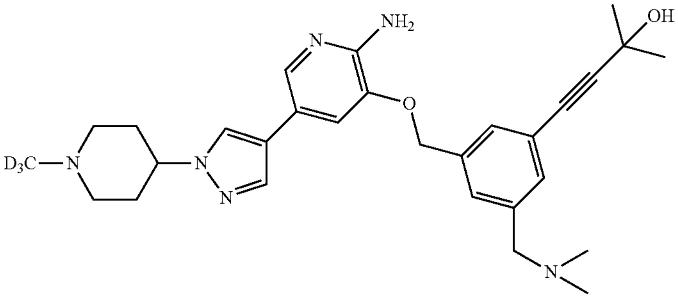
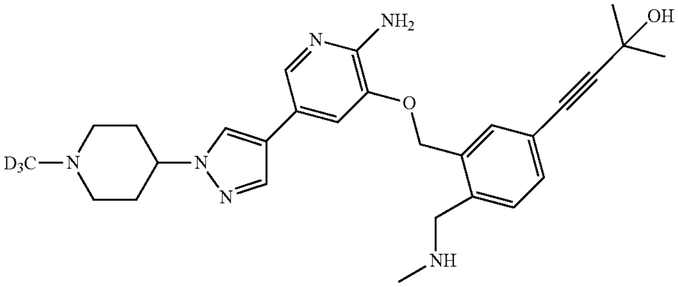
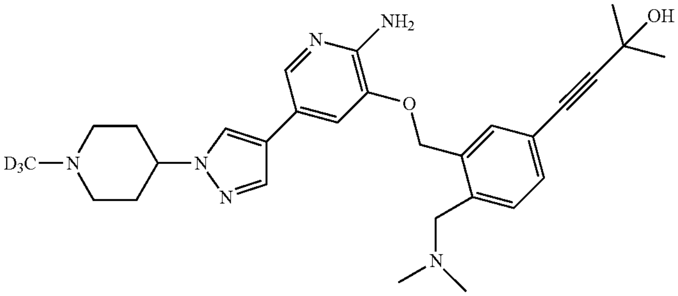
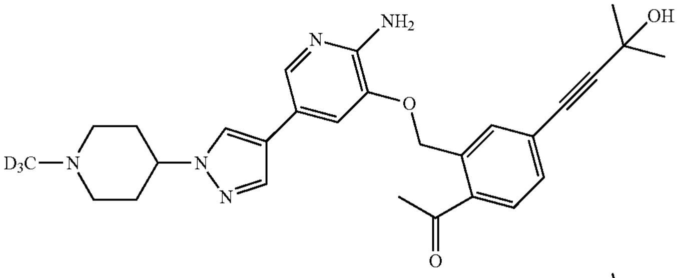
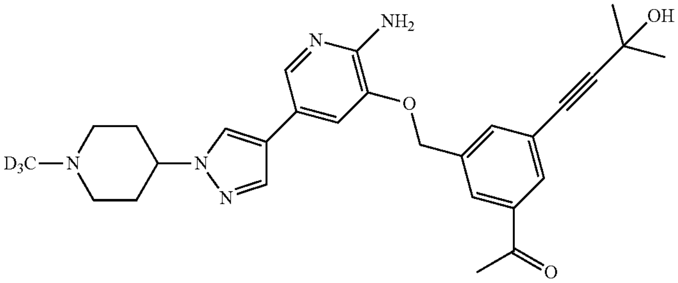

-continued
(3)
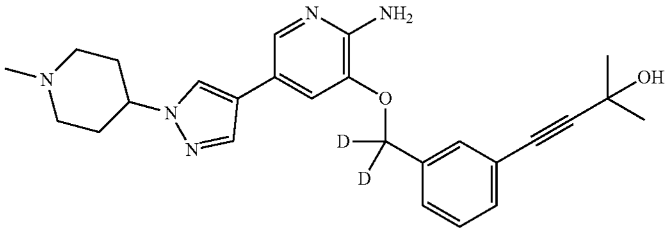
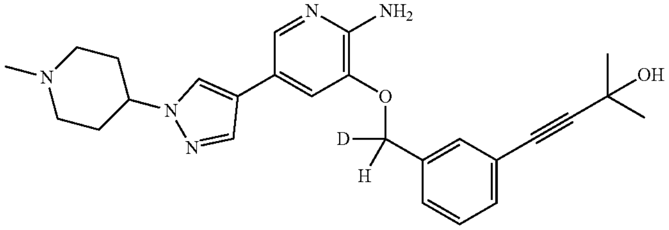
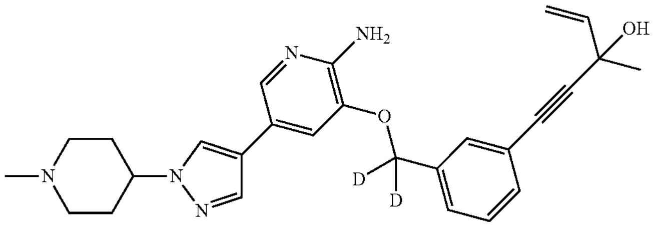
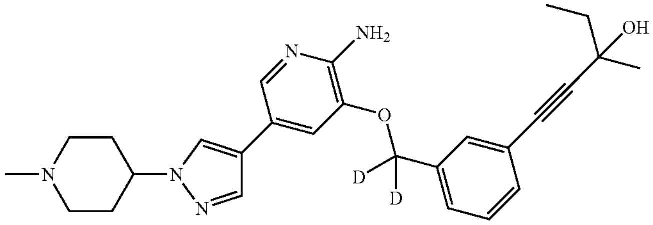
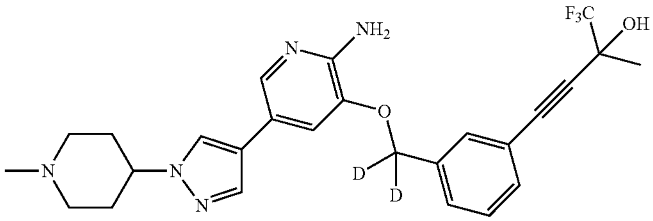
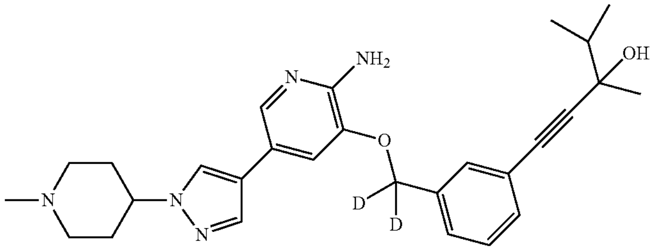
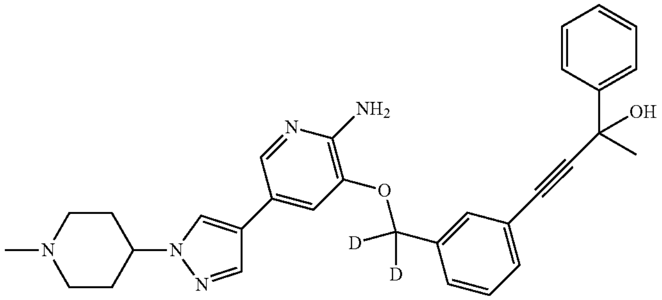

-continued
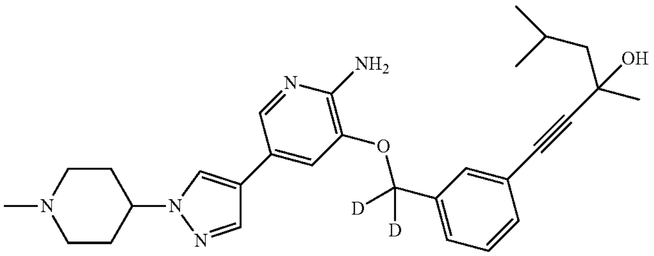
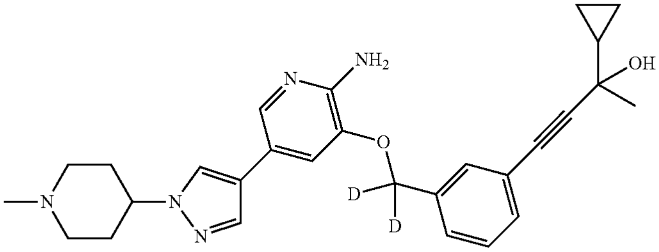
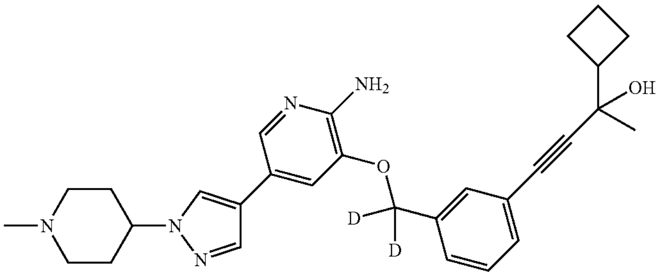
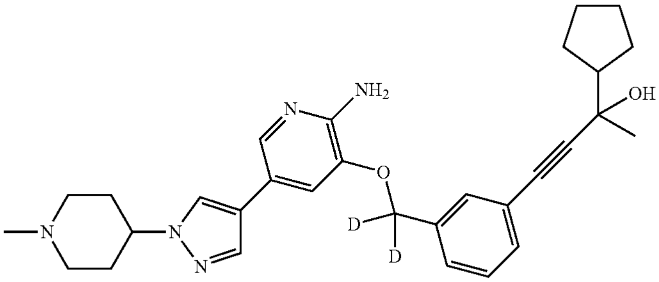
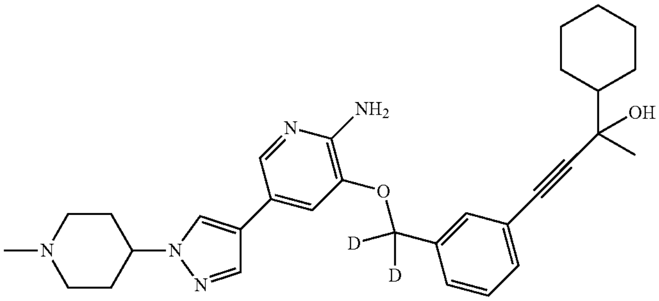
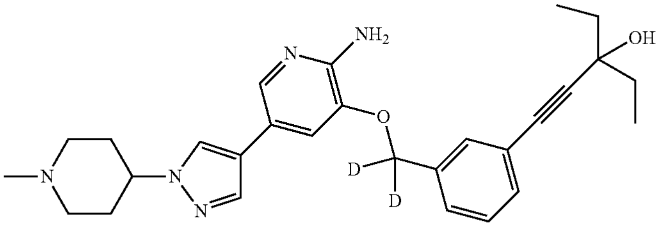

-continued
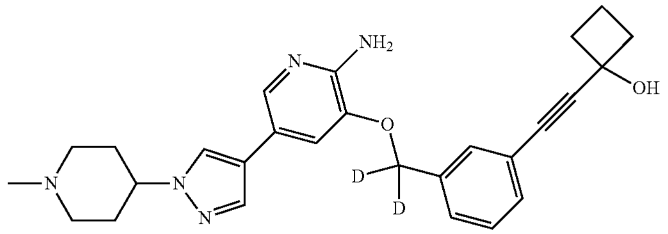
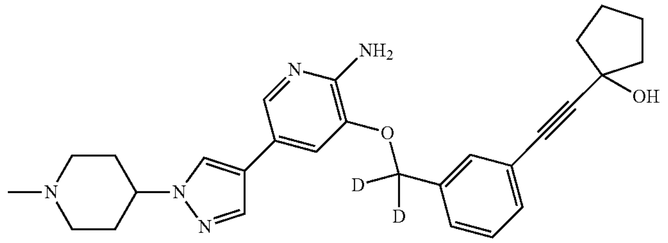
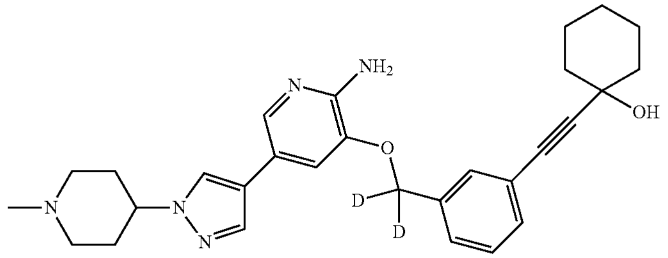
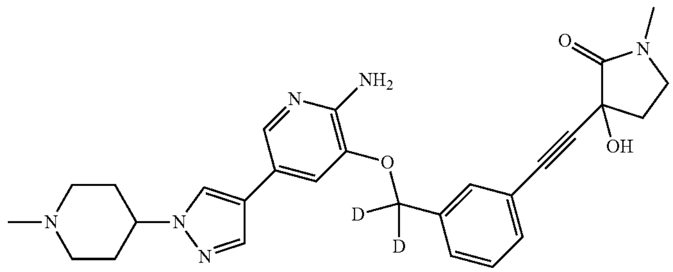
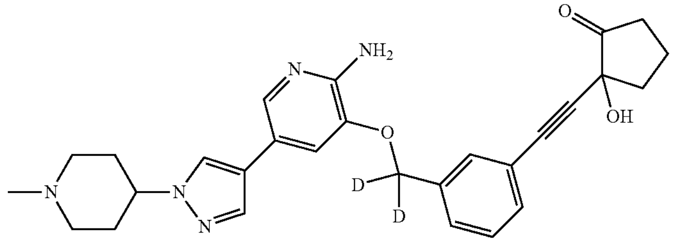
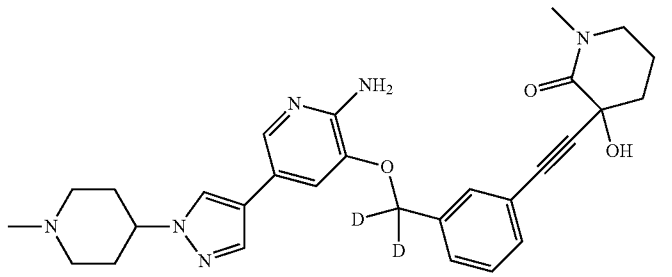

-continued
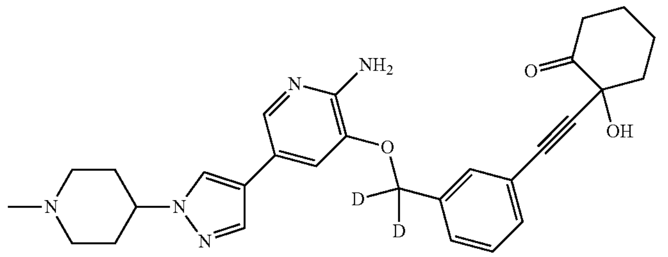
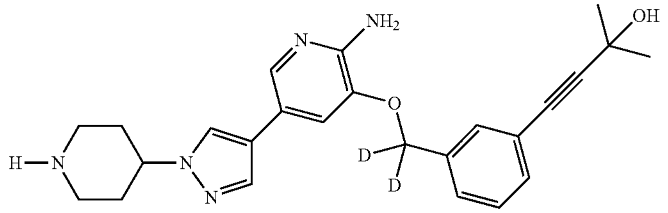
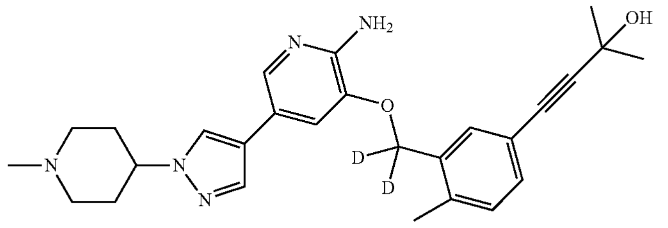
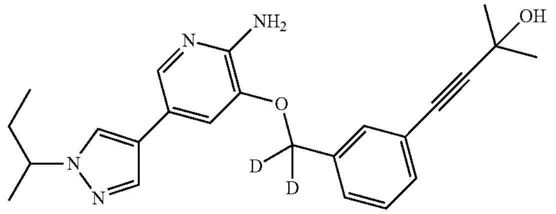
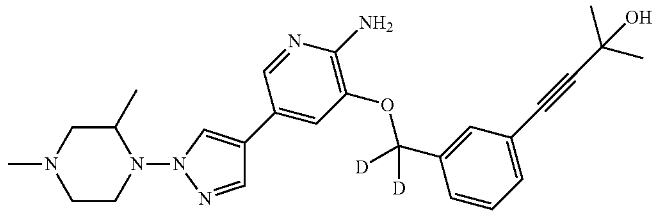
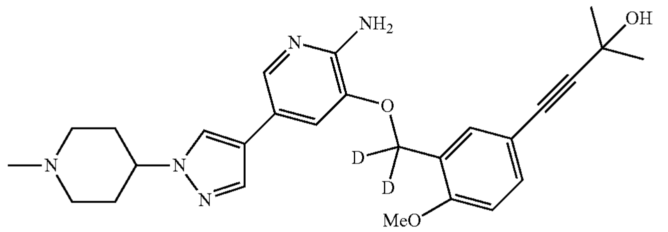
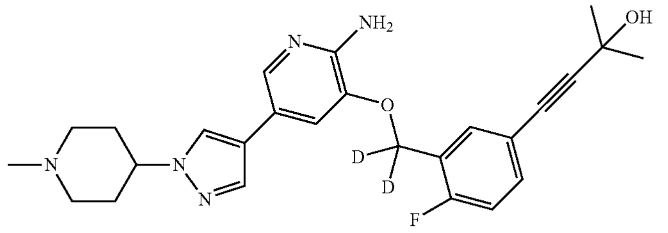

-continued
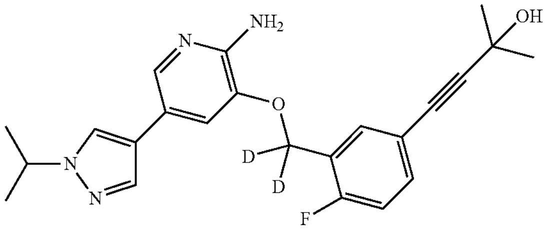
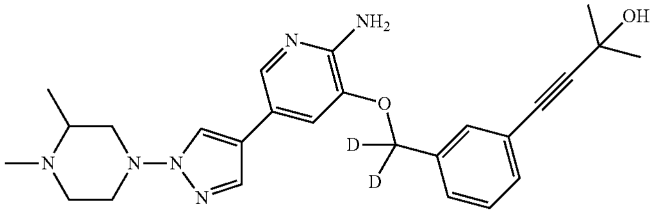
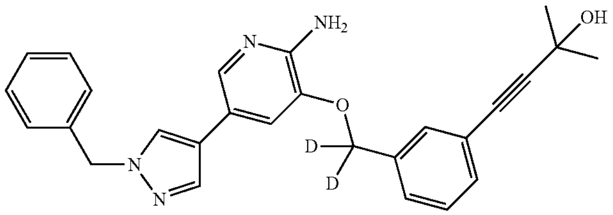
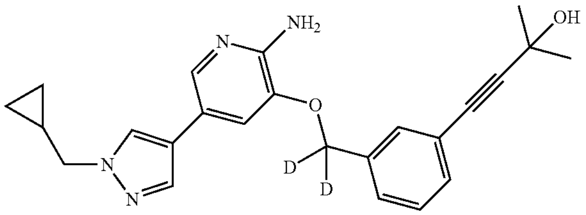
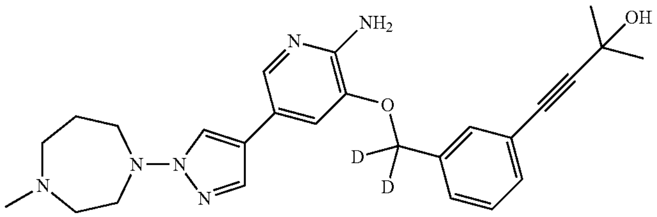
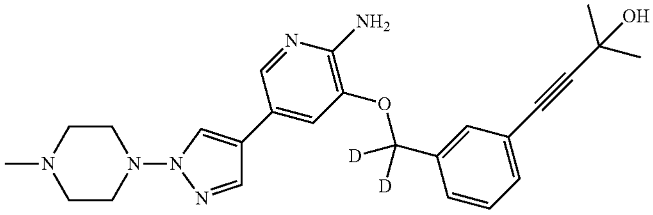
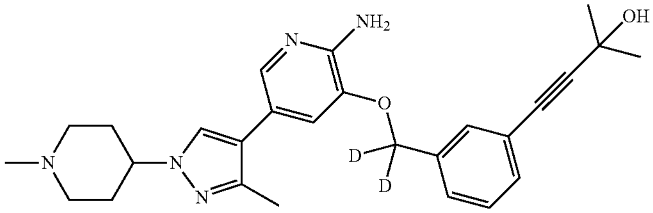
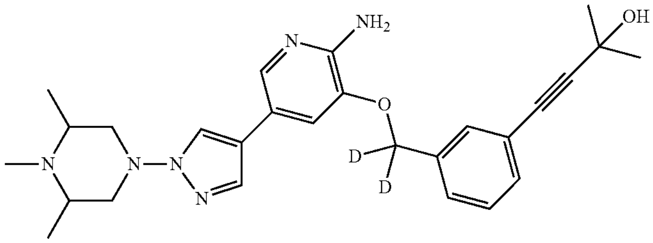

-continued
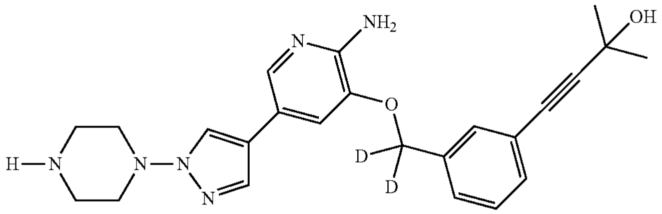
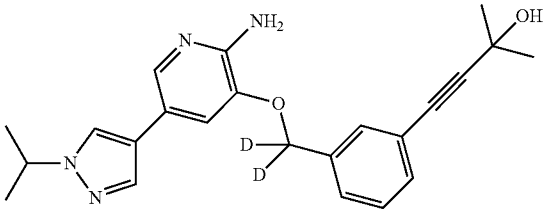
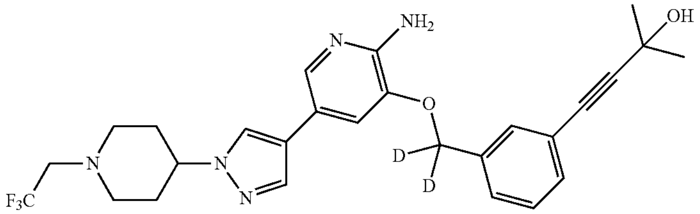
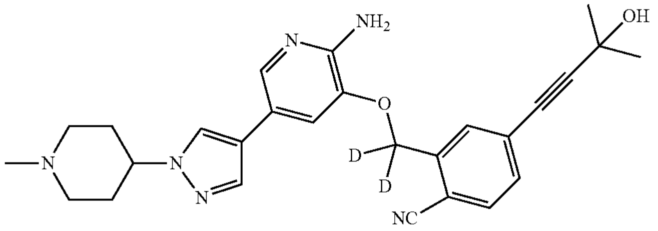
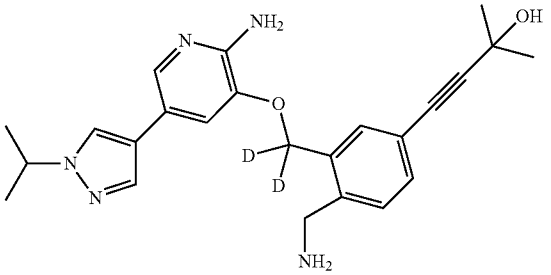
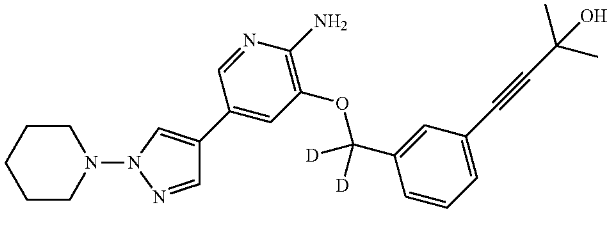
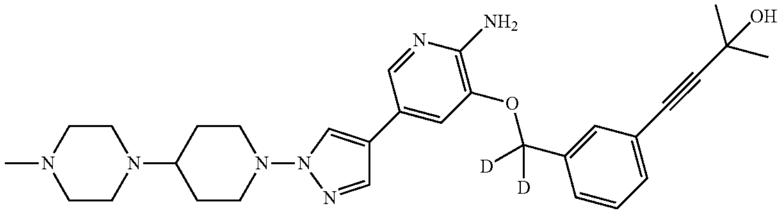

-continued
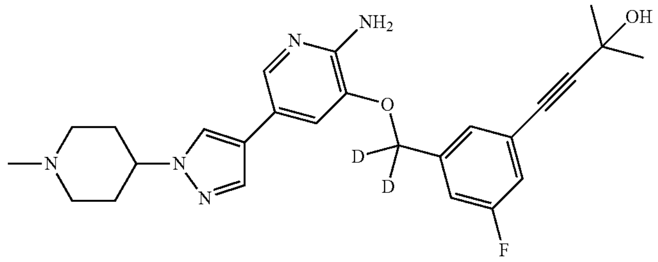
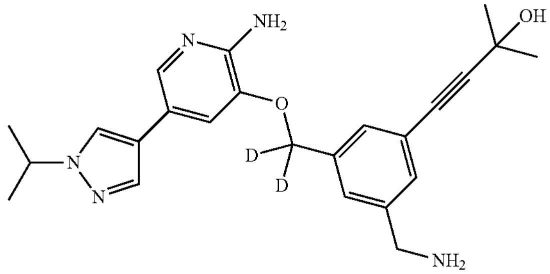
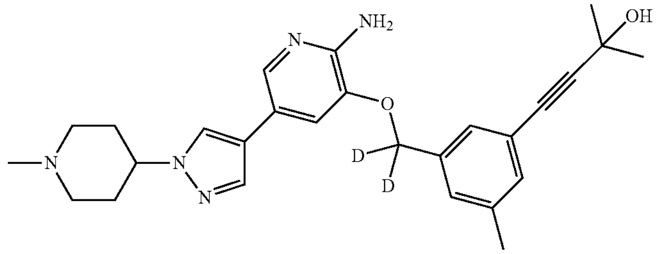
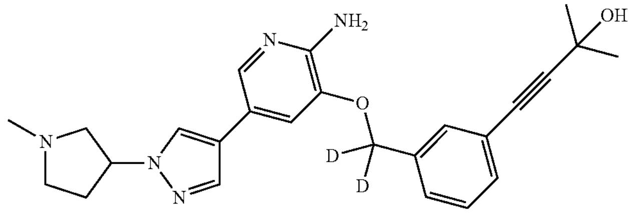
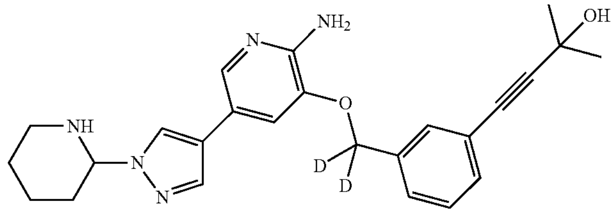
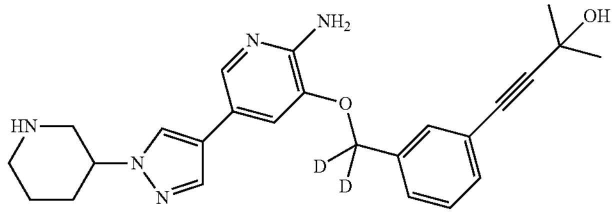
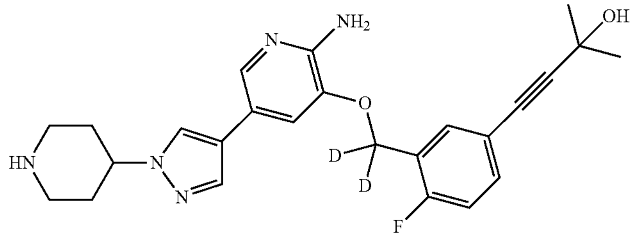

-continued
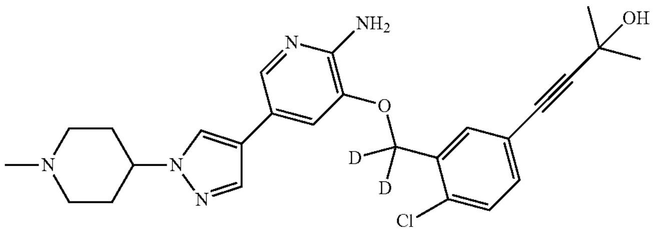
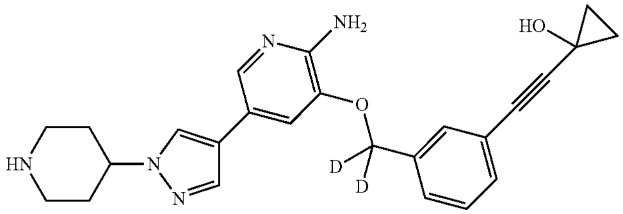
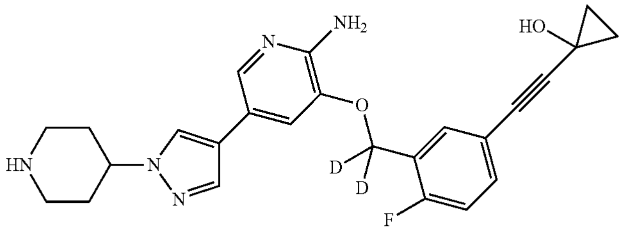
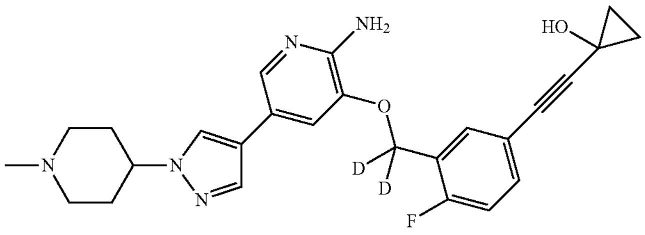
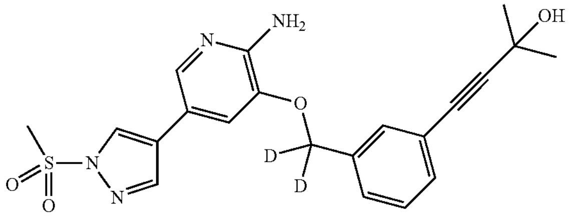
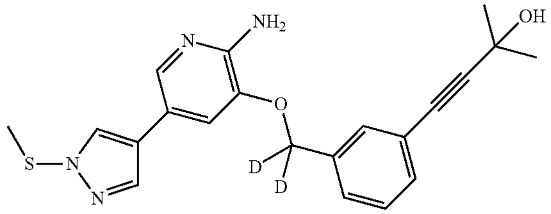
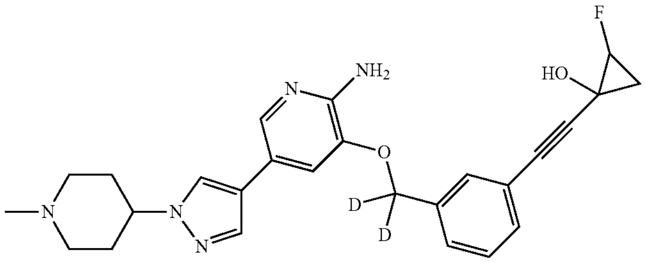
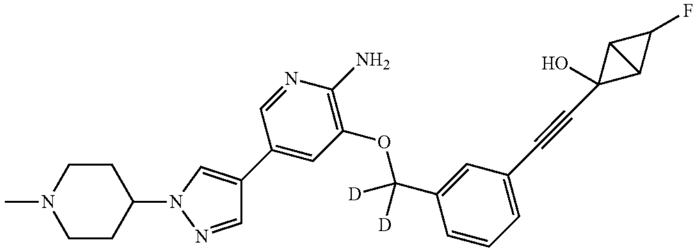

-continued
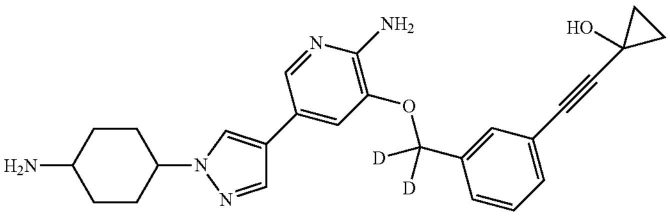
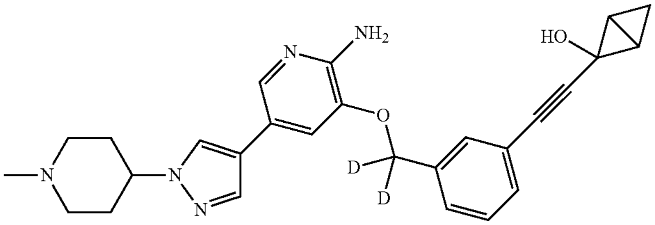
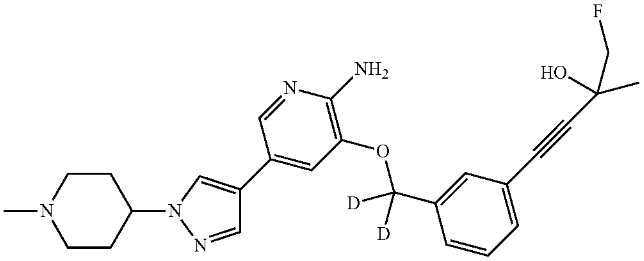
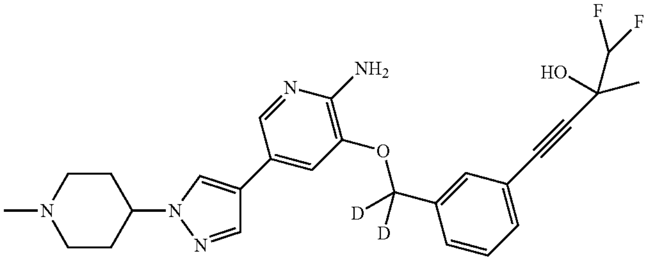
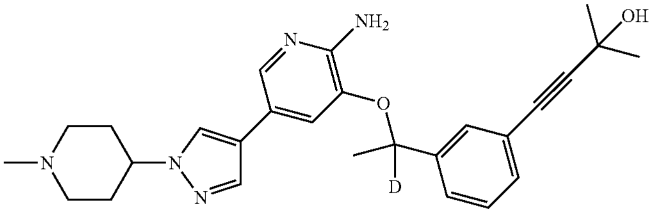
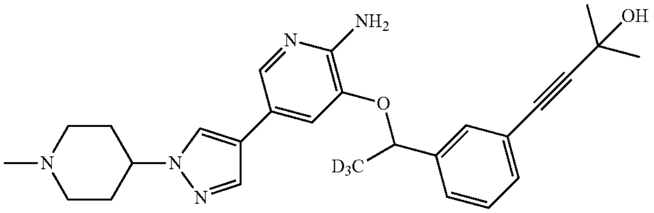
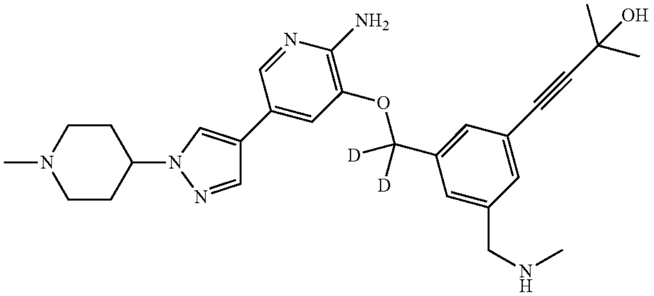

-continued
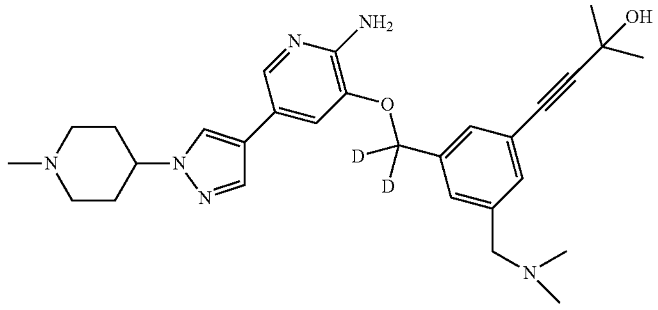
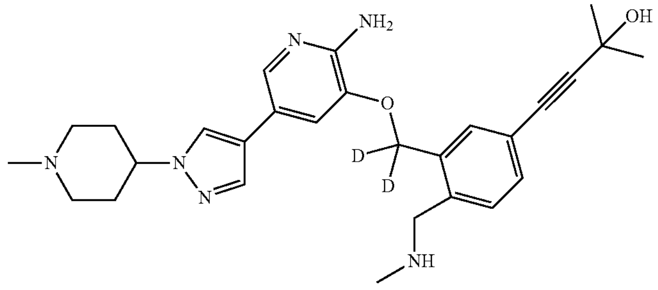
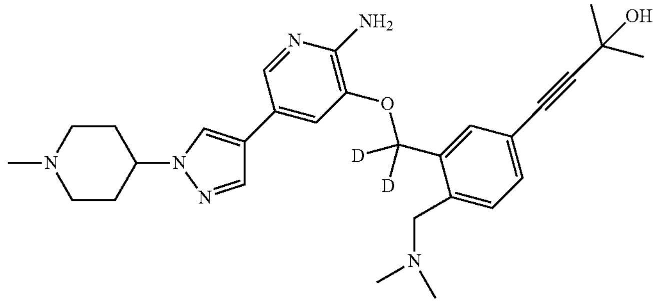
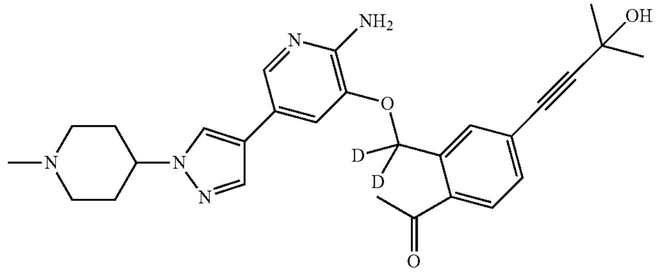
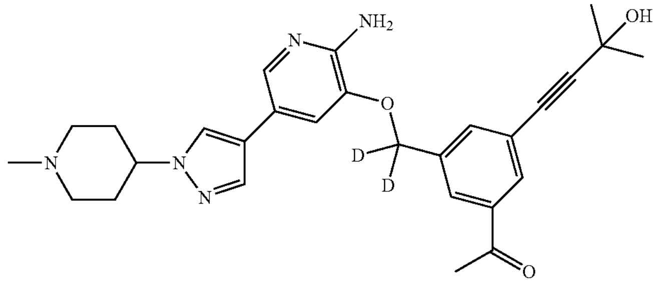
(4)
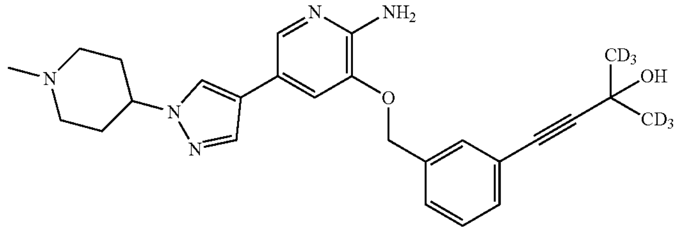

-continued
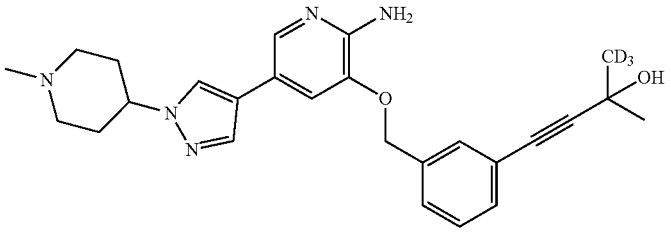
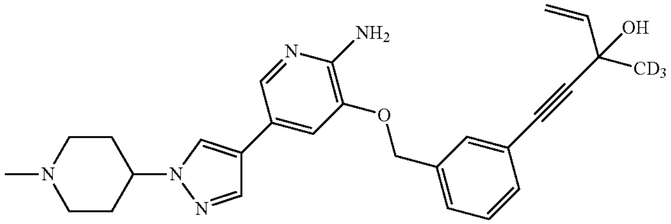
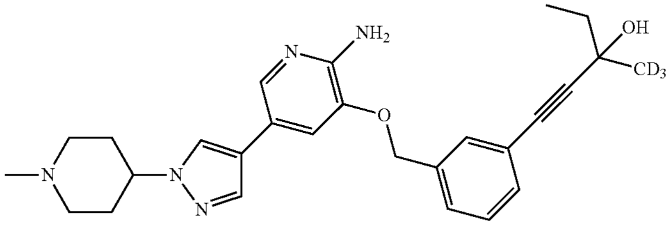
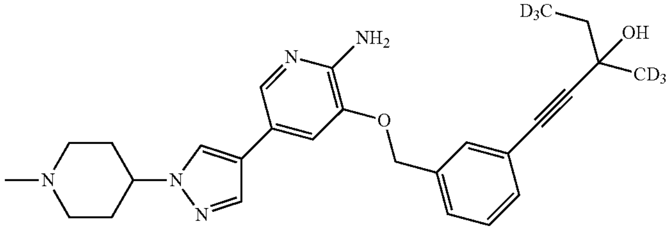
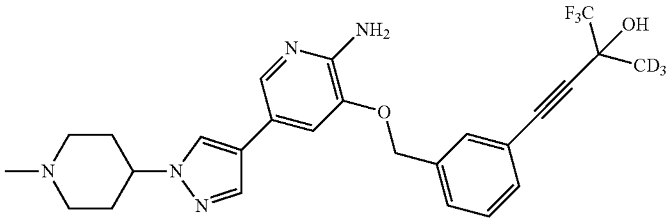
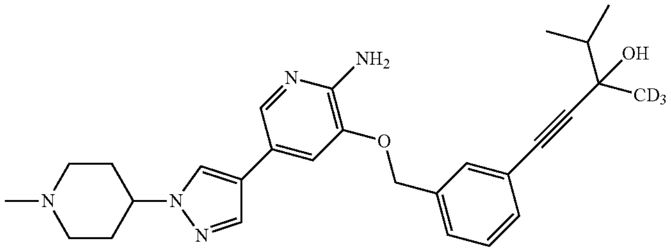
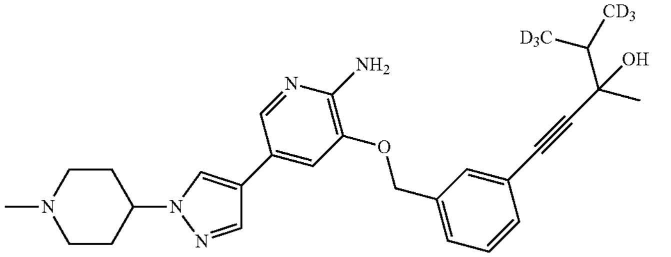

-continued
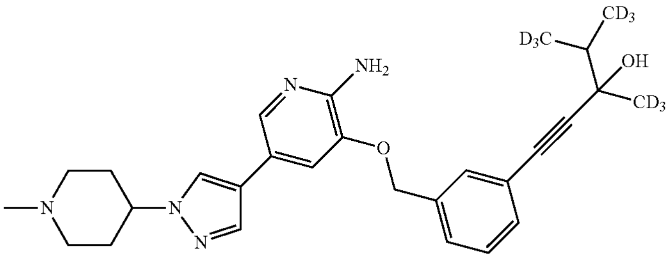
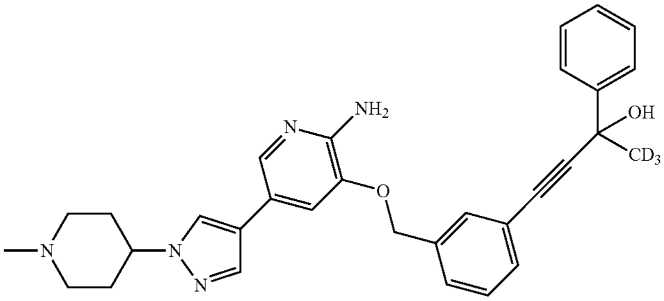
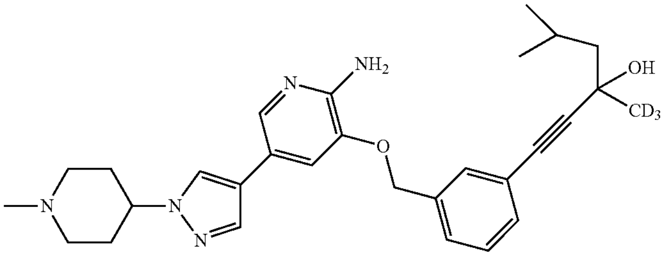
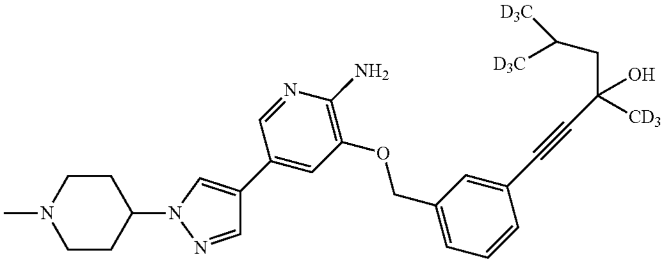
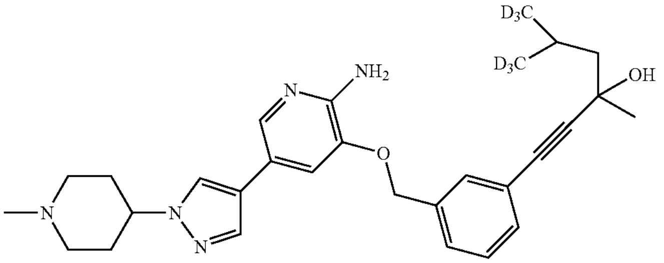
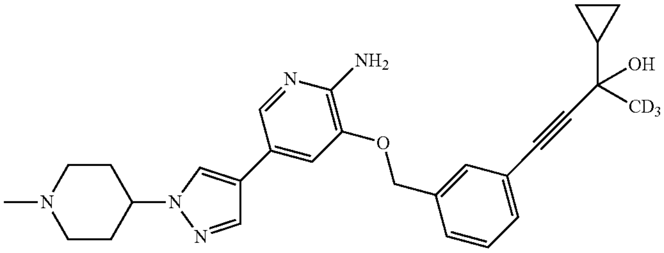

-continued
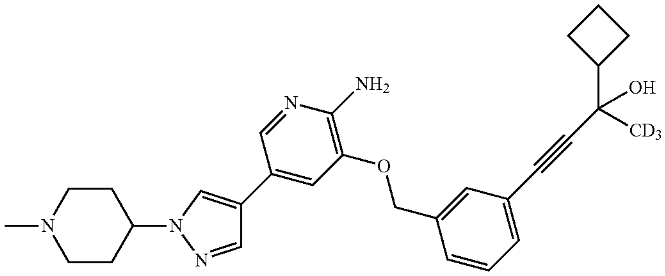
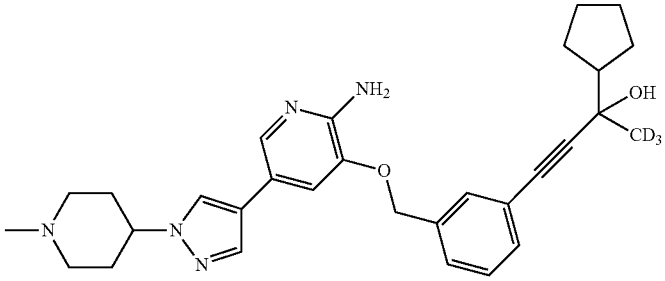
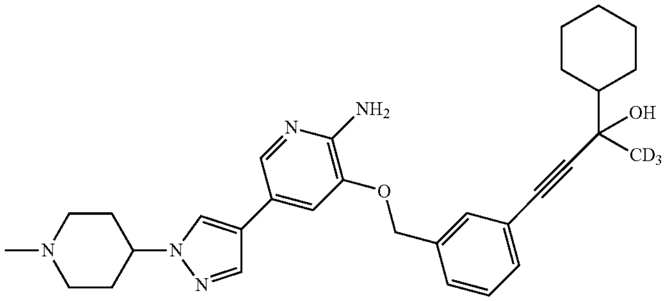
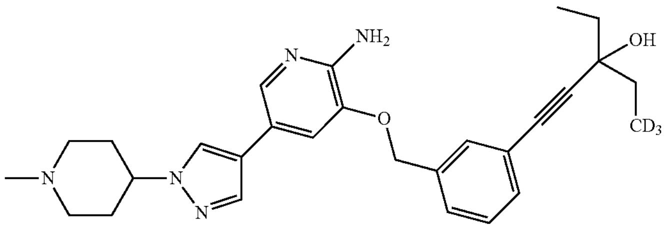
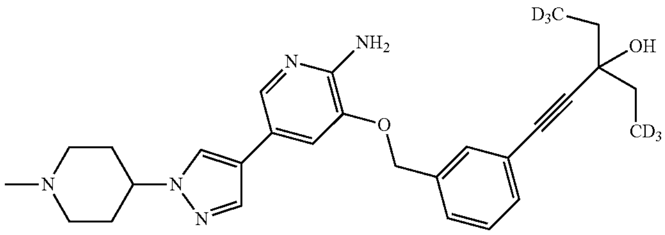
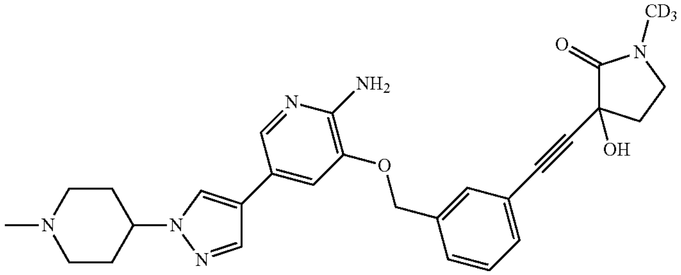

-continued
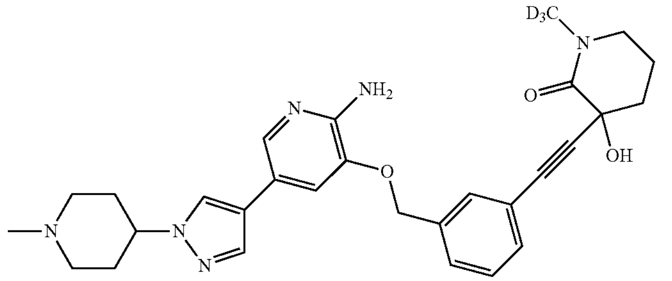
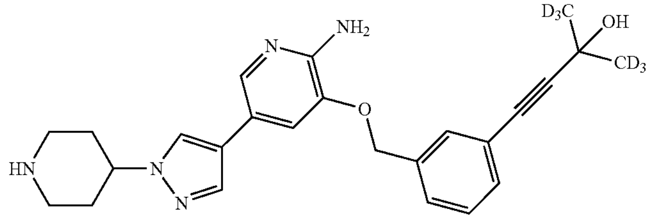
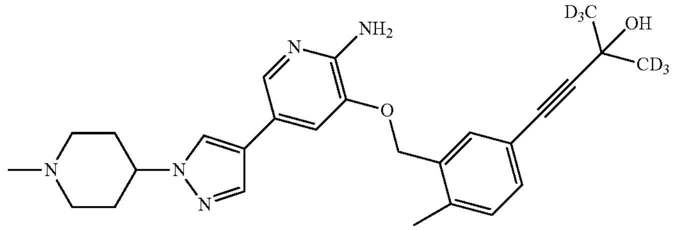
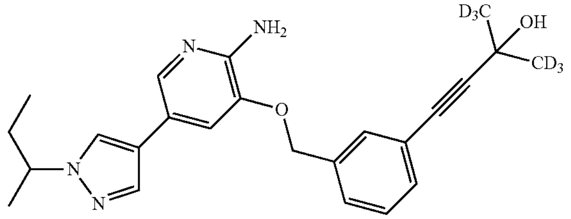
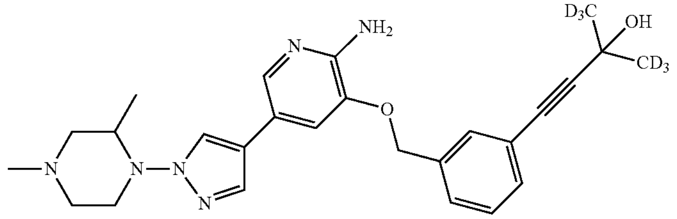
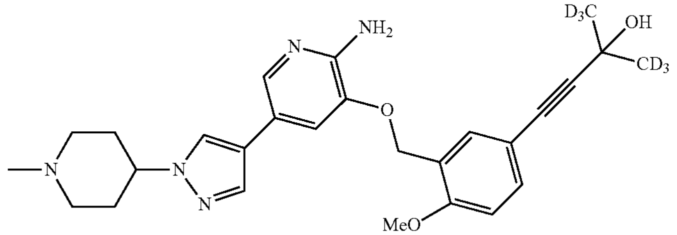
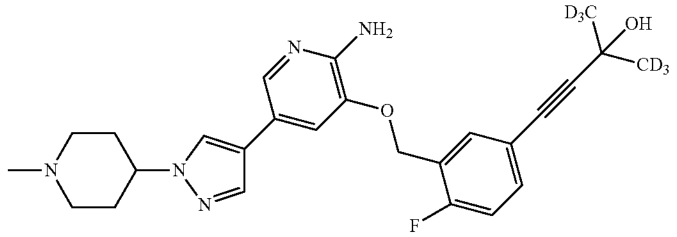

-continued
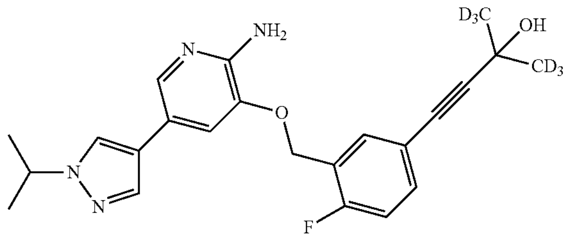
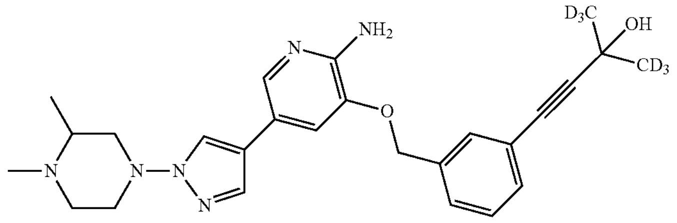
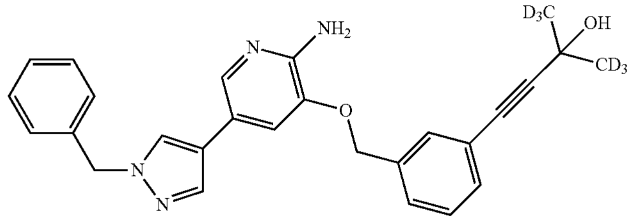
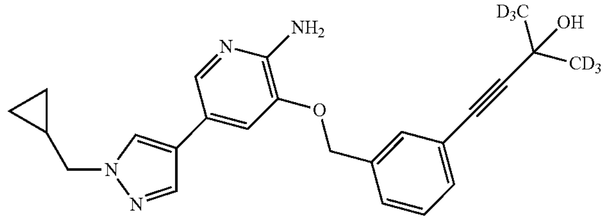
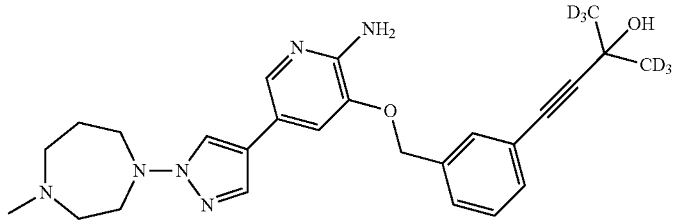
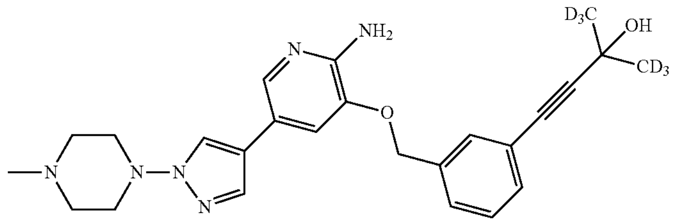
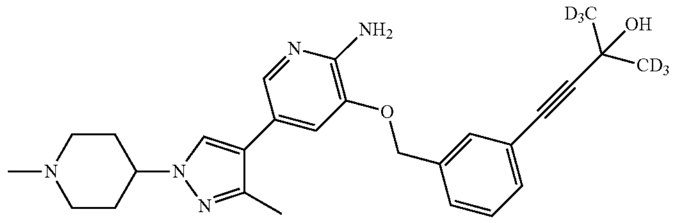

-continued
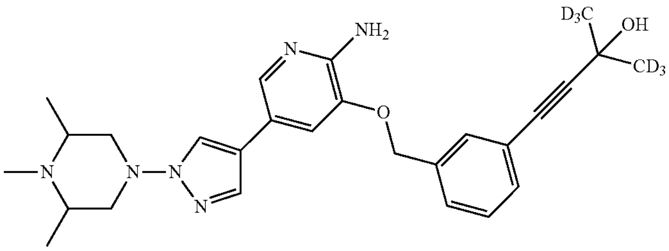
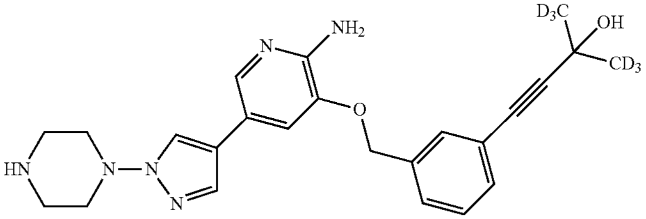
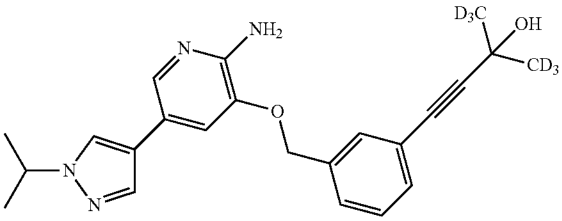
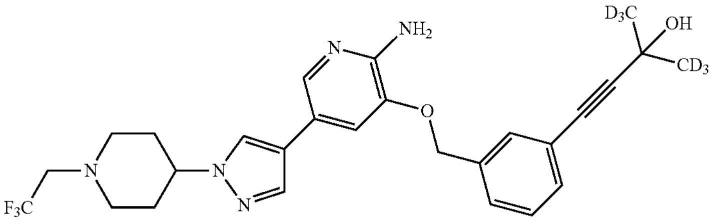
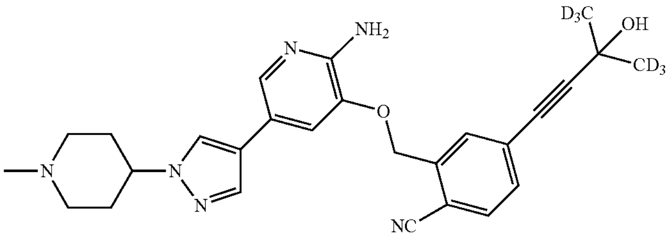
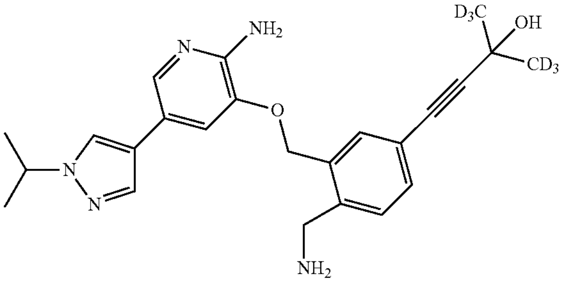
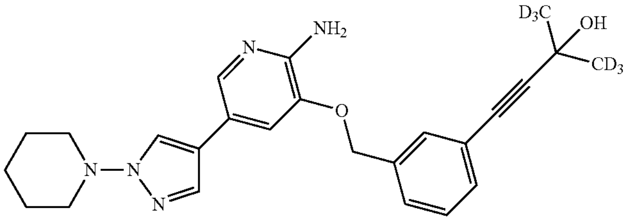

-continued
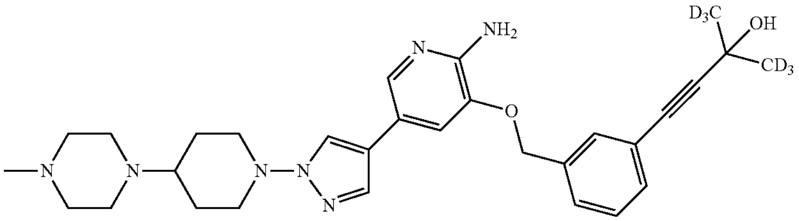
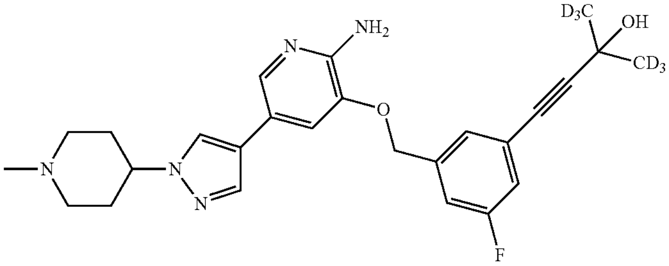
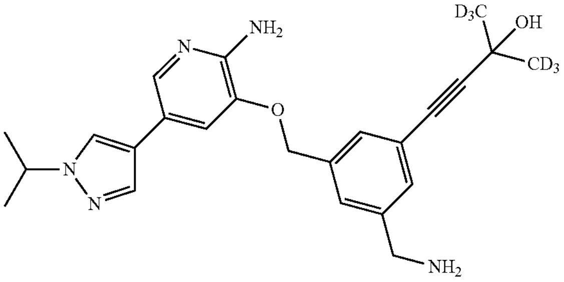
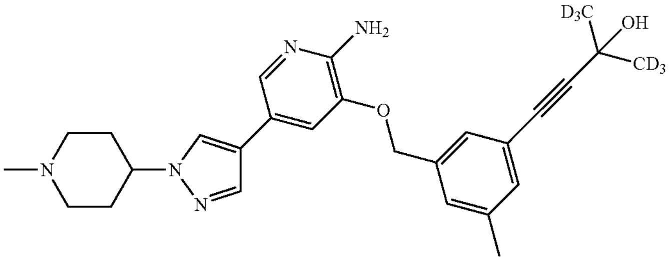
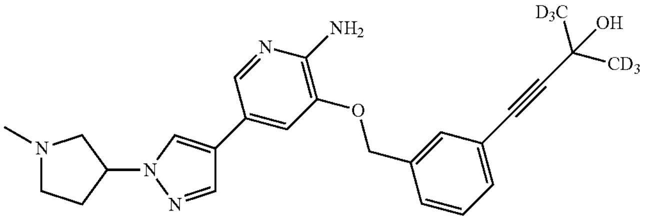
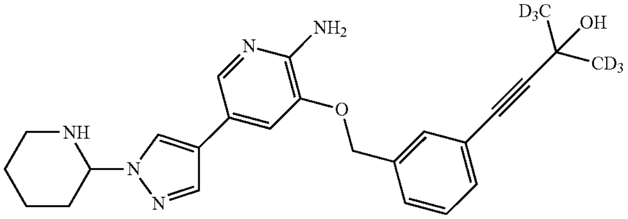
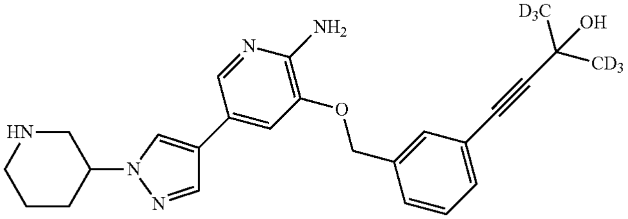

-continued
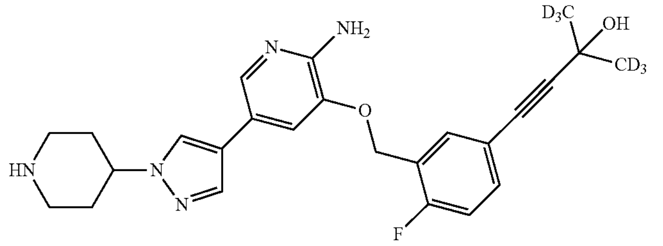
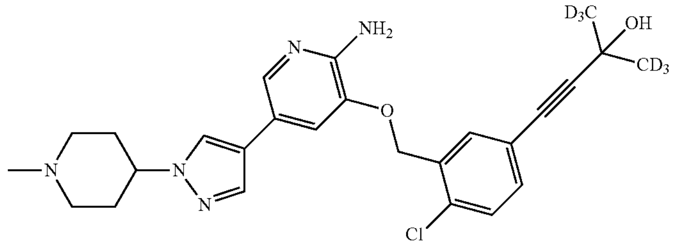
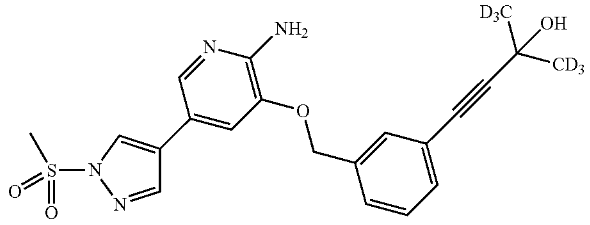
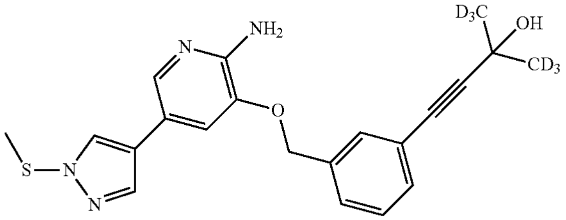
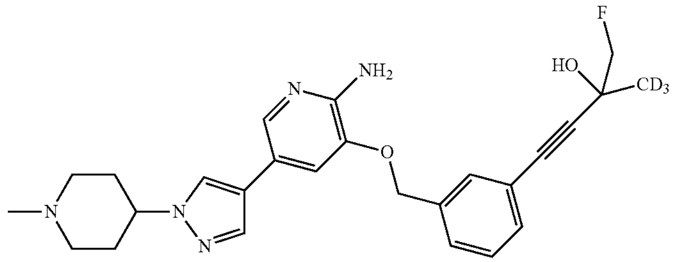
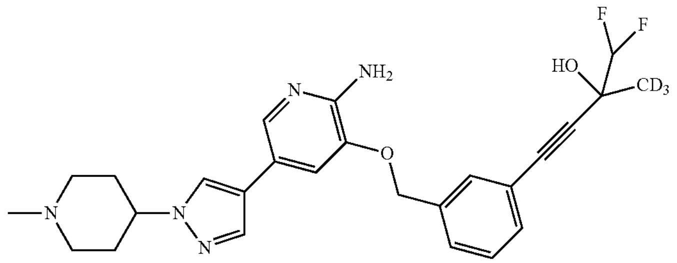
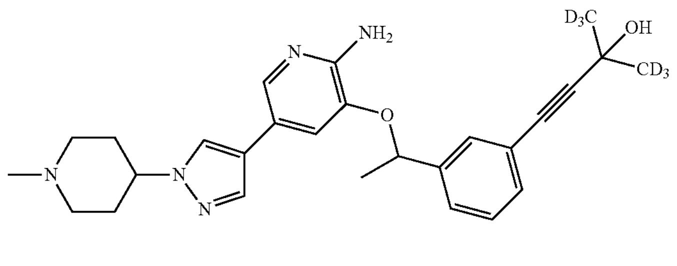

-continued
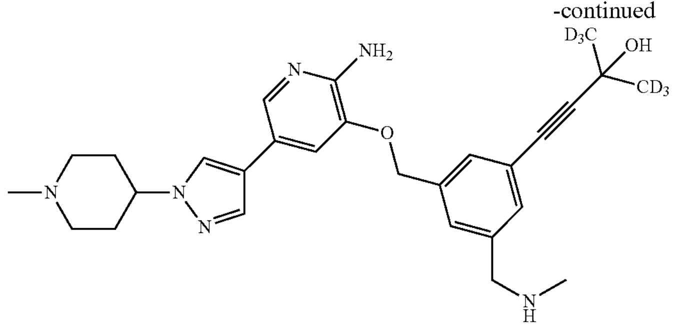
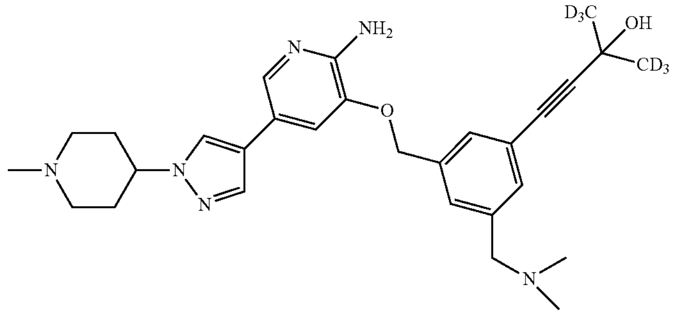
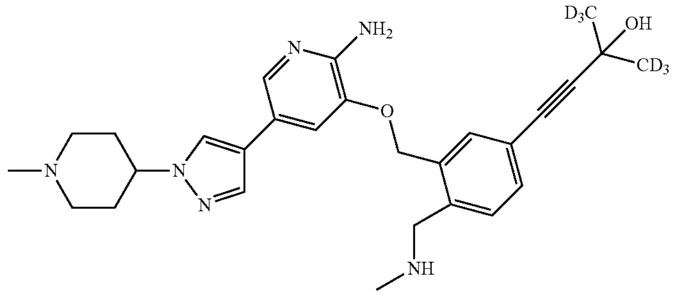
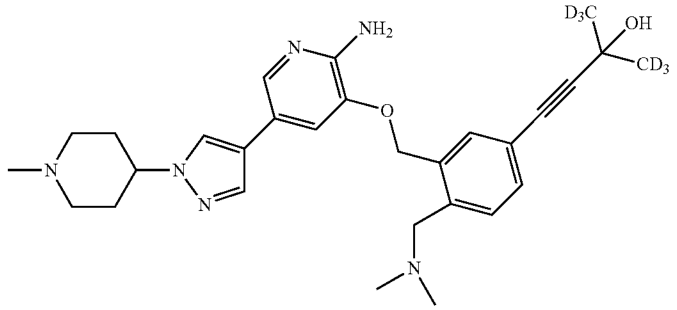
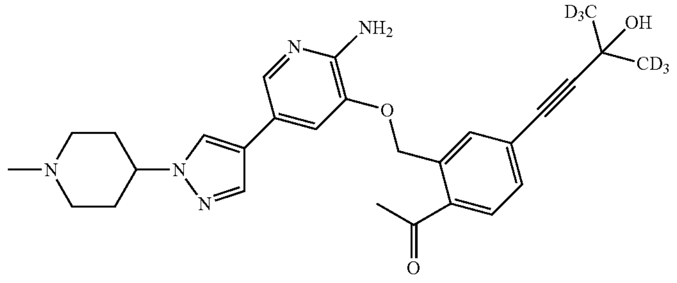

-continued
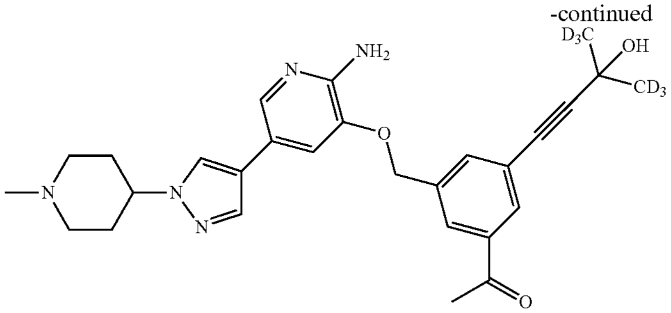
(5)
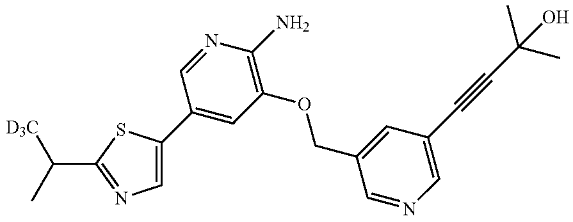
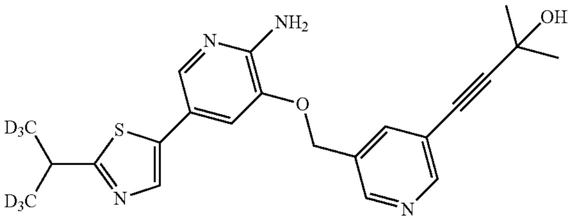
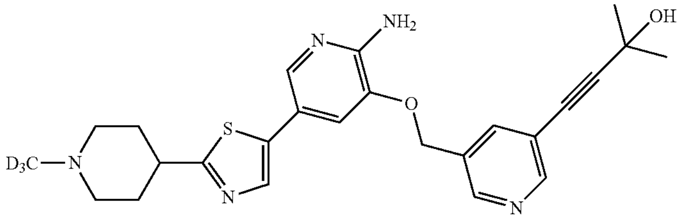
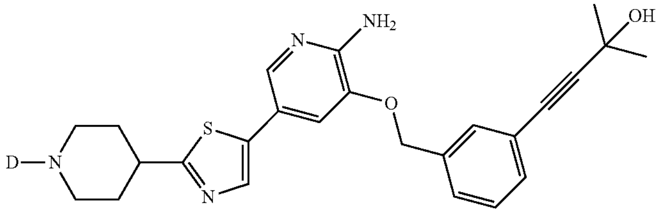
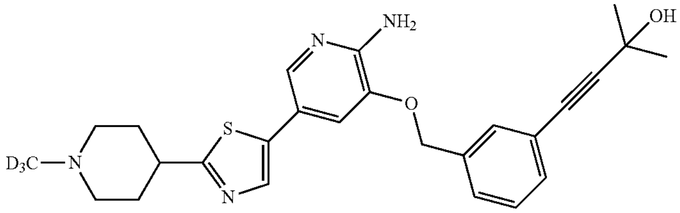
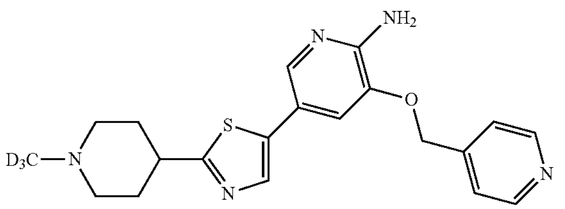
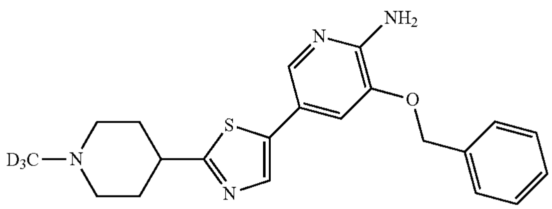
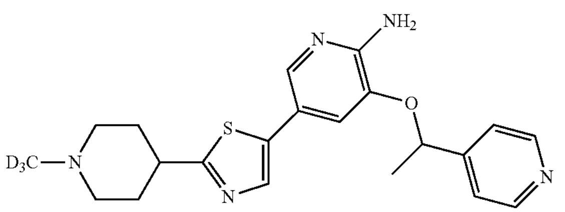
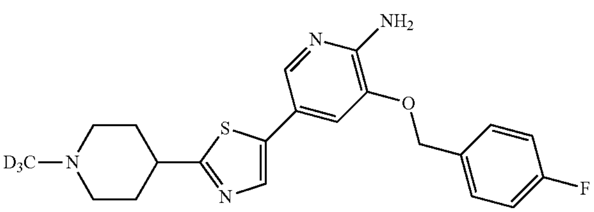

-continued
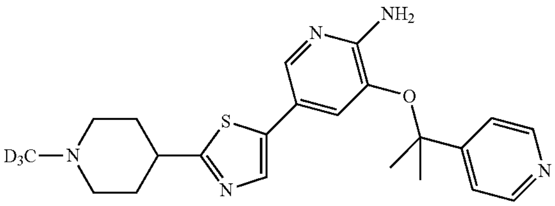
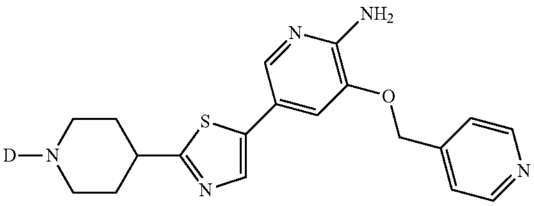
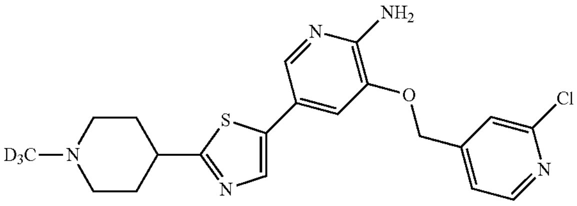
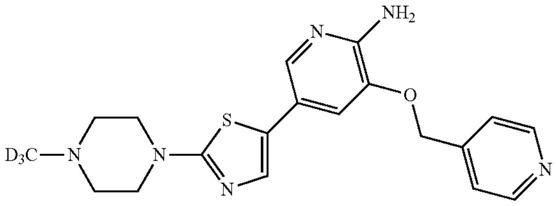
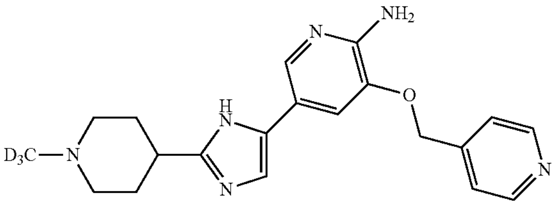
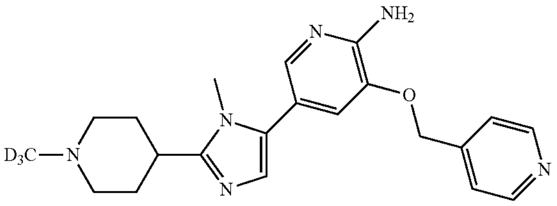
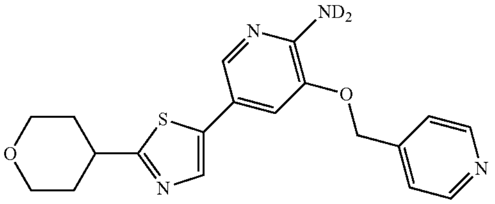
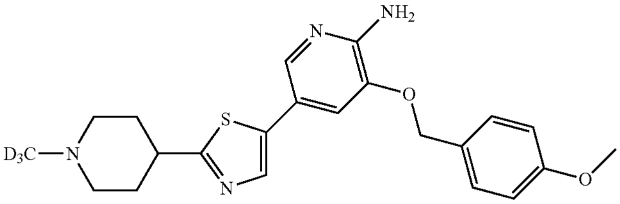
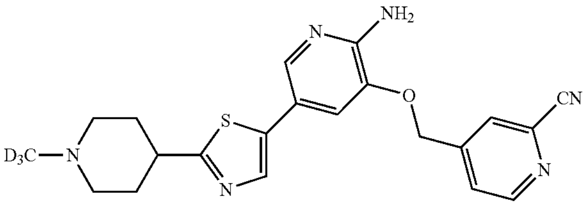
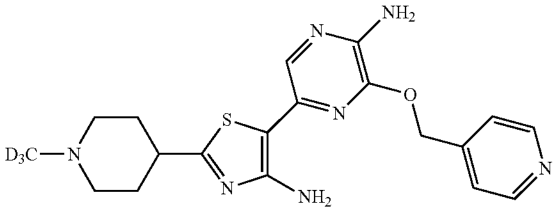
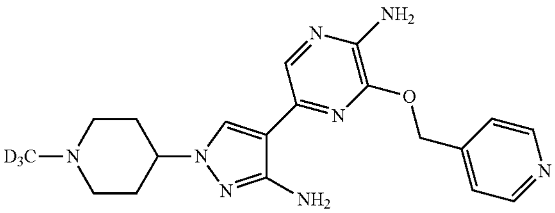
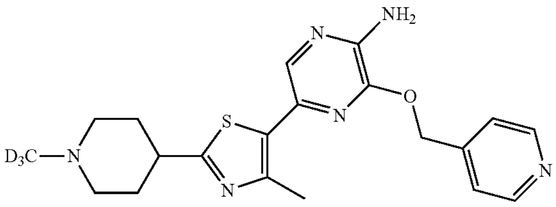
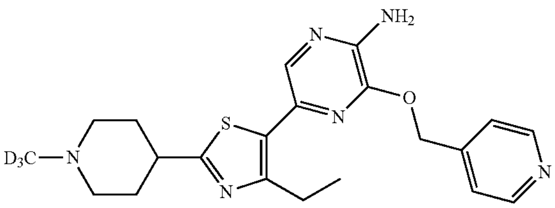
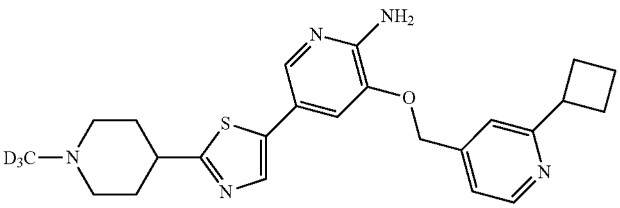
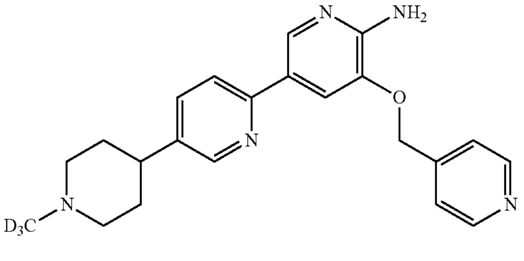

-continued
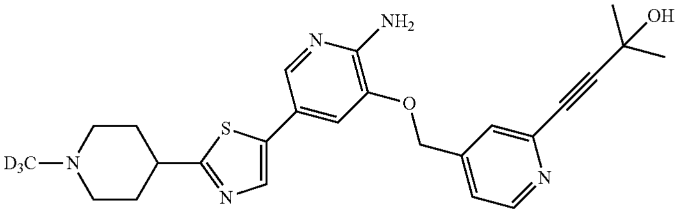
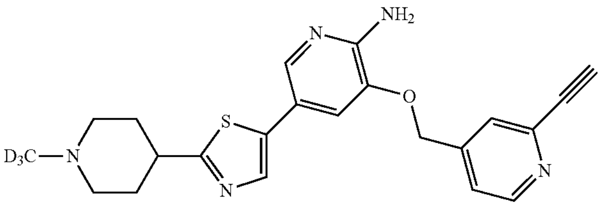
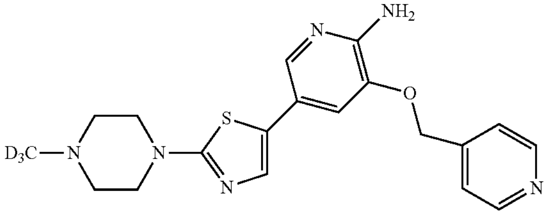
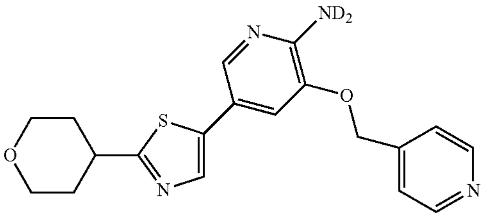
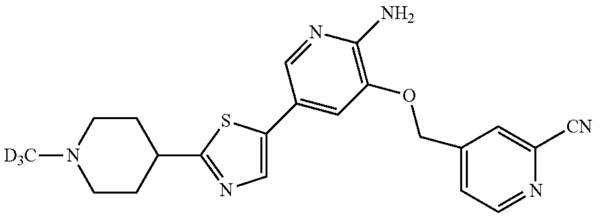
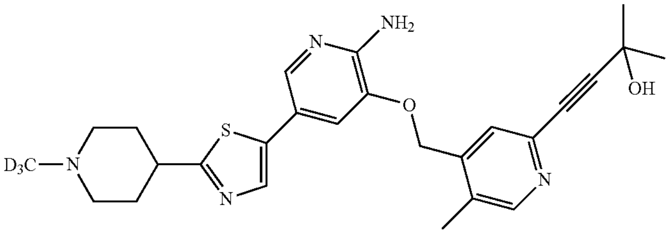
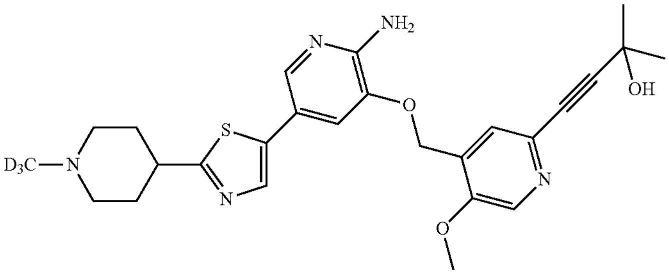
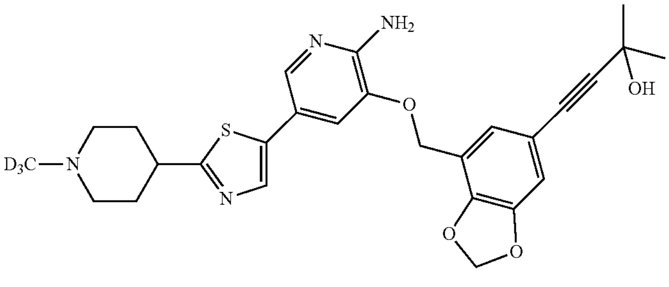
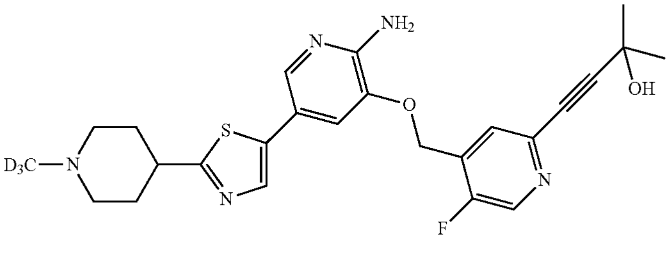
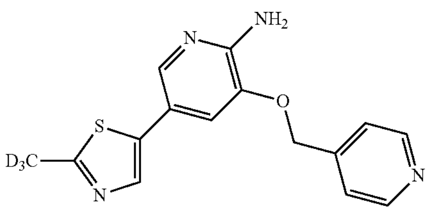

-continued
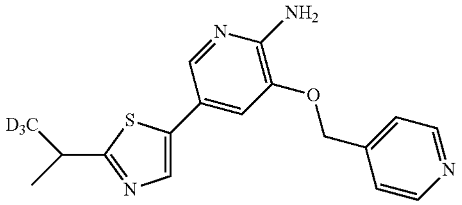
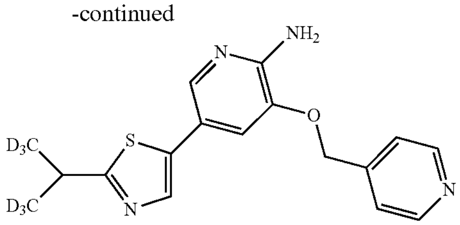
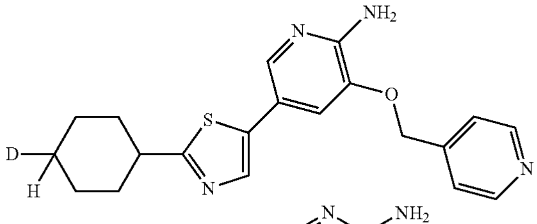
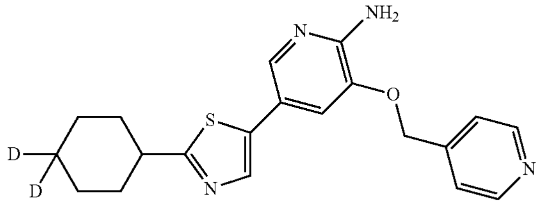
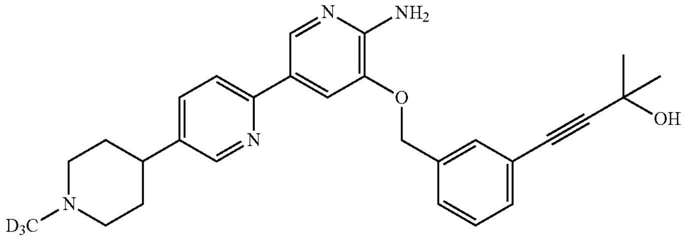
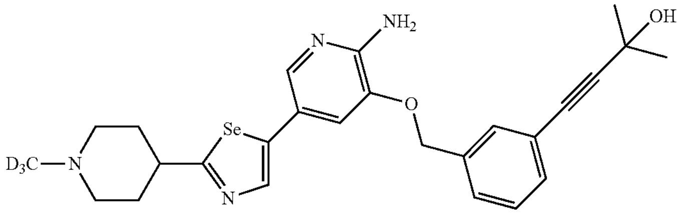
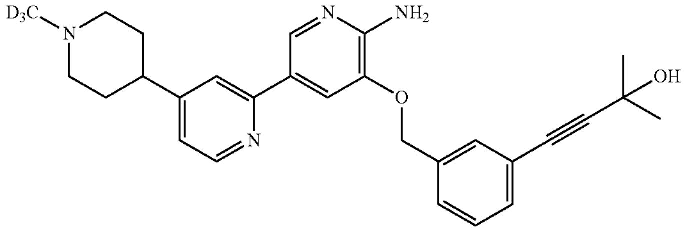
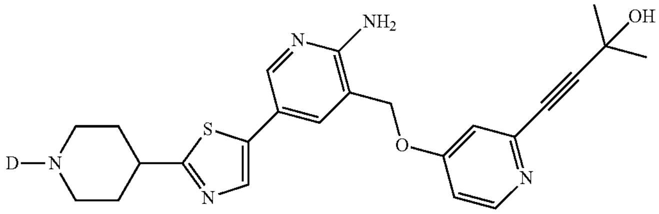
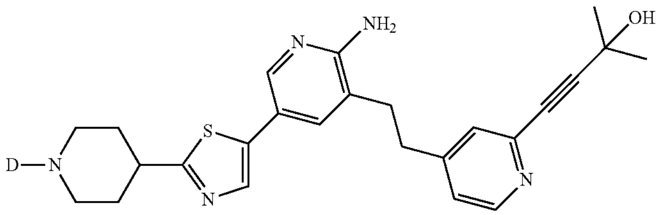
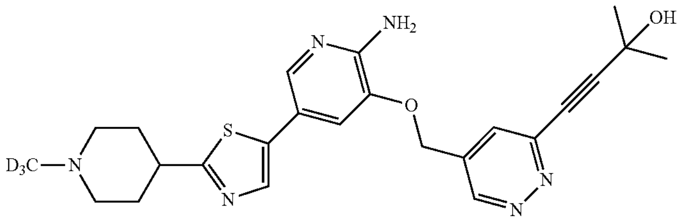

-continued

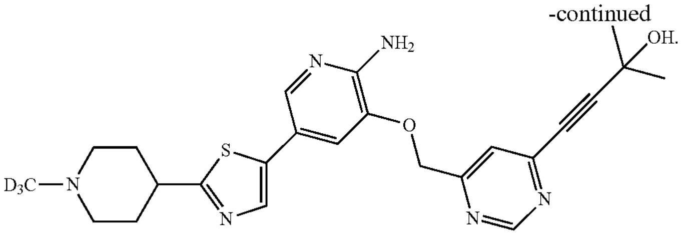

Specifically, in the compound described above, any atom not designated as deuterium exists with its natural isotopic abundance.

Specifically, in the compound described above, the position designated as "deuterium" has at least (for example) 95% deuterium incorporation.

The present invention provides a preparation method of the compound of general formula I, which comprises the following steps:

(1) subjecting

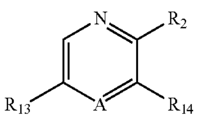

and

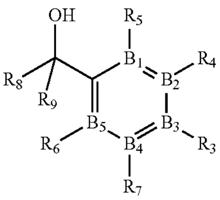

to a condensation reaction to give

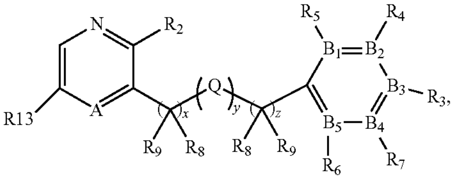

wherein $R_{13}$ is selected from: halogen and

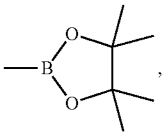

and $R_{14}$ is selected from: —OH and —F; and (2) subjecting

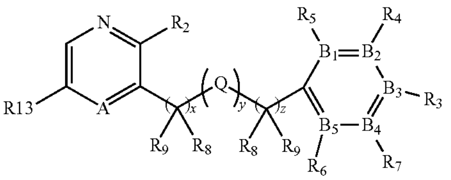

and Ar—$R_{15}$ to a condensation reaction to give

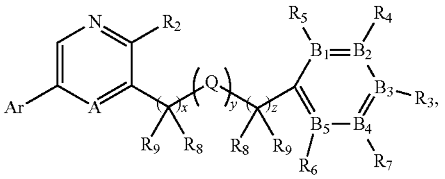

wherein $R_{15}$ is selected from: —Br and —$SnBu_3$.

Specifically, in the step (1) described above, $R_{13}$ is —Br.

Specifically, in the step (2) described above, $R_{13}$ is —Br or

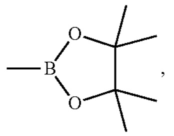

when $R_{13}$ is —Br, $R_{15}$ is —$SnBu_3$, and when $R_{13}$ is

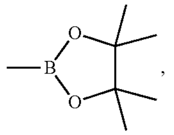

$R_{15}$ is —Br.

The present invention further provides a pharmaceutically acceptable salt, a stereoisomer, an ester, a prodrug and a solvate of the compound of general formula I described above.

Specifically, the pharmaceutically acceptable salt described above includes acid addition salts and base addition salts.

Specifically, The acid addition salts described above include, but are not limited to, salts derived from inorganic acids, such as hydrochloric acid, nitric acid, phosphoric acid, sulfuric acid, hydrobromic acid, hydroiodic acid and phosphonic acid, and salts derived from organic acids, such as aliphatic mono-carboxylic acid and aliphatic dicarboxylic acid, phenyl-substituted alkanoic acid, hydroxyalkanoic acid, alkanedioic acid, aromatic acid, aliphatic sulfonic acid and aromatic sulfonic acid. Thus, these salts include, but are not limited to, sulfate, pyrosulfate, bisulfate, sulfite, bisulfite, nitrate, phosphate, monohydrogenphosphate, dihydrogenphosphate, metaphosphate, pyrophosphate, hydrochloride, hydrobromide, iodate, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, tosylate, phenylacetate, citrate, lactate, maleate, tartrate, and methanesulfonate, and salts comprising amino acids such as arginate, gluconate and galacturonate. Acid addition salts can be prepared by contacting the free base form with a sufficient amount of the desired acid to form the salt in a conventional manner. The free base form can be regenerated by contacting the salt form with a base and isolating the free base in a conventional manner.

Specifically, the base addition salts described above are formed with metals or amines, such as hydroxides of alkali metals and alkaline earth metals, or with organic amines. Examples of metals useful as cations include, but are not limited to, sodium, potassium, magnesium and calcium. Examples of suitable amines include, but are not limited to, N,N'-dibenzylethylenediamine, chloroprocaine, choline, diethanolamine, ethylenediamine(ethane-1,2-diamine), N-methylglucamine and procaine. Base addition salts can be prepared by contacting the free acid form with a sufficient amount of the desired base to form the salt in a conventional manner. The free acid form can be regenerated by contacting the salt form with an acid and isolating the free acid in a conventional manner.

In one embodiment of the present invention, the pharmaceutically acceptable salt described above is hydrochloride.

Specifically, the stereoisomer described above includes enantiomeric, diastereomeric and geometric isomer forms. Some of the compounds of the present invention have cycloalkyl which may be substituted on more than one carbon atom, in which case all geometric forms thereof, including cis and trans, and mixtures thereof, are within the scope of the present invention.

Specifically, the solvate described above refers to a physical association of the compound of the present invention with one or more solvent molecules. The physical association includes various degrees of ionic and covalent bonding, including hydrogen bonding. In some cases, the solvate can be isolated, for example, when one or more solvent molecules are incorporated into the crystal lattice of a crystalline solid. The "solvate" includes both solution phases and isolatable solvates. Representative solvates include ethanolates, methanolates, and the like. The "hydrate" is a solvate in which one or more solvent molecules are $H_2O$.

Specifically, the prodrug described above refers to forms of the compound of formula I (including acetals, esters, and zwitterions) which are suitable for administration to patients without undue toxicity, irritation, allergic response and the like, and which are effective for the intended use thereof. The prodrug is converted in vivo (e.g. by hydrolysis in blood), to give the parent compound of the above formula.

The present invention further provides a crystalline form of the compound of general formula I and the pharmaceutically acceptable salt, the stereoisomer, the ester, the prodrug and the solvates thereof described above.

Specifically, the present invention provides a crystalline form of 4-(3-(((2-amino-S-(1-(1-trideuteromethylpiperidin-4-yl)-1H-pyrazol-4-yl)pyridin-3-yl)oxy)methyl)phenyl)-2-methylbut-3-yn-2-ol (having the following structure).

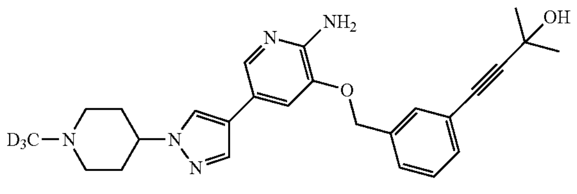 [SMILES: [2H]C([2H])([2H])N1CCC(n2cc(-c3cnc(N)c(OCc4cccc(C#CC(C)(C)O)c4)c3)cn2)CC1]

Specifically, the crystalline form described above is crystalline form A with an XRPD pattern having characteristic peaks (main characteristic diffraction peaks) at at least three (or all) of positions having 2θ values of 13.1°±0.2°, 16.3°±0.2°, 17.5°±0.2° and 23.8°±0.2°.

Specifically, the XRPD pattern of crystalline form A described above further has characteristic peaks (secondary characteristic diffraction peaks) at at least three (at least four, at least five, at least six, at least seven, or all) of positions having 2θ values of 8.1°±0.2°, 12.2°±0.2°, 15.3°±0.2°, 18.0°±0.2°, 19.3°±0.2°, 19.5°±0.2°, 21.3°±0.2° and 21.6°±0.2°.

Specifically, the crystalline form A described above has an XRPD pattern substantially as shown in FIG. 1.

Specifically, a DSC pattern of the crystalline form A described above has an endothermic peak at about 168.8° C.

Specifically, the crystalline form A described above has a DSC pattern substantially as shown in FIG. 2.

Specifically, the weight loss of the crystalline form A described above upon heating from room temperature to 170° C. is about 1.1%.

Specifically, the crystalline form A described above has a TGA pattern substantially as shown in FIG. 2.

Specifically, the crystalline form A described above is an anhydrous crystalline form.

Specifically, the crystalline form described above is crystalline form B with an XRPD pattern having characteristic peaks (main characteristic diffraction peaks) at at least three (or all) of positions having 2θ values of 5.7°±0.2°, 11.3°±0.2°, 22.7°±0.2° and 23.5°±0.2°.

Specifically, the XRPD pattern of the crystalline form B described above further has characteristic peaks (secondary characteristic diffraction peaks) at at least three (at least four, at least five, or all) of positions having 2θ values of 7.1°±0.2°, 8.8°±0.2°, 14.1°±0.2°, 17.0°±0.2°, 18.0°±0.2° and 18.8°±0.2°.

Specifically, the crystalline form B described above has an XRPD pattern substantially as shown in FIG. 6.

Specifically, a DSC pattern of the crystalline form B described above has an endothermic peak at at least one of about 59.5° C., 95.6° C., 150.8° C. and 160.9° C.

Specifically, the crystalline form B described above has a DSC pattern substantially as shown in FIG. 7.

Specifically, the weight loss of the crystalline form B described above is about 13.2% upon heating from room temperature to 70° C. and about 8.5% upon continued heating to 170° C.

Specifically, the crystalline form B described above has a TGA pattern substantially as shown in FIG. 7.

Specifically, the crystalline form B described above is an EtOAc solvate.

Specifically, the present invention further provides a crystalline form of 4-(3-(((2-amino-S-(1-(1-trideuteromethylpiperidin-4-yl)-1H-pyrazol-4-yl)pyridin-3-yl)oxy)methyl)phenyl)-2-methylbut-3-yn-2-ol hydrochloride.

Specifically, the crystalline form described above is crystalline form A with an XRPD pattern having characteristic peaks (main characteristic diffraction peaks) at at least three (at least four, or all) of positions having 2θ values of 13.0°±0.2°, 16.3°±0.2°, 17.5°±0.2°, 19.4°±0.2°, 23.8°±0.2°.

Specifically, the XRPD pattern of the crystalline form A described above further has characteristic peaks (secondary characteristic diffraction peaks) at at least three (at least four, or all) of positions having 2θ values of 8.1°±0.2°, 12.1°±0.2°, 15.3°±0.2°, 18.0°±0.2° and 21.4°±0.2°.

Specifically, the crystalline form A described above has an XRPD pattern substantially as shown in FIG. 11.

Specifically, a DSC pattern of the crystalline form A described above has an endothermic peak at about 81.9° C. and about 156.0° C.

Specifically, the crystalline form A described above has a DSC pattern substantially as shown in FIG. 12.

Specifically, the weight loss of the crystalline form A described above upon heating from room temperature to 150° C. is about 8.6%.

Specifically, the crystalline form A described above has a TGA pattern substantially as shown in FIG. 12.

The present invention further provides a preparation method of the crystalline form described above.

Specifically, the preparation method described above is selected from one or a combination of two or more of: anti-solvent addition, anti-anti-solvent addition, gas-solid diffusion, suspension with stirring at room temperature, suspension with stirring at 5° C., slow volatilization, slow cooling, gas-liquid diffusion, and high polymer induction.

Specifically, the method for anti-solvent addition described above comprises: dissolving a target product with a good solvent, and then adding an anti-solvent to the resulting solution (which is then, for example, volatilized at room temperature to give a solid, or stirred at −20° C. to give a solid).

Specifically, the method for anti-anti-solvent addition described above comprises: dissolving a target product with a good solvent, and then adding an anti-solvent to the resulting solution (which is then, for example, volatilized at room temperature to give a solid, or stirred at −20° C. to give a solid).

Specifically, the methods for gas-solid diffusion, suspension with stirring at room temperature, suspension with stirring at 5° C., slow volatilization, slow cooling, and gas-liquid diffusion described above all comprise: dissolving a target product with a solvent and then drying to give a solid.

Specifically, the method for high polymer induction described above comprises: dissolving a target product with a solvent, adding a high polymer, and volatilizing at room temperature to give a solid.

Specifically, the preparation method for the crystalline form A of 4-(3-(((2-amino-S-(1-(1-trideuteromethylpiperidin-4-yl)-1H-pyrazol-4-yl)pyridin-3-yl)oxy)methyl)phenyl)-2-methylbut-3-yn-2-ol described above is selected from one or a combination of two or more of: anti-solvent addition, anti-anti-solvent addition, gas-solid diffusion, suspension with stirring at room temperature, suspension with stirring at 5° C., slow volatilization, slow cooling, gas-liquid diffusion, and high polymer induction.

Specifically, for the preparation of the crystalline form A described above, in the method for anti-solvent addition, the good solvent may be selected from: MeOH, acetone, DMSO, EtOAc, EtOH, DCM, $CHCl_3$, THF, IPA, ACN and 1,4-dioxane, and the anti-solvent may be selected from: MTBE, toluene, n-heptane and water.

In one embodiment of the present invention, in the method for anti-solvent addition, the good solvent may be selected from: MeOH, acetone and DMSO, and the anti-solvent is MTBE.

In another embodiment of the present invention, in the method for anti-solvent addition, the good solvent may be selected from: EtOH and DCM, and the anti-solvent is toluene.

In another embodiment of the present invention, in the method for anti-solvent addition, the good solvent may be selected from: $CHCl_3$, THF and IPA, and the anti-solvent is n-heptane.

In another embodiment of the present invention, in the method for anti-solvent addition, the good solvent may be selected from: acetone, ACN and 1,4-dioxane, and the anti-solvent is water.

Specifically, for the preparation of the crystalline form A described above, in the method for anti-anti-solvent addition, the good solvent may be selected from: MeOH, MIBK, acetone, anisole, EtOH, THF, EtOAc and DCM, and the anti-solvent may be selected from: toluene, n-heptane, water and MTBE.

In one embodiment of the present invention, in the method for anti-anti-solvent addition, the good solvent may be MIBK, and the anti-solvent may be toluene.

In another embodiment of the present invention, in the method for anti-anti-solvent addition, the good solvent may be selected from: acetone and anisole, and the anti-solvent may be n-heptane.

In another embodiment of the present invention, in the method for anti-anti-solvent addition, the good solvent may be selected from: EtOH and THF, and the anti-solvent may be water.

In another embodiment of the present invention, in the method for anti-anti-solvent addition, the good solvent may be selected from: EtOAc and DCM, and the anti-solvent may be MTBE.

Specifically, for the preparation of the crystalline form A described above, in the method for gas-solid diffusion, the solvent may be selected from: water, DCM, EtOH, MeOH, ACN, THF, $CHCl_3$, acetone, DMSO, EtOAc, 1,4-dioxane and IPA.

Specifically, for the preparation of the crystalline form A described above, in the method for suspension with stirring at room temperature, the solvent may be selected from: MTBE, IPAc, n-heptane, toluene, water, EtOH/toluene (e.g., at a ratio of 1:3, v/v), DMSO/MTBE (e.g., at a ratio of 1:4, v/v), acetone/water (e.g., at a ratio of 1:4, v/v), IPA/n-heptane (e.g., at a ratio of 1:4, v/v), EtOAc/n-heptane (e.g., at a ratio of 1:4, v/v), anisole/toluene (e.g., at a ratio of 1:4, v/v), DMAc/water (e.g., at a ratio of 1:4, v/v), and THF/water (e.g., at a ratio of 1:4, v/v).

Specifically, for the preparation of the crystalline form A described above, in the method for suspension with stirring at 5° C., the solvent may be selected from: MTBE, toluene, water, IPA/n-heptane (e.g., at a ratio of 1:2, v/v), MEK/n-heptane (e.g., at a ratio of 1:2, v/v), EtOAc/toluene (e.g., at a ratio of 1:2, v/v), CPME/toluene (e.g., at a ratio of 1:2, v/v), NMP/water (e.g., at a ratio of 1:4, v/v), THF/water (e.g., at a ratio of 1:4, v/v), ACN/water (e.g., at a ratio of 1:2, v/v), IPAc/DCM (e.g., at a ratio of 1:1, v/v), MeOH/toluene (e.g., at a ratio of 1:4, v/v), DCM/MTBE (e.g., at a ratio of 1:4, v/v), and THF/n-heptane (e.g., at a ratio of 1:4, v/v).

Specifically, for the preparation of the crystalline form A described above, in the method for slow volatilization, the solvent may be selected from: EtOH, acetone, IPAc, THF, CPME, anisole, ACN/water (e.g., at a ratio of 9:1, v/v), MeOH/DCM (e.g., at a ratio of 1:1, v/v), acetone/EtOAc (e.g., at a ratio of 2:1, v/v), and THF/water (e.g., at a ratio of 4:1, v/v).

Specifically, for the preparation of the crystalline form A described above, in the method for slow cooling, the solvent may be selected from: CPME, toluene, ACN/toluene (e.g., at a ratio of 1:2, v/v), acetone/n-heptane (e.g., at a ratio of 1:1, v/v), THF/toluene (e.g., at a ratio of 1:2, v/v), MeOH/water (e.g., at a ratio of 1:1, v/v), and $CHCl_3$/MTBE (e.g., at a ratio of 1:1, v/v).

Specifically, for the preparation of the crystalline form A described above, in the method for gas-liquid diffusion, the good solvent may be selected from: EtOH, THF and DMSO, and the anti-solvent may be selected from: n-heptane, MTBE, toluene, cyclohexane and water.

In one embodiment of the present invention, in the method for gas-liquid diffusion, the good solvent is EtOH, and the anti-solvent may be selected from: n-heptane, MTBE and toluene.

In another embodiment of the present invention, in the method for gas-liquid diffusion, the good solvent is THF, and the anti-solvent may be selected from: n-heptane, cyclohexane and MTBE.

In another embodiment of the present invention, in the method for gas-liquid diffusion, the good solvent is DMSO, and the anti-solvent may be selected from: toluene, MTBE and water.

Specifically, for the preparation of the crystalline form A described above, in the method for high polymer induction, the solvent may be selected from: MEK, ACN/toluene (e.g., at a ratio of 4:1, v/v), THF/water (e.g., at a ratio of 9:1, v/v), EtOAc, acetone/2-MeTHF (e.g., at a ratio of 1:1, v/v), and MeOH/DCM (e.g., at a ratio of 1:1, v/v), and the high polymer may be selected from one or a combination of two or more of: polyvinylpyrrolidone, polyvinyl alcohol, polyvinyl chloride, polyvinyl acetate, hydroxypropyl methylcellulose, methylcellulose, polycaprolactone, polyethylene glycol, polymethyl methacrylate, sodium alginate and hydroxyethylcellulose.

In one embodiment of the present invention, in the method for high polymer induction, the high polymer is a mixture of polyvinylpyrrolidone, polyvinyl alcohol, polyvinyl chloride, polyvinyl acetate, hydroxypropyl methylcellulose and methylcellulose (e.g., at a mass ratio of 1:1:1:1:1), and the solvent may be selected from: MEK, ACN/toluene (e.g., at a ratio of 4:1, v/v), and THF/water (e.g., at a ratio of 9:1, v/v).

In another embodiment of the present invention, in the method for high polymer induction, the high polymer is a mixture of polycaprolactone, polyethylene glycol, polymethyl methacrylate, sodium alginate and hydroxyethylcellulose (e.g., at a mass ratio of 1:1:1:1:1), and the solvent may be selected from: EtOAc and acetone/2-MeTHF (e.g., at a ratio of 1:1, v/v).

Specifically, the preparation method for the crystalline form B of 4-(3-(((2-amino-S-(1-(1-trideuteromethylpiperidin-4-yl)-1H-pyrazol-4-yl)pyridin-3-yl)oxy)methyl)phenyl)-2-methylbut-3-yn-2-ol described above is the method for anti-solvent addition.

In one embodiment of the present invention, for the preparation of the crystalline form B described above, the good solvent is EtOAc, and the anti-solvent is toluene.

The present invention further provides a pharmaceutical composition comprising the compound of general formula I or the pharmaceutically acceptable salt, the stereoisomer, the ester, the prodrug and the solvate thereof described above, or the crystalline form described above, and a pharmaceutically acceptable excipient.

Specifically, the excipient described above is selected from one or more of: a carrier, a diluent, a binder, a lubricant, a wetting agent, and the like. Specifically, the pharmaceutical composition described above comprises a therapeutically effective amount of the compound of general formula I. In certain embodiments, these pharmaceutical compositions may be useful for treating HPK1 kinase-mediated diseases or conditions.

Specifically, the pharmaceutical composition described above may be a tablet (e.g., sugar coated tablet, film coated tablet, sublingual tablet, oral disintegrating tablet, buccal tablet, etc.), a pill, a powder, a granule, a capsule (e.g., soft capsule and microcapsule), a lozenge, a syrup, an emulsion, a suspension, a controlled release formulation (e.g., instantaneous release formulation, sustained release formulation, sustained release microcapsule), an aerosol, a film (e.g., oral disintegrating film, oral mucosa-adherent film), an injection (e.g., subcutaneous injection, intravenous injection, intramuscular injection, intraperitoneal injection), an intravenous drip infusion, a transdermal formulation, an ointment, a lotion, an adhesive formulation, a suppository (e.g., rectal suppository, vaginal suppository), a pellet, a nasal formulation, a pulmonary formulation (inhalant), an eye drop, etc.

Specifically, various dosage forms of the pharmaceutical composition described above can be prepared according to conventional production methods in the pharmaceutical field. For example, the active ingredient may be mixed with one or more excipients and then prepared into the desired dosage form.

Specifically, the pharmaceutical composition described above may comprise 0.1%-99.5% (such as, 0.1%, 1%, 5%, 10%, 20%, 30%, 40%, 50%, 60%, 70%, 80%, 90%, 95%, 99% or 99.5%) by weight of the active ingredient.

The present invention further provides use of the compound of general formula I, and the pharmaceutically acceptable salt, the stereoisomer, the ester, the prodrug and the solvate thereof described above, or the crystalline form described above, or the pharmaceutical composition described above in preparing a medicament for preventing and/or treating a tumor.

The present invention further provides use of the compound of general formula I, and the pharmaceutically acceptable salt, the stereoisomer, the ester, the prodrug and the solvate thereof described above, the crystalline form described above in combination with PD-1, PD-L1, CTLA-4, TIM-3, TGF-β and receptors thereof, LAG3 antagonists or TLR4, TLR7, TLR8, TLR9, and STING agonists in tumor immunotherapy.

The present invention further provides use of the compound of general formula I, and the pharmaceutically acceptable salt, the stereoisomer, the ester, the prodrug and the solvate thereof described above and the crystalline form described above in combination with CAR-T immunotherapy in tumor immunotherapy.

Specifically, the CAR-T immunotherapy described above refers to the chimeric antigen receptor T cell immunotherapy, whose basic principle is to eliminate cancer cells by utilizing immune cells in the patient himself, which belongs to a cell therapy.

Specifically, the tumor described above is a malignancy, including, but not limited to: lymphoma, blastoma, medulloblastoma, retinoblastoma, sarcoma, liposarcoma, synovial cell sarcoma, neuroendocrine tumor, carcinoid tumor, gastrinoma, islet cell carcinoma, mesothelioma, schwannoma, acoustic neuroma, meningioma, adenocarcinoma, melanoma, leukemia and lymphoid malignancy, squamous cell carcinoma, epithelial squamous cell carcinoma, lung carcinoma, small cell lung carcinoma, non-small cell lung carcinoma, adenocarcinoma lung carcinoma, squamous lung carcinoma, peritoneal carcinoma, hepatocellular carcinoma, gastric carcinoma, intestinal carcinoma, pancreatic carcinoma, glioblastoma, cervical carcinoma, ovarian carcinoma, bladder carcinoma, liver carcinoma, breast carcinoma, metastatic breast carcinoma, colon carcinoma, rectal carcinoma, colorectal carcinoma, uterine carcinoma, salivary gland carcinoma, kidney carcinoma, prostate carcinoma, vulval carcinoma, thyroid carcinoma, anal carcinoma, penile carcinoma, Merkel cell carcinoma, esophageal carcinoma, biliary tract carcinoma, head and neck carcinoma, and hematological malignancies.

The present invention further provides use of the compound of general formula I, and the pharmaceutically acceptable salt, the stereoisomer, the ester, the prodrug and the solvate thereof described above, or the crystalline form described above or the pharmaceutical composition described above in preparing a medicament for preventing and/or treating a disease caused by or associated with pathogen infection.

Specifically, the pathogen described above may be a microorganism, a parasite (protozoon, worm, or the like) or any other vector. Specifically, the microorganism described above may be selected from one or more of: viruses, chlamydias, rickettsiae, mycoplasmas, bacteria, spirochaetes, fungi, etc.

In one embodiment of the present invention, the pathogen described above is a virus, for example, but not limited to, Adenoviridae (e.g., adenovirus), Herpesviridae (e.g., HSV1 (herpes of mouth), HSV2 (herpes of external genitalia), VZV (chicken pox), EBV (Epstein-Barr virus), CMV (cytomegalovirus)), Poxviridae (e.g., smallpox virus, vaccinia virus), Papovavirus (e.g., human papilloma virus (HPV)), Parvoviridae (e.g., B19 virus), Hepadnaviridae (e.g., hepatitis B virus (HBV)), Polyomaviridae (e.g., polyomavirus), Reoviridae (e.g., reovirus, rotavirus), Picornaviridae (e.g., enterovirus, foot-and-mouth disease virus), Caliciviridae (e.g., Norwalk virus, hepatitis E virus), Togaviridae (e.g., rubella virus), Arenaviridae (e.g., lymphocytic choriomeningitis virus), Retroviridae (HIV), Flaviviridae (e.g., Dengue virus, Zika virus, encephalitis B virus, Chikungunya virus, yellow fever virus, hepatitis C virus (HCV), West Nile virus, etc.), Orthomyxoviridae (e.g., influenza virus (e.g., influenza A virus, influenza B virus, influenza C virus, etc.)), Paramyxoviridae (e.g., human parainfluenza virus type 1 (HPV), HPV type 2, HPV type 3, HPV type 4, Sendai virus, mumps virus, measles virus, respiratory syncytial virus, Newcastle disease virus, etc.), Bunyaviridae (e.g., California encephalitis virus, Hantavirus), Rhabdoviridae (e.g., rabies virus), Filoviridae (e.g., Ebola virus, Marburg virus), Coronaviridae (e.g., HCoV-229E, HCoV-OC43, HCoV-NL63, HCoV-HKU1, SARS-CoV, MERS-CoV, SARS-CoV-2, etc.), Astroviridae (e.g., astrovirus), and Bornaviridae (e.g., Borna virus).

Specifically, in the use described above, the virus is HBV, HIV, HCV, HPV, Ebola virus, Marburg virus, influenza virus, parainfluenza virus, Dengue virus, SARS-CoV, SARS-CoV-2, etc.

Specifically, the disease caused by or associated with pathogen infection described above includes, but is not limited to, influenza, SARS, COVID-19, viral hepatitis (e.g., hepatitis B, hepatitis C, etc.), AIDS, Dengue fever, Ebola virus disease, Marburg virus disease, etc.

The present invention further provides a method for preventing and/or treating a tumor, which comprises a step of administering to a subject in need thereof an effective amount of the compound of general formula I and the pharmaceutically acceptable salt, the stereoisomer, the ester, the prodrug and the solvate thereof described above, or the crystalline form described above, or the pharmaceutical composition described above in the present invention.

Specifically, the tumor has the corresponding definition described above in the present invention.

The present invention further provides a method for preventing and/or treating a disease caused by or associated with pathogen infection, which comprises a step of administering to a subject in need thereof an effective amount of the compound of general formula I and the pharmaceutically acceptable salt, the stereoisomer, the ester, the prodrug and the solvate thereof described above, or the crystalline form thereof described above, or the pharmaceutical composition described above in the present invention.

Specifically, the pathogen and the disease have the corresponding definitions described above in the present invention.

DETAILED DESCRIPTION OF THE INVENTION

Figure 1:
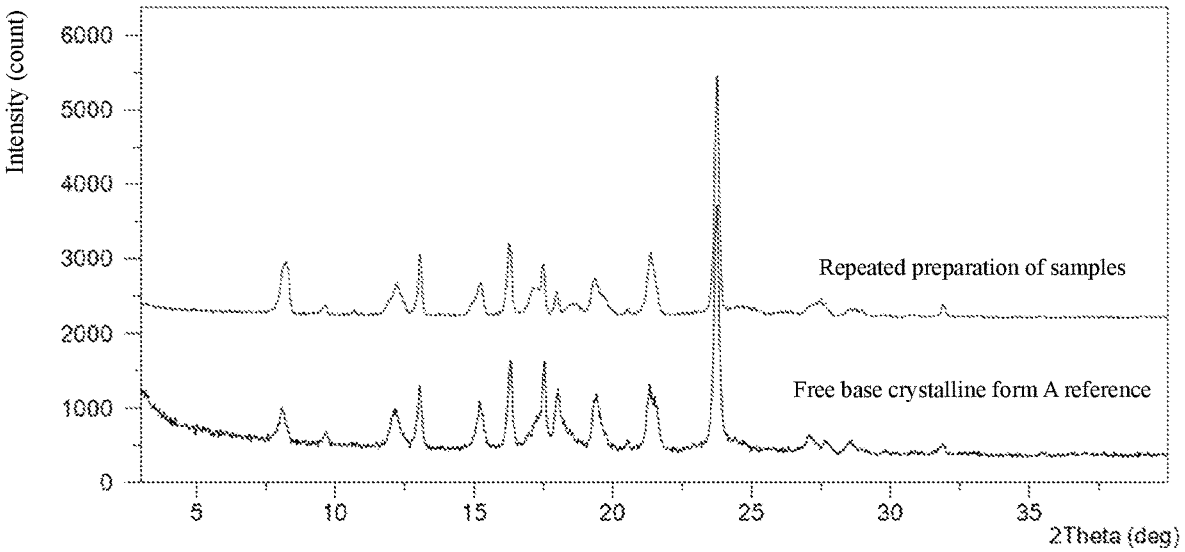
FIG. 1 shows the XRPD pattern of free base crystalline form A of compound A2.

Unless otherwise defined, all scientific and technical terms used herein have the same meaning as commonly understood by those skilled in the art to which the present invention relates.

For the term "$C_{0-10}$ alkyl" described herein, $C_0$ alkyl refers to H, and thus $C_{0-10}$ alkyl comprises H, $C_1$ alkyl, $C_2$ alkyl, $C_3$ alkyl, $C_4$ alkyl, $C_5$ alkyl, $C_6$ alkyl, $C_7$ alkyl, $C_8$ alkyl, $C_9$ alkyl and $C_{10}$ alkyl.

The term "$C_{1-10}$ linear/branched alkyl" described herein comprises methyl, ethyl, $C_3$ linear/branched alkyl, $C_4$ linear/branched alkyl, $C_5$ linear/branched alkyl, $C_6$ linear/branched alkyl, $C_7$ linear/branched alkyl, $C_8$ linear/branched alkyl, $C_9$ linear/branched alkyl and $C_{10}$ linear/branched alkyl.

The term "$C_{3-10}$ branched alkyl" described herein comprises isopropyl, isobutyl, tert-butyl and isoamyl.

The term "$C_{3-10}$ cycloalkyl" described herein comprises $C_3$ cycloalkyl, $C_4$ cycloalkyl, $C_5$ cycloalkyl, $C_6$ cycloalkyl, $C_7$ cycloalkyl, $C_8$ cycloalkyl, $C_9$ cycloalkyl and $C_{10}$ cycloalkyl.

The term "$C_{3-8}$ cycloalkyl" described herein comprises $C_3$ cycloalkyl, $C_4$ cycloalkyl, $C_5$ cycloalkyl, $C_6$ cycloalkyl, $C_7$ cycloalkyl and $C_8$ cycloalkyl.

The term "$C_{4-8}$ cycloalkyl" described herein comprises $C_4$ cycloalkyl, $C_5$ cycloalkyl, $C_6$ cycloalkyl, $C_7$ cycloalkyl and $C_8$ cycloalkyl.

The term "$C_{4-6}$ cycloalkyl" described herein comprises $C_4$ cycloalkyl, $C_5$ cycloalkyl and $C_6$ cycloalkyl.

The term "halogen" described herein comprises fluorine, chlorine, bromine and iodine.

The term "heterocycloalkyl" described herein refers to a non-aromatic saturated monocyclic or polycyclic ring system containing 3 to 10 ring atoms, preferably 5 to 10 ring atoms, wherein one or more ring atoms are not carbon atoms, but are, for example, nitrogen, oxygen or sulfur atoms. Preferred heterocycloalkyl contains 5 to 6 ring atoms. The prefix aza, oxa or thia before heterocycloalkyl means that there is at least one nitrogen, oxygen or sulfur atom as a ring atom.

The term "heterocycloaryl" described herein refers to an aromatic monocyclic or polycyclic ring system containing 5 to 14 ring atoms, preferably 5 to 10 ring atoms, wherein one or more ring atoms are not carbon atoms, but are, for example, nitrogen, oxygen or sulfur atoms. Preferred heterocycloaryl contains 5 to 6 ring atoms. Representative heterocycloaryl includes pyrazinyl, furyl, thienyl, pyridinyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, 2,3-naphthyridinyl, imidazo [1,2-a]pyridine, imidazo[2,1-b]thiazolyl, benzofurazanyl, indolyl, azaindolyl, benzimidazolyl, benzothienyl, quinolyl, imidazolyl, thienopyridinyl, quinazolinyl, thienopyrimidinyl, pyrrolopyridinyl, imidazopyridinyl, isoquinolyl, benzoazaindolyl, 1,2,4-triazinyl, benzothiazolyl, and the like.

In the present invention, "D" represents deuterium; "deuterated" means that one or more hydrogen atoms are substituted with the corresponding number of deuterium atoms.

It should be appreciated that there are some variations in the abundance of natural isotopes in the synthesized compounds, depending on the sources of the chemical materials used in the synthesis. Therefore, the compound of the present invention will inherently contain a small amount of deuterated isotopologues. Despite this variation, the concentration of such naturally abundant stable hydrogen and carbon isotopes is very low and inconsequential compared to the degree to which the compound of the present invention is substituted with stable isotopes. See, e.g., Wada, E et. al., Seikagaku, 1994, 66: 15; and Gannes, L Z et. al., Comp Biochem Physiol Mol Integr Physiol, 1998, 119: 725.

In the compound of the present invention, any atom not designated as deuterium is present at its natural isotopic abundance level. Unless otherwise stated, when "H" or "hydrogen" is specifically designated to a position, that position should be construed as having hydrogen composed of isotopes according to their natural abundance levels. Likewise, unless otherwise stated, when "D" or "deuterium" is specifically designated to a position, that position should be construed as having deuterium at an abundance level that is higher than the natural abundance level of deuterium (0.015%) by at least 3000 times (that is, at least 45% deuterium is incorporated).

The term "isotopic enrichment factor" as used herein refers to a ratio between the isotopic abundance and the natural abundance of a particular isotope.

In other embodiments, the isotopic enrichment factor for each designated deuterium atom in the compound of the present invention is at least 3500 (52.5% deuterium is incorporated at each designated deuterium atom), at least 4000 (60% deuterium incorporated), at least 4500 (67.5% deuterium incorporated), at least 5000 (75% deuterium incorporated), at least 5500 (82.5% deuterium incorporated), at least 6000 (90% deuterium incorporated), at least 6333.3 (95% deuterium incorporated), at least 6466.7 (97% deuterium incorporated), at least 6600 (99% deuterium incorporated), or at least 6633.3 (99.5% deuterium incorporated).

The term "isotopologue" refers to a substance of which the chemical structure differs from that of a particular compound of the present invention only in isotopic composition.

The term "compound", when referring to a compound of the present invention, refers to a collection of molecules having the same chemical structure except that there may be isotopic variations among the constituent atoms of the molecules. It is therefore clear to those skilled in the art that the compounds represented by specific chemical structures containing the indicated deuterium atoms also contain a small amount of isotopologues having hydrogen atoms at one or more of the indicated deuterium positions of the structure. The relative amount of such isotopologues in the compound of the present invention will depend on a variety of factors, including the isotopic purity of the deuteration reagent used to prepare the compound and the efficiency of deuterium incorporation during every synthetic step used to prepare the compound. However, as described above, the overall relative amount of such isotopologues will be less than 49.9% of the compound. In other embodiments, the overall relative amount of such isotopologues will be less than 47.5%, less than 40%, less than 32.5%, less than 25%, less than 17.5%, less than 10%, less than 5%, less than 3%, less than 1%, or less than 0.5% of the compound.

Some of the abbreviations used in the present invention are explained as follows:

XRPD: X-ray powder diffraction

DSC: differential scanning calorimetry

TGA: thermogravimetric analysis $^1$H NMR: liquid nuclear magnetic hydrogen spectrum In the present invention, the term "crystalline form" is confirmed by X-ray powder diffraction pattern characterization. Those skilled in the art can appreciate that the physicochemical properties discussed herein can be characterized with experimental error depending on the conditions of the instrument, sample preparation, purity of the sample, etc. In particular, it is well known to those skilled in the art that the X-ray diffraction pattern will generally vary with the conditions of the instrument. It is particularly noted that the relative intensities of the X-ray powder diffraction patterns may also vary with the experimental conditions, so that the order of the peak intensities cannot be the only or decisive factor. Indeed, the relative intensities of the diffraction peaks in the XRPD pattern are related to the preferred orientation of the crystals, and the peak intensities shown herein are illustrative and not for absolute comparison. In addition, experimental errors in peak angles are typically 5% or less, and these angles should also be taken into account, typically allowing errors of ±0.2°. In addition, due to the influence of experimental factors such as sample thickness, an overall shift in peak angle is caused, and a certain shift is usually allowed. Thus, it can be understood by those skilled in the art that the X-ray powder diffraction pattern of a crystalline form of the present invention is not required to be identical to that of the examples referred to herein, that the "XRPD patterns are identical" described herein does not mean absolutely identical, and that the identical peak positions may differ by ±0.2° and a certain variability in peak intensities is permitted. Any crystalline form having the same or similar pattern as the characteristic peaks in these patterns falls within the scope of the present invention. Those skilled in the art can compare the patterns listed in the present invention with a pattern of an unknown crystalline form to confirm whether the two sets of patterns reflect the same or different crystalline forms.

In some embodiments, the crystalline form A of the present invention is pure, single, and substantially free of any other crystalline forms in admixture. In the present invention, "substantially free", when used in reference to a novel crystalline form, means that the crystalline form contains less than 20% by weight of other crystalline forms, in particular less than 10% by weight of other crystalline forms, more particularly less than 5% by weight of other crystalline forms, and even more particularly less than 1% by weight of other crystalline forms.

It needs to be understood that the numerical values and ranges of numerical values set forth herein should not be construed narrowly as to the numerical values or ranges themselves and that those skilled in the art should recognize that the numerical values and ranges of numerical values may be varied around specific numerical values in different technical environments without departing from the spirit and principle of the present invention. In the present invention, the floating range, which can be foreseen by those skilled in the art, is mostly expressed by the term "about". When the term "about" is used in front of a numerical value of the present invention and refers to the numerical value, it means any value within a range of ±10%, preferably within a range of ±5%, more preferably within a range of ±2%, most preferably within a range of ±1%, of the value. For example, "about 10" should be interpreted to mean 9 to 11, preferably 9.5 to 10.5, more preferably 9.8 to 10.2, and more preferably 9.9 to 10.1.

In the present invention, the term "room temperature" means that the temperature of an article is close to or the same as the temperature of a space (e.g., the location of a fume hood in which the article is located). Typically, room temperature is from about 20° C. to about 30° C., or from about 22° C. to 27° C., or about 25° C.

The anti-solvent addition (also called anti-solvent crystallization, precipitation crystallization, salting out, or forcing crystallization) is generally a method comprising precipitating crystals after bringing a solution into a supersaturated state by adding one or more anti-solvents to the solution in which a target product is dissolved with a good solvent, the product being in a slightly soluble state in the solution. The anti-anti-solvent addition is generally a method comprising precipitating crystals after bringing a solution into a supersaturated state by adding one or more anti-solvents to the solution in which a target product is dissolved with a good solvent, the product being in a slightly soluble state in the solution.

The capability of an anti-solvent for dissolving a target product is poorer than that of a good solvent, e.g., by more than 10%, 20%, 30%, 40%, 50%, 60%, 70% or 80%, therefore the anti-solvent in a system is a relative term. The good solvent and the anti-solvent may be polar or non-polar solvents, for example, may be selected from one or more of: dimethylformamide (DMF), dimethyl sulfoxide (DMSO), water, alcoholic solvents, ether solvents, ketone solvents, ester solvents, alkane solvents, aromatic solvents and nitrile solvents, wherein the alcoholic solvents include, but are not limited to, methanol, ethanol, propanol, isopropanol or 1,3-propanediol, 1,2-propanediol or chlorobutanol or a combination thereof; ether solvents include, but are not limited to, such as tetrahydrofuran, methyl tert-butyl ether or 1,4-dioxane or a combination thereof; ketone solvents include, but are not limited to, acetone, methyl ethyl ketone or 4-methyl-2-pentanone or a combination thereof; ester solvents include, but are not limited to, ethyl acetate, isopropyl acetate, n-butyl acetate or tert-butyl acetate or a combination thereof; alkane solvents include, but are not limited to, dichloromethane, chloroform, n-hexane, cyclohexane or pentane or n-heptane or a combination thereof; aromatic solvents include, but are not limited to, benzene and toluene or a combination thereof; and nitrile solvents include, but are not limited to, acetonitrile and malononitrile.

The anti-solvent addition and anti-anti-solvent addition may be performed by batch, semi-batch or continuous crystallization operations. The addition of an anti-solvent to a solution (anti-solvent crystallization) or the addition of a product solution to an anti-solvent (anti-anti-solvent crystallization) may either be dropwise addition at a constant rate or be dropwise addition slowly at the beginning and then gradually increasing in rate.

The disclosures of the various publications, patents, and published patent specifications cited herein are hereby incorporated by reference in their entirety.

The technical schemes of the present invention will be clearly and completely described below with reference to the examples of the present invention, and it is obvious that the described examples are only a part of the examples of the present invention but not all of them. Based on the examples of the present invention, all other examples obtained by those of ordinary skill in the art without creative work shall fall within the protection scope of the present invention.

Example 1: Synthesis of Compound A2

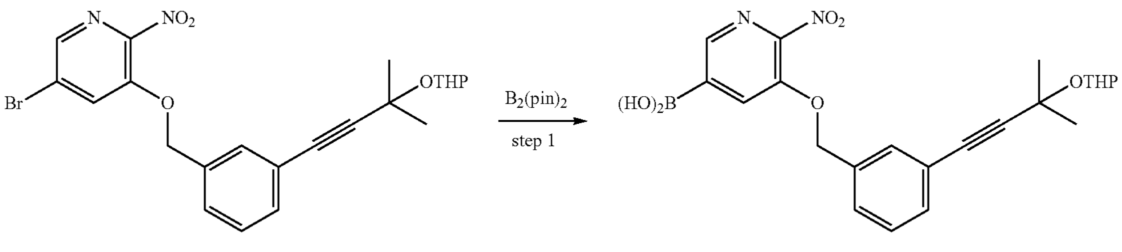

1 2

-continued
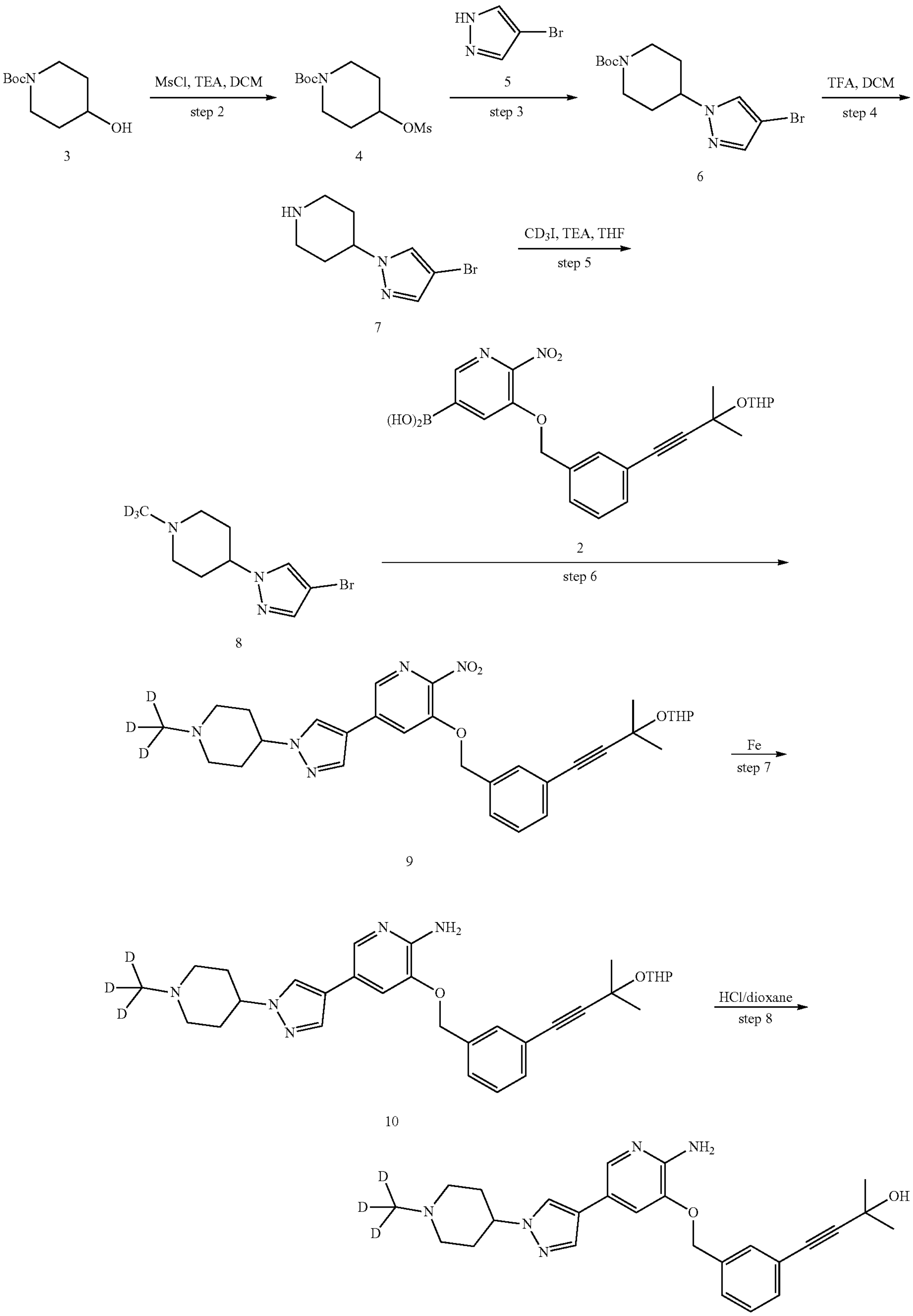

The experimental procedures were as follows:

Step 1:

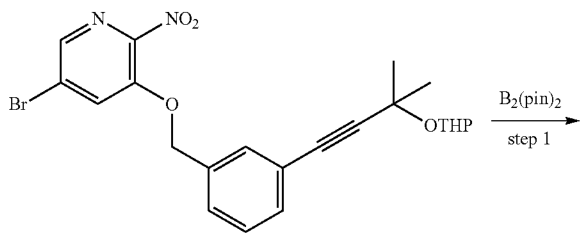

1

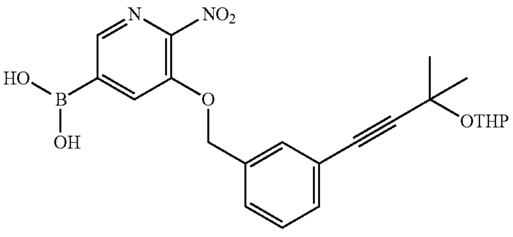

2

To a 500 mL single-necked flask were added 1 (11.3 g, 23.7 mmol), bis(pinacolato)diboron (9.06 g, 35.6 mmol), bis(diphenylphosphino)ferrocene palladium dichloride (1.74 g, 2.37 mmol), potassium acetate (6.99 g, 71.3 mmol) and dimethyl sulfoxide (150 mL), and the mixture was reacted at 95° C. for 16 h under nitrogen atmosphere, quenched with water (300 mL), and extracted with ethyl acetate (150 mL×3). The extract was washed with saturated brine (150 mL×2) and subjected to rotary evaporation to give the target product as a black solid (13.0 g, crude). LC-MS: 463 $[M+Na]^+$.

Step 2:

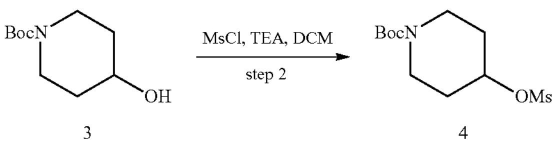 [SMILES: CC(C)(C)OC(=O)N1CCC(O)CC1 ; CC(C)(C)OC(=O)N1CCC(OS(C)(=O)=O)CC1]

3 4

To a 500 mL three-necked flask were added 3 (15 g, 74.6 mmol), triethylamine (22.7 g, 223.8 mmol) and dichloromethane (150 mL), and the mixture was added with methanesulfonyl chloride (12.1 g, 111.9 mmol) in an ice bath and reacted in the ice bath for 1 h, quenched with water (300 mL) and extracted with dichloromethane (100 mL×3). The extract was washed with saturated brine, dried over anhydrous sodium sulfate and subjected to rotary evaporation, and the residue was purified by column chromatography (petroleum ether:ethyl acetate=40:1) to give the target product as a yellow solid (20.7 g, crude). LC-MS: 280 $[M+H]^+$.

Step 3:

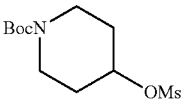

4

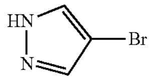

5

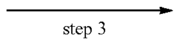

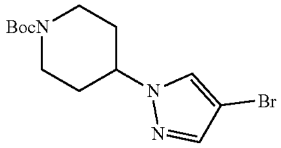

6

To a 500 mL single-necked flask were added 5 (7.27 g, 49.4 mmol) and DMF (200 mL), 60% NaH (2.96 g, 74.1 mmol) was added portionwise at 0° C., and the mixture was reacted at room temperature for 1 h, followed by addition of 4 (20.7 g, 74.1 mmol), and reacted at 70° C. for 16 h under nitrogen atmosphere, quenched with water (500 mL), and extracted with ethyl acetate (200 mL×3). The organic phase was washed with saturated brine (200 mL×2), dried over anhydrous sodium sulfate, and subjected to rotary evaporation, and the residue was separated by column chromatography (petroleum ether:ethyl acetate=30:1) to give the target product as a white solid (9.8 g, yield: 61.2%). LC-MS: 330 $[M+H]^+$.

Step 4:

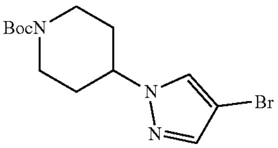

6

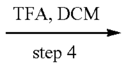

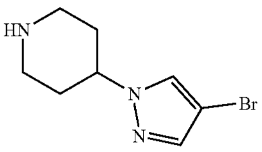

7

In a 500 mL single-necked flask, 6 (9.8 g, 35.8 mmol) was dissolved in DCM (80 mL), TFA (16 mL) was added dropwise at 0° C., and the mixture was reacted at room temperature for 16 h, concentrated at a low temperature, diluted with DCM (200 mL), quenched with ice water, adjusted to pH=10 with aqueous ammonia at 0° C., and extracted with DCM (200 mL×3). The organic phase was washed with saturated brine (200 mL×2), dried over anhydrous sodium sulfate and subjected to rotary evaporation to give the target product as a white solid (6.59 g, yield: 96.6%). LC-MS: 230 $[M+H]^+$.

Step 5:

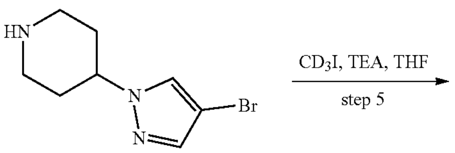

7

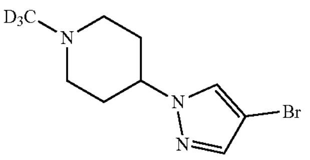

8

In a 250 mL three-necked flask, 7 (5.53 g, 24.0 mmol) and TEA (10 mL, 72.1 mmol) were dissolved in THE (80 mL), and the mixture was reacted at room temperature for 1 h, cooled to 0° C. in an ice bath, added dropwise with $CD_3I$ (1.65 mL, 26.4 mmol), reacted at room temperature for 2 h under nitrogen atmosphere, quenched with water, and extracted with DCM (100 mL×3). The organic phase was washed with saturated brine (100 mL×2), dried over anhydrous sodium sulfate and subjected to rotary evaporation to give the target product as a yellow oil (3.1 g, yield: 52.2%). LC-MS: 248 $[M+H]^+$.

Step 6:

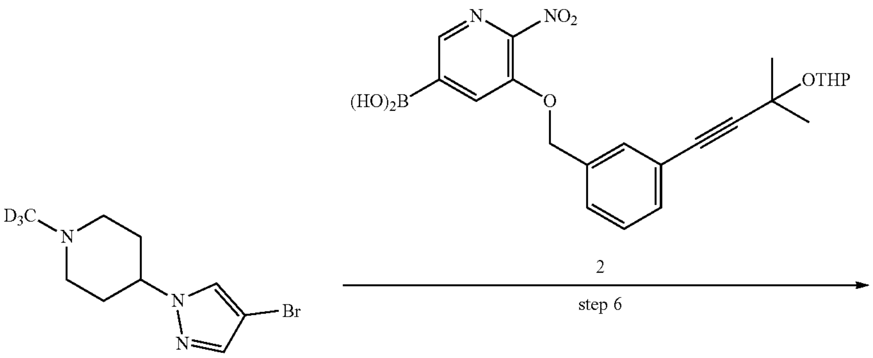

8

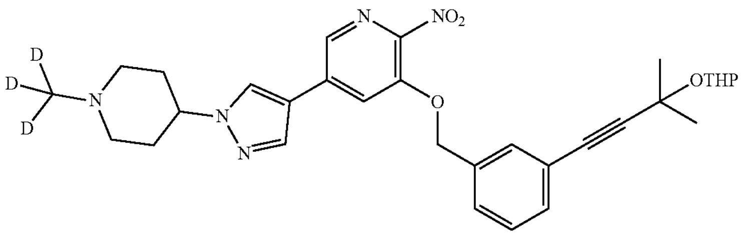

9

To a 500 mL single-necked flask were added 2 (7.13 g, 16.2 mmol), 8 (2.67 g, 10.8 mmol), xphosPdGII (850 mg, 1.08 mmol), XPhos (515 mg, 1.08 mmol), potassium phosphate (4.58 g, 21.6 mmol) and DMF/$H_2O$ (150 mL/30 mL), and the mixture was reacted at 95° C. for 2.5 h under nitrogen atmosphere, quenched with water (300 mL), and extracted with ethyl acetate (150 mL×3). The organic phase was washed with saturated brine (150 mL×2), dried over anhydrous sodium sulfate and subjected to rotary evaporation, and the residue was purified by flash chromatography to give the target product as a black oil (3.3 g, crude). LC-MS: 563 $[M+H]^+$.

Step 7:

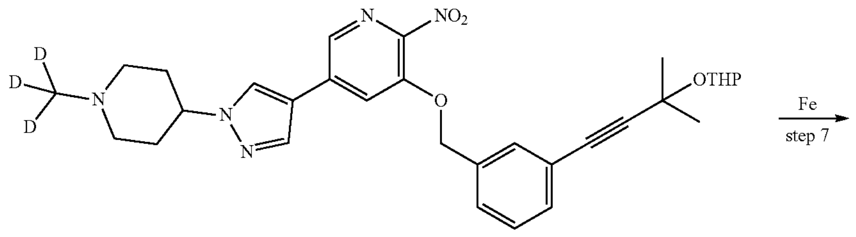

9

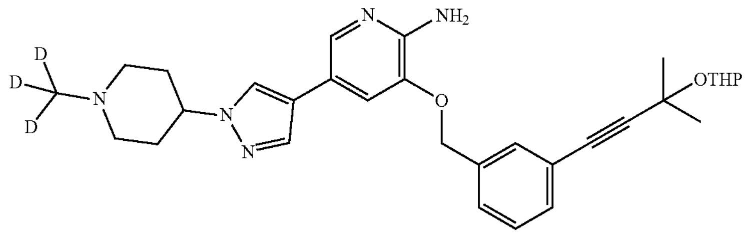

10

To a 250 mL three-necked flask were added 9 (3.3 g, 7.14 mmol), Fe (2.0 g, 35.7 mmol), ammonium chloride (1.9 g, 35.7 mmol), ethanol (40 mL) and water (8 mL), and the mixture was reacted at 85° C. for 2.5 h, and filtered under vacuum, and the filtrate was concentrated to give the target product as a black solid (3.5 g, crude). LC-MS: 533 $[M+H]^+$.

Step 8:

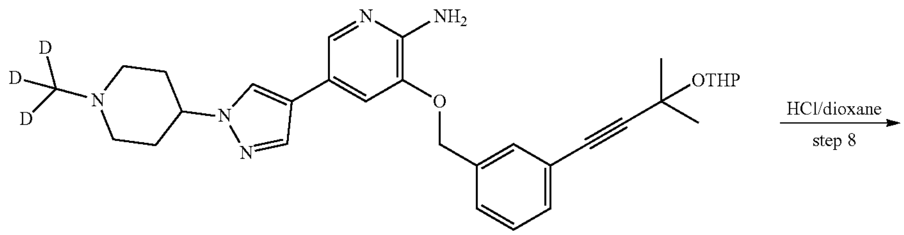

10

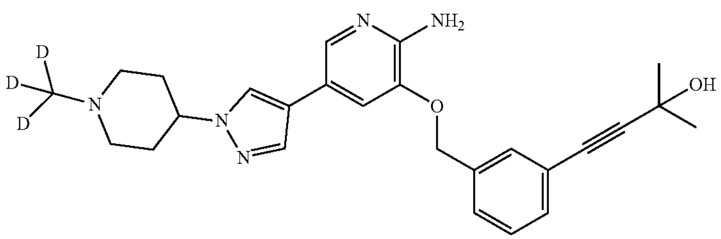

In a 250 mL three-necked flask, 10 (3.5 g, 6.55 mmol) was dissolved in tetrahydrofuran (40 mL), HCl/Dioxane (8 mL) was added dropwise at 0° C., and the mixture was reacted at room temperature for 1 h, concentrated at a low temperature, diluted with DCM (100 mL), quenched with ice water, adjusted to pH=10 with aqueous ammonia at 0° C., and extracted with DCM (100 mL×3). The organic phase was washed with saturated brine (100 mL×2), dried over anhydrous sodium sulfate and subjected to rotary evaporation, and the residue was purified by Prep-HPLC to give the target product as a white solid (450 mg, yield: 15.3%). LC-MS: 449 $[M+H]^+$, 1H NMR (400 MHz, MeOD) δ 8.38 (s, 1H), 8.01 (s, 1H), 7.81 (s, 1H), 7.73 (d, J=1.5 Hz, 1H), 7.54 (s, 1H), 7.48 (td, J=4.7, 1.7 Hz, 1H), 7.38 (s, 2H), 5.21 (s, 2H), 4.51 (t, J=6.9 Hz, 1H), 3.59 (d, J=12.6 Hz, 2H), 3.19 (s, 2H), 2.37-2.32 (m, 4H), 1.56 (s, 6H).

Example 2: Synthesis of Compound B2
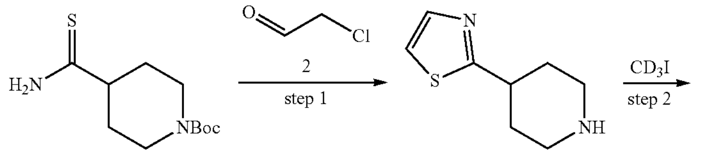
1 3
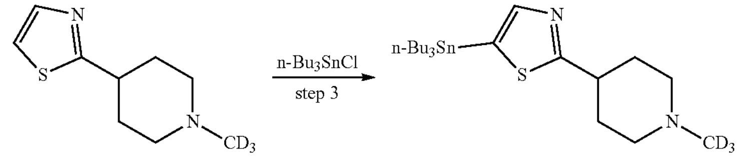
4 5
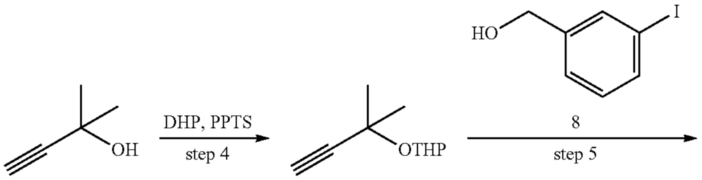
6 7
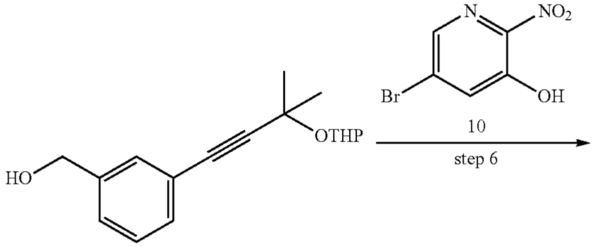
9
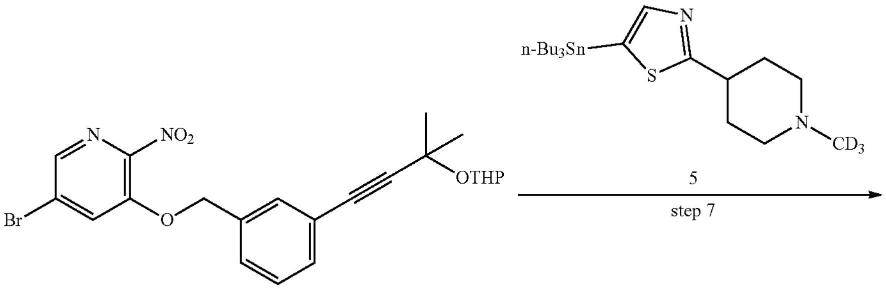
11
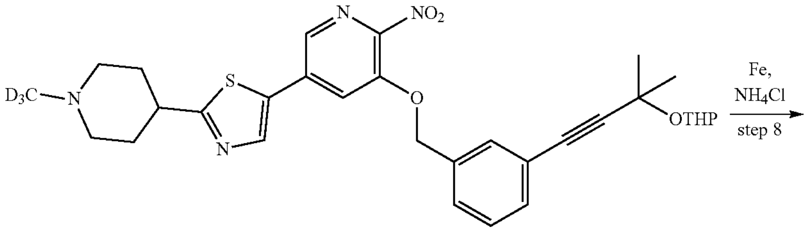
12

-continued

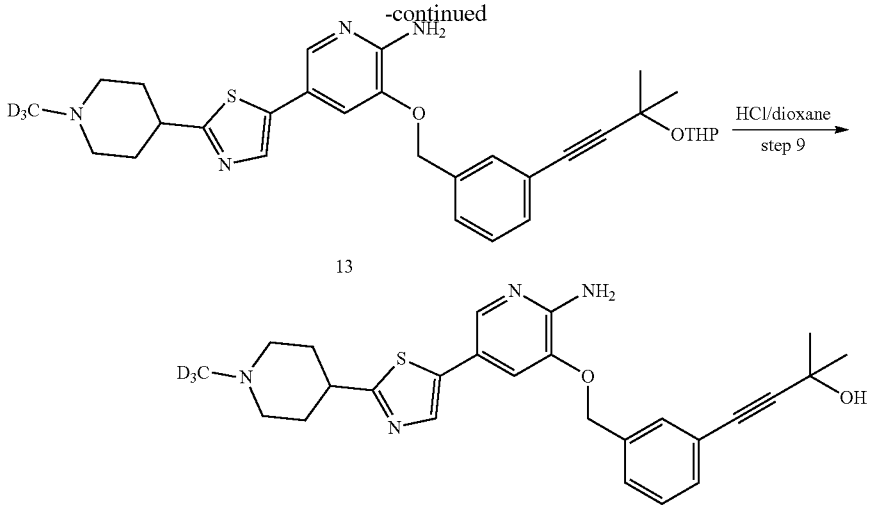

13

The experimental procedures were as follows:

Step 1:

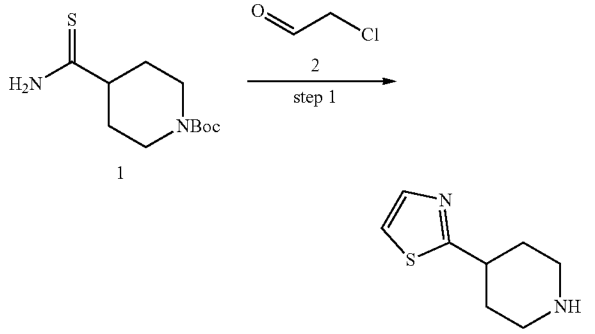

1

3

To a 2000 mL single-necked flask were added 1 (25.0 g, 102 mmol), an aqueous solution of chloroacetaldehyde (12.0 g, 154 mmol), and acetone (500 mL), and the mixture was reacted at 50° C. for 16 h, and subjected to rotary evaporation, and the residue was separated by column chromatography (MeOH in DCM, from 0% to 10%, v/v) to give the target product as a yellow oil (9.20 g, yield: 53.4%). LC-MS: 169 $[M+H]^+$.

Step 2:

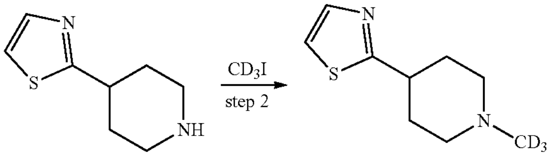

3 4

To a 1000 mL single-necked flask were added 3 (4.00 g, 23.8 mmol), triethylamine (6.01 g, 59.5 mmol) and tetrahydrofuran (200 mL), deuterated iodomethane (3.62 g, 25.0 mmol) was added at room temperature, and the mixture was stirred at room temperature for 2 h, quenched with water (250 mL) and subjected to rotary evaporation, and extracted with ethyl acetate (150 mL×3). The organic phase was dried over anhydrous sodium sulfate and subjected to rotary evaporation, and the residue was separated by column chromatography (MeOH in DCM, from 0% to 10%, v/v) to give the target product as a yellow solid (2.70 g, yield: 61.3%). LC-MS: 186 $[M+H]^+$.

Step 3:

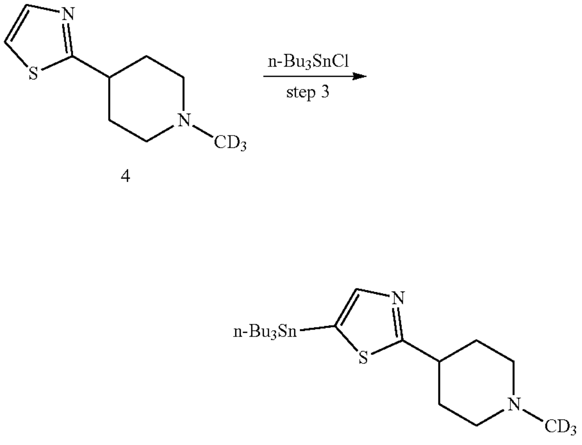

4

5

To a 500 mL three-necked flask were added 4 (2.70 g, 14.6 mmol) and tetrahydrofuran (100 mL), n-butyllithium (2.4 M in tetrahydrofuran, 7.30 mL, 17.5 mmol) was added dropwise at −78° C. under nitrogen atmosphere, and the mixture was stirred for 1 h while maintaining the temperature, added dropwise with tri-n-butylstannous chloride (7.14 g, 21.9 mmol), and then reacted at −78° C. for 1 h. After the reaction was completed, the reaction solution was quenched with saturated aqueous ammonium chloride (100 mL), and extracted with ethyl acetate (120 mL×3). The organic layer was washed with saturated brine, dried over anhydrous sodium sulfate, filtered under vacuum, and concentrated under reduced pressure to give the target product as a yellow oil (7.05 g, crude), which could be directly used in the next step. LC-MS: 476 $[M+H]^+$.

Step 4:

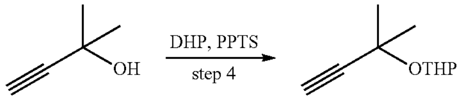

6 7

To a 3 L single-necked flask were added 6 (59.4 g, 707 mmol) and tetrahydrofuran (1.5 L) DHP (68.4 g, 813 mmol) and PPTS (3.55 g, 14.1 mmol) were added separately, and the mixture was reacted at room temperature for 16 h, quenched and washed with saturated sodium bicarbonate (1000 mL×3), washed with saturated brine (500 mL), dried over anhydrous sodium sulfate, and subjected to rotary evaporation to give the target product as a colorless oil (120 g, crude), which could be directly used in the next step. LC-MS: 169 $[M+H]^+$.

Step 5:

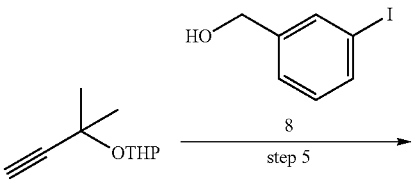

7

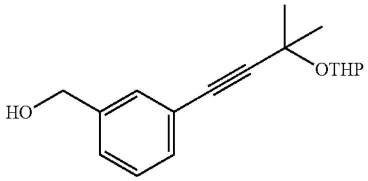

9

To a 3 L single-necked flask were added 7 (35.8 g, 213.15 mmol), 8 (47.5 g, 203.00 mmol), trans-dichlorobis(triphenyl-phosphine)palladium(II) (1.43 g, 2.03 mmol), cuprous iodide (1.93 g, 10.16 mmol), triethylamine (40.01 g, 406.00 mmol) and anhydrous dichloromethane (1 L), and the mixture was reacted at room temperature for 16 h under nitrogen atmosphere, washed with saturated ammonium chloride (1000 mL×3) and saturated brine (500 mL), dried over anhydrous sodium sulfate, and subjected to rotary evaporation to give the target compound as a yellow oil (59.4 g, crude), which could be directly used in the next step. LC-MS: 275 $[M+H]^+$.

Step 6:

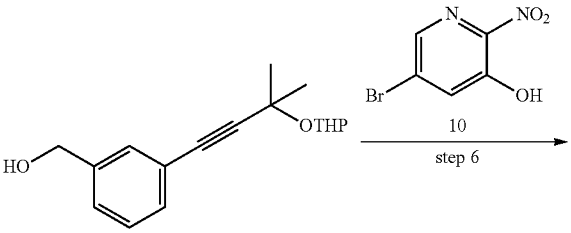

9

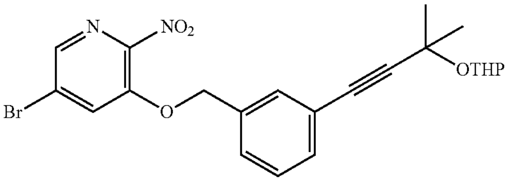

11

To a 2000 mL three-necked flask were added 9 (50.3 g, 184 mmol), tetrahydrofuran (500 mL), 10 (40.1 g, 184 mmol) and triphenylphosphine (72.3 g, 276 mmol), diethyl azodicarboxylate (55.8 g, 276 mmol) was added under nitrogen atmosphere while stirring at room temperature, and the mixture was reacted at room temperature for 16 h and subjected to rotary evaporation, and the residue was subjected to column chromatography (petroleum ether:ethyl acetate=10:1) to give the target product as a yellow solid (70.2 g, yield: 80.6%). LC-MS: 476 $[M+H]^+$.

Step 7:

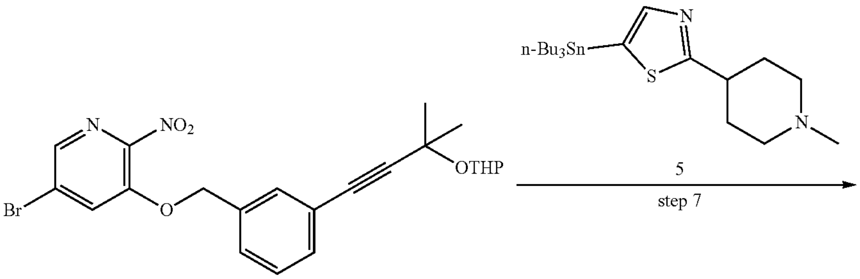

11

-continued

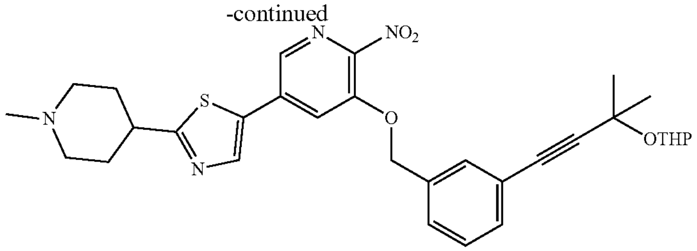

12

To a 1000 mL single-necked flask were added 11 (5.05 g, 10.7 mmol), 5 (9.15 g, 19.3 mmol), trans-dichlorobis(triphenyl-phosphine)palladium(II) (376 mg, 0.535 mmol), cuprous iodide (305 mg, 1.61 mmol) and 1,4-dioxane (200 mL), and the mixture was stirred at 90° C. for 5 h under nitrogen atmosphere, diluted with ethyl acetate (400 mL), washed with saturated aqueous ammonium chloride (300 mL×3), and subjected to rotary evaporation. The residue was separated by column chromatography (MeOH in DCM, from 0% to 5%, v/v) to give the target product as a yellow solid (2.50 g, yield: 40.5%); LC-MS: 580 $[M+H]^+$.

Step 8:

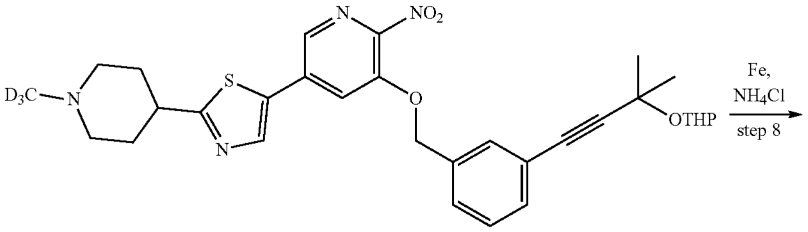

12

13

To a 500 mL single-necked flask were added 12 (2.50 g, 4.32 mmol), reduced iron powder (1.21 g, 21.6 mmol), ammonium chloride (1.14 g, 21.6 mmol), ethanol (100 mL) and water (20 mL), and the mixture was reacted at 80° C. for 2 h, diluted with dichloromethane (100 mL), filtered under vacuum, and subjected to rotary evaporation, and the residue was separated by column chromatography (MeOH in DCM, from 0% to 12%, v/v) to give the target product as a yellow solid (1.40 mg, 59.1%). LC-MS: 550 $[M+H]^+$.

Step 9:

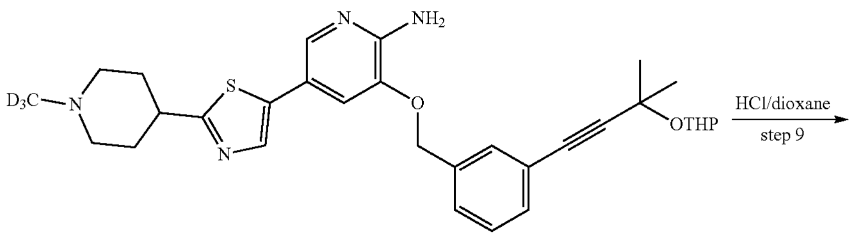

13

-continued

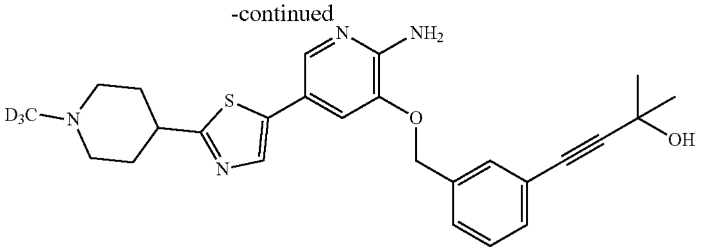

To a 250 mL single-necked flask were added 13 (1.02 g, 1.86 mmol) and tetrahydrofuran (25 mL), and the mixture was stirred in an ice bath, then added dropwise with 4 M/L solution of hydrogen chloride (5 mL) in 1,4-dioxane, reacted at room temperature for 20 min, subjected to rotary evaporation, dissolved in dichloromethane, adjusted to pH=9 with ammonia water, and subjected to rotary evaporation with dichloromethane (30 mL×3). The residue was subjected to preparative high performance liquid chromatography to give the target product as a pale yellow solid (350 mg, 40.5%).

LC-MS: 466 $[M+H]^+$, $^1H$ NMR (400 MHz, DMSO) δ 7.88 (s, 1H), 7.77 (d, J=1.8 Hz, 1H), 7.54 (d, J=5.4 Hz, 2H), 7.42-7.37 (m, 1H), 7.34 (dd, J=5.4, 1.6 Hz, 2H), 6.10 (s, 2H), 5.50 (s, 1H), 5.22 (s, 2H), 2.96-2.78 (m, 3H), 2.02 (dd, J=16.9, 6.7 Hz, 4H), 1.72 (qd, J=12.5, 3.6 Hz, 2H), 1.47 (s, 6H).

Example 3: Synthesis of Compound C

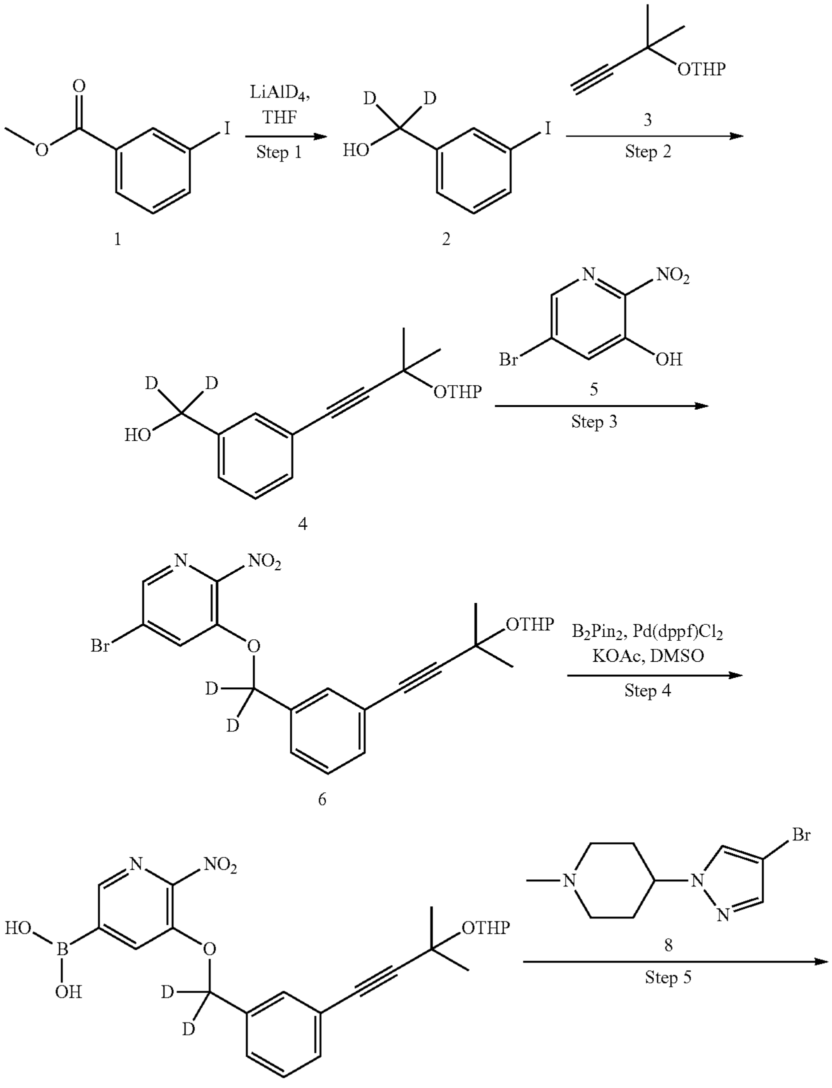

7

-continued

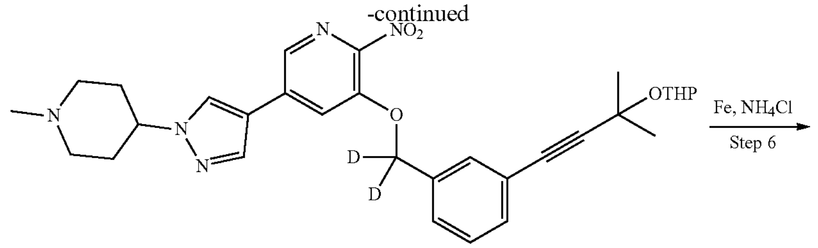

9

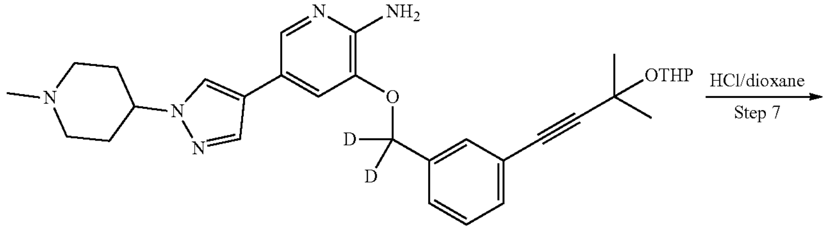

10

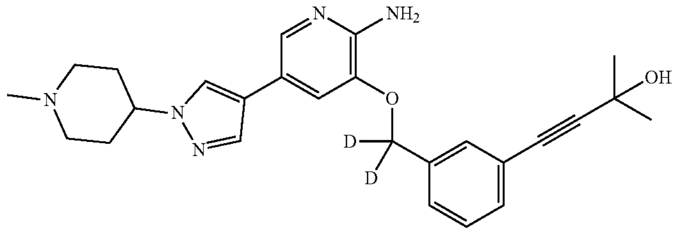

The experimental procedures were as follows:

Step 1:

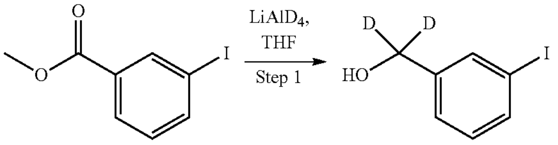

1 2

To a 2000 mL single-necked flask were added 1 (7.86 g, 30.0 mmol) and tetrahydrofuran (500 mL), deuterated lithium aluminum hydride (3.15 g, 75.0 mmol) was added portionwise at 0° C., and the mixture was reacted at 0° C. for 1 h, quenched with acetic acid (50 mL) and extracted with ethyl acetate (500 mL×3). The organic phase was washed with saturated brine (500 mL×3) and subjected to rotary evaporation to give the target product as a yellow solid (3.50 g, crude). LC-MS: 259 $[M+Na]^+$.

Step 2:

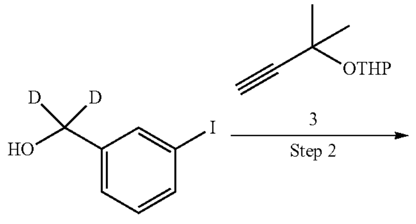

2

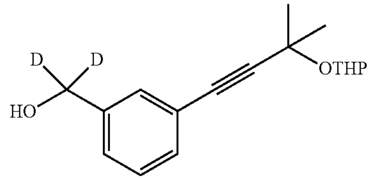

4

To a 250 mL three-necked round bottom flask were added 3 (3.50 g, 14.8 mmol), trans-dichlorobis(triphenyl-phosphine)palladium(II) (519 mg, 0.740 mmol), cuprous iodide (281 mg, 1.48 mmol), triethylamine (4.48 g, 44.4 mmol) and dichloromethane (60 mL), 3 (2.50 g, 14.8 mmol) was added at room temperature under nitrogen atmosphere, and the mixture was reacted at room temperature for 16 h, diluted with dichloromethane (400 mL), washed with saturated aqueous ammonium chloride solution (300 mL×3), and subjected to rotary evaporation. The residue was subjected to column chromatography (petroleum ether:ethyl acetate=4:1) to give the target product as a yellow solid (1.03 g, yield: 25.2%). LC-MS: 299 [M+Na]+.

Step 3:

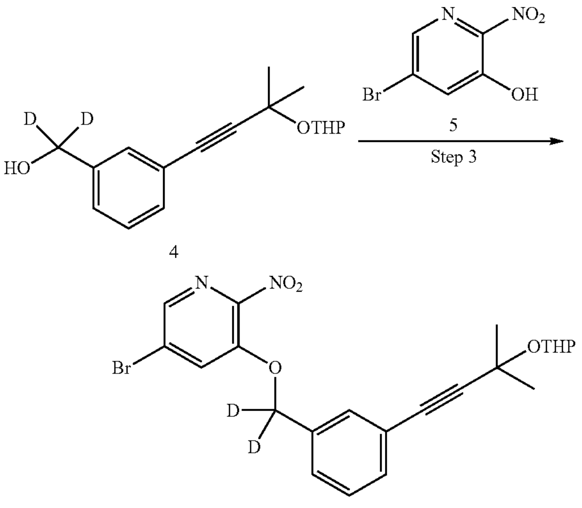

4

6

To a 250 mL three-necked flask were added 4 (1.03 g, 3.73 mmol), tetrahydrofuran (30 mL), 5 (854 mg, 3.92 mmol) and triphenylphosphine (1.47 g, 5.60 mmol), diisopropyl azodicarboxylate (1.13 g, 5.60 mmol) was added dropwise at 0° C. under nitrogen atmosphere, and the mixture was reacted at room temperature for 16 h under nitrogen atmosphere, and subjected to rotary evaporation. The residue was subjected to column chromatography (petroleum ether:ethyl acetate=10:1) to give the target product as a yellow solid (1.30 g, yield: 73.2%). LC-MS: 499 $[M+Na]^+$.

Step 4:

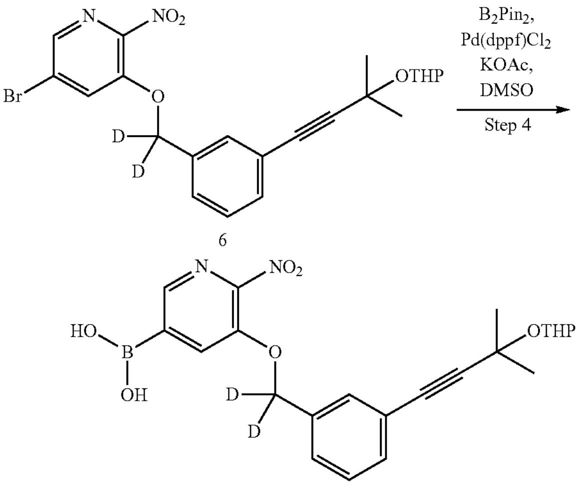

6

7

To a 100 mL single-necked flask were added 6 (300 mg, 0.630 mmol), bis(pinacolato)diboron (240 mg, 0.945 mmol), $Pd(dppf)Cl_2$ (23.5 mg, 0.0315 mmol), potassium acetate (154 mg, 1.58 mmol) and dimethyl sulfoxide (10 mL), and the mixture was reacted at 90° C. for 16 h under nitrogen atmosphere, quenched with water (80 mL), and extracted with ethyl acetate (50 mL×3). The organic phase was washed with saturated brine (50 mL×2), dried over anhydrous sodium sulfate and subjected to rotary evaporation to give the target product as a brown oil (400 mg, crude). LC-MS: 443 $[M+H]^+$.

Step 5

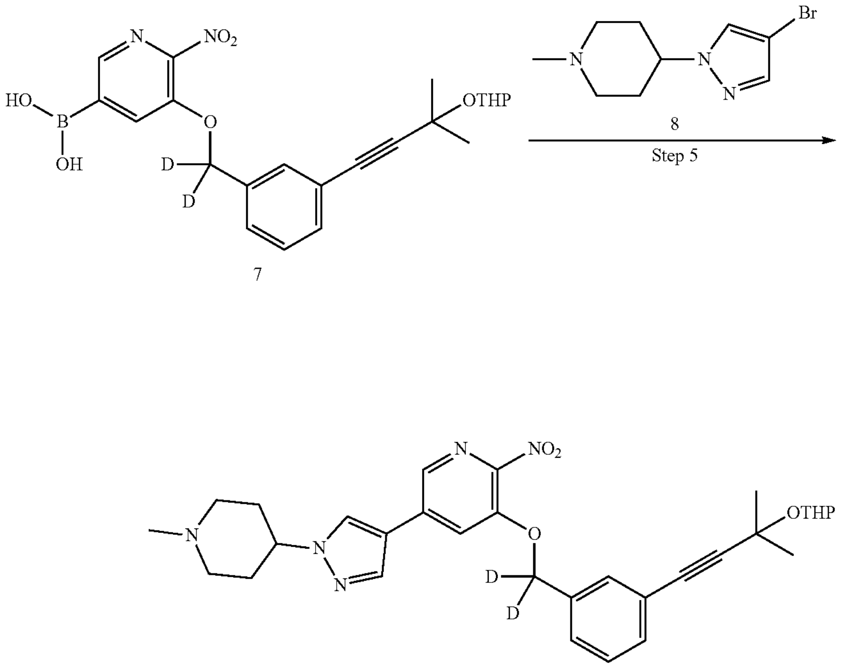

7

9

To a 100 mL single-necked flask were added 7 (400 mg, 0.905 mmol), 8 (200 mg, 0.905 mmol), XPhosPdG2 (35.6 mg, 0.0453 mmol), XPhos (43.2 mg, 0.0905 mmol), potassium phosphate (384 mg, 1.81 mmol), DMF (10 mL) and water (2 mL), and the mixture was reacted at 90° C. for 2 h under nitrogen atmosphere, quenched with water (80 mL), and extracted with ethyl acetate (50 mL×3). The organic phase was washed with saturated brine (50 mL×2), dried over anhydrous sodium sulfate, and subjected to rotary evaporation, and the residue was subjected to column chromatography (dichloromethane:methanol=18:1) to give the target product as a yellow solid (250 mg, yield: 49.2%). LC-MS: 562 $[M+H]^+$.

Step 6:

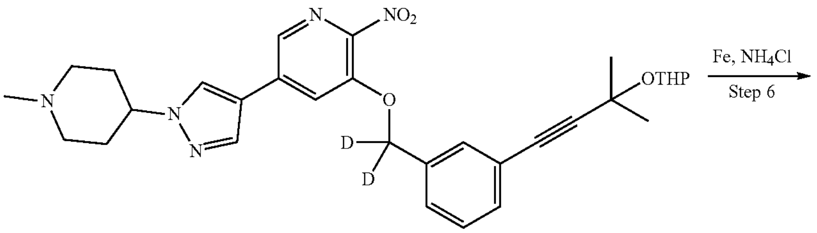

9

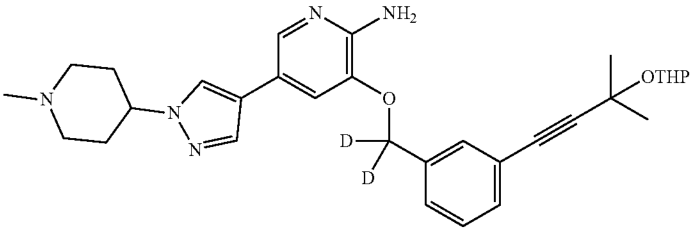

10

To a 100 mL single-necked flask were added 9 (250 mg, 0.446 mmol), reduced iron powder (125 mg, 2.23 mmol), ammonium chloride (118 mg, 2.23 mmol), ethanol (10 mL) and water (2 mL), and the mixture was reacted at 80° C. for 2 h, diluted with dichloromethane (50 mL), filtered under vacuum, and subjected to rotary evaporation. The residue was separated by column chromatography (dichloromethane:methanol=10:1) to give the target product as a yellow solid (220 mg, 93.0%). LC-MS: 532 $[M+H]^+$.

Step 7:

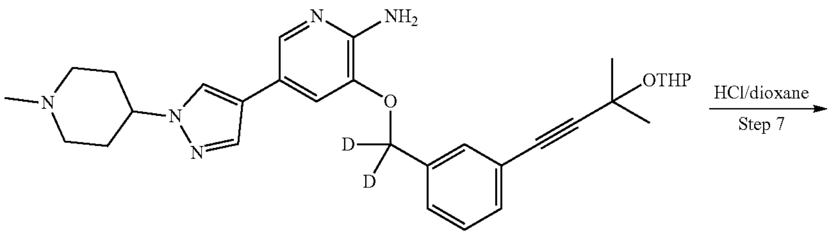

10

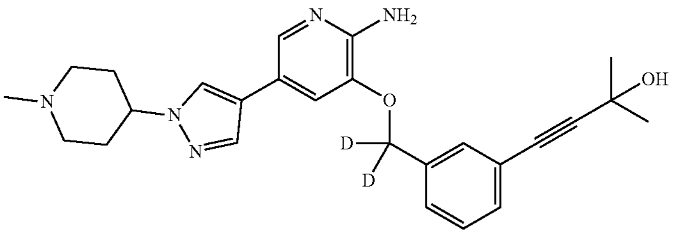

To a 250 mL single-necked flask were added 10 (220 mg, 0.414 mmol) and tetrahydrofuran (10 mL), and the mixture was stirred in an ice bath, then added dropwise with 4 M/L solution of hydrochloric acid in 1,4-dioxane (3 mL), reacted at room temperature for 20 min, subjected to rotary evaporation, dissolved in dichloromethane, adjusted to pH=9 with ammonia water, and subjected to rotary evaporation with dichloromethane (30 mL×3). The residue was subjected to preparative high performance liquid chromatography to give the target product as a pale yellow solid (85.0 mg, 45.9%). LC-MS: 448 $[M+H]^+$, $^1H$ NMR (400 MHz, DMSO) δ 8.10 (s, 1H), 7.79 (d, J=1.8 Hz, 1H), 7.75 (s, 1H), 7.58-7.49 (m, 2H), 7.44-7.30 (m, 3H), 5.66 (s, 2H), 5.49 (s, 1H), 4.14-4.00 (m, 1H), 2.86 (d, J=11.5 Hz, 2H), 2.21 (s, 3H), 1.99 (d, J=3.1 Hz, 6H), 1.46 (s, 6H).

Example 4: Synthesis of Compound D

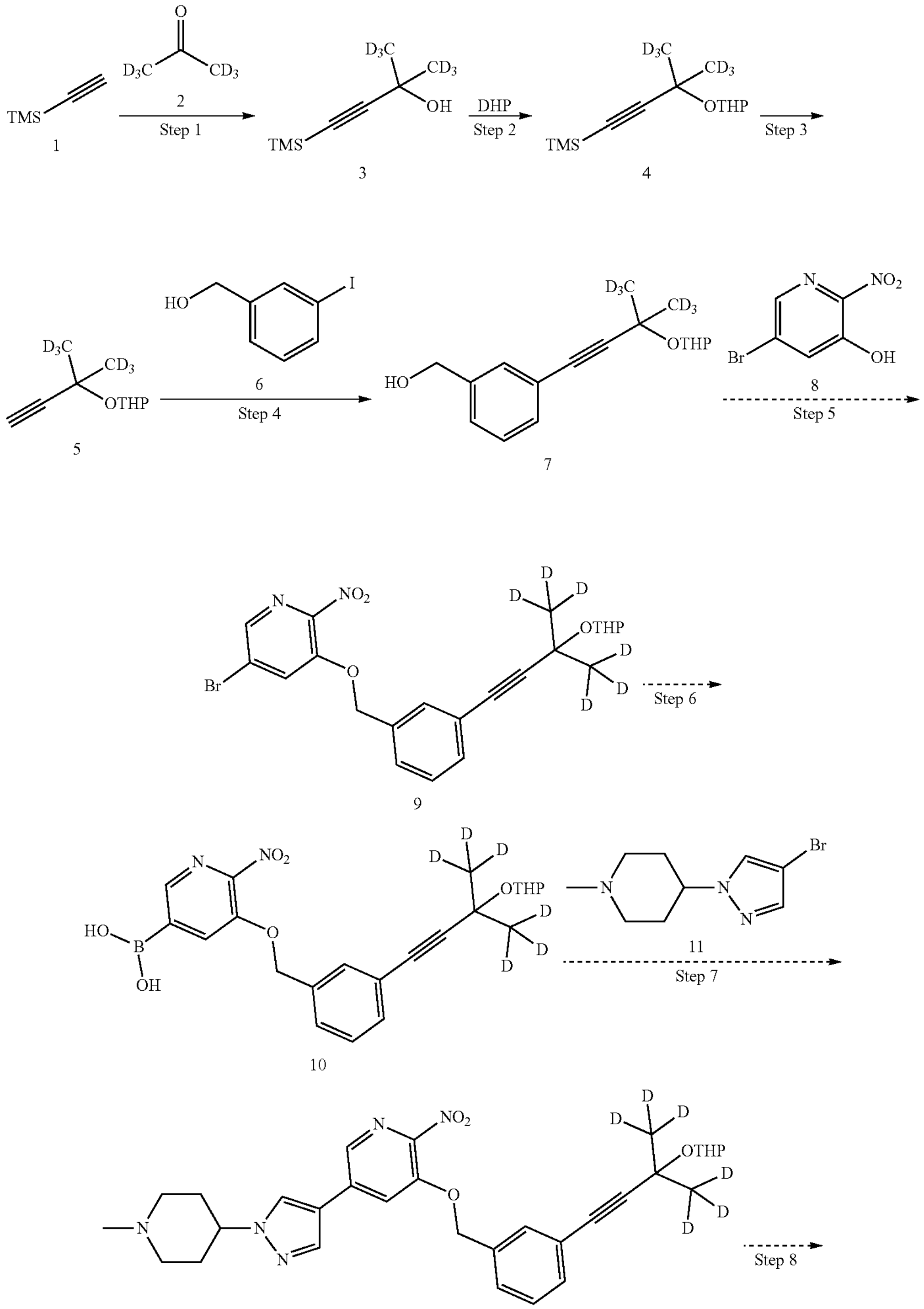

12

-continued

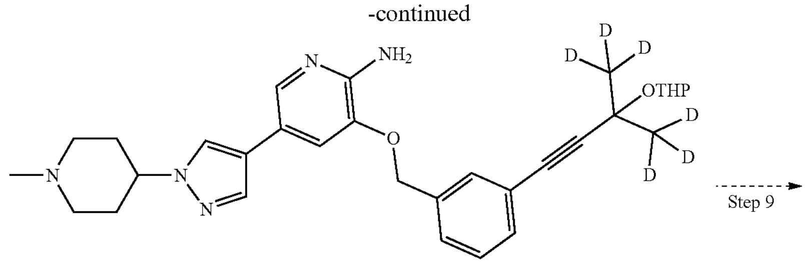

13

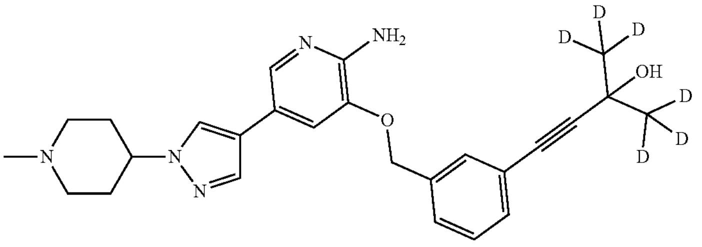

The experimental procedures were as follows:

Step 1:

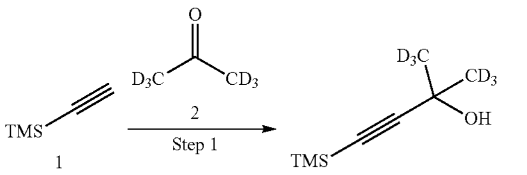

1 3

To a 100 mL three-necked flask were added 1 (3.0 g, 30.61 mmol) and tetrahydrofuran (30 mL), n-butyllithium (2.4 M in tetrahydrofuran, 12.75 mL, 30.61 mmol) was added dropwise at −78° C. under nitrogen atmosphere, and the mixture was stirred for 1 h while maintaining the temperature, added dropwise with 2 (2.0 g, 30.61 mmol), then reacted at −78° C. for 1 h, and heated to room temperature and reacted for 2 h. After the reaction was completed, the reaction solution was quenched with saturated aqueous ammonium chloride (30 mL), and extracted with ethyl acetate (100 mL×3). The organic layer was washed with saturated brine, dried over anhydrous sodium sulfate, filtered under vacuum, and concentrated under reduced pressure to give the target product as a yellow oil (6.1 g, crude), which could be directly used in the next step. LC-MS: 163 $[M+H]^+$.

Step 2:

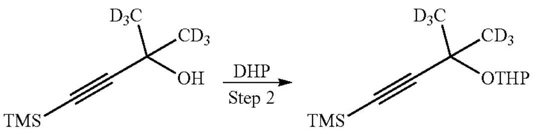

3 4

To a 250 mL single-necked flask were added 3 (6.1 g, 37.65 mmol) and tetrahydrofuran (50 mL), DHP (4.76 g, 56.63 mmol) and PPTS (158.8 mg, 0.63 mmol) were added separately, and the mixture was reacted at room temperature for 16 h, quenched and washed with saturated sodium bicarbonate (100 mL×3), washed with saturated brine (100 mL), dried over anhydrous sodium sulfate, and subjected to rotary evaporation to give the target product as a colorless oil (8.5 g, crude), which could be directly used in the next step. LC-MS: 247 $[M+H]^+$.

Step 3:

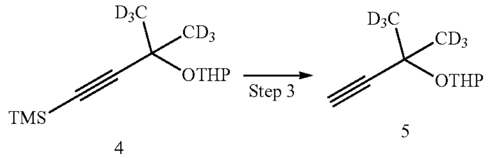

4 5

To a 250 mL single-necked flask were added 4 (8.5 g, 34.55 mmol), methanol and dichloromethane (10 mL/10 mL) and potassium carbonate (7.15 g, 51.83 mmol), and the mixture was reacted at room temperature for 3 h, and filtered under vacuum, and the filtrate was concentrated, and subjected to rotary evaporation to give the target product as a colorless oil (6.3 g, crude), which could be directly used in the next step. LC-MS: 175 $[M+H]^+$.

Step 4:

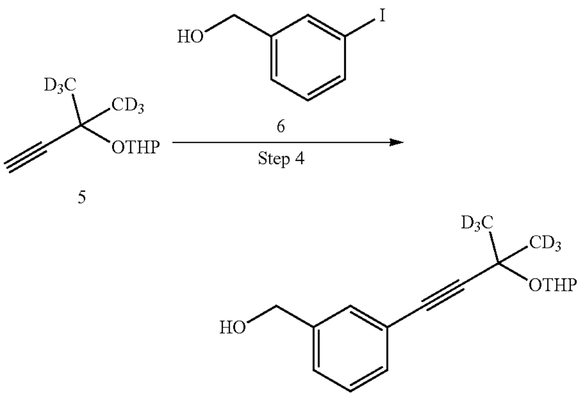

5

7

To a 250 mL single-necked flask were added 5 (6.3 g, 36.21 mmol), 6 (8.05 g, 34.40 mmol), trans-dichlorobis (triphenyl-phosphine)palladium(II) (238 mg, 0.34 mmol), cuprous iodide (322 mg, 1.69 mmol), triethylamine (6.95 g, 68.8 mmol) and anhydrous dichloromethane (80 mL), and the mixture was reacted at room temperature for 16 h under nitrogen atmosphere, washed with saturated ammonium chloride (200 mL×3) and saturated brine (100 mL), dried over anhydrous sodium sulfate, and subjected to rotary evaporation. The residue was subjected to column chromatography (petroleum ether:ethyl acetate=10:1) to give the target compound as a yellow oil (3.2 g); LC-MS: 281 $[M+H]^+$.

Step 5:

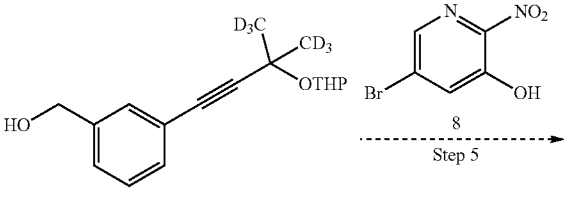

7 8

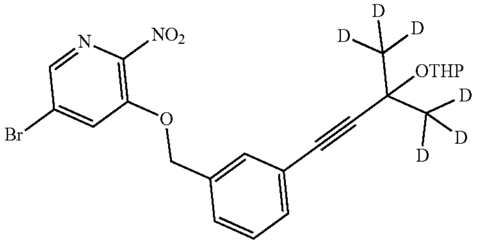

9

To a 100 mL three-necked flask were added 7 (1.5 g, 5.36 mmol), 8 (1.752 g, 8.04 mmol), triphenylphosphine (2.106 g, 8.04 mmol) and anhydrous tetrahydrofuran (20 mL), diisopropyl azodicarboxylate (1.624 g, 8.04 mmol) was added at room temperature under nitrogen atmosphere while stirring at room temperature, and the mixture was reacted at room temperature for 16 h, and subjected to rotary evaporation. The residue was subjected to column chromatography (petroleum ether:ethyl acetate=4:1) to give the target product as a yellow solid (450 mg, yield: 17.50%). LC-MS: 481 $[M+H]^+$.

Step 6:

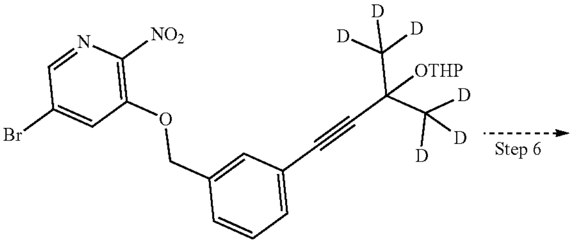

9

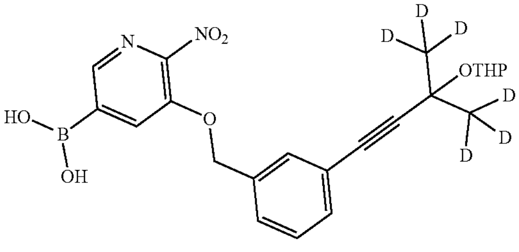

10

To a 100 mL single-necked flask were added 9 (450 mg, 0.94 mmol), bis(pinacolato)diboron (359 mg, 1.41 mmol), bis(diphenylphosphino)ferrocene palladium dichloride (35 mg, 0.047 mmol), potassium acetate (276 mg, 2.82 mmol) and dimethyl sulfoxide (10 mL), and the mixture was reacted at 90° C. for 16 h under nitrogen atmosphere, quenched with water (30 mL), and extracted with ethyl acetate (50 mL×3). The organic phase was washed with saturated brine (100 mL×2) and subjected to rotary evaporation to give the target product as a black solid (500 mg, crude). LC-MS: 447 $[M+H]^+$.

Step 7:

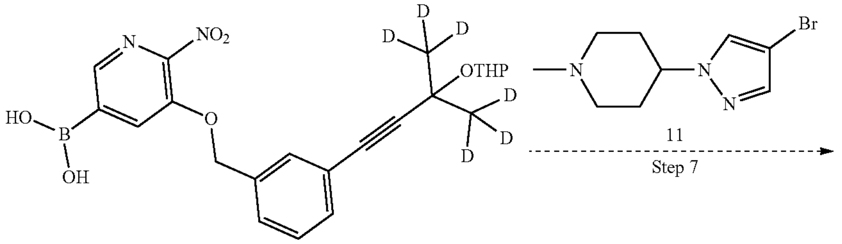

10 11

-continued

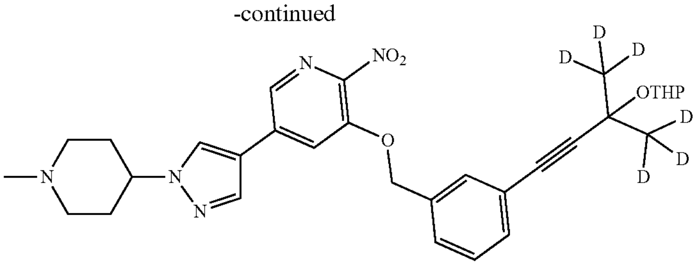

12

To a 100 mL single-necked flask were added 10 (363 mg, 0.81 mmol), 11 (178 g, 0.73 mmol), chloro(2-dicyclohexylphosphino-2',4',6'-triisopropyl-1,1'-biphenyl)[2-(2'-amino-1,1'-biphenyl)]palladium (II) (59 mg, 0.081 mmol), 2-dicyclohexylphosphorus-2,4,6-triisopropylbiphenyl (39 mg, 0.082 mmol) and potassium phosphate (343 mg, 1.62 mmol), DMF (10 mL) and $H_2O$ (2 mL) were added, and the mixture was stirred at 95° C. for 1.5 h under nitrogen atmosphere, quenched with water (30 mL), and extracted with ethyl acetate (100 mL×3). The organic phases were combined and washed with saturated brine (100 mL×3), dried over anhydrous sodium sulfate, and subjected to rotary evaporation, and the residue was separated by TCL (dichloromethane:methanol=15:1) to give the target product as a brown liquid (266 mg, yield: 57.9%); LC-MS: 566 $[M+H]^+$.

Step 8:

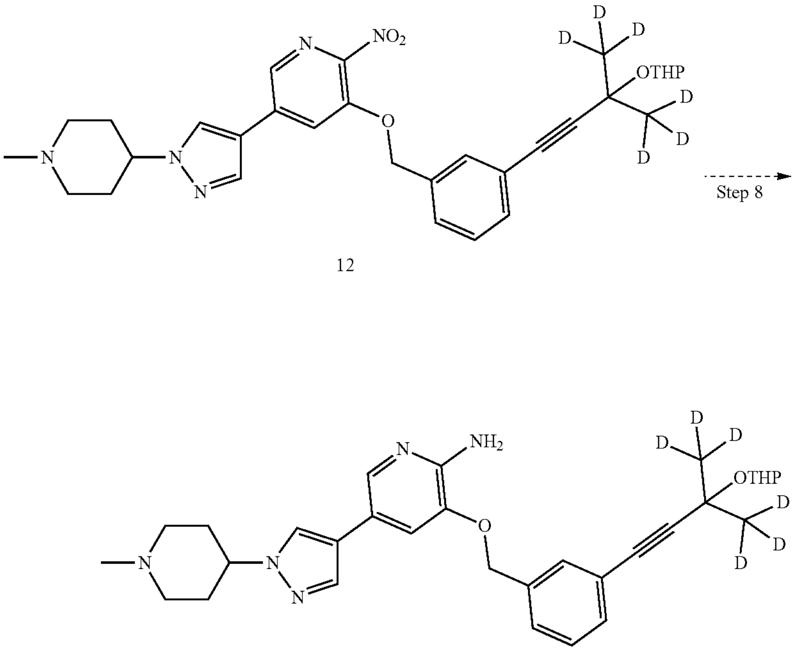

12

13

To a 100 mL single-necked flask were added 12 (266 mg, 0.47 mmol), iron powder (201 mg, 3.77 mmol), ammonium chloride (203 mg, 3.77 mmol), ethanol (10 mL) and water (2 mL), and the mixture was reacted at 80° C. for 1 h, cooled to room temperature, and filtered under vacuum, and the filtrate was concentrated, and separated by TLC (methanol: dichloromethane=1:10, v/v) to give the target product as a yellow solid (95 mg, 37.6%); LC-MS: 536 $[M+H]^+$.

Step 9:

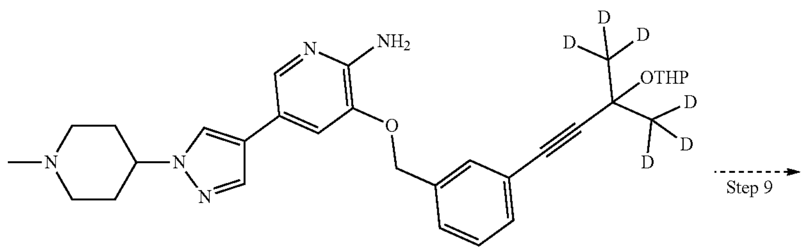

13

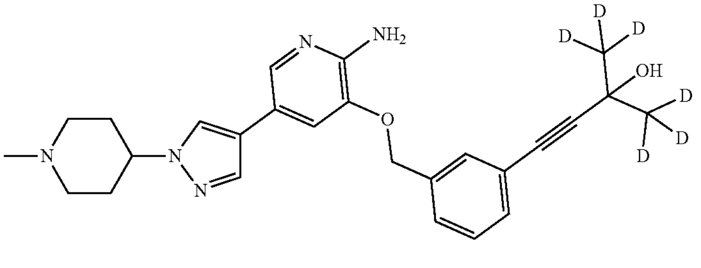

To a 50 mL single-necked flask were added 13 (95 mg, 0.17 mmol) and tetrahydrofuran (5 mL) and the mixture was stirred in an ice bath, then added dropwise with 4 M/L solution of hydrochloric acid in 1,4-dioxane (0.01 mL, 0.34 mmol), reacted at room temperature for 1 h, and subjected to rotary evaporation at 0° C. The residue was subjected to preparative high performance liquid chromatography to give the target product as a black solid (15 mg, 18.7%). LC-MS: 452 $[M+H]^+$, $^1H$ NMR (400 MHz, DMSO) δ 8.20 (s, 1H), 8.10 (s, 1H), 7.80 (d, J=1.7 Hz, 1H), 7.76 (s, 1H), 7.52 (d, J=1.4 Hz, 2H), 7.40 (s, 1H), 7.35-7.32 (m, 2H), 5.67 (s, 2H), 5.18 (s, 2H), 4.09 (dd, J=10.4, 5.1 Hz, 1H), 2.89 (d, J=11.1 Hz, 2H), 2.24 (s, 3H), 2.10 (d, J=11.3 Hz, 2H), 2.00 (d, J=3.3 Hz, 4H).

Example 5: Free Base Crystalline Form A of Compound A2

Compound A2 prepared in Example 1 was purified by a silica gel column to give 1.6 g of crude product (purity: about 80%), then separated by preparative high performance liquid chromatography, concentrated to 100 mL, adjusted to pH=9 with sodium bicarbonate solution, and extracted with dichloromethane (100 mL×3). The organic phase was washed once with saturated sodium chloride solution (80 mL), dried over sodium sulfate and subjected to rotary evaporation to give a pale yellow solid (570 mg, purity: 97%). The solid was slurried with 50 mL of petroleum ether/ethyl acetate (3:1) and filtered to give an off-white solid (460 mg, purity: >99%).

The preparation process was repeated:

(1) 230.9 mg of the free base sample described above was weighed into a 20 mL glass bottle, and 1 mL of IPAc was added to give a clear solution;

(2) after stirring (at 1000 rpm) at room temperature for about 5 min, a large amount of solid precipitated, and 1 mL of IPAc was added;

(3) after suspension with stirring at room temperature for about 1 day, the mixture was centrifuged (at 10000 rpm, for 2 min) to give a solid; and (4) after drying under vacuum at room temperature for 3 h, a total of 195.4 mg of sample was collected (recovery: 84.6%).

The XRPD pattern of the sample described above is shown in FIG. 1, and the XRPD test parameters and the result data table of the sample are respectively shown in Tables 1 and 2, which indicate that the sample is a crystal and is named as free crystalline form A and can be repeatedly prepared. The entire list of peaks or corresponding d values in Table 2 or a subset thereof, and the XRPD pattern substantially similar to FIG. 1 are sufficient to characterize the crystalline form.

Figure 2:
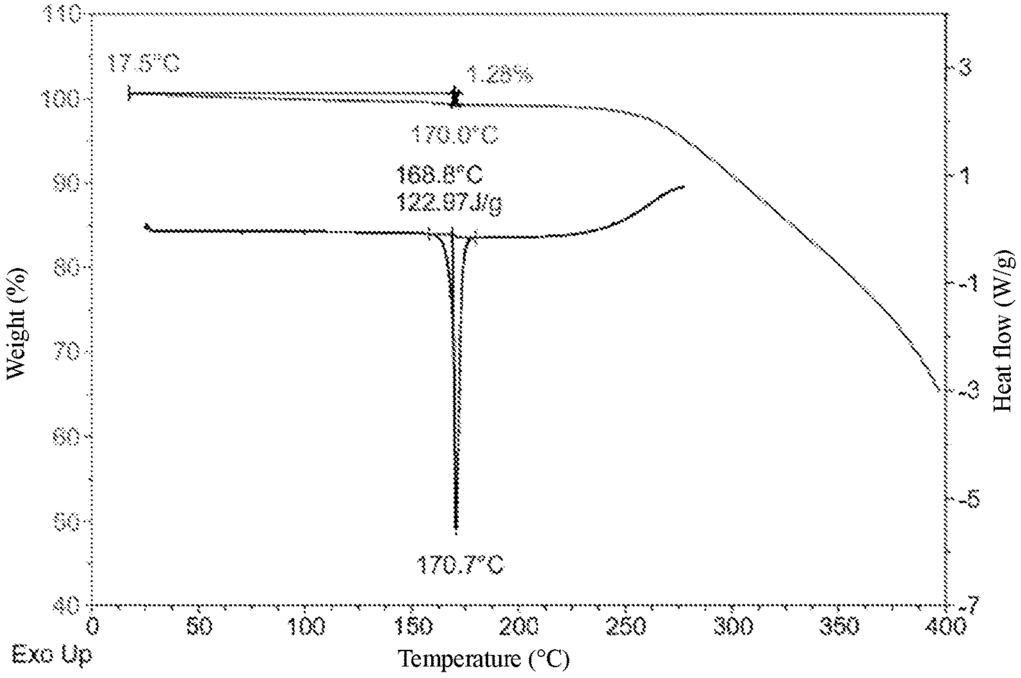
FIG. 2 shows the TGA/DSC pattern of free base crystalline form A of compound A2.

The TGA/DSC pattern of free base crystalline form A of compound A2 is shown in FIG. 2, and the test parameters of TGA and DSC are shown in Table 3. In FIG. 2, the TGA result shows a weight loss of 1.3% upon heating from room temperature to 170° C.; the DSC result shows a sharp endothermic peak at 168.8° C. (initial temperature).

Figure 3:
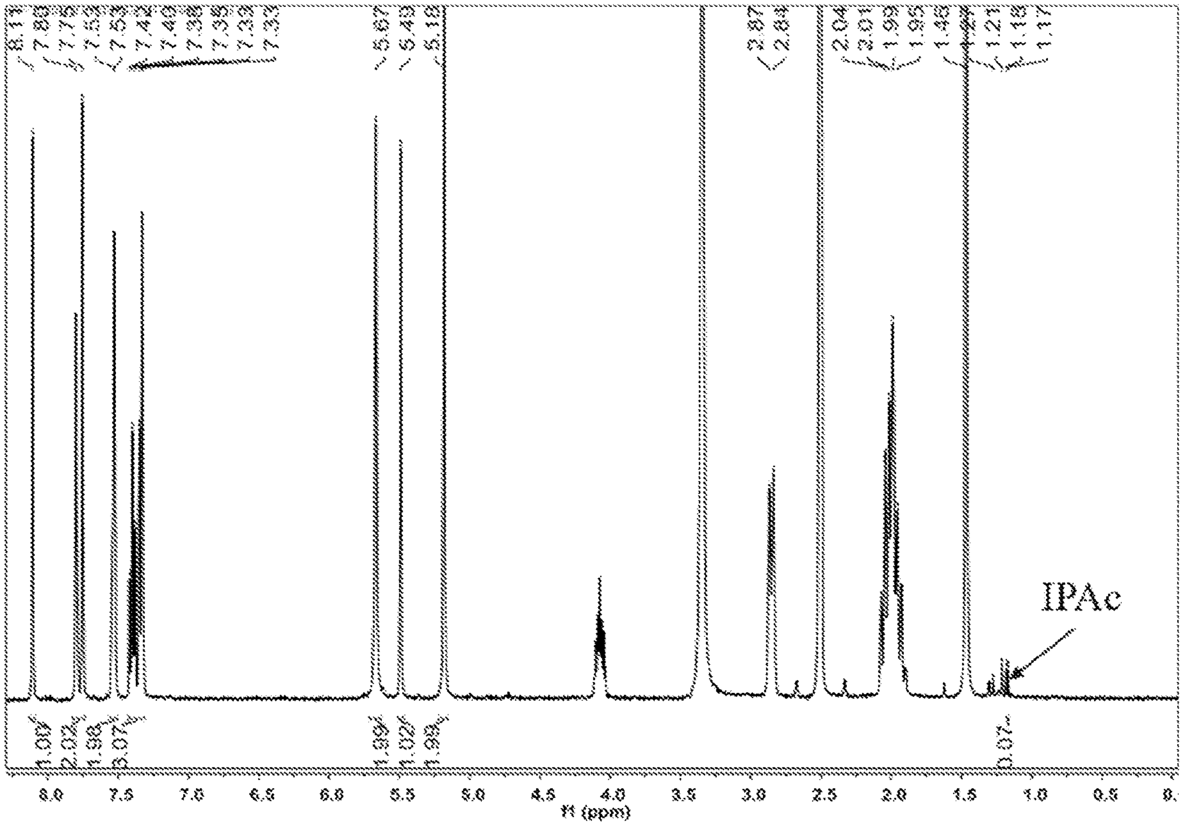
FIG. 3 shows the $^1$H NMR spectrum of free base crystalline form A of compound A2.

The $^1H$ NMR spectrum of free base crystalline form A of compound A2 is shown in FIG. 3. The $^1H$ NMR results indicate that a molar ratio of residual solvent IPAc to free base crystalline form A is 0.01:1 (corresponding to a weight loss of TGA being 0.2%).

Figure 4:
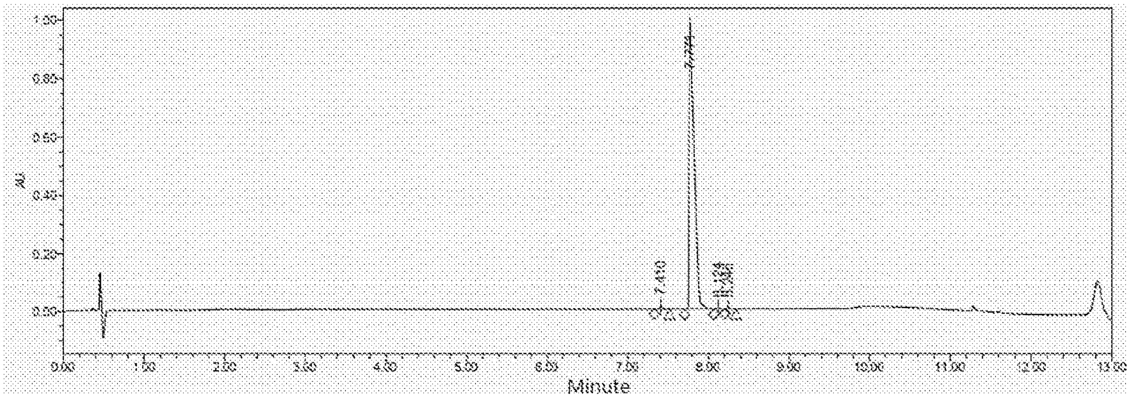
FIG. 4 shows the HPLC chromatogram of free base crystalline form A of compound A2.

The HPLC chromatogram of free base crystalline form A of compound A2 is shown in FIG. 4, and the results are shown in Table 4.

The free base crystalline form A of compound A2 is presumed to be an anhydrous crystalline form.

TABLE 1

| Test parameters of XRPD | |
|---|---|
| Model of instrument | X'Pert$^3$ |
| X-ray | Cu, Kα; Kα1 (Å): 1.540598<br>Kα2 (Å): 1.544426<br>Intensity ratio Kα2/Kα1: 0.50 |
| Settings of X-ray tube | 45 kV, 40 mA |
| Divergent slit | 1/8° |
| Scanning mode | Continuous |
| Scanning range (°2TH) | 3°~40° |
| Scanning step length (°2TH) | 0.0263 |
| Scanning time of each step (s) | 46.665 |
| Scanning time (s) | 5 min 04 s |

TABLE 2

| XRPD data table for free base crystalline form A of compound A2 | | |
|---|---|---|
| Diffraction angle (°2θ) | d value (Å) | Relative intensity (%) |
| 8.056970 | 10.97382 | 15.13 |
| 9.692430 | 9.12550 | 5.99 |
| 12.171430 | 7.27188 | 16.70 |
| 13.057630 | 6.78028 | 32.80 |
| 15.305380 | 5.78921 | 16.44 |
| 16.324030 | 5.43018 | 33.09 |
| 17.530630 | 5.05905 | 32.94 |
| 18.025570 | 4.92125 | 16.88 |
| 19.336490 | 4.59047 | 16.94 |
| 19.450710 | 4.56377 | 17.83 |
| 20.519450 | 4.32842 | 2.47 |
| 21.306330 | 4.17031 | 18.82 |
| 21.588990 | 4.11634 | 16.08 |
| 23.778260 | 3.74208 | 100.00 |
| 27.036990 | 3.29800 | 4.69 |
| 27.711080 | 3.21928 | 3.95 |
| 28.487430 | 3.13329 | 2.77 |
| 31.912120 | 2.80443 | 3.52 |

TABLE 3

| Test parameters of TGA and DSC | | |
|---|---|---|
| Parameter | TGA | DSC |
| Method | Linear heating | Linear heating |
| Sample dish | Aluminum dish, open | Aluminum dish, closed |
| Temperature range | Room temperature to 350° C. | 25-350° C. |
| Rate of heating | 10° C./min | 10° C./min |
| Protective gas | Nitrogen | Nitrogen |

TABLE 4

| HPLC results of free base crystalline form A of compound A2 | | |
|---|---|---|
| Peak | RRT | Area (%) |
| 1 | 0.95 | 0.42 |
| 2 | 1.00 | 99.26 |
| 3 | 1.05 | 0.22 |
| 4 | 1.06 | 0.10 |

Solid State Stability of Free Base Crystalline Form A

Figure 5:
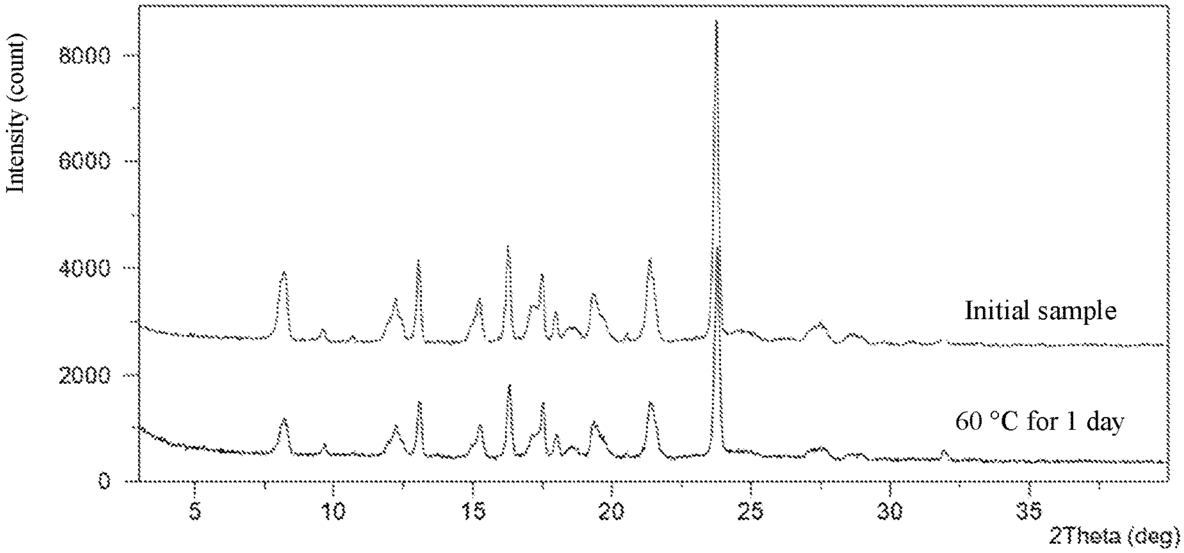
FIG. 5 shows the XRPD pattern of a starting sample of free base crystalline form A of compound A2 and the free base crystalline form A of compound A2 after 1 day of standing in a closed space at 60° C.

The XRPD patterns of an initial sample of the free base crystalline form A described above and the free base crystalline form A after 1 day of standing in a closed space at 60° C. are shown in FIG. 5, and the HPLC results are shown in Table 5.

TABLE 5

| HPLC results of free base crystalline form A of compound A2 | | | |
|---|---|---|---|
| | | Area (%) | |
| Peak | RRT | Initial sample | 60° C./1 day |
| 1 | 0.95 | 0.42 | 0.41 |
| 2 | 1.00 | 99.26 | 99.33 |
| 3 | 1.05 | 0.22 | 0.17 |
| 4 | 1.06 | 0.10 | 0.09 |

Example 6: Free Base Crystalline Form B of Compound A2

(1) 9.9 mg of the free base sample (as described in Example 5) was weighed into a 20 mL glass bottle, and 2 mL of EtOAc was added to dissolve the sample, followed by filtration with a 0.45 μm PTFE filter membrane to give a clear API solution;

(2) the API solution was added dropwise with an anti-solvent toluene while magnetically stirring (at 1000 rpm), and a total of 10 mL of toluene was added;

(3) the resulting clear solution was stirred at room temperature for 2 h, then transferred to 5° C., and stirred for about 15 h to give a clear solution;

(4) the resulting solution was transferred to −20° C. and stirred for about 6 h, it was still a clear solution; and (5) the clear solution was transferred to room temperature and evaporated for 8 d to give a solid.

The XRPD pattern of the sample described above is shown in FIG. 6, and the XRPD test parameters and the result data table of the sample are respectively shown in Tables 1 and 6, which indicate that the sample is a crystal and is named as free crystalline form B. The entire list of peaks or corresponding d values in Table 6 or a subset thereof, and the XRPD pattern substantially similar to FIG. 5 are sufficient to characterize the crystalline form.

TABLE 6

| XRPD data table for free base crystalline form B of compound A2 | | |
|---|---|---|
| Diffraction angle (°2θ) | d value (Å) | Relative intensity (%) |
| 5.683550 | 15.54998 | 87.55 |
| 7.085257 | 12.47650 | 19.72 |
| 8.848269 | 9.99413 | 46.82 |
| 11.330050 | 7.80994 | 100.00 |
| 13.025680 | 6.79684 | 3.84 |
| 14.152280 | 6.25821 | 29.61 |
| 14.979470 | 5.91443 | 6.30 |
| 17.004010 | 5.21453 | 36.50 |
| 17.683430 | 5.01568 | 10.18 |
| 18.091520 | 4.90345 | 30.51 |
| 18.752700 | 4.73203 | 18.19 |
| 21.597990 | 4.11465 | 8.09 |
| 22.297300 | 3.98716 | 3.65 |
| 22.731990 | 3.91189 | 96.70 |
| 23.470920 | 3.79038 | 94.14 |
| 24.190420 | 3.67924 | 4.18 |
| 26.220830 | 3.39877 | 7.82 |

Figure 7:
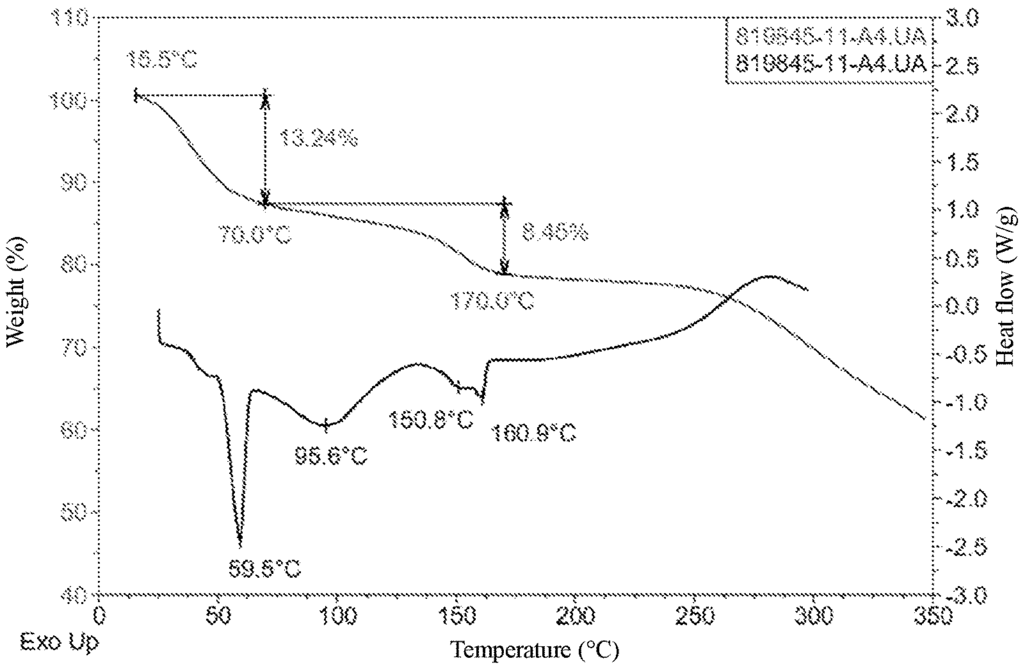
FIG. 7 shows the TGA/DSC pattern of free base crystalline form B of compound A2.

The TGA/DSC pattern of free base crystalline form B of compound A2 is shown in FIG. 7, and the test parameters of TGA and DSC are shown in Table 3. The TGA results indicate that the sample has a weight loss of 13.2% upon heating from room temperature to 70° C. and a weight loss of 8.5% upon continuous heating to 170° C. The DSC results indicate that the sample has four endothermic peaks at 59.5° C., 95.6° C., 150.8° C. and 160.9° C. (peak temperature).

Figure 8:
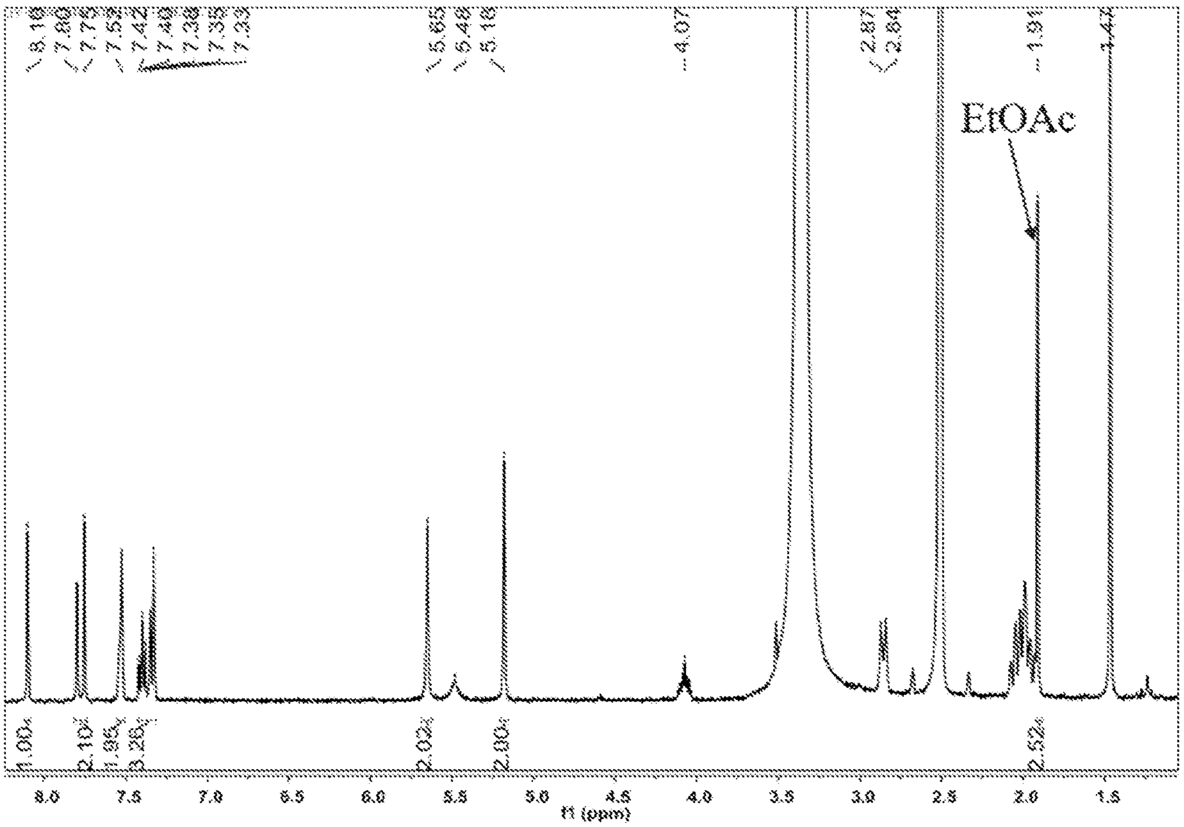
FIG. 8 shows the $^1$H NMR spectrum of free base crystalline form B of compound A2.

The $^1$H NMR spectrum of free base crystalline form B of compound A2 is shown in FIG. 8. The $^1$H NMR results indicate that a molar ratio of residual solvent EtOAc to the free base is 0.8:1 (corresponding to a weight loss of TGA being 18.1%).

Figure 9:
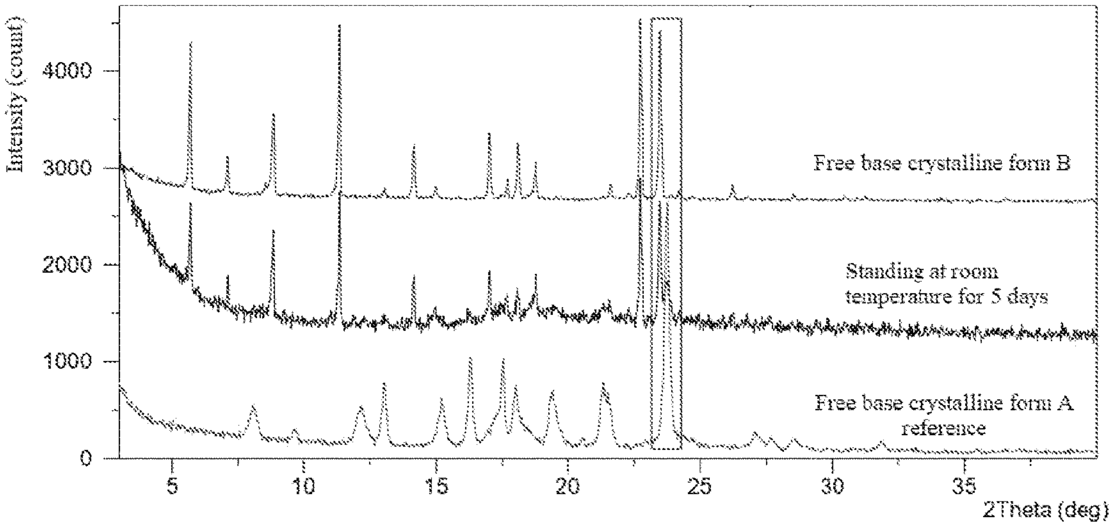
FIG. 9 shows the XRPD pattern of free base crystalline form B of compound A2 before and after standing at room temperature.

The XRPD patterns of free base crystalline form B of compound A2 before and after standing at room temperature are shown in FIG. 9. The results show that after the free base crystalline form B was placed in a closed space for 5 days at room temperature, a diffraction peak of free base crystalline form A appeared, indicating that the free base crystalline form B has a tendency of converting into the free base crystalline form A after being placed at room temperature.

Figure 10:
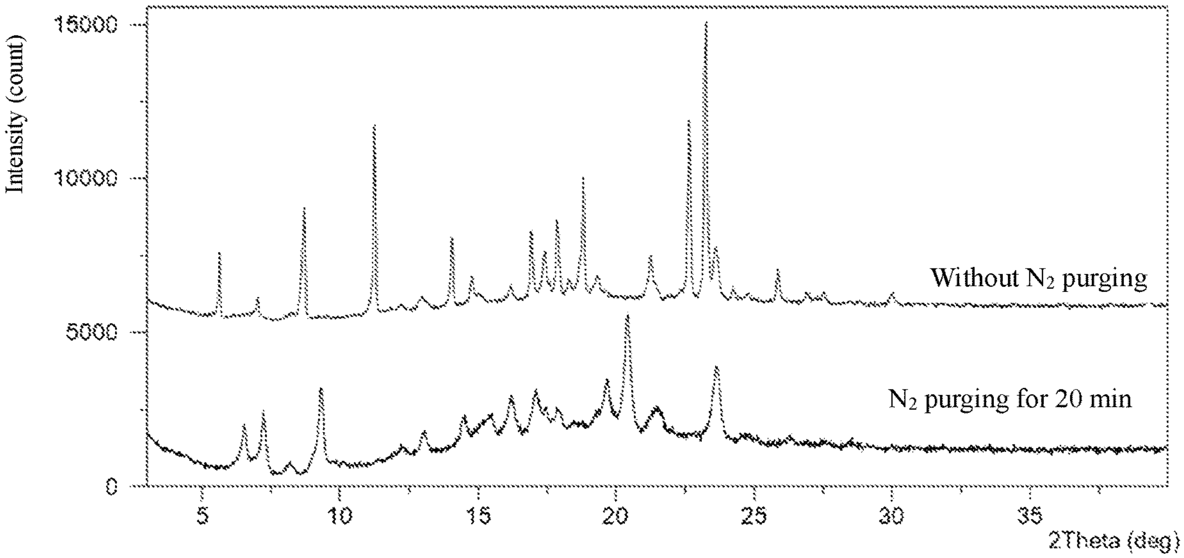
FIG. 10 shows the XRPD pattern of free base crystalline form B of compound A2 before and after nitrogen purging.

The XRPD patterns of free base crystalline form B of compound A2 before and after nitrogen purging are shown in FIG. 10. The results show that the free base crystalline form B (containing one diffraction peak of crystalline form A) has a conversion in crystalline forms after nitrogen purging at 30° C. for 20 minutes. The free base crystalline form B is presumed to have a conversion in crystalline forms with the removal of EtOAc after nitrogen purging.

The comprehensive characterization results suggest that the free base crystalline form B is EtOAc solvate.

Example 7: Preparation of Compound A2 Hydrochloride 100 mg (0.223 mmol) of Compound A2 was weighed and dissolved in 5 mL of anhydrous dichloromethane, the mixture was stirred at room temperature for 5 min, 1.11 mL of a solution of hydrochloric acid in ethyl ether (1N) was added dropwise, and after the dropwise addition was completed, the reaction solution was stirred at room temperature for 30 min. After the starting materials were consumed as shown in TLC, nitrogen was introduced for 10 min, and the reaction solution was concentrated under reduced pressure at 10° C. to give an off-white solid (purity: >99%). The solid was placed in a lyophilizer for 12 h to give 108 mg of A2 hydrochloride (off-white, purity: >99%).

Figure 11:
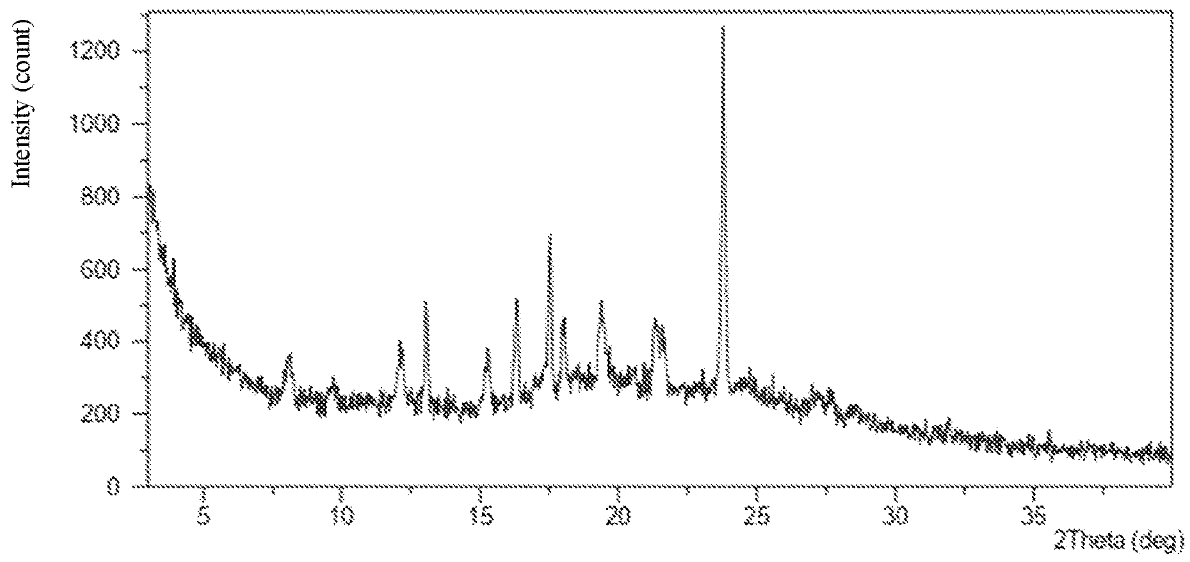
FIG. 11 shows the XRPD pattern of compound A2 hydrochloride.

The XRPD pattern of compound A2 hydrochloride is shown in FIG. 11, the XRPD test parameters are shown in Table 1 of Example 5, and the XRPD result data table is shown in Table 7, which indicate that it is a crystal and is named as hydrochloride crystalline form A. The entire list of peaks or corresponding d values in Table 7 or a subset thereof, and the XRPD pattern substantially similar to FIG. 11 are sufficient to characterize the crystalline form.

Figure 12:
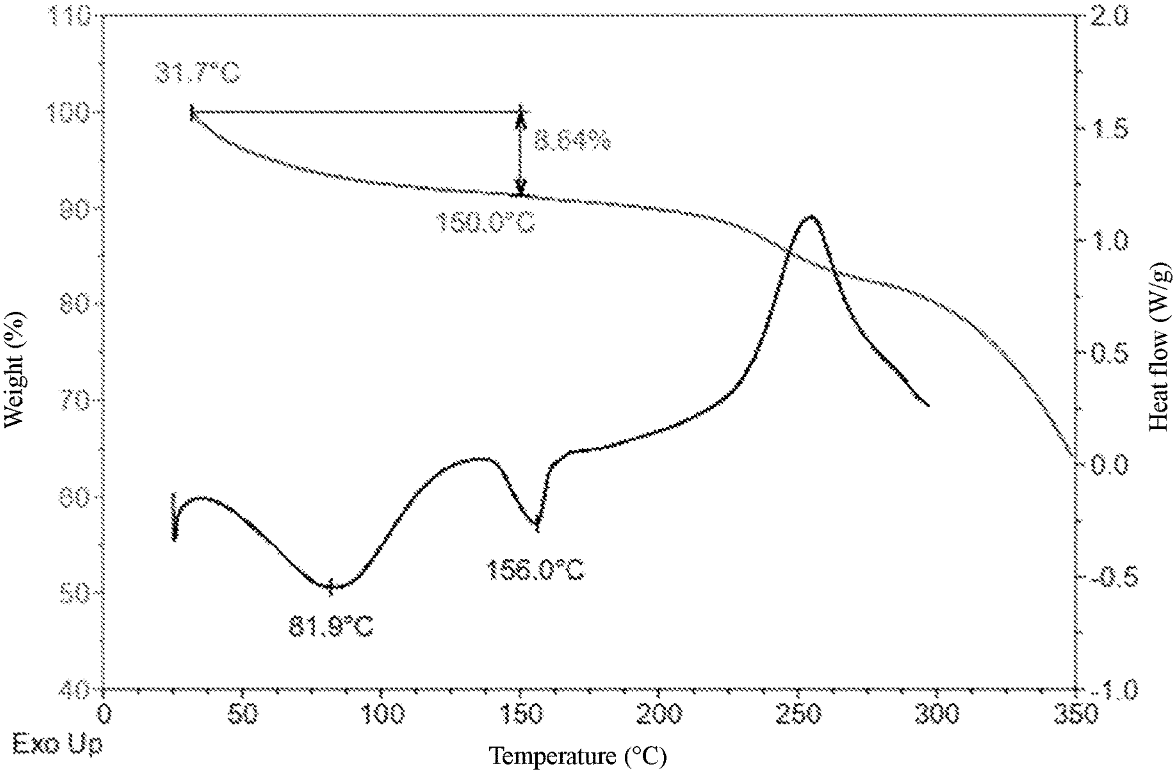
FIG. 12 shows the TGA/DSC pattern of compound A2 hydrochloride.

The TGA/DSC pattern of the hydrochloride of compound A2 is shown in FIG. 12, and the TGA and DSC test parameters are shown in Table 3 of Example 5. The TGA result shows a weight loss of 8.6% upon heating from room temperature to 150° C.; the DSC result shows two endothermic peaks at 81.9° C. and 156.0° C. (peak temperature).

TABLE 7

XRPD data table for compound A2 hydrochloride

| Diffraction angle (°2θ) | d value (Å) | Relative intensity (%) |
|---|---|---|
| 8.138280 | 10.86436 | 10.23 |
| 12.12130 | 7.29535 | 13.51 |
| 13.048080 | 6.78522 | 28.41 |
| 15.250920 | 5.80976 | 13.92 |
| 16.320850 | 5.43123 | 26.84 |
| 17.509650 | 5.06507 | 43.49 |
| 17.990580 | 4.93074 | 20.44 |
| 19.378850 | 4.58053 | 27.22 |
| 21.438430 | 4.14491 | 17.23 |
| 23.765500 | 3.74406 | 100.00 |
| 27.305560 | 3.26617 | 2.56 |

Figure 13:
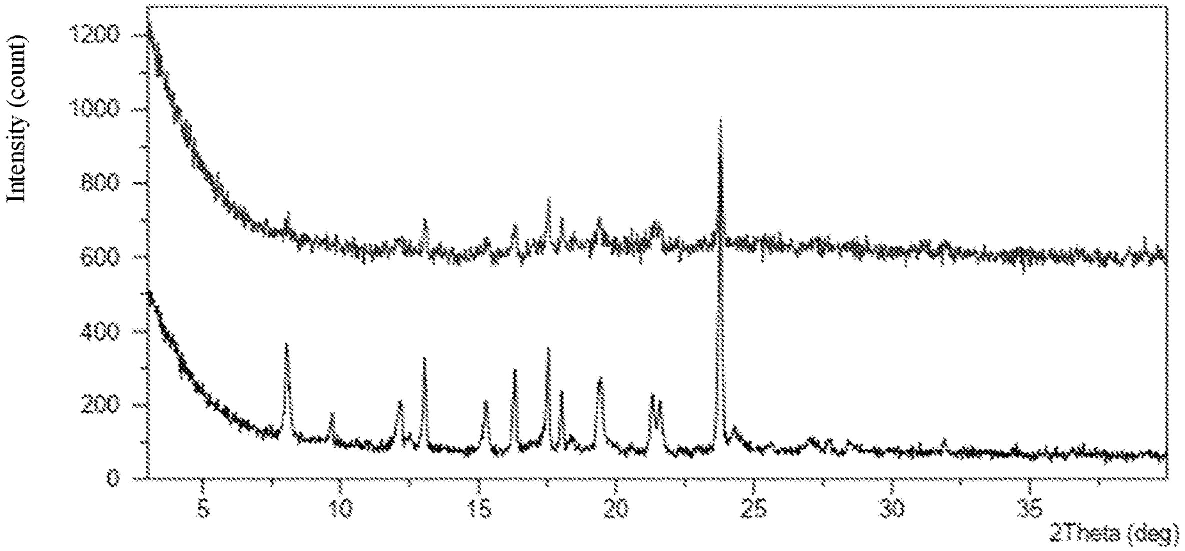
FIG. 13 shows the XRPD pattern overlay of free base crystalline form A of compound A2 and compound A2 hydrochloride.

The XRPD pattern overlay of free base crystalline form A of compound A2 and compound A2 hydrochloride is shown in FIG. 13, and the XRPD results are substantially the same for the two, but the crystallinity of the hydrochloride salt is lower.

Example 8

The operation steps for microsome metabolite identification were as follows:

The compounds (test compounds with numbers shown below, wherein compounds A1 and $B_1$ were prepared by referring the relevant methods disclosed in CN110396087A) were weighed and dissolved in dimethyl sulfoxide to prepare a 20 mM solution, and the compound stock solution was diluted with 50% acetonitrile aqueous solution (v/v) to 1.0 mM concentration to give a working solution; the liver microsomes (20 mg/mL) were diluted to 1.27 mg/mL with 50 mM dipotassium phosphate buffer as a liver microsome working solution; reduced coenzyme was weighed, and 3307 μL of phosphate buffer (50 mM) was added to dissolve the reduced coenzyme to 5.0 mM to give a reduced coenzyme working solution. For the sample with T=60 min, 4 μL of the test sample working solution (1.0 mM), 316 μL of the liver microsome working solution (1.27 mg/mL) and 80 μL of the reduced coenzyme working solution were added sequentially to start the reaction; for the sample with T=0 min, 316 μL of the liver microsome working solution (1.27 mg/mL) was added, and 80 μL of the reduced coenzyme working solution was added to start the reaction, with no test sample incubation; after incubation at 37° C. for 60 min, 1200 μL of stop buffer was added to stop the enzymatic reaction; and for the sample with T=0 min, 4 μL of the test sample working solution (1.0 mM) was added. The sample plate was placed on a vortexer and vortexed at 600 rpm for 5 min. The mixture was centrifuged at 4000 rpm for 10 min, and the supernatant was removed, mixed and purged with nitrogen to dryness at room temperature. The resulting solution was re-dissolved with 300 μL of 10% acetonitrile (0.1% FA), the residue was purged with nitrogen to dryness and then centrifuged at 4000 rpm for 15 min, and the supernatant was transferred to a detection plate for mass spectrometry. Mass spectrometry was performed using an LC/Q-Exactive plus. 7-ethoxycoumarin (10 μM) was selected as a positive control compound, using the procedure same as that of the compounds.

A1

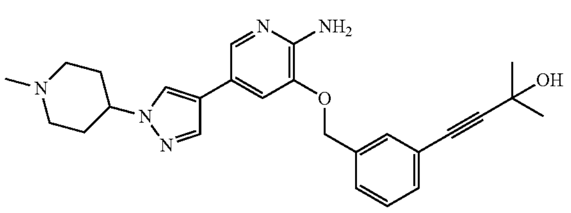

B1

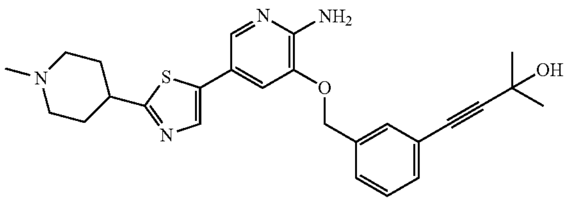

A2

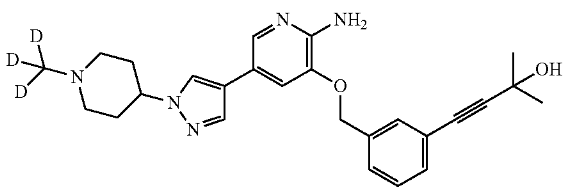

-continued

B2

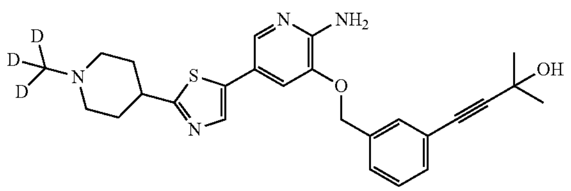

The remaining percentage of the parent nucleus after 60 min is shown in the table below:

TABLE 8

| Stability test results for compounds | | | | |
|---|---|---|---|---|
| Test species | A1 (%) | A2 (%) | B1 (%) | B2 (%) |
| Mouse | 1.13 | 55.0 | 1.24 | 42.8 |
| Rat | 2.44 | 52.1 | 11.21 | 43.9 |
| Beagle | 0.17 | 7.0 | 0.12 | 8.9 |
| Cynomolgus monkey | 0.36 | 29.6 | 9.11 | 23.4 |
| Human | 43.84 | 83.9 | 51.82 | 70.4 |

Example 9: Pharmacokinetic Experiment

Pharmacokinetic Experiment in Rats 6 male Sprague Dawley rats were administered intravenously (iv, n=3) and orally (po, n=3) separately at a single dose once. For intravenous injection, the compounds were prepared into 0.25 mg/mL or 0.5 mg/mL solution with 10% DMSO/30% PEG400/60% water, and the solution was administered at a volume of 2 mL/kg. For oral administration, the compounds were prepared into 0.6 mg/mL or 2.0 mg/mL homogeneous suspension with 0.5% methylcellulose, and the suspension was administered at a volume of 5 mL/kg. The specific dosage is shown in the table below.

TABLE 9

| Dosage | | |
|---|---|---|
| Compound | iv (mg/kg) | po (mg/kg) |
| A1 | 1 | 10 |
| A2 | 1 | 10 |
| C | 0.5 | 3 |
| D | 0.3 | 2 |

After administration, blood samples for intravenous injection and oral administration were collected at 0.0833 h, 0.25 h, 0.5 h, 1 h, 2 h, 4 h, 8 h and 24 h, and concentrations of the compounds in the samples were measured using LC-MS/MS with a lower limit of quantitation of 1 ng/mL, and the pharmacokinetic parameters of the compounds were calculated using the WinNolin non-compartmental model.

The structures and numbers of the compounds involved in the example are shown as follows:

A1

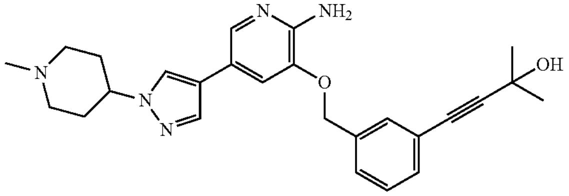

A2

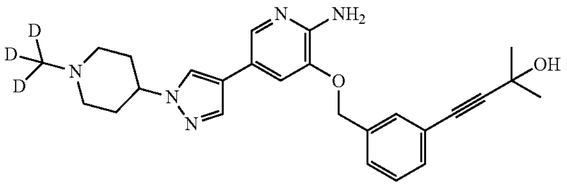

C

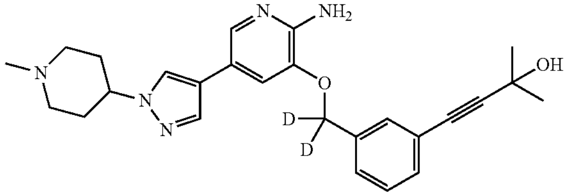

D

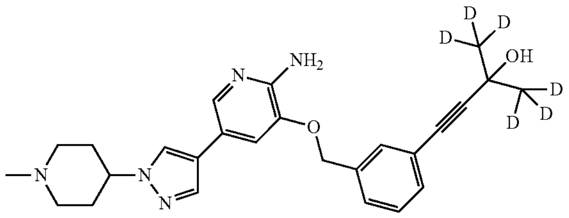

Results

After intravenous administration, the in vivo exposures ($AUC_{last}$) of A1, A2, C and D were 116 hr*ng/mL, 247 hr*ng/mL, 74.8 hr*ng/mL and 28.7 hr*ng/mL, respectively, and the average total clearances (CLs) were 129 mL/min/kg, 71 mL/min/kg, 101 mL/min/kg and 151 mL/min/kg, respectively.

After oral administration, the in vivo exposures ($AUC_{last}$) of A1, A2, C and D were 79.8 ng*hr/mL, 572 ng*hr/mL, 42.8 ng*hr/mL and 9.94 ng*hr/mL, respectively. Compared to the intravenous injection data, the oral bioavailabilities in rats were 6.84%, 23.2%, 9.52% and 5.2%, respectively.

Pharmacokinetic Experiment in Cynomolgus Monkeys 3 male cynomolgus monkeys were administered intravenously (iv, 1 mg/kg, n=3) at a single dose once, followed by elution for one week, and then were administered orally (po, 10 mg/kg, n=3). For intravenous injection, the compounds were prepared into a 1.0 mg/mL solution with water or 10% DMSO/30% PEG400/water, and the solution was administered at a volume of 1 mL/kg. For oral administration, the compounds were prepared into a 2.0 mg/mL solution or suspension with water or 0.5% methylcellulose/1.7 meq 1 N hydrochloric acid, and the solution or suspension was administered at a volume of 5 mL/kg.

After administration, blood samples for intravenous injection and oral administrations were collected at 0.0833 h, 0.25 h, 0.5 h, 1 h, 2 h, 4 h, 8 h, 12 h and 24 h, and concentrations of the compounds in the samples were measured using LC-MS/MS with a lower limit of determination of 1 ng/mL, and the pharmacokinetic parameters of the compounds were calculated using the WinNolin non-compartmental model.

Results

After intravenous administration, the in vivo exposures ($AUC_{last}$) of A1 and A2 were 881 hr*ng/mL and 949 hr*ng/mL, respectively, and the average total clearances (CLs) were 18.9 mL/min/kg and 16.7 mL/min/kg, respectively.

After oral administration, the in vivo exposures ($AUC_{last}$) of A1 and A2 were 388 ng*hr/mL and 1758 ng*hr/mL, respectively. Compared to the date of intravenous injection, the oral bioavailabilities in cynomolgus monkeys were 4.61% and 18.8%, respectively.

The above description is only for the purpose of illustrating the preferred example of the present invention, and is not intended to limit the scope of the present invention. Any modifications, equivalents and the like made without departing from the spirit and principle of the present invention should be included in the protection scope of the present invention.

The foregoing examples and methods described herein may vary based on the abilities, experience, and preferences of those skilled in the art.

The certain order in which the steps of the method are listed in the present invention does not constitute any limitation on the order of the steps of the method.

The invention claimed is:

1. A compound selected from the following structures, or a pharmaceutically acceptable salt thereof:

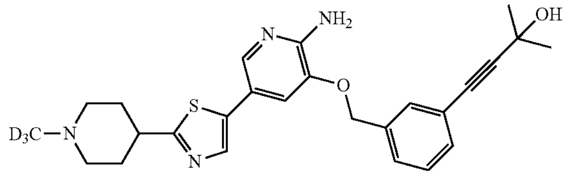

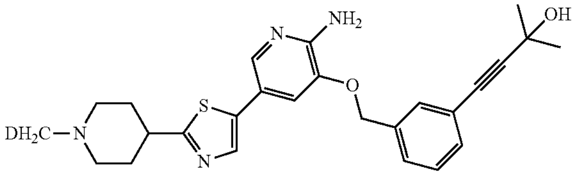

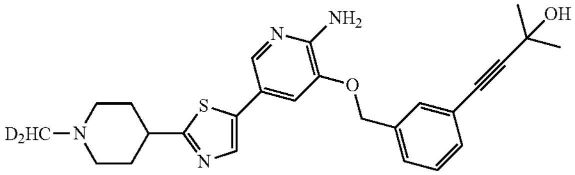

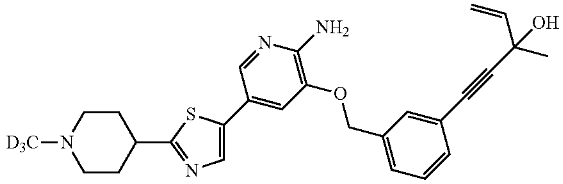

-continued

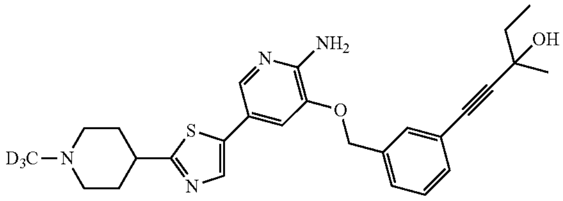

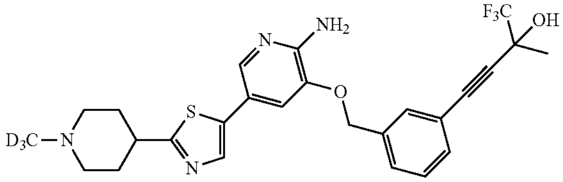

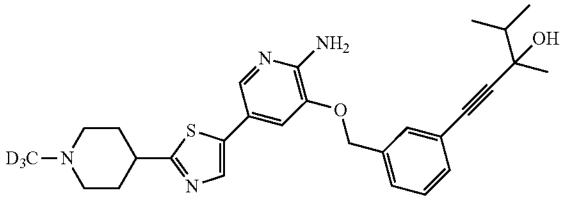

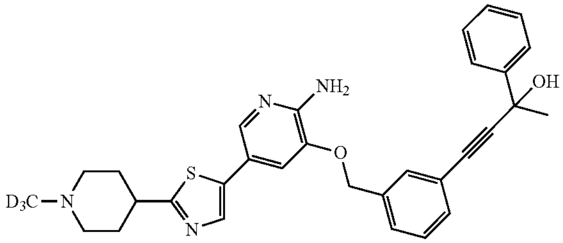

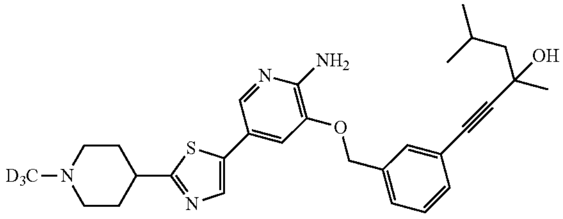

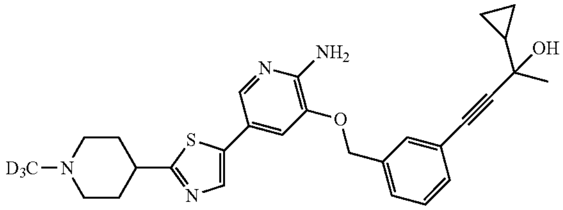

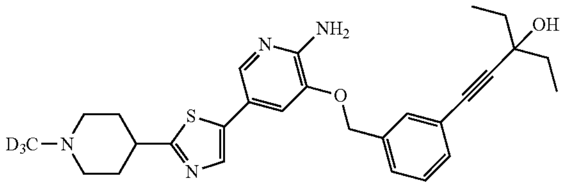

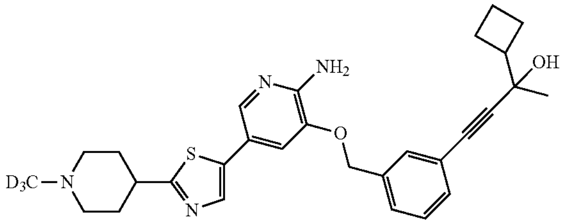

-continued
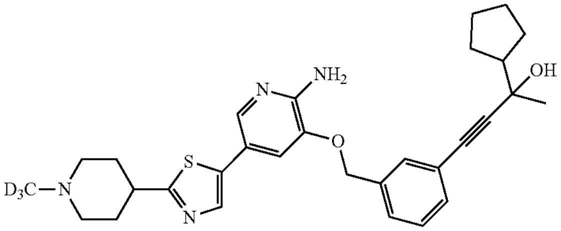
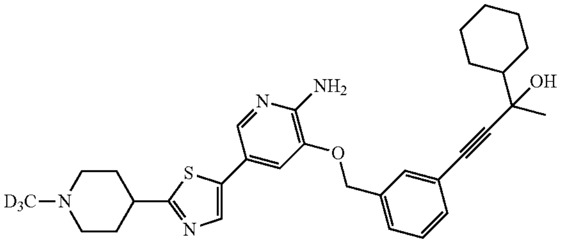
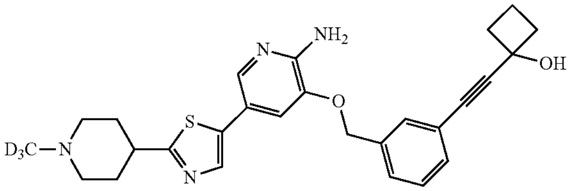
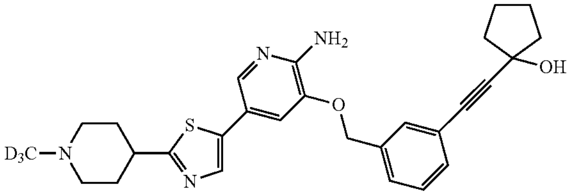
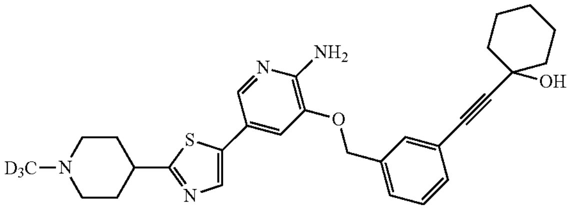
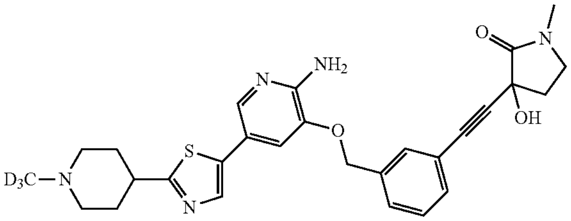
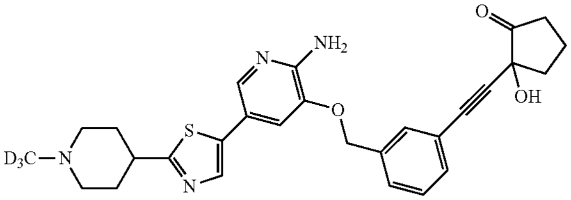
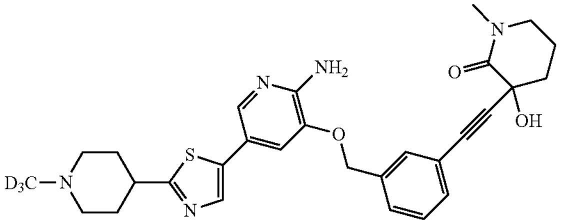
-continued
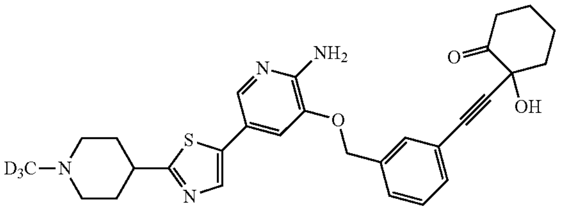
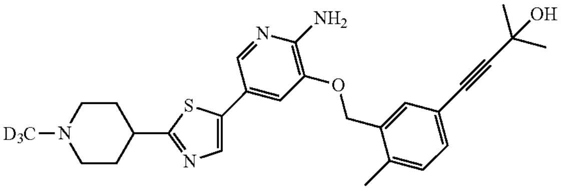
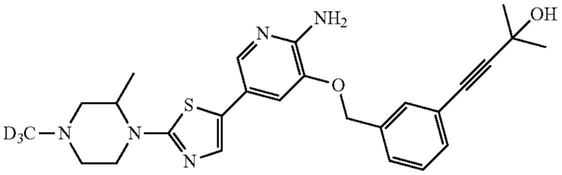
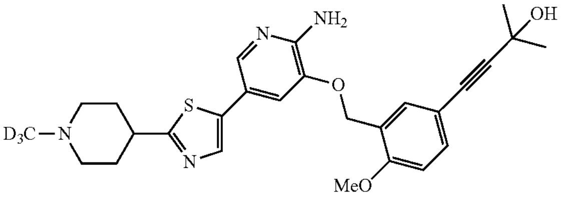 [SMILES: [2H]C([2H])([2H])N1CCC(c2ncc(-c3cnc(N)c(OCc4cc(C#CC(C)(C)O)ccc4C#N)c3)s2)CC1]
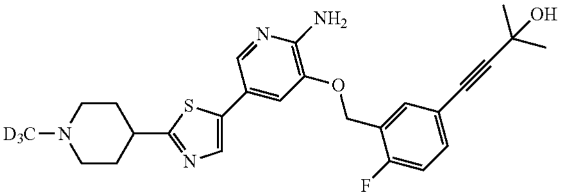 [SMILES: [2H]C([2H])([2H])N1CCC(c2ncc(-c3cnc(N)c(OCc4cc(C#CC(C)(C)O)ccc4Cl)c3)s2)CC1]
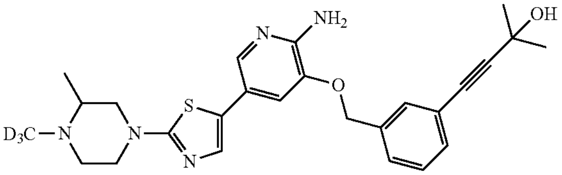
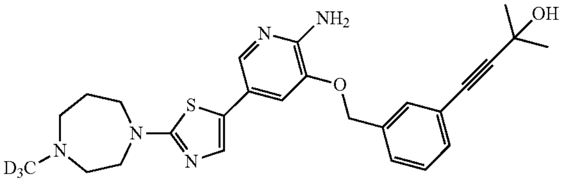
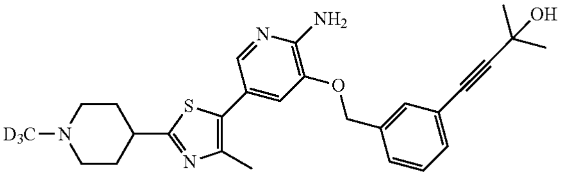
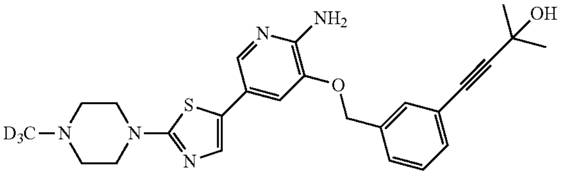

-continued
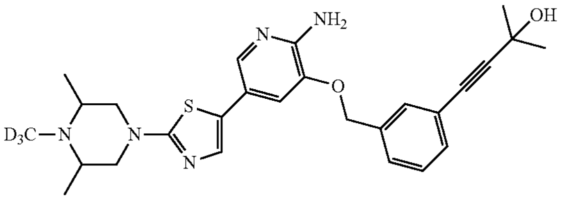
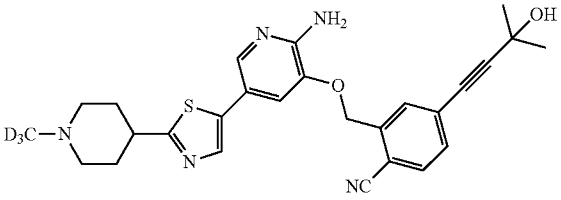
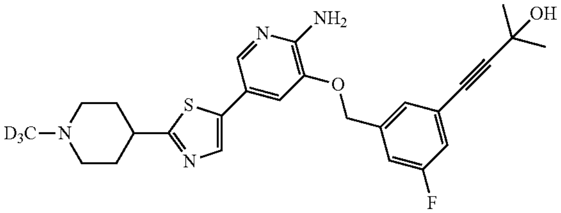
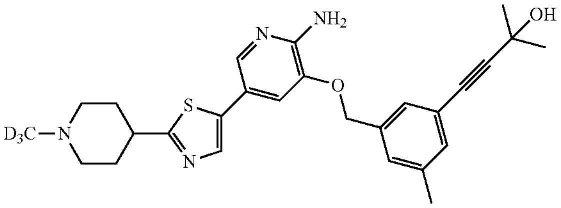
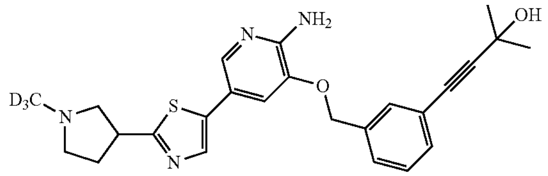
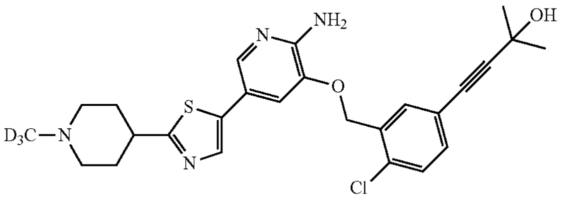
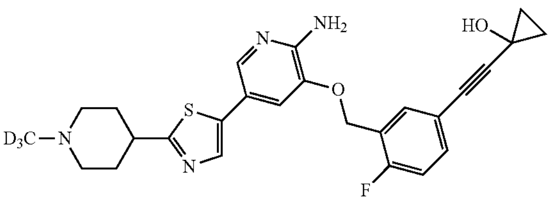
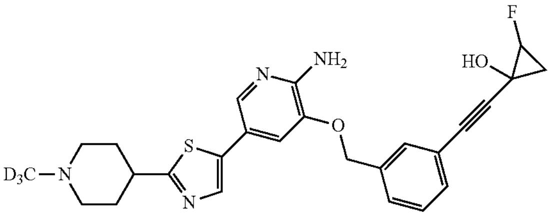
-continued
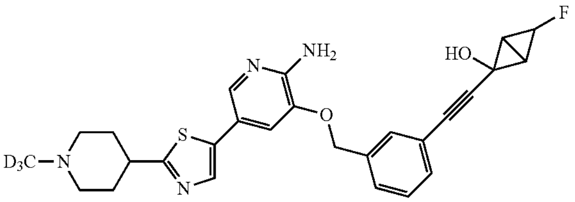
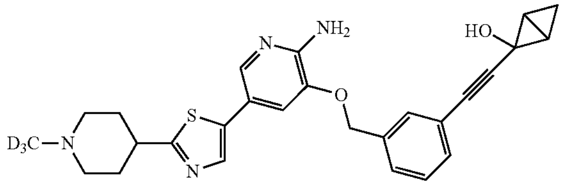
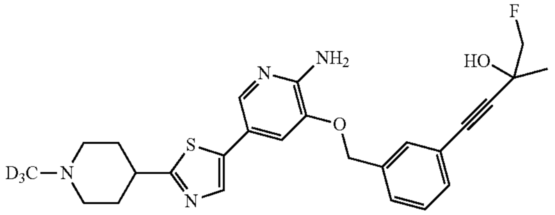
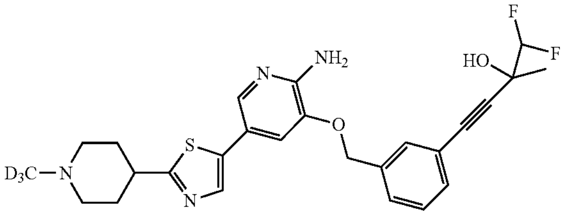
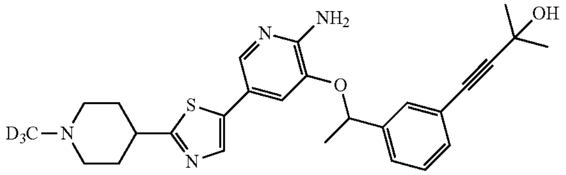
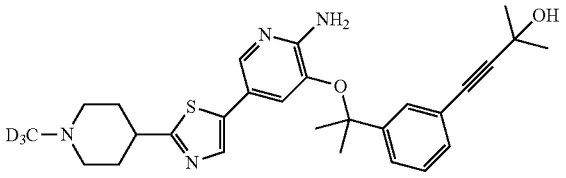
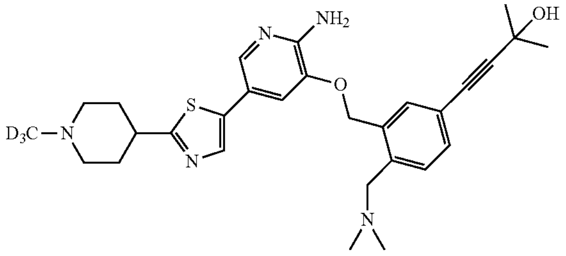
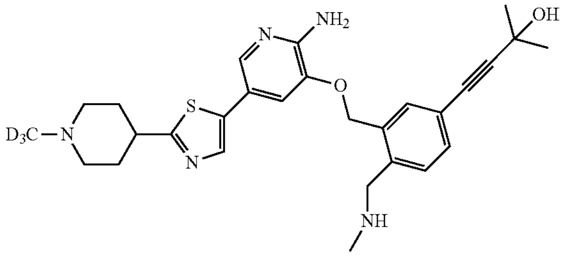

-continued
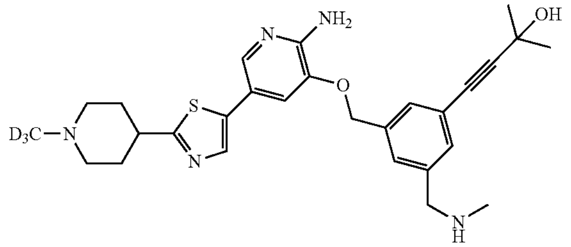
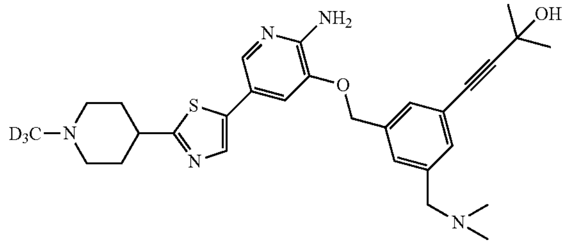
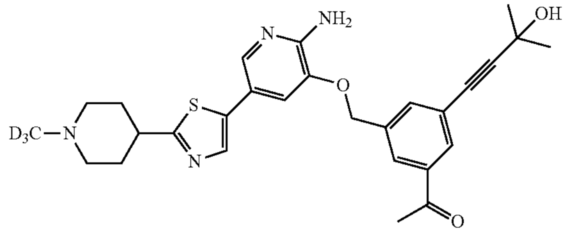
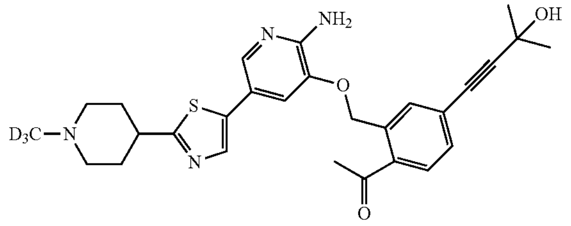
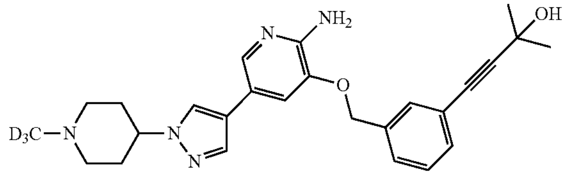
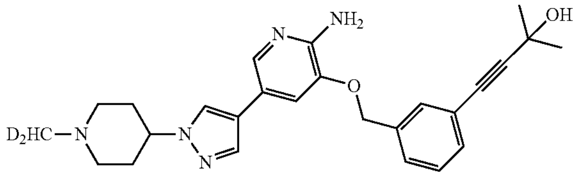
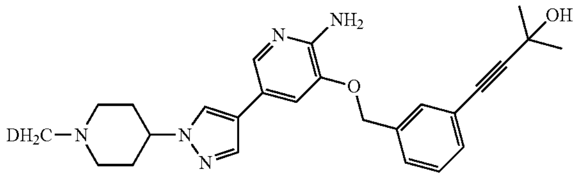
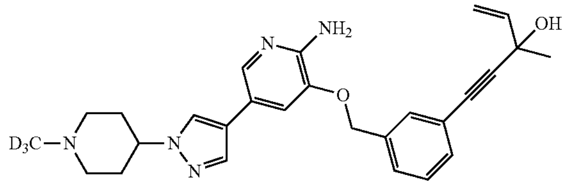
-continued
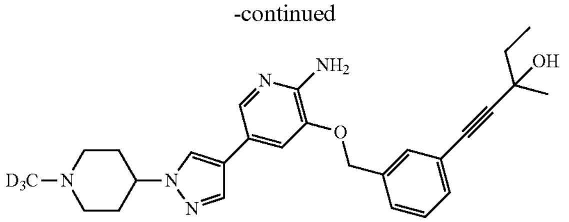
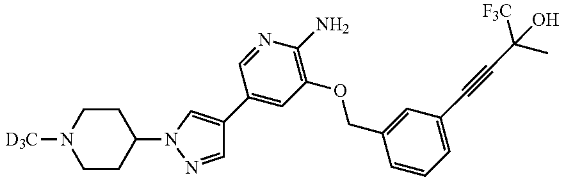
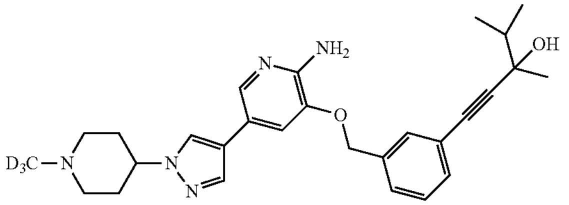
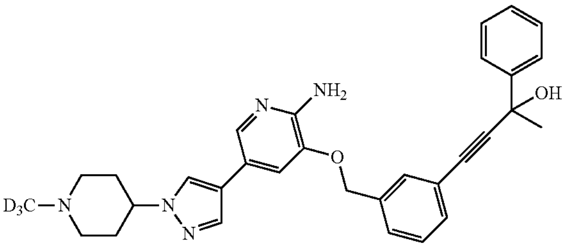
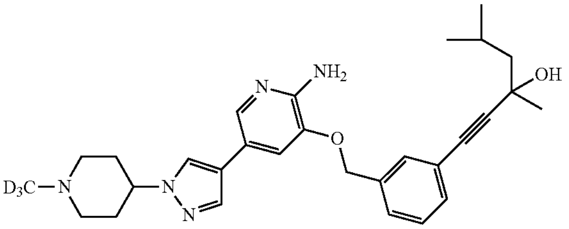
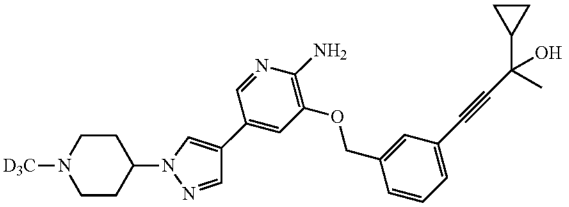
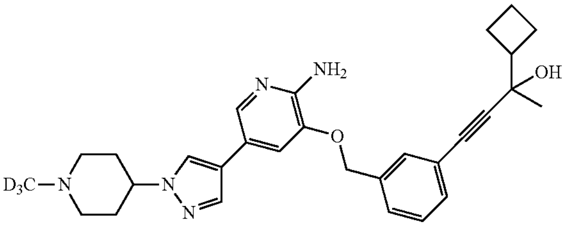
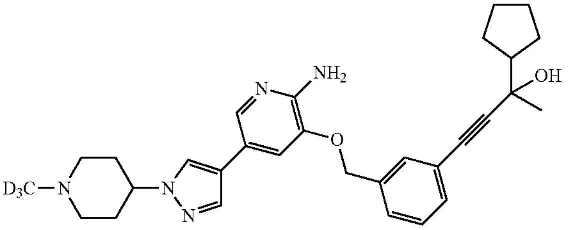

-continued
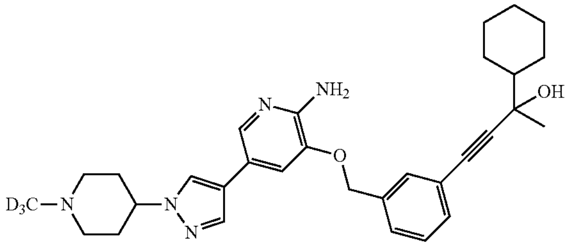
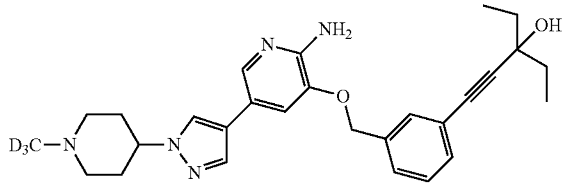
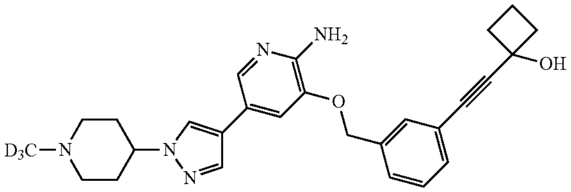
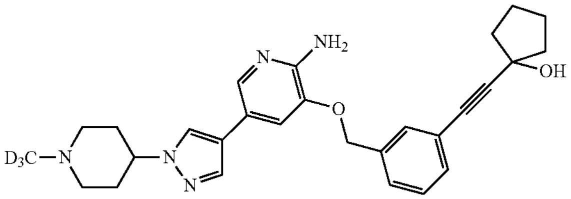
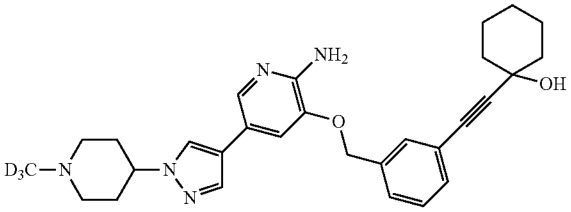
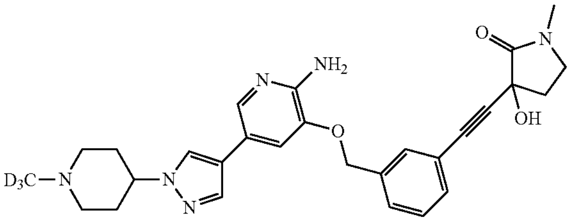
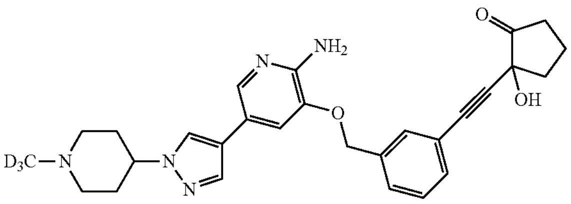
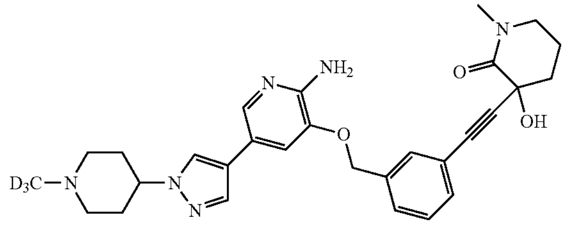
-continued
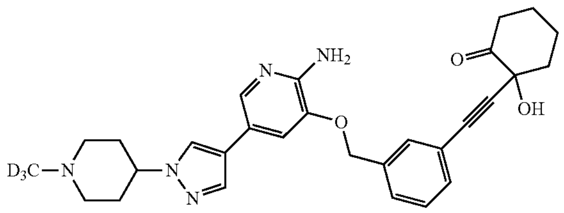
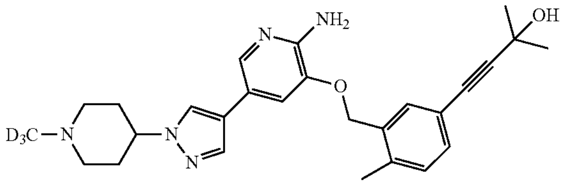
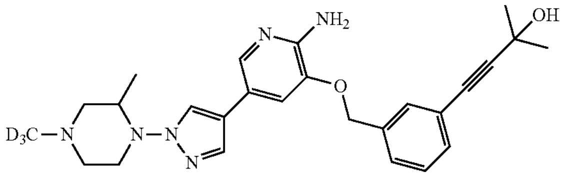
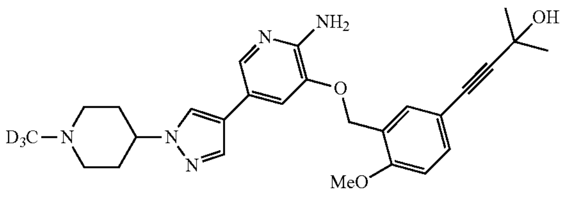
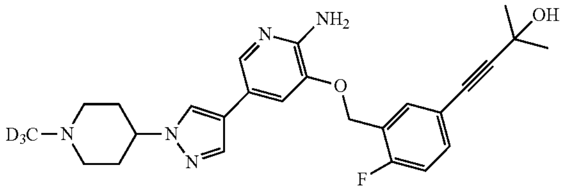
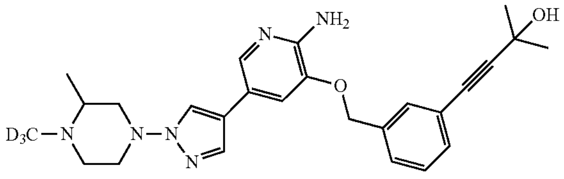
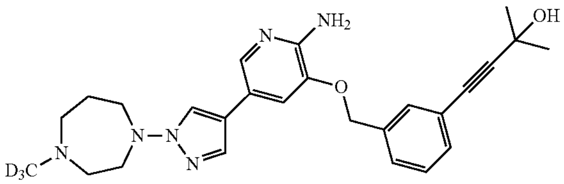
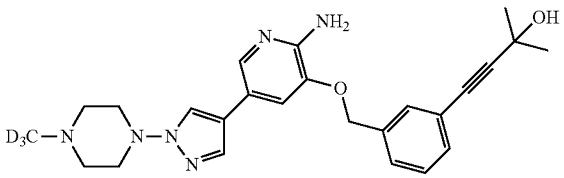
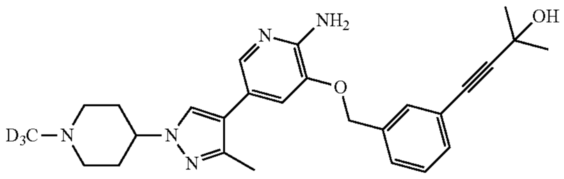

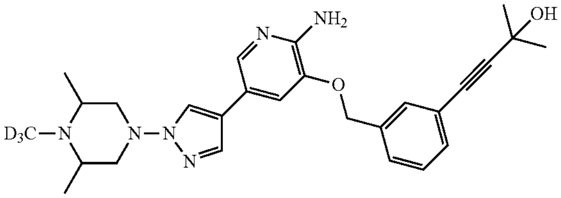
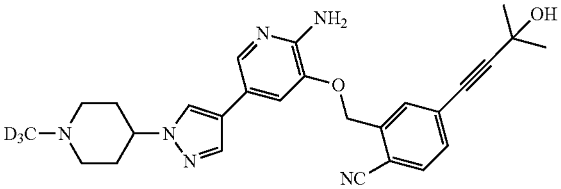
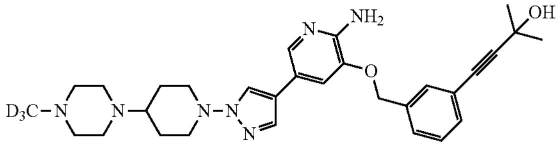
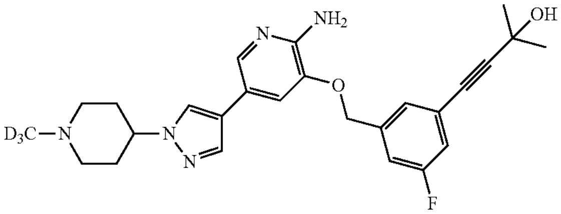
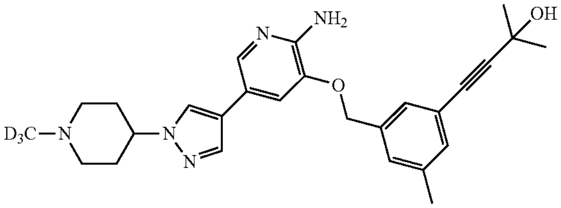
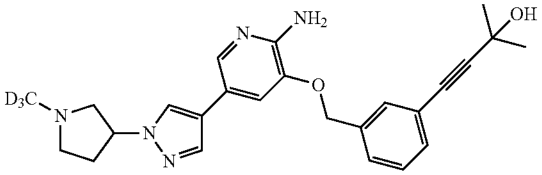
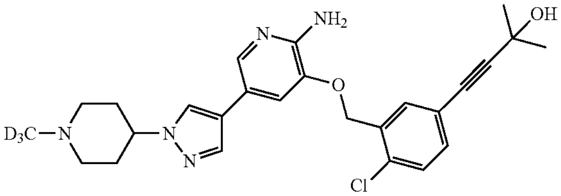
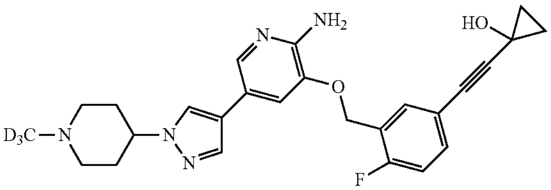
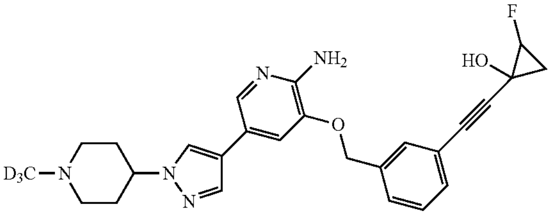
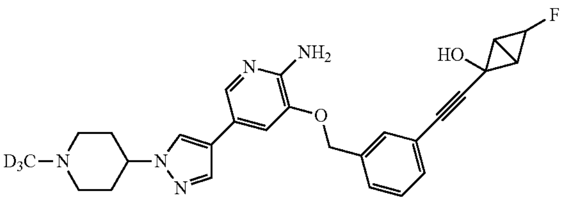
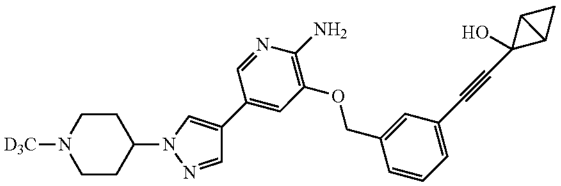
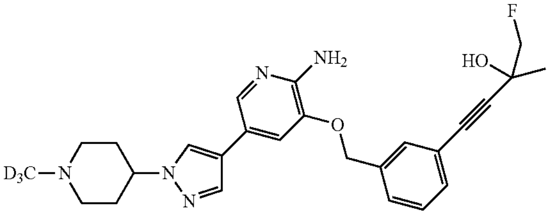
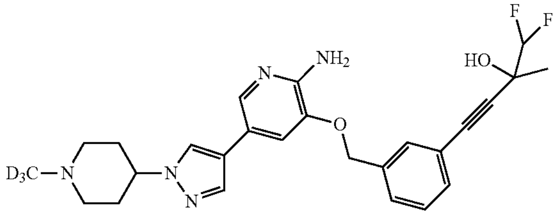
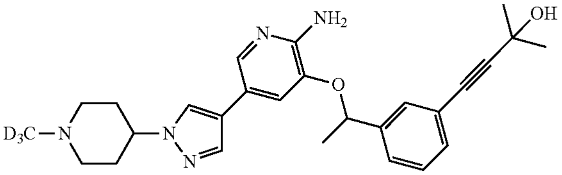
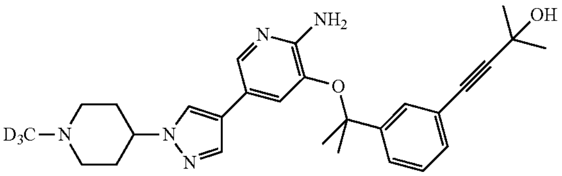
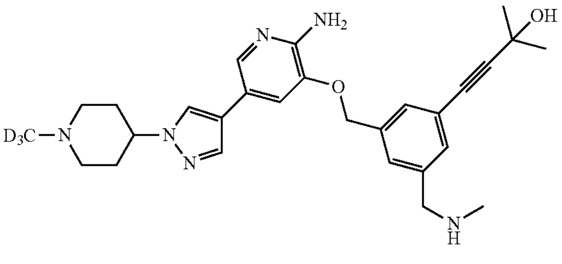
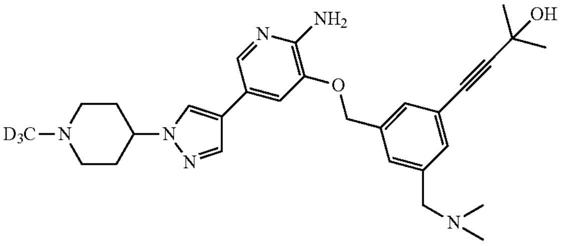

-continued
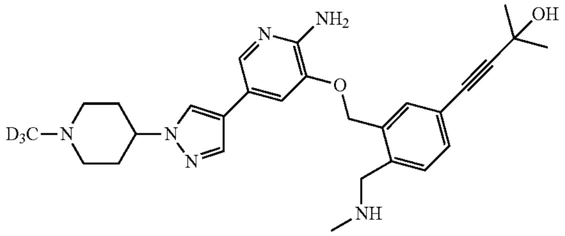
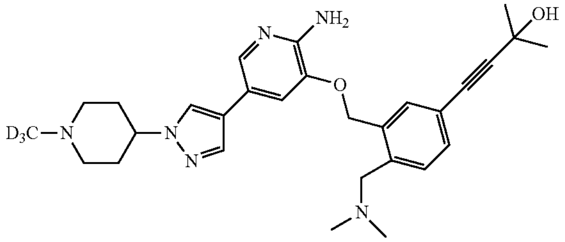
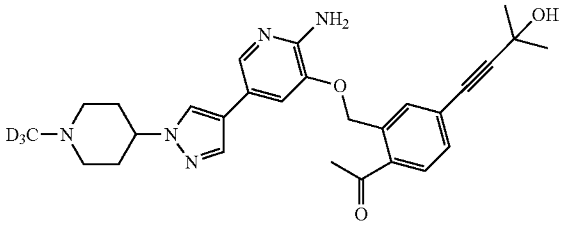
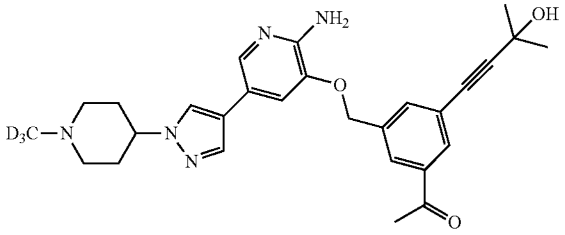
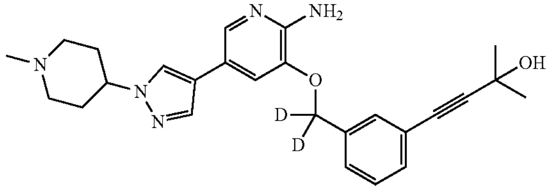
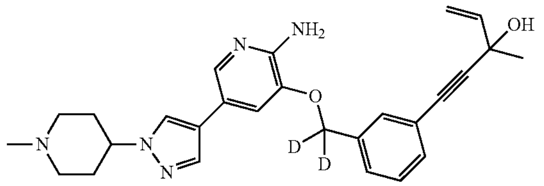
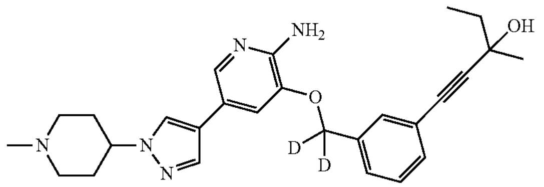
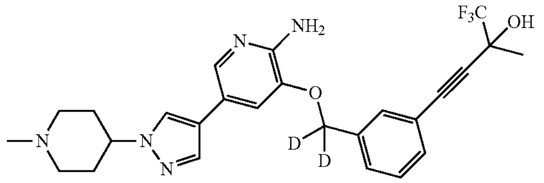
-continued
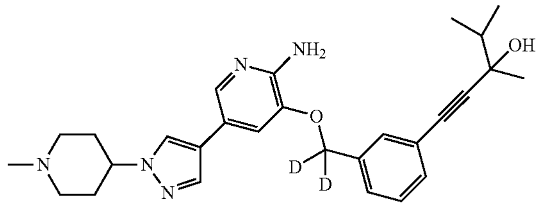
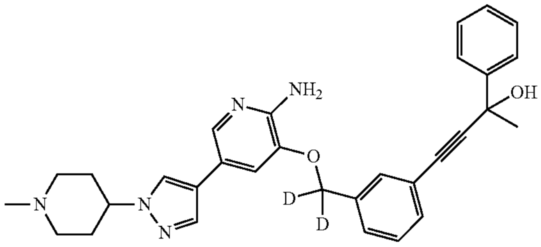
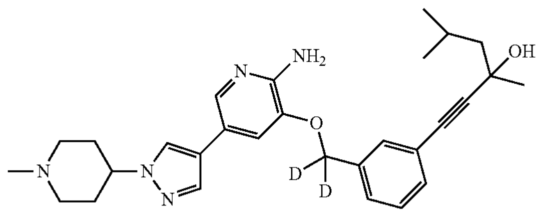
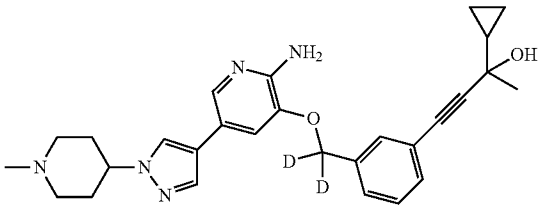
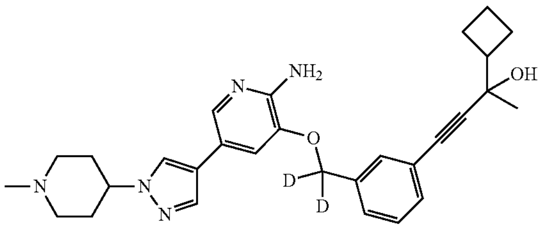
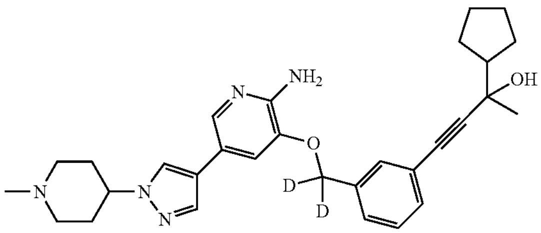
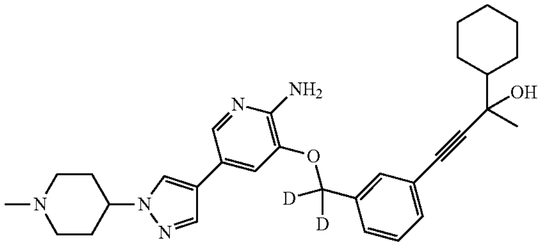

-continued
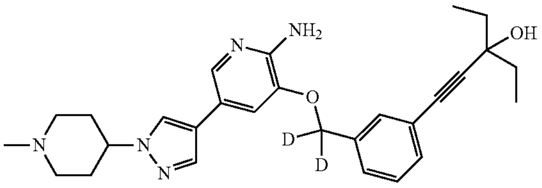
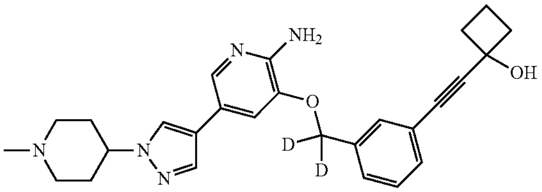
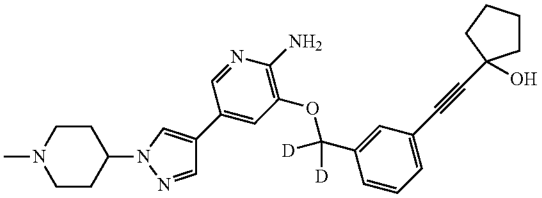
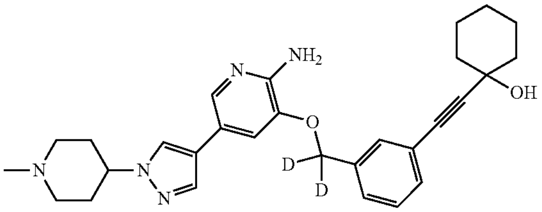
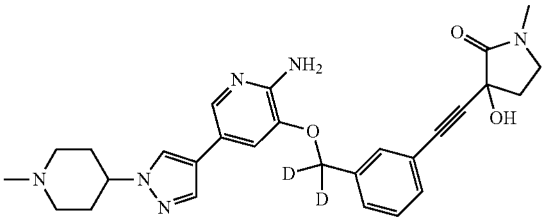
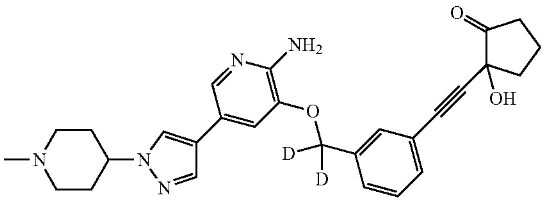
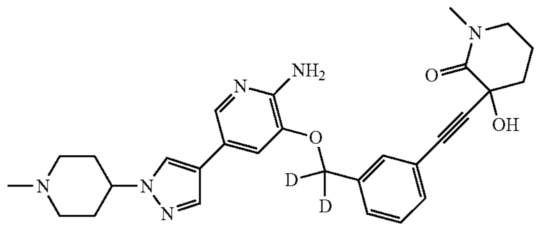
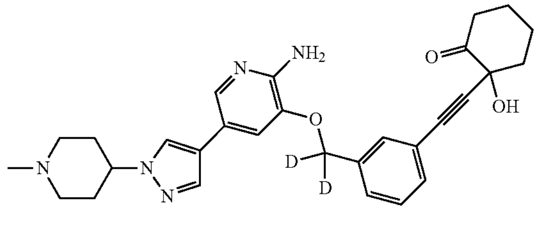
-continued
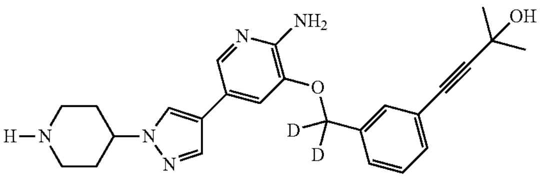
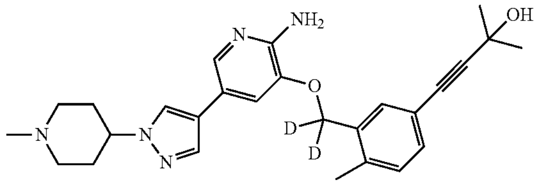
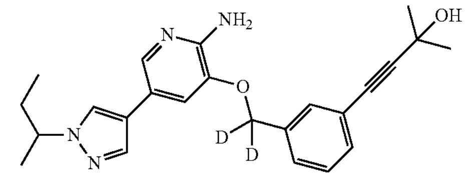
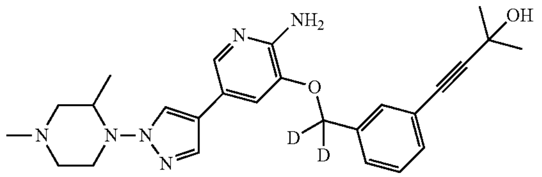
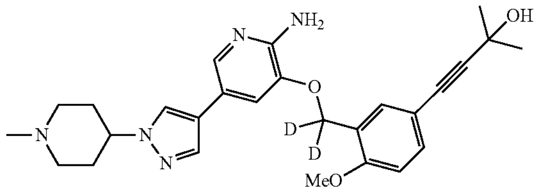
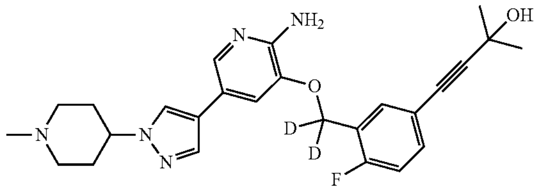
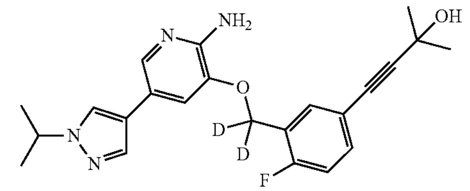
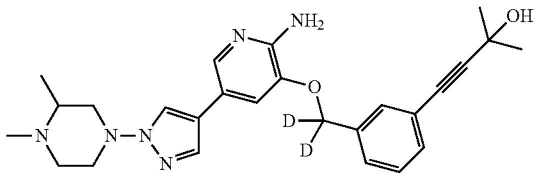
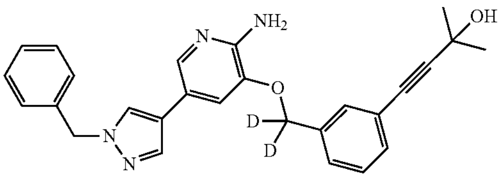

-continued
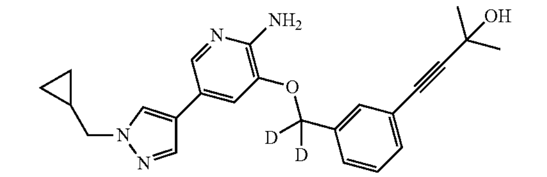
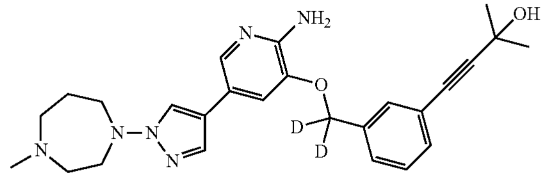
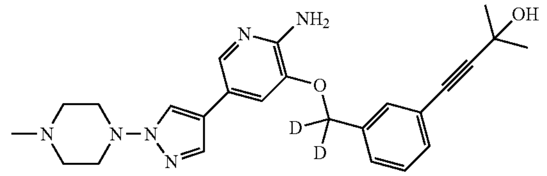
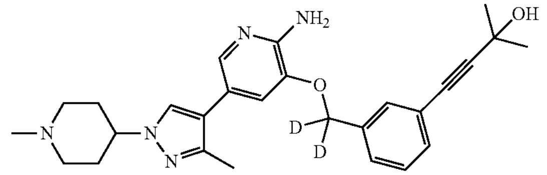
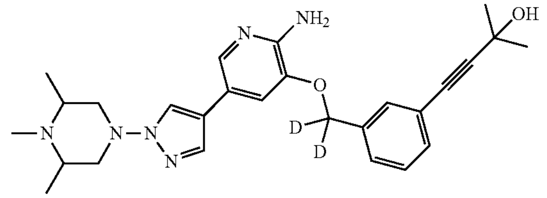
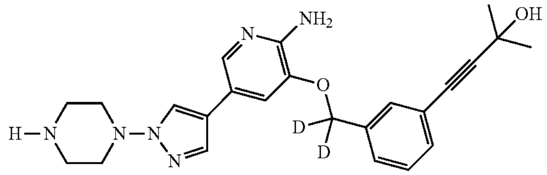
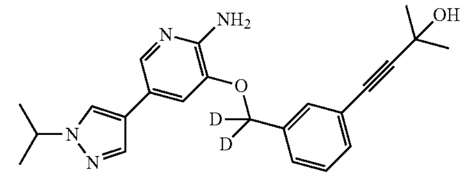
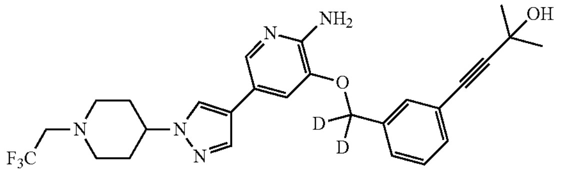
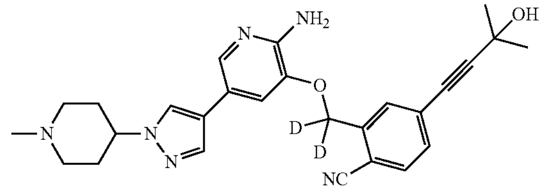
-continued
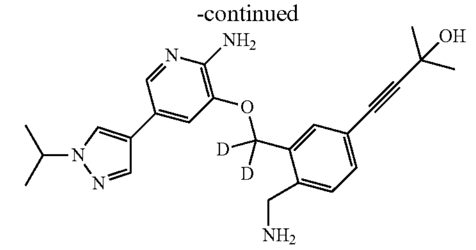
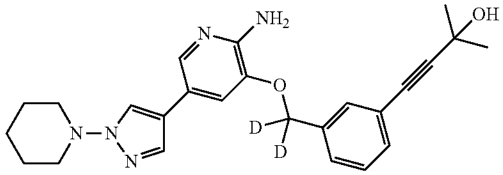
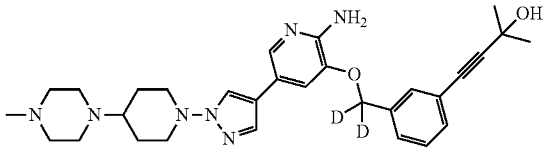
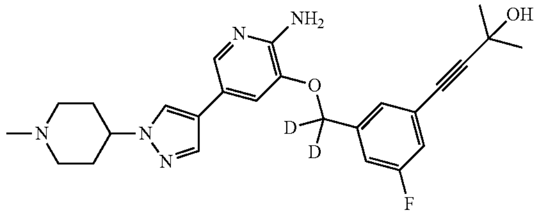
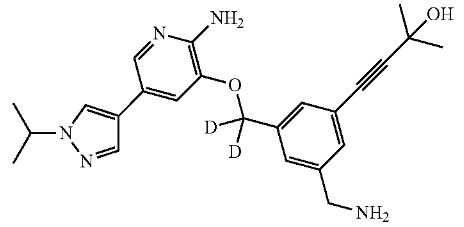
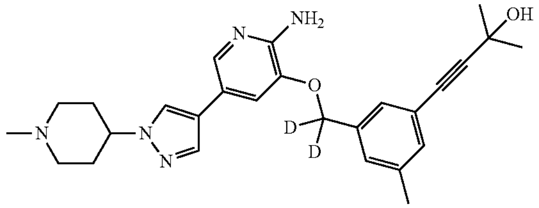
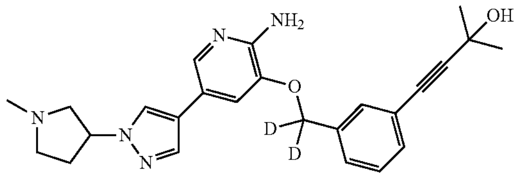
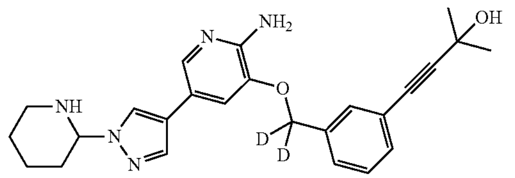
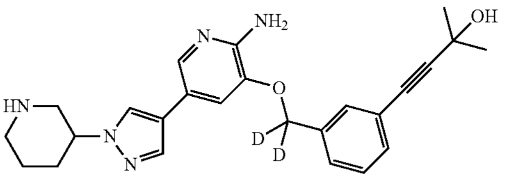

-continued
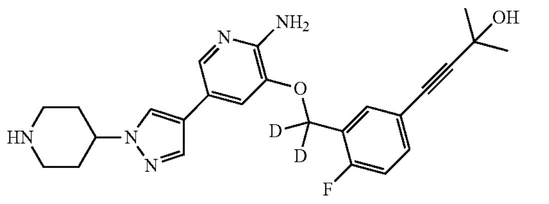
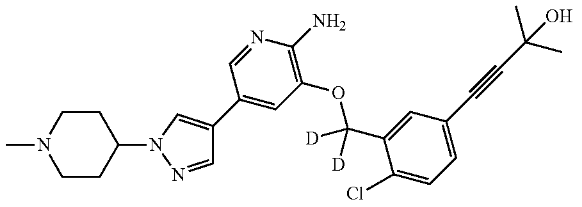
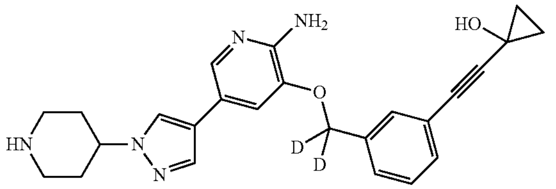
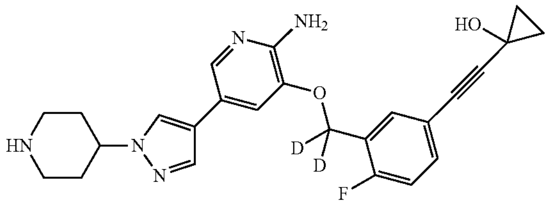
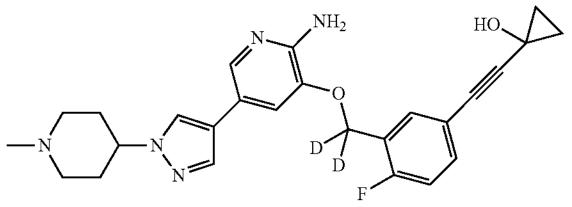
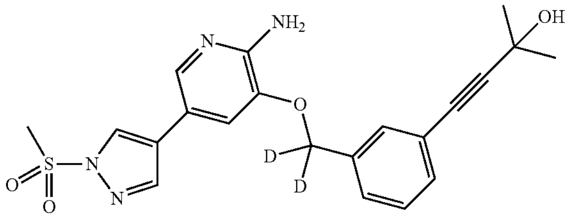
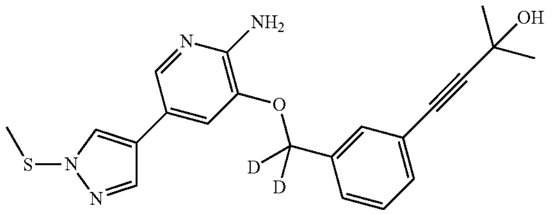
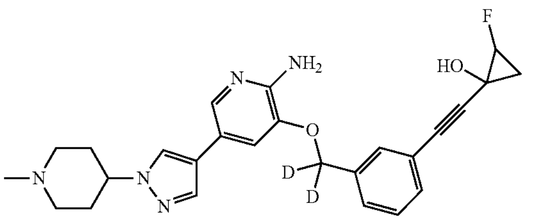
-continued
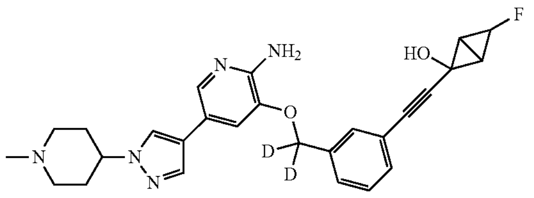
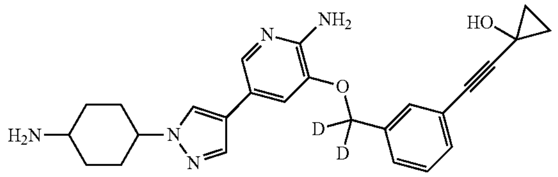
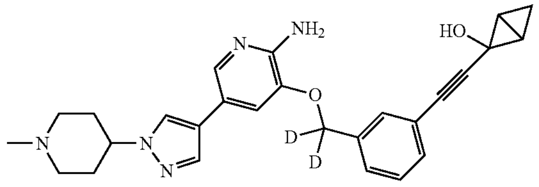
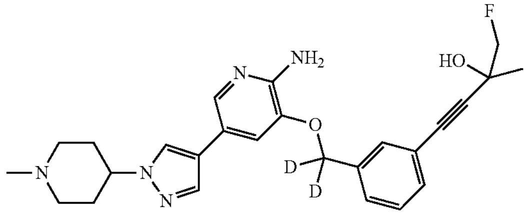
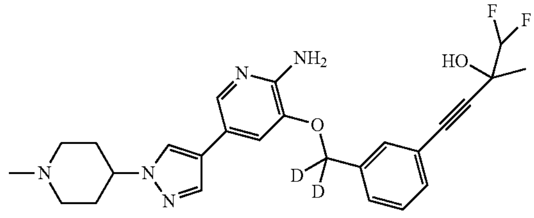
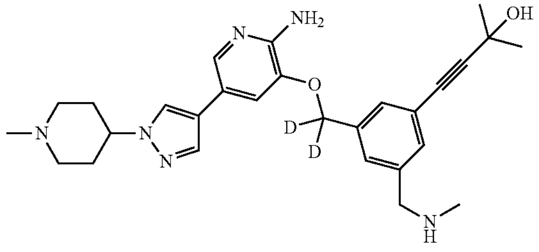
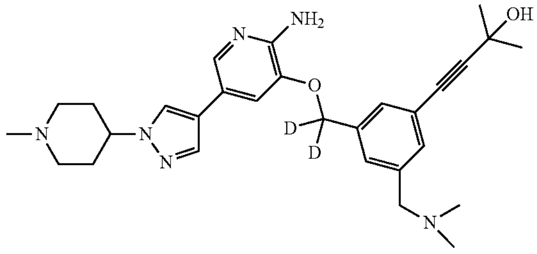
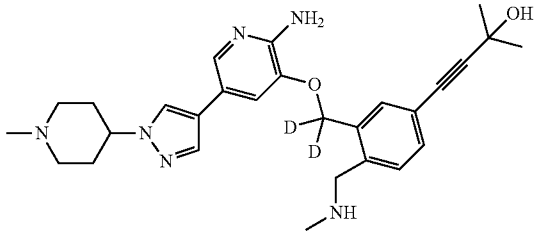

-continued
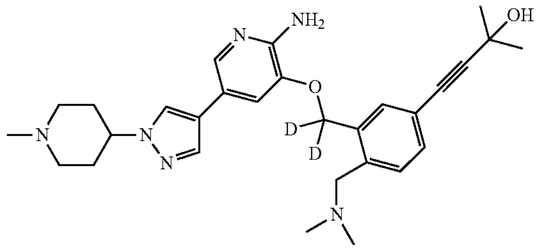
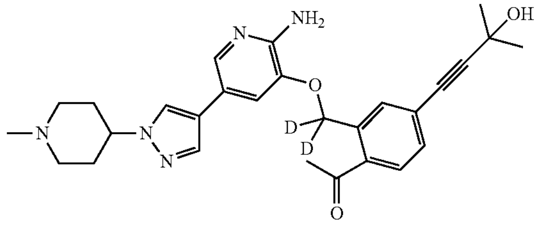
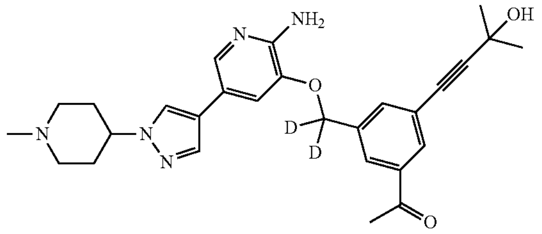
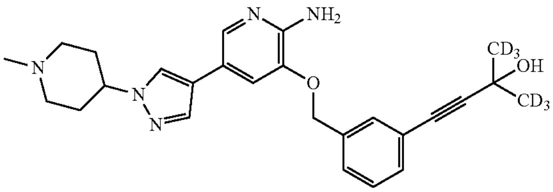
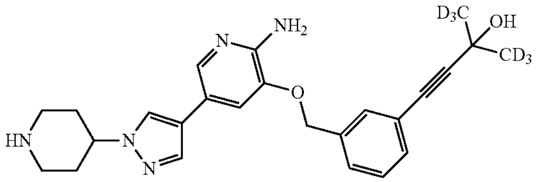
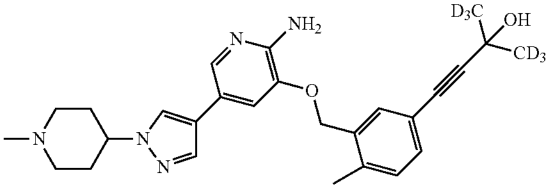
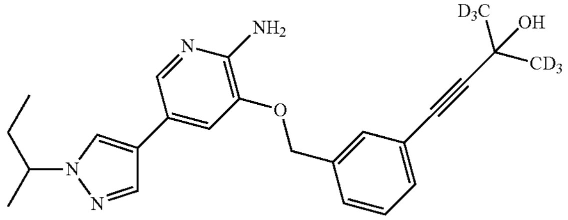
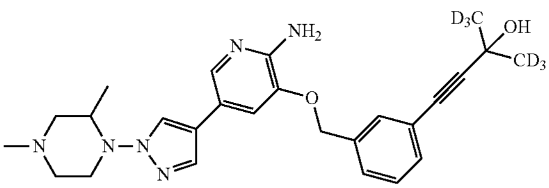
-continued
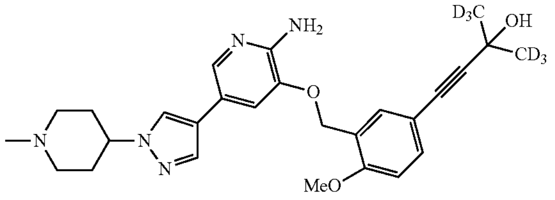
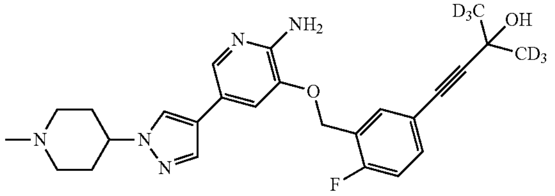
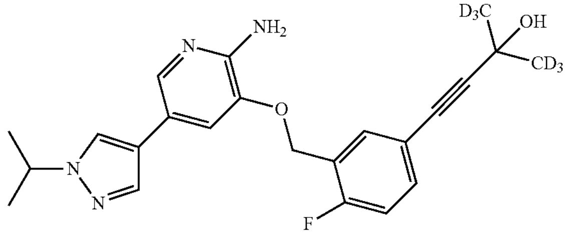
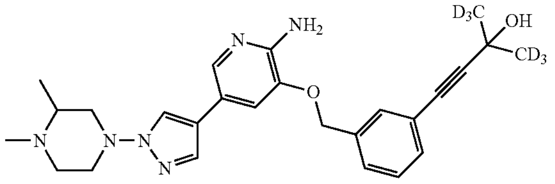
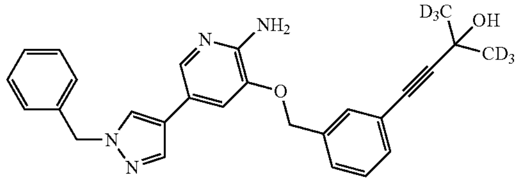
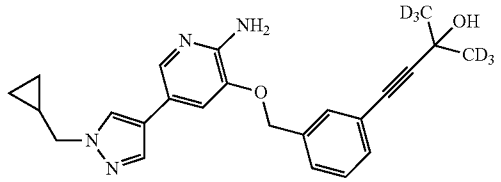
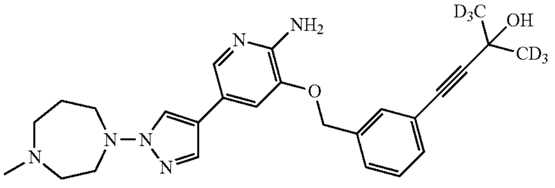
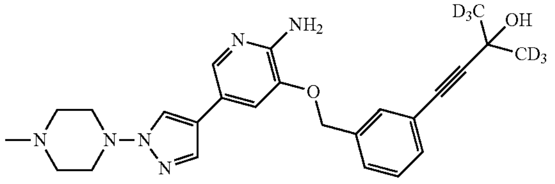
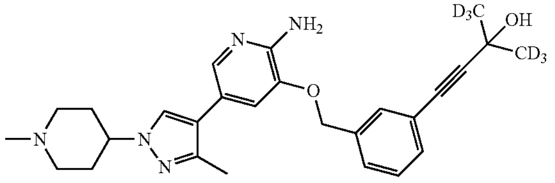

-continued
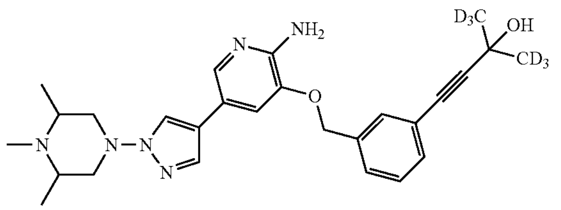
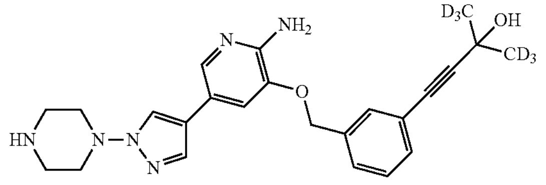
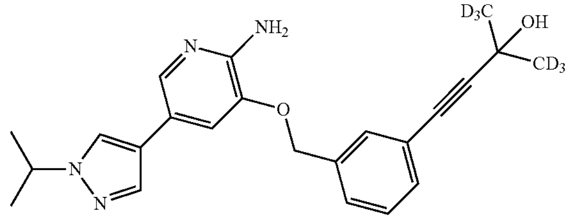
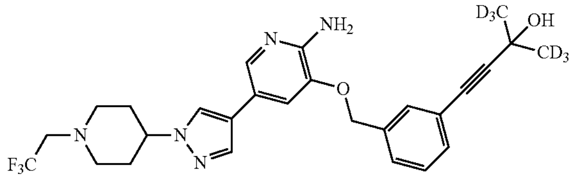
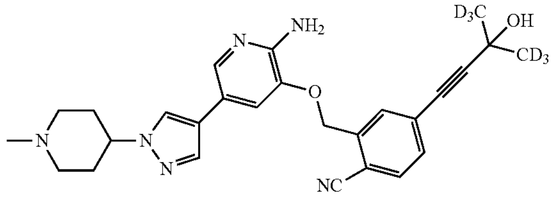
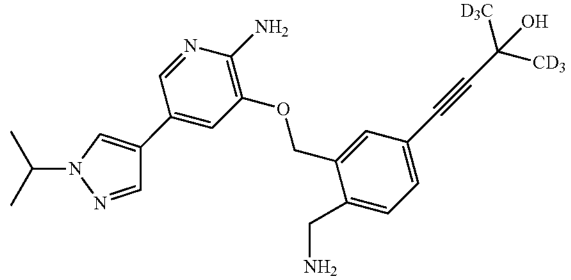
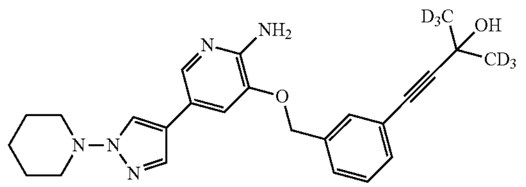
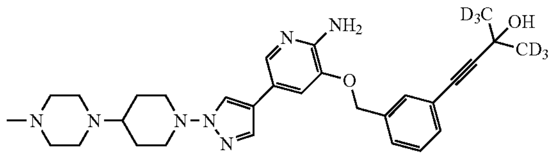
-continued
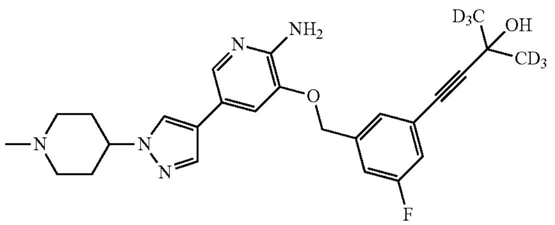
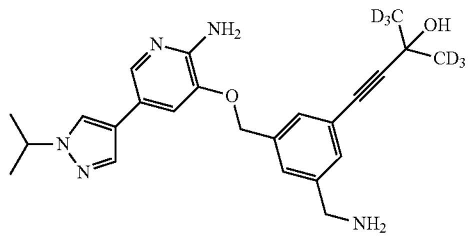
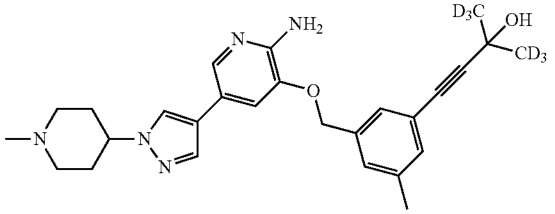
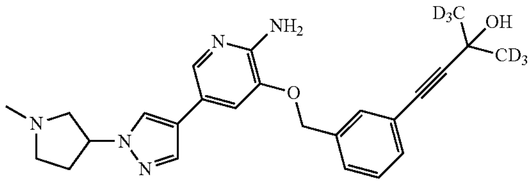
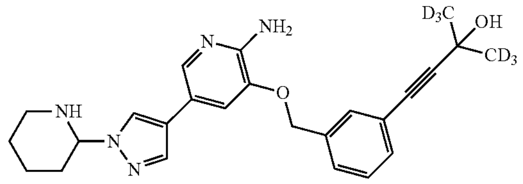
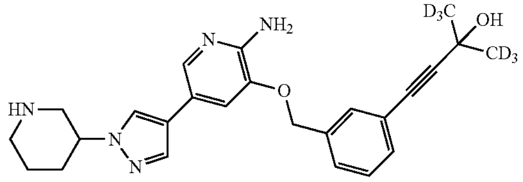
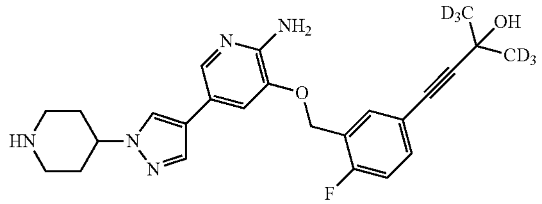
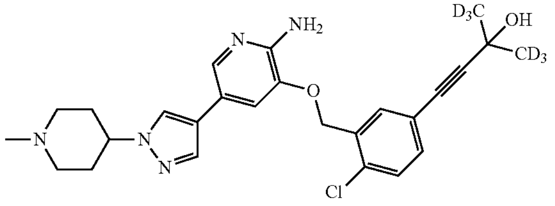

-continued
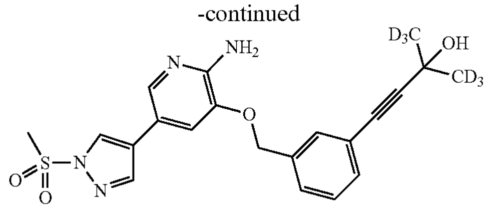
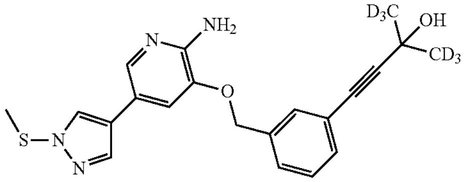
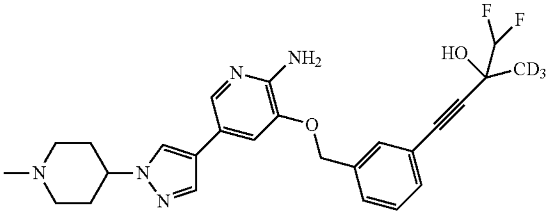
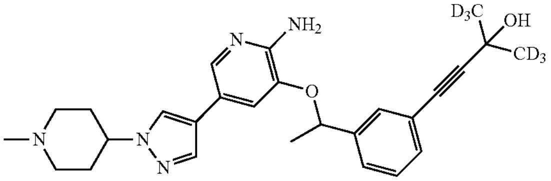
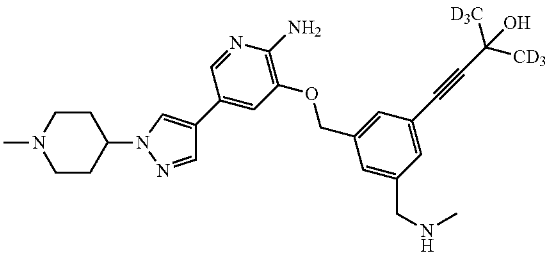
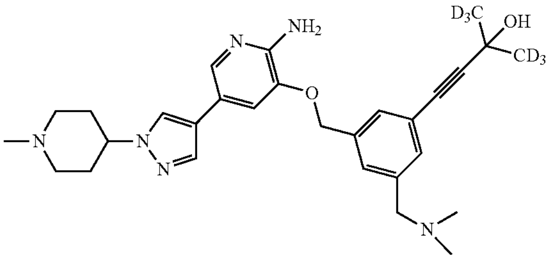
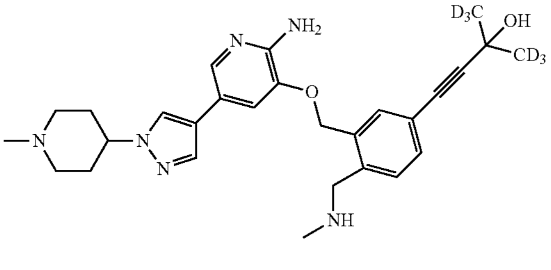
-continued
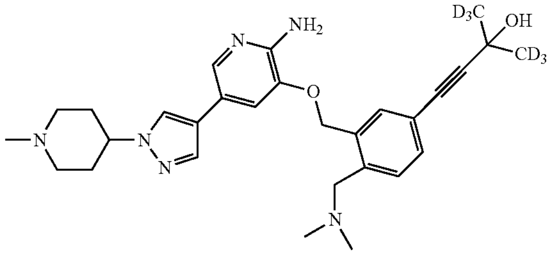
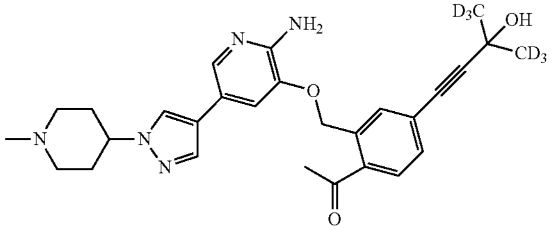
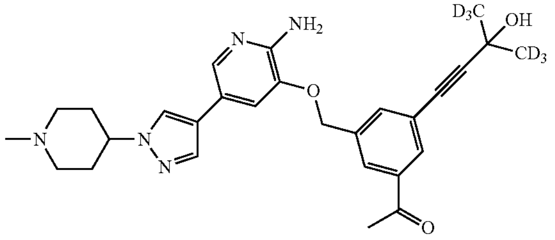
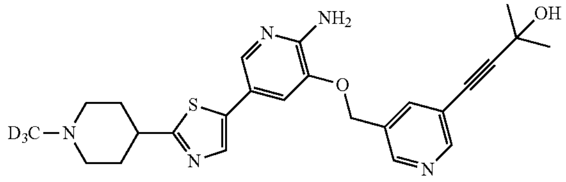
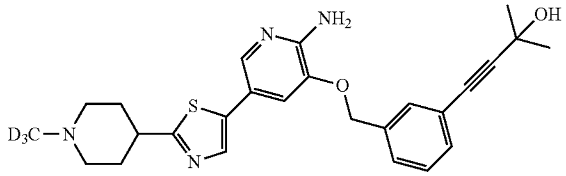
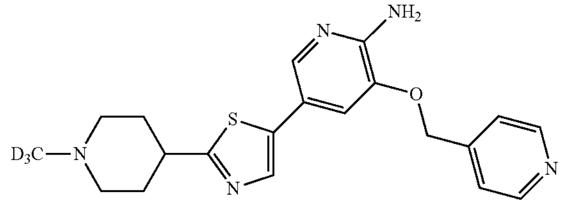
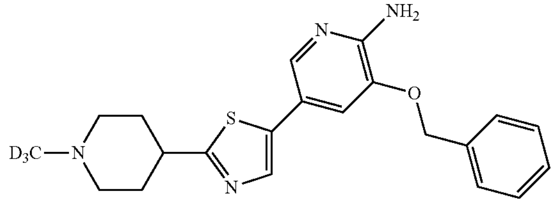
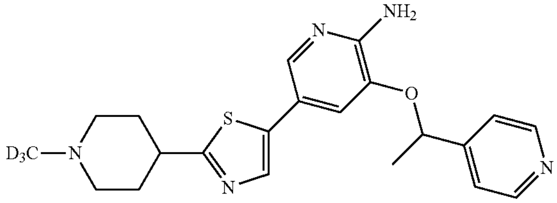

-continued
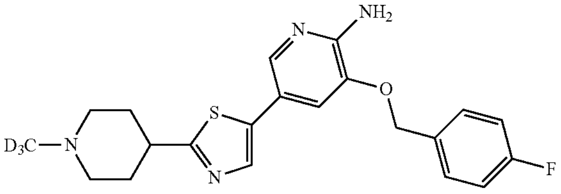
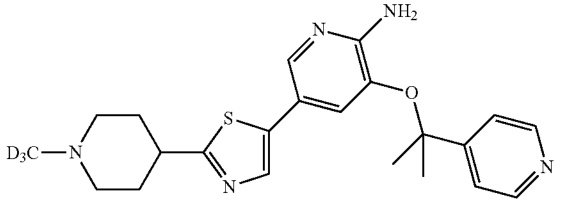
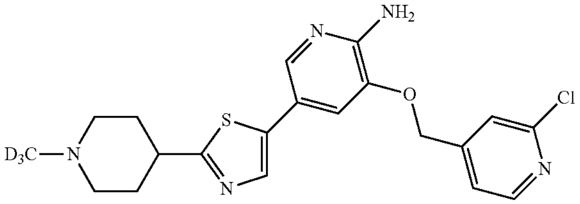
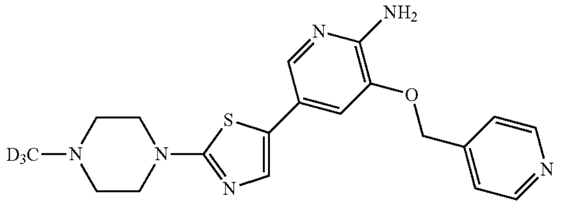
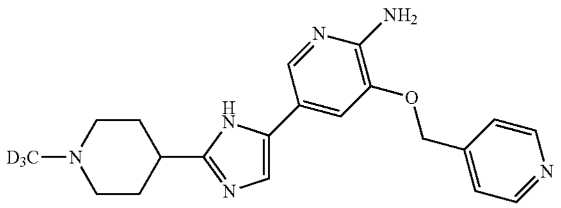
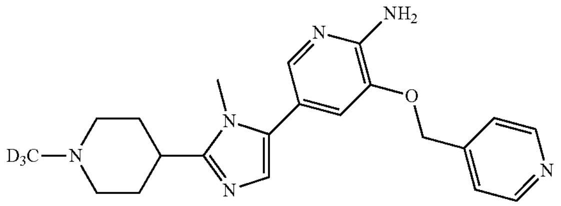
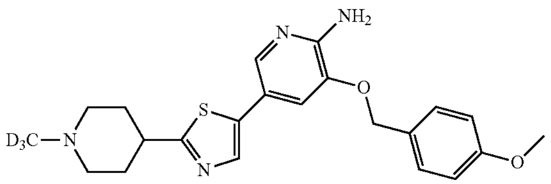
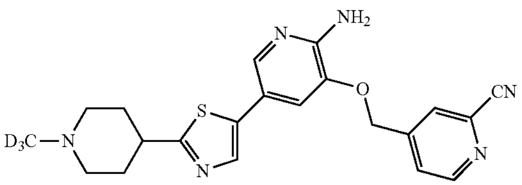
-continued
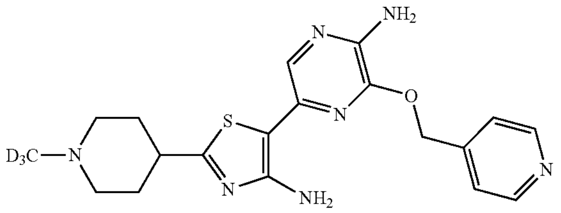
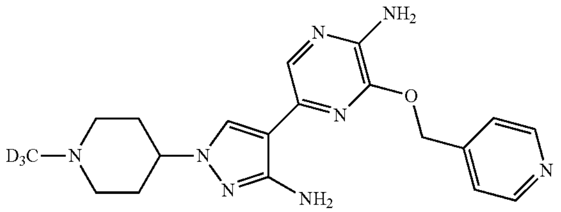
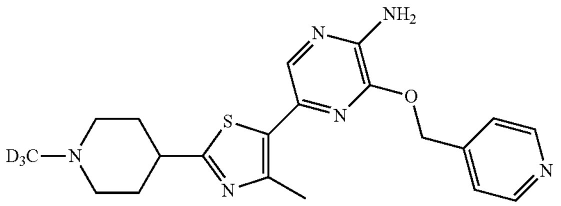
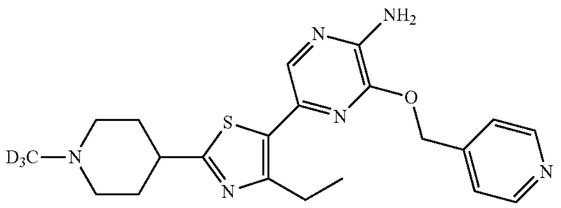
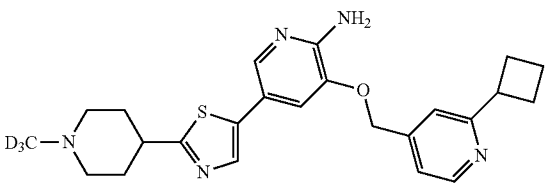
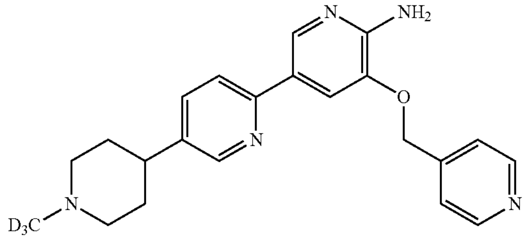
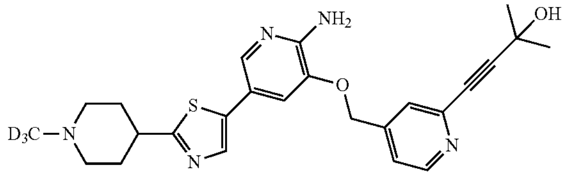
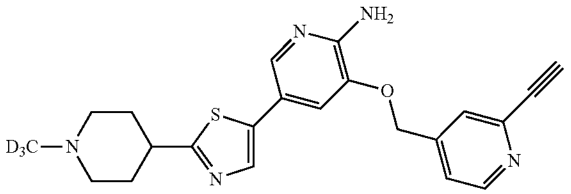

-continued

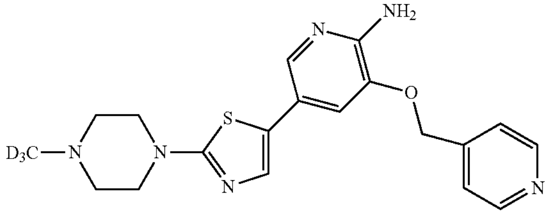

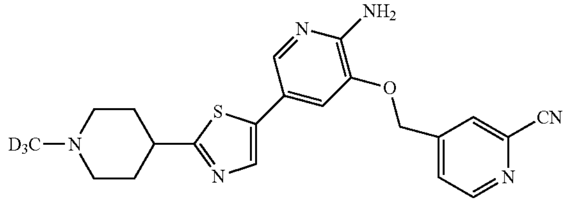

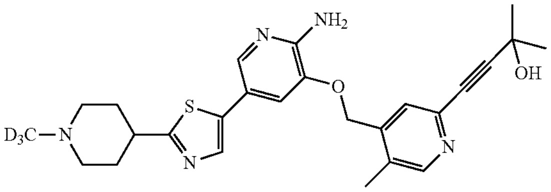

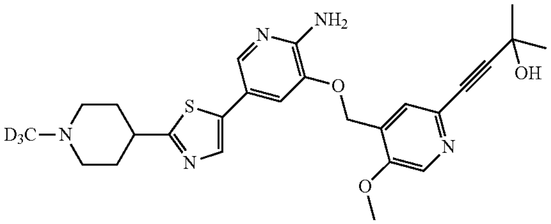

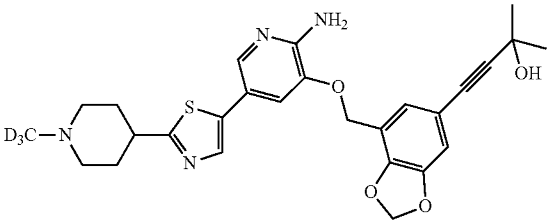

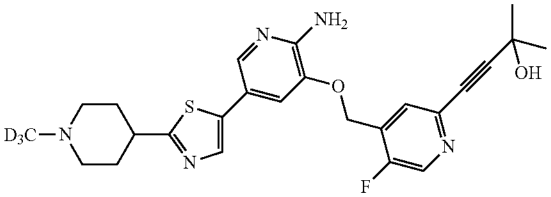

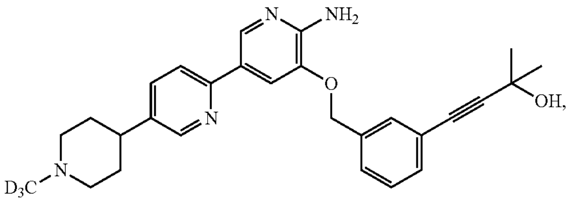

,

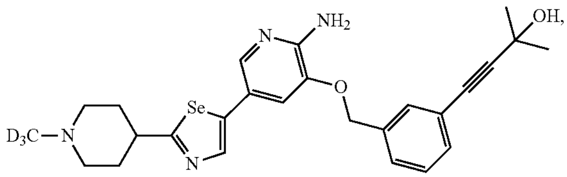

-continued

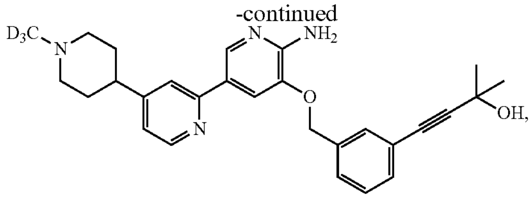

, and

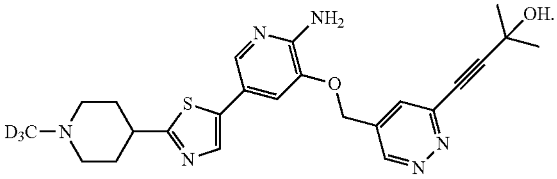

.

2. A crystalline form of 4-(3-(((2-amino-5-(1-(1-trideuteromethylpiperidin-4-yl)-1H-pyrazol-4-yl)pyridin-3-yl)oxy)methyl)phenyl)-2-methylbut-3-yn-2-ol, characterized by an XRPD pattern having characteristic peaks at at least three of positions having 2θ values of 13.1°±0.2°, 16.3°±0.2°, 17.5°±0.2° and 23.8°±0.2°.

3. The crystalline form according to claim 2, wherein the XRPD pattern of the crystalline form further has characteristic peaks at at least three of positions having 2θ values of 8.1°±0.2°, 12.2°±0.2°, 15.3°±0.2°, 18.0°±0.2°, 19.3°±0.2°, 19.5°±0.2°, 21.3°±0.2° and 21.6°±0.2°.

4. The crystalline form according to claim 2, wherein the crystalline form has an XRPD pattern substantially as shown in FIG. 1.

5. A crystalline form of 4-(3-(((2-amino-5-(1-(1-trideuteromethylpiperidin-4-yl)-1H-pyrazol-4-yl)pyridin-3-yl)oxy)methyl)phenyl)-2-methylbut-3-yn-2-ol, characterized by an XRPD pattern having characteristic peaks at at least three of positions having 2θ values of 5.7°±0.2°, 11.3°±0.2°, 22.7°±0.2° and 23.5°±0.2°.

6. The crystalline form according to claim 5, wherein the XRPD pattern of the crystalline form further has characteristic peaks at at least three of positions having 2θ values of 7.1°±0.2°, 8.8°±0.2°, 14.1°±0.2°, 17.0°±0.2°, 18.0°±0.2° and 18.8°±0.2°.

Figure 6:
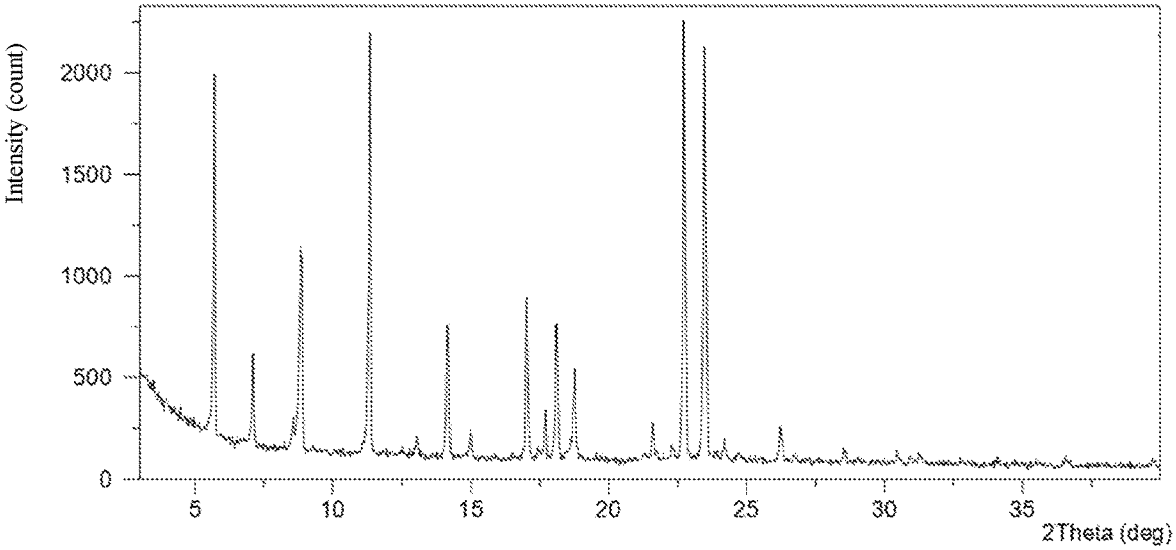
FIG. 6 shows the XRPD pattern of free base crystalline form B of compound A2.

7. The crystalline form according to claim 5, wherein the crystalline form has an XRPD pattern substantially as shown in FIG. 6.

8. A crystalline form of 4-(3-(((2-amino-5-(1-(1-trideuteromethylpiperidin-4-yl)-1H-pyrazol-4-yl)pyridin-3-yl)oxy)methyl)phenyl)-2-methylbut-3-yn-2-ol hydrochloride, characterized by an XRPD pattern having characteristic peaks at at least three of positions having 2θ values of 13.0°±0.2°, 16.3°±0.2°, 17.5°±0.2°, 19.4°±0.2° and 23.8°±0.2°.

9. The crystalline form according to claim 8, wherein the XRPD pattern of the crystalline form further has characteristic peaks at at least three of positions having 2θ values of 8.1°±0.2°, 12.1°±0.2°, 15.3°±0.2°, 18.0°±0.2° and 21.4°±0.2°.

10. The crystalline form according to claim 8, wherein the crystalline form has an XRPD pattern substantially as shown in FIG. 11.

11. The compound of claim 1, which is

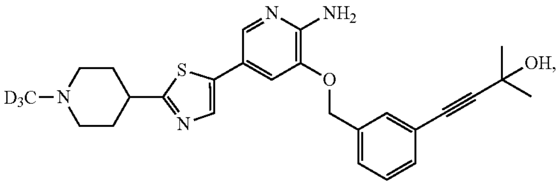

,

-continued

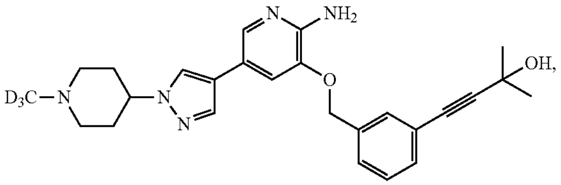

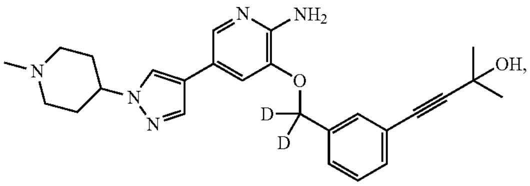

or

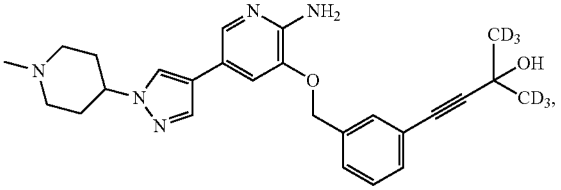

or a pharmaceutically acceptable salt thereof.

12. The compound of claim 1, which is

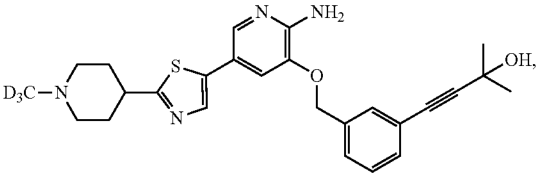

or

-continued

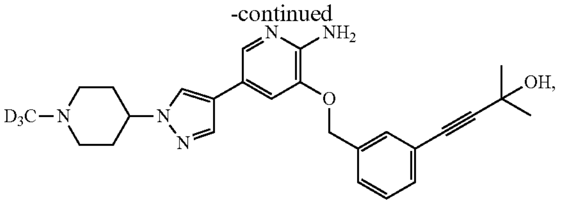

or a pharmaceutically acceptable salt thereof.

13. The compound of claim 1, which is

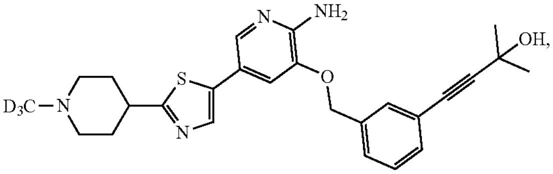 [SMILES: [2H]C([2H])([2H])N1CCC(c2ncc(-c3cnc(N)c(OCc4cccc(C#CC(C)(C)O)c4)c3)s2)CC1]

or a pharmaceutically acceptable salt thereof.

14. The compound of claim 1, which is

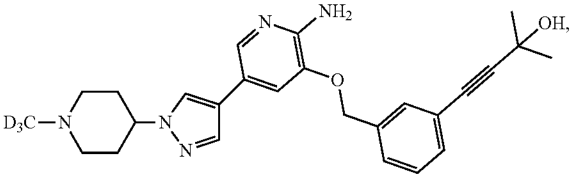 [SMILES: [2H]C([2H])([2H])N1CCC(n2cc(-c3cnc(N)c(OCc4cccc(C#CC(C)(C)O)c4)c3)cn2)CC1]

or a pharmaceutically acceptable salt thereof.

15. A pharmaceutical composition comprising the compound or the pharmaceutically acceptable salt thereof according to claim 1, and a pharmaceutically acceptable excipient.

* * * * *